（12）United States Patent
Bakker et al.

US009005624B2

(10) Patent No.: US 9,005,624 B2
(45) Date of Patent: *Apr. 14, 2015

(54) **BINDING MOLECULES CAPABLE OF NEUTRALIZING RABIES VIRUS AND US

(56) References Cited

FOREIGN PATENT DOCUMENTS

| WO | WO 98/15833 | 4/1998 |
| WO | WO 03/016501 | 2/2003 |
| WO | WO 2004/009618 | 1/2004 |
| WO | WO 2005/118644 | 12/2005 |
| WO | 2006112838 A1 | 10/2006 |
| WO | 2008068246 A1 | 6/2008 |

OTHER PUBLICATIONS

Dietzschold et al., "Biological Characterization of Human Monoclonal Antibodies to Rabies Virus," Journal of Virology, vol. 64, No. 6: pp. 3087-3090 (1990).*
Rudikoff et al., "Single amino acid substitution altering antigen-binding specificity," Proc Natl Acad Sci USA 79:1979-1983 (1982).*
Lafon et al., "Human monoclonal antibodies specific for the rabies virus glycoprotein and N protein," Journal of General Virology, 71: 1689-1696 (1990).*
Danielsson et al., "One-step purification of monoclonal IgG antibodies from mouse ascites," Journal of Immunological Methods 115: pp. 79-88 (1988).*
Li et al., "Synergistic Neutralization of Simian-Human Immunodeficiency Virus SHIV-vpu+ by Triple and Quadruple Combinations of Human Monoclonal Antibodies and High-Titer Anti-Human Immunodeficiency Virus Type 1 Immunoglobulins," J. Virol. 72(4):3235 (1998).*
Xiaoling et al., Construction of human phage-displayed scFv library and selection of the ScFv against rabies virus, Chinese Journal of Cellular and Molecular Immunology, Apr. 30, 2004, pp. 243-247, vol. 20, No. 2, (with English translation).
Benmansour et al., Journal of Virology, 1991, pp. 4198-4203, vol. 65.
Champion et al., "The development of monoclonal human rabies virus-neutralizing antibodies as a substitute for pooled human immune globulin in the prophylactic treatment of rabies virus exposure," Journal of Immunological Methods, 2000, pp. 81-90, vol. 235.
Database Genbank NCBI; Jun. 26, 2003, Prosniak, M. et al., "*Homo sapiens* anti-rabies S057 immunoglobulin heavy chain mRNA" XP 002356864, retrieved from http://www.ncbi.nlr.nih.gov, Database accession No. AY172957.
Database Genbank NCBI; Jun. 26, 2003, Prosniak, M. et al., "*Homo sapiens* anti-rabies S057 immunoglobulin lambda light chain mRNA" XP 002356865, retrieved from http://www.ncbi.nlr.nih.gov, Database accession No. AY172960.
De Haard et al., A Large Non-immunized Human Fab Fragment Phage Library That Permits Rapid Isolation and Kinetic Analysis of High Affinity Antibodies, 1999, Journal of Biological Chemistry, pp. 18218-18230, vol. 274, No. 26.
De Kruif et al., "Selection and Application of Human Single Chain Fv Antibody Fragments from a Semi-synthetic Phage Antibody Display Library with Designed CDR3 Regions," J. Mol. Biol., 1995, pp. 97-105, vol. 248.
De Kruif et al., Rapid selection of cell subpopulation-specific human monoclonal antibodies from a synthetic phage antibody library, 1995, Proceedings of the national Academy of Sciences of the United States of America, vol. 92, pp. 3938-3942.
Dietzschold et al., "Biological Characterization of Human Monoclonal Antibodies to Rabies Virus," Journal of Virology, Jun. 1990, pp. 3087-3090, vol. 64, No. 6.
Hanlon et al., "Experimental utility of rabies virus-neutralizing human monoclonal antibodies in post-exposure prophylaxis," Vaccine, 2001, pp. 3834-3842, vol. 19.
Heitner et al., Selection of cell binding and internalizing epidermal growth factor receptor antibodies from a phage display library, Journal of Immunological Methods, 2001, pp. 17-30, vol. 248.
Ikematsu et al., Sequences of the Vh genes of human IgM, IgG and IgA to rabies virus reveal preferential utilization of VhIII segments and somatic hypermutation, 1993, The Journal of Immunology, pp. 1325-1337, vol. 150.
Jones et al., "High-level Expression of Recombinant IgG in the Human Cell Line Per.C6," Biotechnol. Prog., 2003, pp. 163-168, vol. 19.
Kramer et al., Abstract, Immunity to infection: The human antibody repertoire specific for rabies virus glycoprotein as selected from immune libraries, Eur. J. Immunol., 35: 2131-2145 (2005).
Lang et al., Biologicals, 1998, vol. 26, No. 7-15.
Leucht et at, The B cell superantigen-like interaction of intravenous immunoglobulin (IVIG) with Fab fragments of Vh 3-23 and 3-30/3-30.5 germline gene origin cloned from a patient with Kawasaki disease is enhanced after IVIG therapy, 2001, Clinical Immunology, pp. 18-29, vol. 99.
Marissen et al., Novel Rabies Virus-Neutralizing Epitope Recognized by Human Monoclonal Antibody: Fine Mapping and Escape Mutant Analysis, Journal of Virology, Apr. 2005, pp. 4672-4678, vol. 79, No. 8.
Nicacio et al., Neutralizing human fab fragments against measles virus recovered by phage display, Journal of Virology, 2002, pp. 251-258, vol. 76.
Paul, Fundamental Immunology, (textbook), 1993, pp. 292-295, Lippincott-Raven Publishers, Philadelphia, PA (U.S. Appl. No. 11/978,742).
PCT International Preliminary Report on Patentability, PCT/EP2005/052410, dated Aug. 28, 2006.
PCT International Search Report, PCT/EP2005/052410, dated Jan. 9, 2006.
Prosniak et al., "Development of a Cocktail of Recombinant-Expressed Human Rabies Virus-Neutralizing Monoclonal Antibodies for Postexposure Prophylaxis of Rabies," Journal of Infectious Diseases, Jul. 1, 2003, pp. 53-56, vol. 188.
Ray et al., Selection of single chain variable fragments (scFv) against the glycoprotein antigen of the rabies virus from a human synthetic scFv phage display library and their fusion with the Fc region of human IgG1, Clinical and Experimental Immunology, 2001, pp. 94-101, vol. 125.
Schumacher et al. "Use of mouse anti-rabies monoclonal antibodies in post-exposure treatment of rabies." J. Clin. Invest. 84:971-975 (1989).
U.S. Appl. No. 12/383,330, filed Mar. 23, 2009 Bakker et al. Agonistic Binding Molecules to the Human OX40 Receptor.
Seif et al., Rabies Virulence: Effect on Pathogenicity and Sequence Characterization of Rabies Virus Mutations Affecting Antigenic Site III of the Glycoprotein, Journal of Virology, Mar. 1985, pp. 926-934, vol. 53, No. 3.
Xuan et al., "Biological and immunogenic properties of rabies virus glycoprotein expressed by canine herpesvirus vector," Vaccine, 1998, pp. 969-976, vol. 16, No. 9/10.
PCT International Preliminary Report on Patenability, PCT/EP2004/052043, dated Dec. 21, 2005.
PCT International Search Report, PCT/EP2004/052043. dated Apr. 21, 2005.
Fodor et al., "Nucleotide and deduced amino acid sequences of the glycoprotein gene of rabies virus vaccine strain Vnukovo-32," Archives of Virology, 1994, pp. 451-459, vol. 135, No. 3-4.
Daugherty et al., Formulation and delivery issues for monoclonal antibody therapeutics, Advanced Drug Delivery Reviews, 2006, pp. 686-706, vol. 58, Science Direct.
Database Geneseq 'Online! Dec. 18, 2003, "Wild-type rabies virus G protein." XP002323001, retrieved from EBI accession No. GSN:ACD37470, Database accession No. ADC37470.
Database USPTO Proteins Online! May 14, 2004, "Sequence 59 from patent US 6,706,523," XP002323002, retrieved from EBI accession No. USPOP:AAT21621, Database accession No. AAT21621.
Database Geneseq 'Online! Dec. 18, 2003, "Mutant rabies virus G protein," XP002323003, retrieved from EBI accession No. GSN:ADC37471, Database accession No. ADC37471.
Database USPTO Proteins Online! May 14, 2004, "Sequence 60 from patent US 6,706,523." XP002323004, retrieved from EBI accession No. USPOP:AAT21622, Database accession No. AAT21622.

(56) References Cited

OTHER PUBLICATIONS

Database NCBI 'Online! Jun. 1, 2001, Jayakumar: XP0002323005, retrieved from EBI accession No. Q99AU1, Database accession No. Q99AU1.

Database JPO Proteins 'Online! Apr. 27, 1998, "A recombinant Glycoprotein," XP002323006, retrieved from EBI accession No. JPOP:E61000, Database accession No. E61000.

Database Geneseq 'Online! Mar. 21, 1997, "Recombinant rabies virus G protein," XP002323007, retrieved from EBI accession No. GSN:AAW09380, Database accession No. AAW09380.

Dietzschold et al., "Chemical and Immunological Analysis of the rabies Soluble Glycoprotein," Virology, 1983, pp. 330-337, vol. 124, No. 2.

Dietzschold et al., "New Approaches to the Development of Live Attenuated Rabies Vaccines," Hybridoma and Hybridomics, Apr. 2002, pp. 129-134, vol. 21, No. 2.

Dietzschold et al., "Structural and Immunological Characterization of a Linear Virus-Neutralizing Epitope of the Rabies Virus glycoprotein and its Possible Use in a Synthetic Vaccine," Journal of Virology, Aug. 1990, pp. 3804-3809, vol. 64, No. 8.

Drings et al., "Is there an advantage to including the nucleoprotein in a rabies glycoprotein subunit vaccine?" Vaccine, 1999, pp. 1549-1557, vol. 17, No. 11/12.

Fu et al., "Oral vaccination of raccoons (Procyon lotor) with baculovirus-expressed rabies virus glycoprotein," Vaccine, 1993, pp. 925-928, vol. 11, No. 9.

Luo et al., "A virus-neutralizing epitope on the glycoprotein of rabies virus that contains Trp251 is a linear epitope," Virus Research, 1997, pp. 35-41, vol. 51, No. 1.

McGarvey et al., "Expression of the rabies Virus Glycoprotein in Transgenic Tomatoes," Bio/Technology, Dec. 1995, pp. 1484-1487, Vo. 13.
Morimoto et al., "Shedding of Gs Protein (A Soluble Form of the Viral Glycoprotein) by the Rabies Virus-Infected BHK-21 Cells," Virology, 1993, pp. 541-549, vol. 195, No. 2.
Translated text of Chinese Office Action for Co-pending Chinese Patent Application No. 201110071403.1, dated Sep. 23, 2013.

* cited by examiner

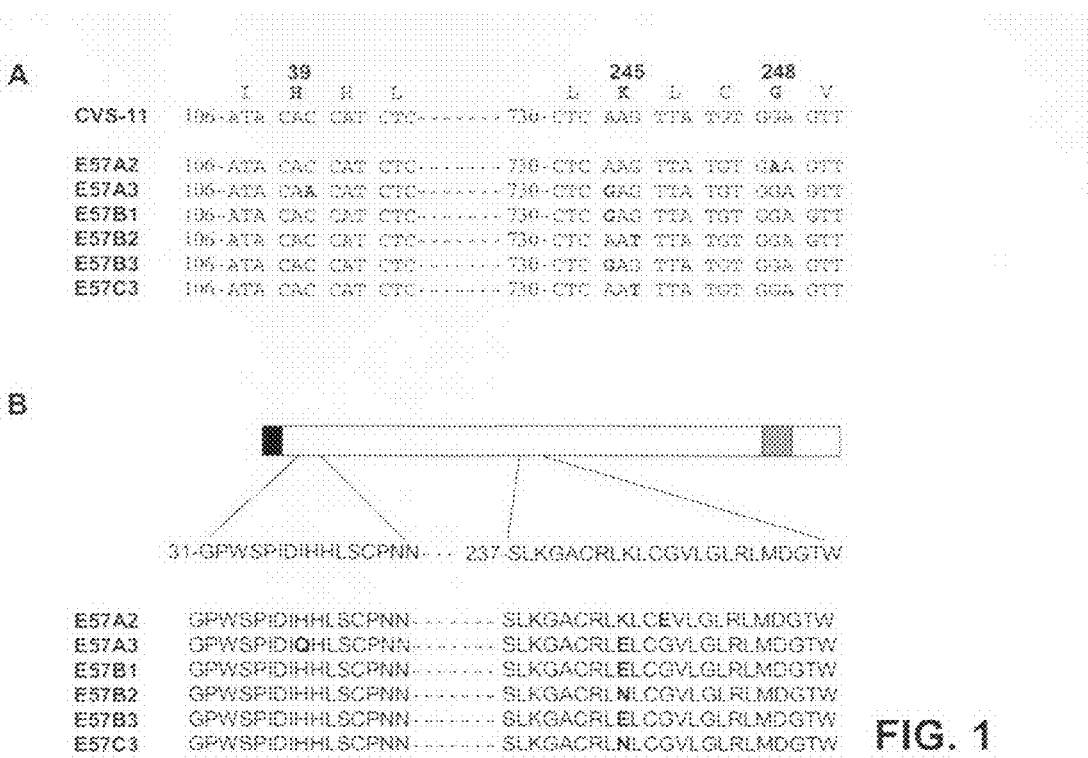
FIG. 1
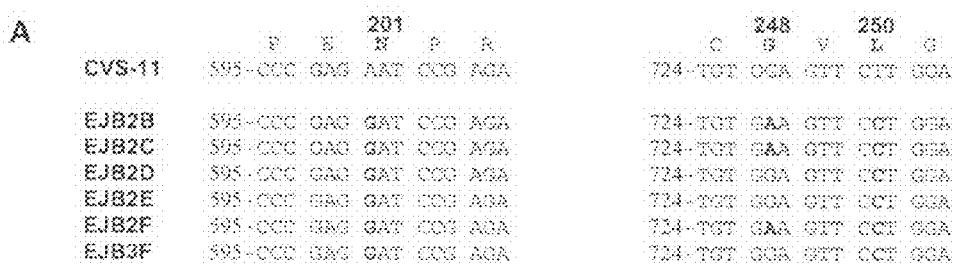
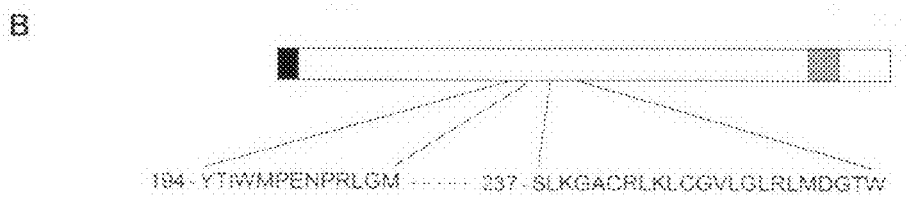
FIG. 2

A   CVS-11          1033
                    CGG ACC TGG AAT GAG ATC ATC
                    (SEQ ID NO:745)

E98-2, 4, 5, 6, 7   CGG ACC TGG GAT GAG ATC ATC
                        (SEQ ID NO:746)

B   CVS-11          336
                    HYKSVRT

BINDING MOLECULES CAPABLE OF NEUTRALIZING RABIES VIRUS AND USES THEREOF

CROSS-REFERENCE TO RELATED APPLICATIONS

This application is a divisional of U.S. patent application Ser. No. 11/978,742, filed Oct. 29, 2007, now U.S. Pat. No. 7,740,852, issued Jun. 22, 2010, which application is a divisional of U.S. patent application Ser. No. 11/590,126, filed Oct. 31, 2006, now U.S. Pat. No. 7,579,446, issued Aug. 25, 2009, which application is a continuation of International Patent Appln. No. PCT/EP2005/052410 filed May 26, 2005, and published in English as PCT Internat'l Publication No. WO 2005/118644 A2, on Dec. 15, 2005, which application claims priority to Internat'l Patent Appln. No. PCT/EP2005/050953 filed Mar. 3, 2005, which application claims priority to Internat'l Patent Appln. No. PCT/EP2005/050310, filed Jan. 25, 2005, which application claims priority to Internat'l Patent Appln. No. PCT/EP2004/052772 filed Nov. 3, 2004, which application claims priority to Internat'l Patent Appln. No. PCT/EP2004/052286 filed Sep. 23, 2004, which application claims priority to Internat'l Patent Appln. No. PCT/EP2004/051661 filed Jul. 29, 2004 which application claims priority to Internat'l Patent Appln. No. PCT/EP2004/050943 filed May 27, 2004, and U.S. Provisional Patent Appln. Ser. No. 60/575,023 filed May 27, 2004, the contents of the entirety of each of which are incorporated herein by this reference.

STATEMENT ACCORDING TO 37 C.F.R. §1.52(e)(5)—SEQUENCE LISTING SUBMITTED ON COMPACT DISC

Pursuant to 37 C.F.R. §1.52(e)(1)(ii), a compact disc containing an electronic version of the Sequence Listing has been submitted concomitant with this application, the contents of which are hereby incorporated herein by reference. A second compact disc is being submitted herewith and is an identical copy of the first compact disc. The discs are labeled "copy 1" and "copy 2," respectively, and each disc contains one file entitled "Sequence Listing 2578-7990US.txt" which is 337 KB and was created on Oct. 30, 2006.

TECHNICAL FIELD

The invention relates generally to biotechnology and medicine. In particular, the invention relates to binding molecules directed against rabies, such as virus-neutralizing binding molecules. The binding molecules are useful in the post-exposure prophylaxis of rabies.

BACKGROUND

Rabies is a viral infection with nearly worldwide distribution that affects principally wild and domestic animals but also involves humans, resulting in a devastating, almost invariably fatal encephalitis. Annually, more than 70,000 human fatalities are estimated, and millions of others require post-exposure treatment.

The rabies virus is a bullet-shaped, enveloped, single-stranded RNA virus classified in the rhabdovirus family and Lyssavirus genus. The genome of rabies virus codes for five viral proteins: RNA-dependent RNA polymerase (L); a nucleoprotein (N); a phosphorylated protein (P); a matrix protein (M) located on the inner side of the viral protein envelope; and an external surface glycoprotein (G).

The G protein (62-67 kDa) is a type-I glycoprotein composed of 505 amino acids that has two to four potential N-glycosylation sites, of which only one or two are glycosylated depending on the virus strains. The G protein forms the protrusions that cover the outer surface of the virion envelope and is known to induce virus-neutralizing antibodies.

Rabies can be treated or prevented by both passive and active immunizations. Rabies post-exposure prophylaxis includes prompt local wound care and administration of both passive (anti-rabies immunoglobulins) and active (vaccines) immunizations.

Currently, the anti-rabies immunoglobulins (RIG) are prepared from the serum samples of either rabies virus-immune humans (HRIG) or rabies virus-immune horses (ERIG). A disadvantage of ERIG as well as HRIG is that they are not available in sufficient amounts and, in case of HRIG, are too expensive. In addition, the use of ERIG might lead to adverse reactions such as anaphylactic shock. The possibility of contamination by known or unknown pathogens is an additional concern associated with HRIG. To overcome these disadvantages it has been suggested to use monoclonal antibodies capable of neutralizing rabies virus in post-exposure prophylaxis. Rabies virus-neutralizing murine monoclonal antibodies are known in the art (see, Schumacher et al., 1989). However, the use of murine antibodies in vivo is limited due to problems associated with administration of murine antibodies to humans, such as short serum half life, an inability to trigger certain human effector functions and elicitation of an unwanted dramatic immune response against the murine antibody in a human (the "human anti-mouse antibody" (HAMA) reaction).

Recently, human rabies virus-neutralizing monoclonal antibodies have been described (see, Dietzschold et al., 1990, Champion et al., 2000, and Hanlon et al., 2001). For human anti-rabies monoclonal antibodies to be as effective as HRIG in post-exposure prophylaxis a mixture of monoclonal antibodies should be used. In such a mixture each antibody should bind to a different epitope or site on the virus to prevent the escape of resistant variants of the virus.

Currently, a significant need still exists for new human rabies virus-neutralizing monoclonal antibodies having improved post-exposure prophylactic potential, particularly antibodies having different epitope-recognition specificities.

SUMMARY OF THE INVENTION

Described are human monoclonal antibodies that offer the potential to be used in mixtures useful in the post-exposure prophylaxis of a wide range of rabies viruses and neutralization-resistant variants thereof.

Herebelow follow definitions of terms as used herein.

DEFINITIONS

Binding molecule: As used herein the term "binding molecule" refers to an intact immunoglobulin including monoclonal antibodies, such as chimeric, humanized or human monoclonal antibodies, or to an antigen-binding and/or variable domain comprising fragment of an immunoglobulin that competes with the intact immunoglobulin for specific binding to the binding partner of the immunoglobulin, e.g., rabies virus or a fragment thereof such as, for instance, the G protein. Regardless of structure, the antigen-binding fragment binds with the same antigen that is recognized by the intact immunoglobulin. An antigen-binding fragment can comprise a peptide or polypeptide comprising an amino acid sequence of at least two contiguous amino acid residues, at least five contiguous amino acid residues, at least ten contiguous amino acid residues, at least 15 contiguous amino acid residues, at least 20 contiguous amino acid residues, at least 25 contiguous amino acid residues, at least 30 contiguous amino acid residues, at least 35 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of the binding molecule.

The term "binding molecule," as used herein includes all immunoglobulin classes and subclasses known in the art. Depending on the amino acid sequence of the constant domain of their heavy chains, binding molecules can be divided into the five major classes of intact antibodies: IgA, IgD, IgE, IgG, and IgM, and several of these may be further divided into subclasses (isotypes), e.g., IgA1, IgA2, IgG1, IgG2, IgG3 and IgG4.

Antigen-binding fragments include, inter alia, Fab, F(ab'), F(ab')$_2$, Fv, dAb, Fd, complementarity determining region (CDR) fragments, single-chain antibodies (scFv), bivalent single-chain antibodies, single-chain phage antibodies, diabodies, triabodies, tetrabodies, (poly)peptides that contain at least a fragment of an immunoglobulin that is sufficient to confer specific antigen binding to the (poly)peptide, etc. The above fragments may be produced synthetically or by enzymatic or chemical cleavage of intact immunoglobulins or they may be genetically engineered by recombinant DNA techniques. The methods of production are well known in the art and are described, for example, in "Antibodies: A Laboratory Manual," edited by E. Harlow and D. Lane (1988), Cold Spring Harbor Laboratory, Cold Spring Harbor, N.Y., which is incorporated herein by reference. A binding molecule or antigen-binding fragment thereof may have one or more binding sites. If there is more than one binding site, the binding sites may be identical to one another or they may be different.

The binding molecule can be a naked or unconjugated binding molecule but can also be part of an immunoconjugate. A naked or unconjugated binding molecule is intended to refer to a binding molecule that is not conjugated, operatively linked or otherwise physically or functionally associated with an effector moiety or tag, such as inter alia a toxic substance, a radioactive substance, a liposome, or an enzyme. It will be understood that naked or unconjugated binding molecules do not exclude binding molecules that have been stabilized, multimerized, humanized or in any other way manipulated, other than by the attachment of an effector moiety or tag. Accordingly, all post-translationally modified naked and unconjugated binding molecules are included herewith, including where the modifications are made in the natural binding molecule-producing cell environment, by a recombinant-binding molecule-producing cell, and are introduced by the hand of man after initial binding molecule preparation. Of course, the term naked or unconjugated binding molecule does not exclude the ability of the binding molecule to form functional associations with effector cells and/or molecules after administration to the body, as some of such interactions are necessary in order to exert a biological effect. The lack of associated effector group or tag is therefore applied in definition to the naked or unconjugated binding molecule in vitro, not in vivo.

Complementarily determining regions (CDR): The term "complementarity determining regions" as used herein means sequences within the variable regions of binding molecules, such as immunoglobulins, that usually contribute to a large extent to the antigen-binding site which is complementary in shape and charge distribution to the epitope recognized on the antigen. The CDR regions can be specific for linear epitopes, discontinuous epitopes, or conformational epitopes of proteins or protein fragments, either as present on the protein in its native conformation or, in some cases, as present on the proteins as denatured, e.g., by solubilization in SDS. Epitopes may also consist of post-translational modifications of proteins.

Functional variant: The term "functional variant," as used herein, refers to a binding molecule that comprises a nucleotide and/or amino acid sequence that is altered by one or more nucleotides and/or amino acids compared to the nucleotide and/or amino acid sequences of the parent binding molecule and that is still capable of competing for binding to the binding partner, e.g., rabies virus or a fragment thereof, with the parent binding molecule. In other words, the modifications in the amino acid and/or nucleotide sequence of the parent binding molecule do not significantly affect or alter the binding characteristics of the binding molecule encoded by the nucleotide sequence or containing the amino acid sequence, i.e., the binding molecule is still able to recognize and bind its target. The functional variant may have conservative sequence modifications including nucleotide and amino acid substitutions, additions and deletions. These modifications can be introduced by standard techniques known in the art, such as site-directed mutagenesis and random PCR-mediated mutagenesis, and may comprise natural as well as non-natural nucleotides and amino acids.

Conservative amino acid substitutions include the ones in which the amino acid residue is replaced with an amino acid residue having similar structural or chemical properties. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine, tryptophan), nonpolar side chains (e.g., glycine, alanine, valine, leucine, isoleucine, proline, phenylalanine, methionine), beta-branched side chains (e.g., threonine, valine, isoleucine) and aromatic side chains (e.g., tyrosine, phenylalanine, tryptophan). It will be clear to the skilled artisan that other classifications of amino acid residue families than the one used above can also be employed. Furthermore, a variant may have non-conservative amino acid substitutions, e.g., replacement of an amino acid with an amino acid residue having different structural or chemical properties. Similar minor variations may also include amino acid deletions or insertions, or both. Guidance in determining which amino acid residues may be substituted, inserted, or deleted without abolishing immunological activity may be found using computer programs well known in the art.

A mutation in a nucleotide sequence can be a single alteration made at a locus (a point mutation), such as transition or transversion mutations, or alternatively, multiple nucleotides may be inserted, deleted or changed at a single locus. In addition, one or more alterations may be made at any number of loci within a nucleotide sequence. The mutations may be performed by any su Host: The term "host," as used herein, is intended to refer to an organism or a cell into which a vector such as a cloning vector or an expression vector has been introduced. The organism or cell can be prokaryotic or eukaryotic. It should be understood that this term is intended to refer not only to the particular subject organism or cell, but to the progeny of such an organism or cell as well. Because certain modifications may occur in succeeding generations due to either mutation or environmental influences, such progeny may not, in fact, be identical to the parent organism or cell, but are still included within the scope of the term "host" as used herein.

Human: The term "human," when applied to binding molecules as defined herein, refers to molecules that are either directly derived from a human or based upon a human sequence. When a binding molecule is derived from or based on a human sequence and subsequently modified, it is still to be considered human as used throughout the specification. In other words, the term human, when applied to binding molecules is intended to include binding molecules having variable and constant regions derived from human germline immunoglobulin sequences based on variable or constant regions either or not occurring in a human or human lymphocyte or in modified form. Thus, the human binding molecules may include amino acid residues not encoded by human germline immunoglobulin sequences, comprise substitutions and/or deletions (e.g., mutations introduced by, for instance, random or site-specific mutagenesis in vitro or by somatic mutation in vivo). "Based on" as used herein refers to the situation that a nucleic acid sequence may be exactly copied from a template, or with minor mutations, such as by error-prone PCR methods, or synthetically made matching the template exactly or with minor modifications. Semisynthetic molecules based on human sequences are also considered to be human as used herein.

Monoclonal antibody: The term "monoclonal antibody" as used herein refers to a preparation of antibody molecules of single molecular composition, i.e., primary structure, i.e., having a single amino acid sequence. A monoclonal antibody displays a single binding specificity and affinity for a particular epitope. Accordingly, the term "human monoclonal antibody" refers to an antibody displaying a single binding specificity which has variable and constant regions derived from, or based on, human germline immunoglobulin sequences or derived from completely synthetic sequences. The method of preparing the monoclonal antibody is not relevant.

Nucleic acid molecule: The term "nucleic acid molecule" as used in the invention refers to a polymeric form of nucleotides and includes both sense and antisense strands of RNA, cDNA, genomic DNA, and synthetic forms and mixed polymers of the above. A nucleotide refers to a ribonucleotide, deoxynucleotide or a modified form of either type of nucleotide. The term also includes single- and double-stranded forms of DNA. In addition, a polynucleotide may include either or both naturally occurring and modified nucleotides linked together by naturally occurring and/or non-naturally occurring nucleotide linkages. The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). The above term is also intended to include any topological conformation, including single-stranded, double-stranded, partially duplexed, triplex, hairpinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. A reference to a nucleic acid sequence encompasses its complement unless otherwise specified. Thus, a reference to a nucleic acid molecule having a particular sequence should be understood to encompass its complementary strand, with its complementary sequence. The complementary strand is also useful, e.g., for antisense therapy, hybridization probes and PCR primers.

Pharmaceutically acceptable excipient: By "pharmaceutically acceptable excipient" is meant any inert substance that is combined with an active molecule such as a drug, agent, or binding molecule for preparing an agreeable or convenient dosage form. The "pharmaceutically acceptable excipient" is an excipient that is non-toxic, or at least of which the toxicity is acceptable for its intended use, to recipients at the dosages and concentrations employed and is compatible with other ingredients of the formulation comprising the drug, agent or binding molecule.

Post exposure prophylaxis: "Post exposure prophylaxis" (PEP) is indicated for persons possibly exposed to a rabid animal. Possible exposures include bite exposure (i.e., any penetration of the skin by teeth) including animal bites, and non-bite exposure. Non-bite exposures include exposure to large amounts of aerosolized rabies virus in laboratories or caves and surgical recipients of corneas transplanted from patients who died of rabies. The contamination of open wounds, abrasions, mucous membranes, or theoretically, scratches, with saliva or other potentially infectious material (such as neural tissue) from a rabid animal also constitutes a non-bite exposure. Other contact by itself, such as petting a rabid animal and contact with blood, urine, or feces of a rabid animal, does not constitute an exposure and is not an indication for prophylaxis. PEP should begin as soon as possible after an exposure. If no exposure has occurred post exposure prophylaxis is not necessary. In all post exposure prophylaxis regimens, except for persons previously immunized, active and passive immunizations should be used concurrently.

Specifically Binding: The term "specifically binding," as used herein, in reference to the interaction of a binding molecule, e.g., an antibody, and its binding partner, e.g., an antigen, means that the interaction is dependent upon the presence of a particular structure, e.g., an antigenic determinant or epitope, on the binding partner. In other words, the antibody preferentially binds or recognizes the binding partner even when the binding partner is present in a mixture of other molecules or organisms. The binding may be mediated by covalent or non covalent interactions or a combination of both. In yet other words, the term "specifically binding" means immunospecifically binding to an antigen or a fragment thereof and not immunospecifically binding to other antigens. A binding molecule that immunospecifically binds to an antigen may bind to other peptides or polypeptides with lower affinity as determined by, e.g., radioimmunoassays (RIA), enzyme linked immunosorbent assays (ELISA), BIACORE®, or other assays known in the art. Binding molecules or fragments thereof that immunospecifically bind to an antigen may be cross reactive with related antigens. In certain embodiments, binding molecules or fragments thereof that immunospecifically bind to an antigen do not cross react with other antigens.

Therapeutically effective amount: The term "therapeutically effective amount" refers to an amount of the binding molecule as defined herein that is effective for post-exposure prophylaxis of rabies.

Vector: The term "vector" denotes a nucleic acid molecule into which a second nucleic acid molecule can be inserted for introduction into a host where it will be replicated, and in some cases expressed. In other words, a vector is capable of transporting a nucleic acid molecule to which it has been linked. Cloning as well as expression vectors are contemplated by the term "vector," as used herein. Vectors include, but are not limited to, plasmids, cosmids, bacterial artificial chromosomes (BAC) and yeast artificial chromosomes (YAC) and vectors derived from bacteriophages or plant or animal (including human) viruses. Vectors comprise an origin of replication recognized by the proposed host and in case of expression vectors, promoter and other regulatory regions recognized by the host. A vector containing a second nucleic acid molecule is introduced into a cell, for example, by transformation, transfection, or by making use of bacterial or viral entry mechanisms. Other ways of introducing nucleic acid into cells are known, such as electroporation or particle bombardment often used with plant cells, and the like. The method of introducing nucleic acid into cells depends among other things on the type of cells, and so forth. This is not critical to the invention. Certain vectors are capable of autonomous replication in a host into which they are introduced (e.g., vectors having a bacterial origin of replication can replicate in bacteria). Other vectors can be integrated into the genome of a host upon introduction into the host, and thereby are replicated along with the host genome.

Provided are binding molecules capable of specifically binding to and neutralizing rabies virus. Furthermore, described are nucleic acid molecules encoding at least the binding region of these binding molecules. The invention further provides for the use of the binding molecules of the invention in the post exposure prophylaxis of a subject at risk of developing a condition resulting from rabies virus.

DESCRIPTION OF THE FIGURES

FIG. 1 shows the comparison of the amino acid sequences of the rabies virus strain CVS-11 and E57 escape viruses. Virus-infected cells were harvested two days post-infection and total RNA was isolated. cDNA was generated and used for DNA sequencing. Regions containing mutations are shown and the mutations are indicated in bold. FIG. 1A shows the comparison of the nucleotide sequences. Numbers above amino acids indicate amino acid numbers from rabies virus glycoprotein including signal peptide. FIG. 1B shows the comparison of amino acid sequences. Schematic drawing of rabies virus glycoprotein is shown on top. The black box indicates the signal peptide, while the gray box indicates the transmembrane domain. The sequences in FIG. 1 are also represented by SEQ ID NOS:130 through 141 of the incorporated SEQUENCE LISTING.

FIG. 2 shows the comparison of the amino acid sequences of the rabies virus strain CVS-11 and EJB escape viruses. Virus-infected cells were harvested two days post-infection and total RNA was isolated. cDNA was generated and used for DNA sequencing. Regions containing mutations are shown and the mutations are indicated in bold. FIG. 2A shows the comparison of the nucleotide sequences. Numbers above amino acids indicate amino acid numbers from rabies virus glycoprotein including the signal peptide. FIG. 2B shows the comparison of amino acid sequences. Schematic drawing of rabies virus glycoprotein is shown on top. The black box indicates the signal peptide, while the gray box indicates the transmembrane domain. The sequences in FIG. 2 are also represented by SEQ ID NOS:142 through 151.

FIG. 8 shows the comparison of the amino acid sequences of CVS-11 and E98 escape viruses. Virus-infected cells were harvested two days post-infection and total RNA was isolated. cDNA was generated and used for DNA sequencing. Region containing a point mutation is shown and the mutation is indicated in bold. FIG. 8A shows the comparison of the nucleotide sequences SEQ ID NOS:745 and 746. The number above the nucleotide indicates the mutated nucleotide (indicated in bold) from rabies virus glycoprotein open reading frame without signal peptide sequence. FIG. 8B shows the comparison of amino acid sequences SEQ ID NOS:747 and 748. The number above the amino acid indicates the mutated amino acid (indicated in bold) from rabies virus glycoprotein without signal peptide sequence.

FIG. 10 shows neutralizing epitopes on rabies glycoprotein. A schematic drawing of the rabies virus glycoprotein is shown depicting the antigenic sites including the novel CR57 epitope. The signal peptide (19 amino acids) and transmembrane domain are indicated by black boxes. Disulfide bridges are indicated. Amino acid numbering is from the mature protein minus the signal peptide sequence.

DETAILED DESCRIPTION OF THE INVENTION

Figure 3:
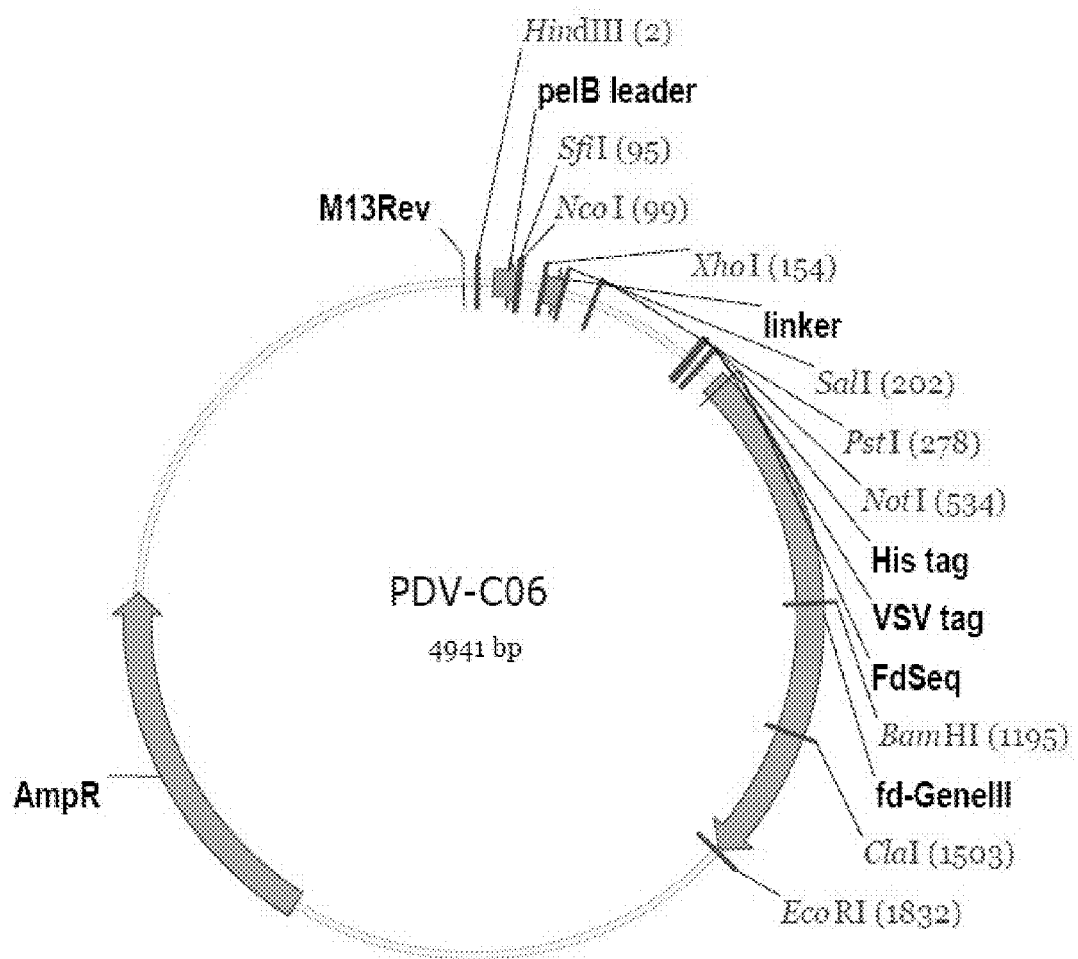
FIG. 3 shows the vector PDV-C06.

In a first aspect, the invention encompasses binding molecules capable of specifically binding to rabies virus. In certain embodiments, the binding molecules of the invention also have rabies virus-neutralizing activity. In certain embodiments, the binding molecules of the invention are human binding molecules. Alternatively, they may also be binding molecules of other animals. Rabies virus is part of the Lyssavirus genus. In total, the Lyssavirus genus includes eleven genotypes: rabies virus (genotype 1), Lagos bat virus (genotype 2), Mokola virus (genotype 3), Duvenhage virus (genotype 4), European bat lyssavirus 1 (genotype 5), European bat lyssavirus 2 (genotype 6), Australian bat lyssavirus (genotype 7), Aravan virus (genotype 8), Khujand virus (genotype 9), Irkut virus (genotype 10) and West Caucasian virus (genotype 11). Besides binding to rabies virus, the binding molecules of the invention may also be capable of binding to other genotypes of the Lyssavirus genus. In certain embodiments, the binding molecules may also be capable of neutralizing other genotypes of the Lyssavirus genus. Furthermore, the binding molecules of the invention may even be capable of binding to and/or neutralizing viruses, other than Lyssaviruses, of the rhabdovirus family. This family includes the genera cytorhabdovirus, ephemerovirus, lyssavirus, nucleorhabdovirus, rhabdovirus and vesiculovirus.

The binding molecules may be capable of specifically binding to rabies virus in its natural form or in its inactivated/attenuated form. Inactivation of rabies virus may be performed by treatment with inter alia beta-propiolactone (BPL) (White and Chappel, 1982), heating at 56° C. for more than 30 minutes, gamma irradiation, treatment with acetylethylenimine or ethylenimine or treatment with ascorbic acid and copper sulfate for 72 hours (Madhusudana et al., 2004). General viral inactivation methods well known to the skilled artisan such as inter alia pasteurization (wet heat), dry heat treatment, vapor heat treatment, treatment with low pH, treatment with organic solvent/detergent, nanofiltration; UV light irradiation may also be used. In certain embodiments, the inactivation is performed by treatment with beta-propiolactone (BPL). Methods to test if rabies virus is still infective or partly or completely inactivated are well known to the person skilled in the art and can among others be found in "Laboratory techniques in rabies," edited by F.-X. Meslin, M. M. Kaplan and H. Koprowski (1996), 4th edition, Chapter 36, World Health Organization, Geneva.

The binding molecules may also be capable of specifically binding to one or more fragments of the rabies virus such as inter alia a preparation of one or more proteins and/or (poly) peptides derived from rabies virus or a cell transfected with a rabies virus protein and/or (poly)peptide. For methods of treatment and/or prevention such as methods for post exposure prophylaxis of rabies virus the binding molecules are preferably capable of specifically binding to surface accessible proteins of rabies virus such as the M (see, Ameyama et al. 2003) or G protein. For diagnostic purposes, the human binding molecules may also be capable of specifically binding to proteins not present on the surface of rabies virus. The amino acid sequence of surface accessible and internal proteins of various known strains of rabies virus can be found in the EMBL-database and/or other databases.

In certain embodiments, the fragment at least comprises an antigenic determinant recognized by the human binding molecules of the invention. An "antigenic determinant" as used herein is a moiety, such as a rabies virus (poly)peptide, (glyco)protein, or analog or fragment thereof, that is capable of binding to a human binding molecule of the invention with sufficiently high affinity to form a detectable antigen-binding molecule complex.

The binding molecules according to the invention can be intact immunoglobulin molecules such as polyclonal or monoclonal antibodies, in particular human monoclonal antibodies, or the binding molecules can be antigen-binding fragments including, but not limited to, Fab, F(ab'), F(ab')$_2$, Fv, dAb, Fd, complementarity determining region (CDR) fragments, single-chain antibodies (scFv), bivalent single-chain antibodies, single-chain phage antibodies, diabodies, triabodies, tetrabodies, and (poly)peptides that contain at least a fragment of an immunoglobulin that is sufficient to confer specific antigen binding to the rabies virus or fragment thereof. The binding molecules of the invention can be used in non-isolated or isolated form. Furthermore, the binding molecules of the invention can be used alone or in a mixture comprising at least one human binding molecule (or variant or fragment thereof). In other words, the binding molecules can be used in combination, e.g., as a pharmaceutical composition comprising two or more binding molecules, variants or fragments thereof. For example, binding molecules having rabies virus-neutralizing activity can be combined in a single therapy to achieve a desired prophylactic, therapeutic or diagnostic effect.

RNA viruses such as rabies virus make use of their own RNA polymerase during virus replication. These RNA polymerases tend to be error-prone. This leads to the formation of so-called quasi-species during a viral infection. Each quasi-species has a unique RNA genome, which could result in differences in amino acid composition of viral proteins. If such mutations occur in structural viral proteins, the virus could potentially escape from the host's immune system due to a change in T or B cell epitopes. The likelihood of this to happen is higher when individuals are treated with a mixture of two binding molecules, such as human monoclonal antibodies, than with a polyclonal antibody mixture (HRIG). Therefore, a prerequisite for a mixture of two human monoclonal antibodies for treatment of rabies is that the two antibodies recognize non-overlapping, non-competing epitopes on their target antigen, i.e., rabies virus glycoprotein. The chance of the occurrence of rabies escape viruses is thereby minimized. As a consequence thereof, the binding molecules of the invention preferably are capable of reacting with different, non-overlapping, non-competing epitopes of the rabies virus, such as epitopes on the rabies virus G protein. The mixture of binding molecules may further comprise at least one other therapeutic agent such as a medicament suitable for the post exposure prophylaxis of rabies.

Typically, binding molecules hereof can bind to their binding partners, i.e., rabies virus or fragments thereof such as rabies virus proteins, with an affinity constant ($K_d$-value) that is lower than $0.2*10^{-4}$ M, $1.0*10^{-5}$ M, $1.0*10^{-6}$ M, $1.0*10^{-7}$ M, preferably lower than $1.0*10^{-8}$ M, more preferably lower than $1.0*10^{-9}$ M, more preferably lower than $1.0*10^{-10}$ M, even more preferably lower than $1.0*10^{-11}$ M, and in particular lower than $1.0*10^{-12}$ M. The affinity constants can vary for antibody isotypes. For example, affinity binding for an IgM isotype refers to a binding affinity of at least about $1.0*10^{-7}$ M. Affinity constants can for instance be measured using surface plasmon resonance, i.e., an optical phenomenon that allows for the analysis of real time biospecific interactions by detection of alterations in protein concentrations within a biosensor matrix, for example, using the BIACORE® system (Pharmacia Biosensor AB, Uppsala, Sweden).

The binding molecules according to the invention may bind to rabies virus in purified/isolated or non-purified/non-isolated form. The binding molecules may bind to rabies virus in soluble form such as, for instance, in a sample or may bind to rabies virus bound or attached to a carrier or substrate, e.g., microtiter plates, membranes and beads, etc. Carriers or substrates may be made of glass, plastic (e.g., polystyrene), polysaccharides, nylon, nitrocellulose, or teflon, etc. The surface of such supports may be solid or porous and of any convenient shape. Alternatively, the binding molecules may also bind to fragments of rabies virus, such as proteins or (poly)peptides of the rabies virus. In certain embodiments, the binding molecules are capable of specifically binding to the rabies virus G protein or fragment thereof. The rabies virus proteins or (poly)peptides may either be in soluble form or may bind to rabies virus bound or attached to a carrier or substrate as described above. In certain embodiments, cells transfected with the G protein may be used as binding partner for the binding molecules.

In certain embodiments, the binding molecules of the invention neutralize rabies virus infectivity. This may be achieved by preventing the attachment of rabies virus to its receptors on host cells, such as inter alia the murine p75 neurotrophin receptor, the neural cell adhesion molecule (CD56) and the acetylcholine receptor, or inhibition of the release of RNA into the cytoplasm of the cell or prevention of RNA transcription or translation. In a specific embodiment, the binding molecules of the invention prevent rabies virus from infecting host cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to infection of host cells by rabies virus in the absence of the binding molecules. Neutralization can, for instance, be measured as described in "Laboratory techniques in rabies," edited by F.-X. Meslin, M. M. Kaplan and H. Koprowski (1996), 4th edition, Chapters 15-17, World Health Organization, Geneva. Furthermore, the human binding molecules of the invention may be complement fixing binding molecules capable of assisting in the lysis of enveloped rabies virus. The human binding molecules of the invention might also act as opsonins and augment phagocytosis of rabies virus either by promoting its uptake via Fc or C3b receptors or by agglutinating rabies virus to make it more easily phagocytosed.

In a preferred embodiment, the binding molecules according to the invention comprise at least a CDR3 region comprising the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23 and SEQ ID NO:24. In certain embodiments, the CDR3 region is a heavy chain CDR3 region.

In yet another embodiment, the binding molecules according to the invention comprise a variable heavy chain comprising essentially an amino acid sequence selected from the group consisting of SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48 and SEQ ID NO:49. In a preferred embodiment, the binding molecules according to the invention comprise a variable heavy chain comprising essentially an amino acid sequence comprising amino acids 1-119 of SEQ ID NO:335.

In a further embodiment, the binding molecules according to the invention comprise a variable heavy chain comprising the amino acid sequence of SEQ ID NO:26 and a variable light chain comprising the amino acid sequence of SEQ ID NO:50, a variable heavy chain comprising the amino acid sequence of SEQ ID NO:27 and a variable light chain comprising the amino acid sequence of SEQ ID NO:51, a variable heavy chain comprising the amino acid sequence of SEQ ID NO:28 and a variable light chain comprising the amino acid sequence of SEQ ID NO:52, a variable heavy chain comprising the amino acid sequence of SEQ ID NO:29 and a variable light chain comprising the amino acid sequence of SEQ ID NO:53, a variable heavy chain comprising the amino acid sequence of SEQ ID NO:30 and a variable light chain comprising the amino acid sequence of SEQ ID NO:54, a variable heavy chain comprising the amino acid sequence of SEQ ID NO:31 and a variable light chain comprising the amino acid sequence of SEQ ID NO:55, a variable heavy chain comprising the amino acid sequence of SEQ ID NO:32 and a variable light chain comprising the amino acid sequence of SEQ ID NO:56, a variable heavy chain comprising the amino acid sequence of SEQ ID NO:33 and a variable light chain comprising the amino acid sequence of SEQ ID NO:57, a variable heavy chain comprising the amino acid sequence of SEQ ID NO:34 and a variable light chain comprising the amino acid sequence of SEQ ID NO:58, a variable heavy chain comprising the amino acid sequence of SEQ ID NO:35 and a variable light chain comprising the amino acid sequence of SEQ ID NO:59, a variable heavy chain comprising the amino acid sequence of SEQ ID NO:36 and a variable light chain comprising the amino acid sequence of SEQ ID NO:60, a variable heavy chain comprising the amino acid sequence of SEQ ID NO:37 and a variable light chain comprising the amino acid sequence of SEQ ID NO:61, a variable heavy chain comprising the amino acid sequence of SEQ ID NO:38 and a variable light chain comprising the amino acid sequence of SEQ ID NO:62, a variable heavy chain comprising the amino acid sequence of SEQ ID NO:39 and a variable light chain comprising the amino acid sequence of SEQ ID NO:63, a variable heavy chain comprising the amino acid sequence of SEQ ID NO:40 and a variable light chain comprising the amino acid sequence of SEQ ID NO:64, a variable heavy chain comprising the amino acid sequence of SEQ ID NO:41 and a variable light chain comprising the amino acid sequence of SEQ ID NO:65, a variable heavy chain comprising the amino acid sequence of SEQ ID NO:42 and a variable light chain comprising the amino acid sequence of SEQ ID NO:66, a variable heavy chain comprising the amino acid sequence of SEQ ID NO:43 and a variable light chain comprising the amino acid sequence of SEQ ID NO:67, a variable heavy chain comprising the amino acid sequence of SEQ ID NO:44 and a variable light chain comprising the amino acid sequence of SEQ ID NO:68, a variable heavy chain comprising the amino acid sequence of SEQ ID NO:45 and a variable light chain comprising the amino acid sequence of SEQ ID NO:69, a variable heavy chain comprising the amino acid sequence of SEQ ID NO:46 and a variable light chain comprising the amino acid sequence of SEQ ID NO:70, a variable heavy chain comprising the amino acid sequence of SEQ ID NO:47 and a variable light chain comprising the amino acid sequence of SEQ ID NO:71, a variable heavy chain comprising the amino acid sequence of SEQ ID NO:48 and a variable light chain comprising the amino acid sequence of SEQ ID NO:72, a variable heavy chain comprising the amino acid sequence of SEQ ID NO:49 and a variable light chain comprising the amino acid sequence of SEQ ID NO:73. In a preferred embodiment, the human binding molecules according to the invention comprise a variable heavy chain comprising the amino acid sequence comprising amino acids 1-119 of SEQ ID NO:335 and a variable light chain comprising the amino acid sequence comprising amino acids 1-107 of SEQ ID NO:337.

In a preferred embodiment, the binding molecules having rabies virus-neutralizing activity of the invention are administered in IgG format, preferably IgG1 format.

Another aspect of the invention includes functional variants of binding molecules as defined herein. Molecules are considered to be "functional variants of a binding molecule according to the invention," if the variants are capable of competing for specific binding to rabies virus or a fragment thereof with the parent binding molecules; in other words, when the functional variants are still capable of binding to rabies virus or a fragment thereof. Functional variants should also still have rabies virus-neutralizing activity. Functional variants include, but are not limited to, derivatives that are substantially similar in primary structural sequence, but which contain e.g., in vitro or in vivo modifications, chemical and/or biochemical, that are not found in the parent binding molecule. Such modifications include inter alia acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI-anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, ubiquitination, and the like.

Alternatively, functional variants can be binding molecules as defined in the invention comprising an amino acid sequence containing substitutions, insertions, deletions or combinations thereof of one or more amino acids compared to the amino acid sequences of the parent binding molecules. Furthermore, functional variants can comprise truncations of the amino acid sequence at either or both the amino or carboxy termini. Functional variants according to the invention may have the same or different, either higher or lower, binding affinities compared to the parent binding molecule but are still capable of binding to rabies virus or a fragment thereof and are still capable of neutralizing rabies virus. For instance, functional variants according to the invention may have increased or decreased binding affinities for rabies virus or a fragment thereof compared to the parent binding molecules or may have a higher or lower rabies virus-neutralizing activity. In certain embodiments, the amino acid sequences of the variable regions, including, but not limited to, framework regions, hypervariable regions, in particular the CDR3 regions, are modified. Generally, the light chain and the heavy chain variable regions comprise three hypervariable regions, comprising three CDRs, and more conserved regions, the so-called framework regions (FRs). The hypervariable regions comprise amino acid residues from CDRs and amino acid residues from hypervariable loops. Functional variants intended to fall within the scope of the invention have at least about 50% to about 99%, preferably at least about 60% to about 99%, more preferably at least about 70% to about 99%, even more preferably at least about 80% to about 99%, most preferably at least about 90% to about 99%, in particular at least about 95% to about 99%, and in particular at least about 97% to about 99% amino acid sequence homology with the parent binding molecules as defined herein. Computer algorithms such as inter alia Gap or Bestfit known to a person skilled in the art can be used to optimally align amino acid sequences to be compared and to define similar or identical amino acid residues.

In certain embodiments, functional variants may be produced when the parent binding molecule comprises a glycosylation site in its sequence that results in glycosylation of the binding molecule upon expression in eukaryotic cells and hence might abrogate the binding to the antigen. The functional variant produced no longer contains the glycosylation site, but will be capable of binding to rabies virus and still have neutralizing activity.

Functional variants can be obtained by altering the parent binding molecules or parts thereof by general molecular biology methods known in the art including, but not limited to, error-prone PCR, oligonucleotide-directed mutagenesis and site-directed mutagenesis. Furthermore, the functional variants may have complement fixing activity, be capable of assisting in the lysis of enveloped rabies virus and/or act as opsonins and augment phagocytosis of rabies virus either by promoting its uptake via Fc or C3b receptors or by agglutinating rabies virus to make it more easily phagocytosed.

In yet a further aspect, the invention includes immunoconjugates, i.e., molecules comprising at least one binding molecule or functional variant thereof as defined herein and further comprising at least one tag, such as inter alia a detectable moiety/agent. Also contemplated in the invention are mixtures of immunoconjugates according to the invention or mixtures of at least one immunoconjugate according to the invention and another molecule, such as a therapeutic agent or another binding molecule or immunoconjugate. In a further embodiment, the immunoconjugates of the invention may comprise one or more tags. These tags can be the same or distinct from each other and can be joined/conjugated non-covalently to the binding molecules. The tag(s) can also be joined/conjugated directly to the binding molecules through covalent bonding, including, but not limited to, disulfide bonding, hydrogen bonding, electrostatic bonding, recombinant fusion and conformational bonding. Alternatively, the tag(s) can be joined/conjugated to the binding molecules by means of one or more linking compounds. Techniques for conjugating tags to binding molecules are well known to the skilled artisan.

The tags of the immunoconjugates of the invention may be therapeutic agents, but preferably they are detectable moieties/agents. Immunoconjugates comprising a detectable agent can be used diagnostically to, for example, assess if a subject has been infected with rabies virus or monitor the development or progression of a rabies virus infection as part of a clinical testing procedure to, e.g., determine the efficacy of a given treatment regimen. However, they may also be used for other detection and/or analytical and/or diagnostic purposes. Detectable moieties/agents include, but are not limited to, enzymes, prosthetic groups, fluorescent materials, luminescent materials, bioluminescent materials, radioactive materials, positron emitting metals, and nonradioactive paramagnetic metal ions.

The tags used to label the binding molecules for detection and/or analytical and/or diagnostic purposes depend on the specific detection/analysis/diagnosis techniques and/or methods used such as inter alia immunohistochemical staining of (tissue) samples, flow cytometric detection, scanning laser cytometric detection, fluorescent immunoassays, enzyme-linked immunosorbent assays (ELISAs), radioimmunoassays (RIAs), bioassays (e.g., neutralization assays), Western blotting applications, etc. For immunohistochemical staining of tissue samples preferred labels are enzymes that catalyze production and local deposition of a detectable product. Enzymes typically conjugated to binding molecules to permit their immunohistochemical visualization are well known and include, but are not limited to, acetylcholinesterase, alkaline phosphatase, beta-galactosidase, glucose oxidase, horseradish peroxidase, and urease. Typical substrates for production and deposition of visually detectable products are also well known to the skilled person in the art. Next to that, immunoconjugates of the invention can be labeled using colloidal gold or they can be labeled with radioisotopes, such as $^{33}P$, $^{32}P$, $^{35}S$, $^{3}H$, and $^{125}I$. Binding molecules of the invention can be attached to radionuclides directly or indirectly via a chelating agent by methods well known in the art.

When the binding molecules of the invention are used for flow cytometric detections, scanning laser cytometric detections, or fluorescent immunoassays, they can usefully be labeled with fluorophores. A wide variety of fluorophores useful for fluorescently labeling the binding molecules of the invention are known to the skilled artisan. When the binding molecules of the invention are used for secondary detection using labeled avidin, streptavidin, captavidin or neutravidin, the binding molecules may be labeled with biotin to form suitable prosthetic group complexes.

When the immunoconjugates of the invention are used for in vivo diagnostic use, the binding molecules can also be made detectable by conjugation to e.g., magnetic resonance imaging (MRI) contrast agents, such as gadolinium diethylenetriaminepentaacetic acid, to ultrasound contrast agents or to X-ray contrast agents, or by radioisotopic labeling.

Furthermore, the binding molecules, functional variants thereof or immunoconjugates of the invention can also be attached to solid supports, which are particularly useful for in vitro immunoassays or purification of rabies virus or a fragment thereof. Such solid supports might be porous or nonporous, planar or nonplanar and include, but are not limited to, glass, cellulose, polyacrylamide, nylon, polystyrene, polyvinyl chloride or polypropylene supports. The human binding molecules can also, for example, usefully be conjugated to filtration media, such as NHS-activated Sepharose or CNBr-activated Sepharose for purposes of immunoaffinity chromatography. They can also usefully be attached to paramagnetic microspheres, typically by biotin-streptavidin interaction. The microspheres can be used for isolation of rabies virus or a fragment thereof from a sample containing rabies virus or a fragment thereof. As another example, the human binding molecules of the invention can usefully be attached to the surface of a microtiter plate for ELISA.

The binding molecules of the invention or functional variants thereof can be fused to marker sequences, such as a peptide to facilitate purification. Examples include, but are not limited to, the hexa-histidine tag, the hemagglutinin (HA) tag, the myc tag or the flag tag.

Alternatively, an antibody can be conjugated to a second antibody to form an antibody heteroconjugate. In another aspect, the human binding molecules of the invention may be conjugated/attached to one or more antigens. In certain embodiments, these antigens are antigens that are recognized by the immune system of a subject to which the binding molecule-antigen conjugate is administered. The antigens may be identical but may also differ from each other. Conjugation methods for attaching the antigens and binding molecules are well known in the art and include, but are not limited to, the use of cross-linking agents. The human binding molecules will bind to rabies virus and the antigens attached to the human binding molecules will initiate a powerful T-cell attack on the conjugate which will eventually lead to the destruction of the rabies virus.

Next to producing immunoconjugates chemically by conjugating, directly or indirectly via, for instance, a linker, the immunoconjugates can be produced as fusion proteins comprising the human binding molecules of the invention and a suitable tag. Fusion proteins can be produced by methods known in the art such as, e.g., recombinantly by constructing nucleic acid molecules comprising nucleotide sequences encoding the human binding molecules in frame with nucleotide sequences encoding the suitable tag(s) and then expressing the nucleic acid molecules.

It is another aspect of the invention to provide a nucleic acid molecule encoding at least a binding molecule or functional variant thereof according to the invention. Such nucleic acid molecules can be used as intermediates for cloning purposes, e.g., in the process of affinity maturation described above. In a preferred embodiment, the nucleic acid molecules are isolated or purified.

One of ordinary skill in the art will appreciate that functional variants of these nucleic acid molecules are also intended to be a part of the invention. Functional variants are nucleic acid sequences that can be directly translated, using the standard genetic code, to provide an amino acid sequence identical to that translated from the parent nucleic acid molecules.

In certain embodiments, the nucleic acid molecules encode binding molecules comprising a CDR3 region, preferably a heavy chain CDR3 region, comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23 and SEQ ID NO:24.

The nucleic acid molecules may encode human binding molecules comprising a variable heavy chain comprising essentially an amino acid sequence selected from the group consisting of SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48 and SEQ ID NO:49. In a particularly preferred embodiment, the nucleic acid molecules encode binding molecules comprising a variable heavy chain comprising essentially an amino acid sequence comprising amino acids 1-119 of SEQ ID NO:335.

In yet another embodiment, the nucleic acid molecules encode binding molecules comprising a variable heavy chain comprising the amino acid sequence of SEQ ID NO:26 and a variable light chain comprising the amino acid sequence of SEQ ID NO:50, or they encode a variable heavy chain comprising the amino acid sequence of SEQ ID NO:27 and a variable light chain comprising the amino acid sequence of SEQ ID NO:51, or they encode a variable heavy chain comprising the amino acid sequence of SEQ ID NO:28 and a variable light chain comprising the amino acid sequence of SEQ ID NO:52, or they encode a variable heavy chain comprising the amino acid sequence of SEQ ID NO:29 and a variable light chain comprising the amino acid sequence of SEQ ID NO:53, or they encode a variable heavy chain comprising the amino acid sequence of SEQ ID NO:30 and a variable light chain comprising the amino acid sequence of SEQ ID NO:54, or they encode a variable heavy chain comprising the amino acid sequence of SEQ ID NO:31 and a variable light chain comprising the amino acid sequence of SEQ ID NO:55, or they encode a variable heavy chain comprising the amino acid sequence of SEQ ID NO:32 and a variable light chain comprising the amino acid sequence of SEQ ID NO:56, or they encode a variable heavy chain comprising the amino acid sequence of SEQ ID NO:33 and a variable light chain comprising the amino acid sequence of SEQ ID NO:57, or they encode a variable heavy chain comprising the amino acid sequence of SEQ ED NO:34 and a variable light chain comprising the amino acid sequence of SEQ ID NO:58, or they encode a variable heavy chain comprising the amino acid sequence of SEQ ID NO:35 and a variable light chain comprising the amino acid sequence of SEQ ID NO:59, or they encode a variable heavy chain comprising the amino acid sequence of SEQ ID NO:36 and a variable light chain comprising the amino acid sequence of SEQ ID NO:60, or they encode a variable heavy chain comprising the amino acid sequence of SEQ ID NO:37 and a variable light chain comprising the amino acid sequence of SEQ ID NO:61, or they encode a variable heavy chain comprising the amino acid sequence of SEQ ID NO:38 and a variable light chain comprising the amino acid sequence of SEQ ID NO:62, or they encode a variable heavy chain comprising the amino acid sequence of SEQ ID NO:39 and a variable light chain comprising the amino acid sequence of SEQ ID NO:63, or they encode a variable heavy chain comprising the amino acid sequence of SEQ ID NO:40 and a variable light chain comprising the amino acid sequence of SEQ ID NO:64, or they encode a variable heavy chain comprising the amino acid sequence of SEQ ID NO:41 and a variable light chain comprising the amino acid sequence of SEQ ID NO:65, or they encode a variable heavy chain comprising the amino acid sequence of SEQ ID NO:42 and a variable light chain comprising the amino acid sequence of SEQ ID NO:66, or they encode a variable heavy chain comprising the amino acid sequence of SEQ ID NO:43 and a variable light chain comprising the amino acid sequence of SEQ ID NO:67, or they encode a variable heavy chain comprising the amino acid sequence of SEQ ID NO:44 and a variable light chain comprising the amino acid sequence of SEQ ID NO:68, or they encode a variable heavy chain comprising the amino acid sequence of SEQ ID NO:45 and a variable light chain comprising the amino acid sequence of SEQ ID NO:69, or they encode a variable heavy chain comprising the amino acid sequence of SEQ ID NO:46 and a variable light chain comprising the amino acid sequence of SEQ ID NO:70, or they encode a variable heavy chain comprising the amino acid sequence of SEQ ID NO:47 and a variable light chain comprising the amino acid sequence of SEQ ID NO:71, or they encode a variable heavy chain comprising the amino acid sequence of SEQ ID NO:48 and a variable light chain comprising the amino acid sequence of SEQ ID NO:72, or they encode a variable heavy chain comprising the amino acid sequence of SEQ ID NO:49 and a variable light chain comprising the amino acid sequence of SEQ ID NO:73. In a preferred embodiment, the nucleic acid molecules encode human binding molecules comprising a variable heavy chain comprising the amino acid sequence comprising amino acids 1-119 of SEQ ID NO:335 and a variable light chain comprising the amino acid sequence comprising amino acids 1-107 of SEQ ID NO:337.

In a specific embodiment of the invention, the nucleic acid molecules encoding the variable heavy chain of the binding molecules of the invention comprise essentially a nucleotide sequence selected from the group consisting of SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96 and SEQ ID NO:97. In certain embodiments, the nucleic acid molecules encoding the variable heavy chain of the binding molecules of the invention comprise essentially a nucleotide sequence comprising nucleotides 1-357 of SEQ ID NO:334.

In yet another specific embodiment of the invention, the nucleic acid molecules encoding the variable light chain of the binding molecules of the invention comprise essentially a nucleotide sequence selected of the group consisting of SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120 and SEQ ID NO:121. In certain embodiments, the nucleic acid molecules encoding the variable light chain of the human binding molecules of the invention comprise essentially a nucleotide sequence comprising nucleotides 1-321 of SEQ ID NO:336.

It is another aspect of the invention to provide vectors, i.e., nucleic acid constructs, comprising one or more nucleic acid molecules according to the invention. Vectors can be derived from plasmids such as inter alia F, R1, RP1, Col, pBR322, TOL, Ti, etc.; cosmids; phages such as lambda, lambdoid, M13, Mu, P1, P22, $Q_\beta$, T-even, T-odd, T2, T4, T7, etc.; plant viruses such as inter alia alfalfa mosaic virus, bromovirus, capillovirus, carlavirus, carmovirus, caulivirus, clostervirus, comovirus, cryptovirus, cucumovirus, dianthovirus, fabavirus, fijivirus, furovirus, geminivirus, hordeivirus, ilarvirus, luteovirus, machlovirus, marafivirus, necrovirus, nepovirus, phytorepvirus, plant rhabdovirus, potexvirus, potyvirus, sobemovirus, tenuivirus, tobamovirus, tobravirus, tomato spotted wilt virus, tombusvirus, tymovirus, etc.; or animal viruses such as inter alia adenovirus, arenaviridae, baculoviridae, birnaviridae, bunyaviridae, calciviridae, cardioviruses, coronaviridae, corticoviridae, cystoviridae, Epstein-Barr virus, enteroviruses, filoviridae, flaviviridae, Foot-and-Mouth disease virus, hepadnaviridae, hepatitis viruses, herpesviridae, immunodeficiency viruses, influenza virus, inoviridae, iridoviridae, orthomyxoviridae, papovaviruses, paramyxoviridae, parvoviridae, picornaviridae, poliovirus, polydnaviridae, poxyiridae, reoviridae, retroviruses, rhabdoviridae, rhinoviruses, Semliki Forest virus, tetraviridae, togaviridae, toroviridae, vaccinia virus, vescular stomatitis virus, etc. Vectors can be used for cloning and/or for expression of the human binding molecules of the invention and might even be used for gene therapy purposes. Vectors comprising one or more nucleic acid molecules according to the invention operably linked to one or more expression-regulating nucleic acid molecules are also covered by the invention. The choice of the vector is dependent on the recombinant procedures followed and the host used. Introduction of vectors in host cells can be effected by inter alia calcium phosphate transfection, virus infection, DEAE-dextran mediated transfection, lipofectamine transfection or electroporation. Vectors may be autonomously replicating or may replicate together with the chromosome into which they have been integrated. In certain embodiments, the vectors contain one or more selection markers. The choice of the markers may depend on the host cells of choice, although this is not critical to the invention as is well known to persons skilled in the art.

They include, but are not limited to, kanamycin, neomycin, puromycin, hygromycin, zeocin, thymidine kinase gene from Herpes simplex virus (HSV-TK), and dihydrofolate reductase gene from mouse (dhfr). Vectors comprising one or more nucleic acid molecules encoding the human binding molecules as described above operably linked to one or more nucleic acid molecules encoding proteins or peptides that can be used to isolate the binding molecules are also covered by the invention. These proteins or peptides include, but are not limited to, glutathione-S-transferase, maltose-binding protein, metal-binding polyhistidine, green fluorescent protein, luciferase and beta-galactosidase.

Hosts containing one or more copies of the vectors mentioned above are an additional subject of the invention. In certain embodiments, the hosts are host cells. Host cells include, but are not limited to, cells of mammalian, plant, insect, fungal or bacterial origin. Bacterial cells include, but are not limited to, cells from Gram positive bacteria such as several species of the genera *Bacillus, Streptomyces* and *Staphylococcus* or cells of Gram negative bacteria such as several species of the genera *Escherichia*, such as *E. coli*, and *Pseudomonas*. In the group of fungal cells preferably yeast cells are used. Expression in yeast can be achieved by using yeast strains such as inter alia *Pichia pastoris, Saccharomyces cerevisiae* and *Hansenula polymorpha*. Furthermore, insect cells such as cells from *Drosophila* and Sf9 can be used as host cells. Besides that, the host cells can be plant cells. Transformed (transgenic) plants or plant cells are produced by known methods, for example, *Agrobacterium*-mediated gene transfer, transformation of leaf discs, protoplast transformation by polyethylene glycol-induced DNA transfer, electroporation, sonication, microinjection or bolistic gene transfer. Additionally, a suitable expression system can be a baculovirus system. Expression systems using mammalian cells, such as Chinese Hamster Ovary (CHO) cells, COS cells, BHK cells or Bowes melanoma cells, are preferred in the invention. Mammalian cells provide expressed proteins with post-translational modifications that are most similar to natural molecules of mammalian origin. Since the invention deals with molecules that may have to be administered to humans, a completely human expression system would be particularly preferred. Therefore, even more preferably, the host cells are human cells. Examples of human cells are inter alia HeLa, 911, AT1080, A549, 293 and HEK293T cells. Preferred mammalian cells are human retina cells such as 911 cells or the cell line deposited at the European Collection of Cell Cultures (ECACC), CAMR, Salisbury, Wiltshire SP4 OJG, Great Britain on 29 Feb. 1996 under number 96022940 and marketed under the trademark PER.C6® (PER.C6® is a registered trademark of Crucell Holland B.V.). For the purposes of this application "PER.C6®" refers to cells deposited under number 96022940 or ancestors, passages up-stream or downstream as well as descendants from ancestors of deposited cells, as well as derivatives of any of the foregoing.

In preferred embodiments, the human producer cells comprise at least a functional part of a nucleic acid sequence encoding an adenovirus E1 region in expressible format. In even more preferred embodiments, the host cells are derived from a human retina and immortalized with nucleic acids comprising adenoviral E1 sequences, such as the cell line deposited at the European Collection of Cell Cultures (ECACC), CAMR, Salisbury, Wiltshire SP4 OJG, Great Britain on 29 Feb. 1996 under number 96022940 and marketed under the trademark PER.C6®. Production of recombinant proteins in host cells can be performed according to methods well known in the art. The use of the cells marketed under the trademark PER.C6® as a production platform for proteins of interest has been described in WO 00/63403, the disclosure of which is incorporated herein by reference in its entirety.

A method of producing a binding molecule or a functional variant according to the invention is an additional part of the invention. The method comprises the steps of (a) culturing a host according to the invention under conditions conducive to the expression of the binding molecule or functional variant thereof, and (b) optionally, recovering the expressed binding molecule or functional variant thereof. The expressed binding molecules or functional variants thereof can be recovered from the cell free extract, but preferably they are recovered from the culture medium. Methods to recover proteins, such as binding molecules, from cell free extracts or culture medium are well known to the man skilled in the art. Binding molecules or functional variants thereof as obtainable by the above described method are also a part of the invention.

Alternatively, next to the expression in hosts, such as host cells, the binding molecules or functional variants thereof of the invention can be produced synthetically by conventional peptide synthesizers or in cell-free translation systems using RNA nucleic acid derived from DNA molecules according to the invention. Binding molecules or functional variants thereof as obtainable by the above described synthetic production methods or cell-free translation systems are also a part of the invention.

In certain embodiments, binding molecules or functional variants thereof, according to the invention, may be generated by transgenic non-human mammals, such as, for instance, transgenic mice or rabbits, that express human immunoglobulin genes. In certain embodiments, the transgenic non-human mammals have a genome comprising a human heavy chain transgene and a human light chain transgene encoding all or a portion of the human binding molecules as described above. The transgenic non-human mammals can be immunized with a purified or enriched preparation of rabies virus or a fragment thereof. Protocols for immunizing non-human mammals are well established in the art. See "Using Antibodies: A Laboratory Manual," edited by E. Harlow, D. Lane (1998), Cold Spring Harbor Laboratory, Cold Spring Harbor, N.Y., and "Current Protocols in Immunology," edited by J. E. Coligan, A. M. Kruisbeek, D. H. Margulies, E. M. Shevach, W. Strober (2001), John Wiley & Sons Inc., New York, the disclosures of which are incorporated herein by reference.

In a further aspect, the invention provides a method of identifying binding molecules such as human monoclonal antibodies or fragments thereof according to the invention or nucleic acid molecules according to the invention capable of specifically binding to rabies virus and comprises the steps of (a) contacting a collection of binding molecules on the surface of replicable genetic packages with the rabies virus or a fragment thereof under conditions conducive to binding, (b) selecting at least once for replicable genetic packages binding to the rabies virus or the fragment thereof, and (c) separating and recovering the replicable genetic packages binding to the rabies virus or the fragment thereof.

The selection step may be performed in the presence of rabies virus. The rabies virus may be isolated or non-isolated, e.g., present in serum and/or blood of an infected individual. In certain embodiments, the rabies virus is inactivated. Alternatively, the selection step may be performed in the presence of a fragment of rabies virus, such as an extracellular part of the rabies virus, one or more (poly)peptides derived from rabies virus, such as the G protein, fusion proteins comprising these proteins or (poly)peptides, and the like. In certain embodiments, cells transfected with rabies virus G protein are used for selection procedures.

In yet a further aspect, the invention provides a method of obtaining a binding molecule or a nucleic acid molecule according to the invention, wherein the method comprises the steps of (a) performing the above described method of identifying binding molecules, such as human monoclonal antibodies or fragments thereof according to the invention, or nucleic acid molecules according to the invention, and (b) isolating from the recovered replicable genetic packages the binding molecule and/or the nucleic acid encoding the binding molecule. Once a new monoclonal antibody has been established or identified with the above mentioned method of identifying binding molecules or nucleic acid molecules encoding the binding molecules, the DNA encoding the scFv or Fab can be isolated from the bacteria or replicable genetic packages and combined with standard molecular biological techniques to make constructs encoding bivalent scFvs or complete human immunoglobulins of a desired specificity (e.g., IgG, IgA or IgM). These constructs can be transfected into suitable cell lines and complete human monoclonal antibodies can be produced (see, Huls et al., 1999; Boel et al., 2000).

A replicable genetic package as used herein can be prokaryotic or eukaryotic and includes cells, spores, bacteria, viruses, (bacterio)phage and polysomes. A preferred replicable genetic package is a phage. The human binding molecules, such as, for instance, single chain Fvs, are displayed on the replicable genetic package, i.e., they are attached to a group or molecule located at an exterior surface of the replicable genetic package. The replicable genetic package is a screenable unit comprising a human binding molecule to be screened linked to a nucleic acid molecule encoding the binding molecule. The nucleic acid molecule should be replicable either in vivo (e.g., as a vector) or in vitro (e.g., by PCR, transcription and translation). In vivo replication can be autonomous (as for a cell), with the assistance of host factors (as for a virus) or with the assistance of both host and helper virus (as for a phagemid). Replicable genetic packages displaying a collection of human binding molecules are formed by introducing nucleic acid molecules encoding exogenous binding molecules to be displayed into the genomes of the replicable genetic packages to form fusion proteins with endogenous proteins that are normally expressed from the outer surface of the replicable genetic packages. Expression of the fusion proteins, transport to the outer surface and assembly results in display of exogenous binding molecules from the outer surface of the replicable genetic packages. In a further aspect, the invention pertains to a human binding molecule capable of binding rabies virus or a fragment thereof and being obtainable by the identification method as described above.

In yet a further aspect, the invention relates to a method of identifying a binding molecule potentially having neutralizing activity against rabies virus, wherein the method comprises the steps of (a) contacting a collection of binding molecules on the surface of replicable genetic packages with the rabies virus under conditions conducive to binding, (b) separating and recovering binding molecules that bind to the rabies virus from binding molecules that do not bind, (c) isolating at least one recovered binding molecule, (d) verifying if the binding molecule isolated has neutralizing activity against the rabies virus, wherein the rabies virus in step a is inactivated. The inactivated rabies virus may be purified before being inactivated. Purification may be performed by means of well-known purification methods suitable for viruses such as, for instance, centrifugation through a glycerol cushion. The inactivated rabies virus in step (a) may be immobilized to a suitable material before use. Alternatively, the rabies virus in step (a) may still be active. In another alternative embodiment, a fragment of a rabies virus, such as a polypeptide of a rabies virus such as the G protein, is used in step (a). In yet another embodiment, cells transfected with rabies virus G protein are used for selecting binding molecule potentially having neutralizing activity against rabies virus. As indicated herein, when cells expressing rabies virus G protein were included in the selection method the number of selected neutralizing antibodies was higher compared to selection methods wherein only purified rabies virus G protein and/or inactivated rabies virus was used.

In a further embodiment, the method of identifying a binding molecule potentially having neutralizing activity against rabies virus as described above further comprises the step of separating and recovering, and optionally isolating, human binding molecules containing a variable heavy 3-30 germline gene. A person skilled in the art can identify the specific germline gene by methods known in the art such as, for instance, nucleotide sequencing. The step of separating and recovering binding molecules containing a variable heavy 3-30 germline gene can be performed before or after step (c). As indicated below, the majority of rabies virus-neutralizing human monoclonal antibodies found in the invention comprise this specific $V_H$ germline gene.

Phage display methods for identifying and obtaining (neutralizing) binding molecules, e.g., antibodies, are by now well-established methods known by the person skilled in the art. They are, e.g., described in U.S. Pat. No. 5,696,108; Burton and Barbas, 1994; de Kruif et al., 1995b; and "Phage Display: A Laboratory Manual," edited by C. F. Barbas, D. R. Burton, J. K. Scott and G. J. Silverman (2001), Cold Spring Harbor Laboratory Press, Cold Spring Harbor, N.Y. All these references are herewith incorporated herein in their entirety.

For the construction of phage display libraries, collections of human monoclonal antibody heavy and light chain variable region genes are expressed on the surface of bacteriophage, preferably filamentous bacteriophage, particles in, for example, single-chain Fv (scFv) or in Fab format (see, de Kruif et al., 1995b). Large libraries of antibody fragment-expressing phages typically contain more than $1.0*10^9$ antibody specificities and may be assembled from the immunoglobulin V regions expressed in the B lymphocytes of immunized- or non-immunized individuals. In a specific embodiment of the invention, the phage library of human binding molecules, preferably scFv phage library, is prepared from RNA isolated from cells obtained from a subject that has been vaccinated against rabies or exposed to a rabies virus. RNA can be isolated from inter alia bone marrow or peripheral blood, preferably peripheral blood lymphocytes. The subject can be an animal vaccinated or exposed to rabies virus, but is preferably a human subject which has been vaccinated or has been exposed to rabies virus. In certain embodiments, the human subject has been vaccinated. A collection of human binding molecules on the surface of replicable genetic packages, such as a scFv phage library, as described above is another aspect of the invention.

Alternatively, phage display libraries may be constructed from immunoglobulin variable regions that have been partially assembled in vitro to introduce additional antibody diversity in the library (semi-synthetic libraries). For example, in vitro assembled variable regions contain stretches of synthetically produced, randomized or partially randomized DNA in those regions of the molecules that are important for antibody specificity, e.g., CDR regions. Rabies virus-specific phage antibodies can be selected from the libraries by immobilizing target antigens such as antigens from rabies virus on a solid phase and subsequently exposing the target antigens to a phage library to allow binding of phages expressing antibody fragments specific for the solid phase-bound antigen(s). Non-bound phages are removed by washing and bound phages eluted from the solid phase for infection of *Escherichia coli* (*E. coli*) bacteria and subsequent propagation. Multiple rounds of selection and propagation are usually required to sufficiently enrich for phages binding specifically to the target antigen(s). If desired, before exposing the phage library to target antigens the phage library can first be subtracted by exposing the phage library to non-target antigens bound to a solid phase. Phages may also be selected for binding to complex antigens, such as complex mixtures of rabies virus proteins or (poly)peptides, host cells expressing one or more rabies virus proteins or (poly)peptides of rabies virus, or (inactivated) rabies virus itself. Antigen-specific phage antibodies can be selected from the library by incubating a solid phase with bound thereon a preparation of inactivated rabies virus with the phage antibody library to let, for example, the scFv or Fab part of the phage bind to the proteins/polypeptides of the rabies virus preparation. After incubation and several washes to remove unbound and loosely attached phages, the phages that have bound with their scFv or Fab part to the preparation are eluted and used to infect *Escherichia coli* to allow amplification of the new specificity. Generally, one or more selection rounds are required to separate the phages of interest from the large excess of non-binding phages. Alternatively, known proteins or (poly)peptides of the rabies virus can be expressed in host cells and these cells can be used for selection of phage antibodies specific for the proteins or (poly)peptides. A phage display method using these host cells can be extended and improved by subtracting non-relevant binders during screening by addition of an excess of host cells comprising no target molecules or non-target molecules that are similar, but not identical, to the target, and thereby strongly enhance the chance of finding relevant binding molecules. (This process is referred to as the MABSTRACT® process. MABSTRACT® is a registered trademark of Crucell Holland B.V. See also, U.S. Pat. No. 6,265,150, which is incorporated herein by reference.)

In yet a further aspect, the invention provides compositions comprising at least one binding molecule, at least one functional variant or fragment thereof, at least one immunoconjugate according to the invention or a combination thereof. The compositions may further comprise inter alia stabilizing molecules, such as albumin or polyethylene glycol, or salts. In certain embodiments, the salts used are salts that retain the desired biological activity of the human binding molecules and do not impart any undesired toxicological effects. If necessary, the human binding molecules of the invention may be coated in or on a material to protect them from the action of acids or other natural or non-natural conditions that may inactivate the binding molecules.

In yet a further aspect, the invention provides compositions comprising at least one nucleic acid molecule as defined in the invention. The compositions may comprise aqueous solutions such as aqueous solutions containing salts (e.g., NaCl or salts as described above), detergents (e.g., SDS) and/or other suitable components.

Furthermore, the invention pertains to pharmaceutical compositions comprising at least one n binding molecule according to the invention, at least one functional variant or fragment thereof, at least one immunoconjugate according to the invention, at least one composition according to the invention, or combinations thereof. The pharmaceutical composition of the invention further comprises at least one pharmaceutically acceptable excipient.

In certain embodiments, a pharmaceutical composition of the invention comprises at least one additional binding molecule, i.e., the pharmaceutical composition can be a cocktail/mixture of binding molecules. The pharmaceutical composition may comprise at least two binding molecules according to the invention or at least one binding molecule according to the invention and at least one further anti-rabies virus binding molecule. The further binding molecule preferably comprises a CDR3 region comprising the amino acid sequence of SEQ ID NO:25. The binding molecule comprising the CDR3 region comprising the amino acid sequence of SEQ ID NO:25 may be a chimeric or humanized monoclonal antibody or functional fragment thereof, but preferably, it is a human monoclonal antibody or functional fragment thereof. In certain embodiments, the binding molecule comprises a heavy chain variable region comprising the amino acid sequence SEQ ID NO:273. In certain embodiments, the binding molecule comprises a light chain variable region comprising the amino acid sequence SEQ ID NO:275. In yet another embodiment, the binding molecule comprises a heavy and light chain comprising the amino acid sequences of SEQ ID NO:123 and SEQ ID NO:125, respectively. The binding molecules in the pharmaceutical composition should be capable of reacting with different, non-competing epitopes of the rabies virus. The epitopes may be present on the G protein of rabies virus and may be different, non-overlapping epitopes. The binding molecules should be of high affinity and should have a broad specificity. In certain embodiments, they neutralize as many fixed and street strains of rabies virus as possible. Even more preferably, they also exhibit neutralizing activity towards other genotypes of the Lyssavirus genus or even with other viruses of the rhabdovirus family, while exhibiting no cross-reactivity with other viruses or normal cellular proteins. In certain embodiments, the binding molecule is capable of neutralizing escape variants of the other binding molecule in the cocktail.

Another aspect of the invention pertains to a pharmaceutical composition comprising at least two rabies virus-neutralizing binding molecules, preferably (human) binding molecules according to the invention, wherein the binding molecules are capable of reacting with different, non-competing epitopes of the rabies virus. In certain embodiments, the pharmaceutical composition comprises a first rabies virus-neutralizing binding molecule which is capable of reacting with an epitope located in antigenic site I of the rabies virus G protein and a second rabies virus-neutralizing binding molecule which is capable of reacting with an epitope located in antigenic site III of the rabies virus G protein. The antigenic structure of the rabies glycoprotein was initially defined by Lafon et al. (1983). The antigenic sites were identified using a panel of mouse mAbs and their respective mAb-resistant virus variants. Since then, the antigenic sites have been mapped by identification of the amino acid mutations in the glycoprotein of mAb-resistant variants (see, Seif et al., 1985; Prehaud et al., 1988; and Benmansour et al., 1991). The majority of rabies-neutralizing mAbs are directed against antigenic site II (see, Benmansour et al., 1991), which is a discontinuous conformational epitope comprising amino acids 34-42 and amino acids 198-200 (see, Prehaud et al., 1988). Antigenic site III is a continuous conformational epitope at amino acids 330-338 and harbors two charged residues, K330 and R333, that affect viral pathogenicity (see, Seif et al., 1985; Coulon et al., 1998; and Dietzschold et al., 1983). The conformational antigenic site I was defined by only one mAb, 509-6, and located at amino acid 231 (see, Benmansour et al., 1991; and Lafon et al., 1983). Antigenic site IV is known to harbor overlapping linear epitopes (see, Tordo, 1996; Bunschoten et at, 1989; Luo et al., 1997; and Ni et al., 1995). Benmansour et al. (1991) also described the presence of a minor site located at position 342-343, which is distinct from antigenic site III despite its close proximity. Alignment of the CR-57 epitope with the currently known linear and conformational-neutralizing epitopes on rabies glycoprotein (FIG. 10) revealed that the CR-57 epitope is located in the same region as the conformational antigenic site I, defined by the single mAb 509-6. Based on nucleotide and amino acid sequences of the glycoprotein of the escape viruses of CR04-098, the epitope recognized by this antibody appears to be located in the same region as the continuous conformational antigenic site III.

In a preferred embodiment, the pharmaceutical composition comprises a first rabies virus-neutralizing binding molecule comprising at least a CDR3 region, preferably heavy chain CDR3 region, comprising the amino acid sequence of SEQ ID NO:25 and a second rabies virus-neutralizing binding molecule comprising at least a CDR3 region, preferably heavy chain CDR3 region, comprising the amino acid sequence selected from the group consisting of SEQ ID NO:4, SEQ ID NO:10, SEQ ID NO:14, SEQ ID NO:15, SEQ ID NO:16 and SEQ ID NO:22. More preferably, the second rabies virus-neutralizing binding molecule comprises at least a CDR3 region, preferably a heavy chain CDR3 region, comprising the amino acid sequence of SEQ ID NO:14. In certain embodiments, the first rabies virus-neutralizing binding molecule comprises a heavy and light chain comprising the amino acid sequences of SEQ ID NO:123 and SEQ ID NO:125, respectively, and the second rabies virus-neutralizing binding molecule comprises a heavy and light chain comprising the amino acid sequences of SEQ ID NO:335 and SEQ ID NO:337, respectively. In certain embodiments, the heavy and light chain of the first rabies virus-neutralizing binding molecule are encoded by SEQ ID NO:122 and SEQ ID NO:124, respectively, and the heavy and light chain of the second rabies virus-neutralizing binding molecule are encoded by SEQ ID NO:334 and SEQ ID NO:336, respectively.

A pharmaceutical composition comprising two binding molecules, wherein the pI of the binding molecules is divergent and may have a problem when choosing a suitable buffer which optimally stabilizes both binding molecules. When adjusting the pH of the buffer of the composition such that it increases the stability of one binding molecule, this might decrease the stability of the other binding molecule. Decrease of stability or even instability of a binding molecule may lead to its precipitation or aggregation or to its spontaneous degradation resulting in loss of the functionality of the binding molecule. Therefore, in another aspect, the invention provides a pharmaceutical composition comprising at least two binding molecules, preferably human binding molecules, wherein the binding molecules have isoelectric points (pI) that differ less than about 1.5, 1.4, 1.3, 1.2, 1.1, 1.0, 0.9, 0.8, 0.7, 0.6, 0.5, 0.4, 0.3, preferably less than (and including) 0.25 pI units from one another. The pI can be measured experimentally, e.g., by means of isoelectric focusing, or be calculated based on the amino acid sequence of the binding molecules. In certain embodiments, the binding molecules are binding molecules according to the invention and the pharmaceutical composition is a pharmaceutical composition according to the invention. In certain embodiments, the binding molecules are monoclonal antibodies, e.g., human monoclonal antibodies such as IgG1 antibodies. In certain embodiments, the binding molecules are capable of binding to and/or neutralizing an infectious agent, e.g., a virus, a bacterium, a yeast, a fungus or a parasite. In certain embodiments, the binding molecules are capable of binding to and/or neutralizing a lyssavirus, e.g., rabies virus. In a specific embodiment, both binding molecules have a calculated pI that is in the range between 8.0-9.5, preferably 8.1-9.2, more preferably 8.2-8.5. In certain embodiments, the binding molecules have the heavy chain CDR3 region of SEQ ID NO:14 and SEQ ID NO:25, respectively.

In certain embodiments, the invention provides a cocktail of two or more human or other animal binding molecules, including but not limited to antibodies, wherein at least one binding molecule is derived from an antibody phage or other replicable package display technique and at least one binding molecule is obtainable by a hybridoma technique. When divergent techniques are being used, the selection of binding molecules having a compatible pI is also very useful in order to obtain a composition, wherein each binding molecule is sufficiently stable for storage, handling and subsequent use.

In certain embodiments, the binding molecules present in the pharmaceutical composition of the invention augment each other's neutralizing activity, i.e., they act synergistically when combined. In other words, the pharmaceutical compositions may exhibit synergistic rabies virus, and even lyssavirus, neutralizing activity. As used herein, the term "synergistic" means that the combined effect of the binding molecules when used in combination is greater than their additive effects when used individually. The ranges and ratios of the components of the pharmaceutical compositions of the invention should be determined based on their individual potencies and tested in in vitro neutralization assays or animal models such as hamsters.

Furthermore, the pharmaceutical composition according to the invention may comprise at least one other therapeutic, prophylactic and/or diagnostic agent. The further therapeutic and/or prophylactic agents may be anti-viral agents such as ribavirin or interferon-alpha.

The binding molecules or pharmaceutical compositions of the invention can be tested in suitable animal model systems prior to use in humans. Such animal model systems include, but are not limited to, mice, rats, hamsters, monkeys, etc.

Typically, pharmaceutical compositions must be sterile and stable under the conditions of manufacture and storage. The human binding molecules, variant or fragments thereof, immunoconjugates, nucleic acid molecules or compositions of the invention can be in powder form for reconstitution in the appropriate pharmaceutically acceptable excipient before or at the time of delivery. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Alternatively, the binding molecules, variant or fragments thereof, immunoconjugates, nucleic acid molecules or compositions of the invention can be in solution and the appropriate pharmaceutically acceptable excipient can be added and/or mixed before or at the time of delivery to provide a unit dosage injectable form. In certain embodiments, the pharmaceutically acceptable excipient used in the invention is suitable to high drug concentration, can maintain proper fluidity and, if necessary, can delay absorption.

The choice of the optimal route of administration of the pharmaceutical compositions will be influenced by several factors including the physico-chemical properties of the active molecules within the compositions, the urgency of the clinical situation and the relationship of the plasma concentrations of the active molecules to the desired therapeutic effect. For instance, if necessary, the human binding molecules of the invention can be prepared with carriers that will protect them against rapid release, such as a controlled release formulation, including implants, transdermal patches, and microencapsulated delivery systems. Biodegradable, biocompatible polymers can inter alia be used, such as ethylene vinyl acetate, poly-anhydrides, poly-glycolic acid, collagen, poly-orthoesters, and poly-lactic acid. Furthermore, it may be necessary to coat the human binding molecules with, or co-administer the binding molecules with, a material or compound that prevents the inactivation of the human binding molecules. For example, the human binding molecules may be administered to a subject in an appropriate carrier, for example, liposomes, or a diluent.

The routes of administration can generally be divided into two main categories, oral and parenteral administration. The preferred administration of the human binding molecules and pharmaceutical compositions of the invention is into and around the wound and intramuscularly in the gluteal region. Formulations of the human binding molecules and pharmaceutical compositions are dependent on the routes of administration.

In a further aspect, the binding molecules, functional variants, immunoconjugates, compositions, or pharmaceutical compositions of the invention can be used as a medicament. Thus, a method of treatment and/or prevention of a lyssavirus infection using the human binding molecules, functional variants, immunoconjugates, compositions, or pharmaceutical compositions of the invention is another part of the invention. The lyssavirus can be a virus from any of the known genotypes, but is preferably rabies virus. The above-mentioned molecules or compositions can be used in the post-exposure prophylaxis of rabies.

The molecules or compositions mentioned above may be employed in conjunction with other molecules useful in diagnosis, prophylaxis and/or treatment of rabies virus. They can be used in vitro, ex vivo or in vivo. For instance, the human binding molecules, functional variants, immunoconjugates or pharmaceutical compositions of the invention can be co-administered with a vaccine against rabies. Alternatively, the vaccine may also be administered before or after administration of the molecules or compositions of the invention. Administration of the molecules or compositions of the invention with a vaccine is suitable for post exposure prophylaxis. Rabies vaccines include, but are not limited to, purified chick embryo cell (PCEC) vaccine (RabAvert), human diploid cell vaccine (HDCV; Imovax vaccine) or rabies vaccine adsorbed (RVA).

The molecules are typically formulated in the compositions and pharmaceutical compositions of the invention in a therapeutically or diagnostically effective amount. Dosage regimens can be adjusted to provide the optimum desired response (e.g., a therapeutic response). A suitable dosage range may, for instance, be 0.1-100 IU/kg body weight, preferably 1.0-50 IU/kg body weight and more preferably 10-30 IU/kg body weight, such as 20 IU/kg body weight.

In certain embodiments, a single bolus of the binding molecules or pharmaceutical compositions of the invention are administered. The molecules and pharmaceutical compositions according to the invention are preferably sterile. Methods to render these molecules and compositions sterile are well known in the art. The dosing regimen of post exposure prophylaxis is administration of five doses of rabies vaccine intramuscularly in the deltoid muscle on days 0, 3, 7, 14 and 28 days after exposure in individuals not previously immunized against rabies virus. The human binding molecules or pharmaceutical compositions according to the invention should be administered into and around the wounds on day 0 or otherwise as soon as possible after exposure, with the remaining volume given intramuscularly at a site distant from the vaccine. Non-vaccinated individuals are advised to be administered anti-rabies virus human binding molecules, but it is clear to the skilled artisan that vaccinated individuals in need of such treatment may also be administered anti-rabies virus human binding molecules.

In another aspect, the invention concerns the use of binding molecules or functional variants thereof, immunoconjugates according to the invention, nucleic acid molecules according to the invention, compositions or pharmaceutical compositions according to the invention in the preparation of a medicament for the diagnosis, prophylaxis, treatment, or combination thereof, of a condition resulting from an infection by a lyssavirus. The lyssavirus can be a virus from any of the known genotypes but is preferably rabies virus. In certain embodiments, the molecules mentioned above are used in the preparation of a medicament for the post exposure prophylaxis of rabies.

Next to that, kits comprising at least one binding molecule according to the invention, at least one functional variant thereof according to the invention, at least one immunoconjugate according to the invention, at least one nucleic acid molecule according to the invention, at least one composition according to the invention, at least one pharmaceutical composition according to the invention, at least one vector according to the invention, at least one host according to the invention or a combination thereof are also a part of the invention. Optionally, the above described components of the kits of the invention are packed in suitable containers and labeled for diagnosis, prophylaxis and/or treatment of the indicated conditions. The above-mentioned components may be stored in unit or multi-dose containers, for example, sealed ampoules, vials, bottles, syringes, and test tubes, as an aqueous, preferably sterile, solution or as a lyophilized, preferably sterile, formulation for reconstitution. The containers may be formed from a variety of materials such as glass or plastic and may have a sterile access port (for example, the container may be an intravenous solution bag or a vial having a stopper pierceable by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. Associated with the kits can be instructions customarily included in commercial packages of therapeutic, prophylactic or diagnostic products, that contain information about, for example, the indications, usage, dosage, manufacture, administration, contraindications and/or warnings concerning the use of such therapeutic, prophylactic or diagnostic products.

Currently, HRIG products are used for post exposure prophylaxis of rabies. An adult dose of HRIG of 1500 IU (75 kg individual, 20 IU/kg) is only available in a volume of 10 ml. More concentrated HRIG products are not possible as the currently obtainable 10 ml dose contains 1-1.5 gram of total IgG. In view thereof the current HRIG products have two drawbacks. Firstly, it is often not anatomically feasible to administer the recommended full dose in and around the bite wounds and secondly the administration of the current volume dose of HRIG is associated with significant pain. The invention gives a solution to these drawbacks as it provides a pharmaceutical composition comprising a full adult dose in a volume of approximately 2 ml or less, if desirable. Such a pharmaceutical composition may comprise, for example, two binding molecules capable of neutralizing rabies virus, preferably CR57 and CR04-098. The pharmaceutical composition further comprises a pharmaceutically acceptable excipient and has a volume of around 2 ml. More is also possible, but less desirable in view of the pain associated with injecting larger volumes. Less than 2 ml is also possible. The pharmaceutical composition comprises the full adult dose (in IU) necessary for successful post exposure prophylaxis. In certain embodiments, the pharmaceutical composition is stored in a 10 ml vial such as, for instance, a 10 ml ready-to-use vial (type I glass) with a stopper. By providing a 10 ml vial the option is given to dilute the pharmaceutical composition towards a higher volume in case an individual presents a large wound surface area. The invention also provides a kit comprising at least a container (such as a vial) comprising the pharmaceutical composition. The kit may further comprise a second container which holds a diluent suitable for diluting the pharmaceutical composition towards a higher volume. Suitable diluents include, but are not limited to, the pharmaceutically acceptable excipient of the pharmaceutical composition and a saline solution. Furthermore, the kit may comprise instructions for diluting the pharmaceutical composition and/or instructions for administering the pharmaceutical composition, whether diluted or not.

Further provided is a method of detecting a rabies virus in a sample, wherein the method comprises the steps of (a) contacting a sample with a diagnostically effective amount of a binding molecule, a functional variant or an immunoconjugate according to the invention, and (b) determining whether the binding molecule, functional variant, or immunoconjugate specifically binds to a molecule of the sample. The sample may be a biological sample including, but not limited to blood, serum, tissue or other biological material from (potentially) infected subjects. The (potentially) infected subjects may be human subjects, but also animals that are suspected as carriers of rabies virus might be tested for the presence of rabies virus using the human binding molecules, functional variants or immunoconjugates of the invention. The sample may first be manipulated to make it more suitable for the method of detection. "Manipulation" means inter alia treating the sample suspected to contain and/or containing rabies virus in such a way that the rabies virus will disintegrate into antigenic components such as proteins, (poly)peptides or other antigenic fragments. In certain embodiments, the binding molecules, functional variants or immunoconjugates are contacted with the sample under conditions which allow the formation of an immunological complex between the human binding molecules and rabies virus or antigenic components thereof that may be present in the sample. The formation of an immunological complex, if any, indicating the presence of rabies virus in the sample, is then detected and measured by suitable means. Such methods include, inter alia, homogeneous and heterogeneous binding immunoassays, such as radioimmunoassays (RIA), ELISA, immunofluorescence, immunohistochemistry, FACS, BIACORE® and Western blot analyses.

Furthermore, the binding molecules of the invention can be used to identify epitopes of rabies virus proteins such as the G protein. The epitopes can be linear, but also structural and/or conformational. In one embodiment, binding of binding molecules of the invention to a series of overlapping peptides, such as 15 mer peptides, of a protein from rabies virus such as the rabies virus G protein can be analyzed by means of PEPSCAN® analysis (see, inter alia WO 84/03564, WO 93/09872, Slootstra et al. 1996). The binding of human binding molecules to each peptide can be tested in a PEPSCAN®-based enzyme linked immunosorbent assay (ELISA). In certain embodiments, a random peptide library comprising peptides from rabies virus proteins can be screened for peptides capable of binding to the human binding molecules of the invention. In the above assays the use of rabies virus neutralizing human binding molecules may identify one or more neutralizing epitopes. The peptides/epitopes found can be used as vaccines and for the diagnosis of rabies.

In a further aspect, the invention provides a method of screening a binding molecule or a functional variant of a binding molecule for specific binding to a different, preferably non-overlapping epitope of rabies virus as the epitope bound by a binding molecule or functional variant of the invention, wherein the method comprises the steps of (a) contacting a binding molecule or a functional variant to be screened, a binding molecule or functional variant of the invention and rabies virus or a fragment thereof (such as for instance the rabies virus G protein), (b) measure if the binding molecule or functional variant to be screened is capable of competing for specifically binding to the rabies virus or fragment thereof with the binding molecule or functional variant of the invention. If no competition is measured the binding molecules or functional variants to be screened bind to a different epitope. In a specific embodiment of the above screening method, human binding molecules, or functional variants thereof, may be screened to identify human binding molecules or functional variants capable of binding a different epitope than the epitope recognized by the binding molecule comprising the CDR3 region comprising the amino acid sequence of SEQ ID NO:25. In certain embodiments, the epitopes are non-overlapping or non-competing. It is clear to the skilled person that the above screening method can also be used to identify binding molecules or functional variants thereof capable of binding to the same epitope. In a further step it may be determined if the screened binding molecules that are not capable of competing for specifically binding to the rabies virus or fragment thereof have neutralizing activity. It may also be determined if the screened binding molecules that are capable of competing for specifically binding to the rabies virus or fragment thereof have neutralizing activity. Neutralizing anti-rabies virus binding molecules or functional variants thereof found in the screening method are another part of the invention. In the screening method "specifically binding to the same epitope" also contemplates specific binding to substantially or essentially the same epitope as the epitope bound by the human binding molecules of the invention. The capacity to block, or compete with, the binding of the human binding molecules of the invention to rabies virus typically indicates that a binding molecule to be screened binds to an epitope or binding site on the rabies virus that structurally overlaps with the binding site on the rabies virus that is immunospecifically recognized by the binding molecules of the invention. Alternatively, this can indicate that a binding molecule to be screened binds to an epitope or binding site which is sufficiently proximal to the binding site immunospecifically recognized by the binding molecules of the invention to sterically or otherwise inhibit binding of the binding molecules of the invention to rabies virus or a fragment thereof.

In general, competitive inhibition is measured by means of an assay, wherein an antigen composition, i.e., a composition comprising rabies virus or fragments (such as G proteins) thereof, is admixed with reference binding molecules and binding molecules to be screened. In certain embodiments, the reference binding molecule may be one of the human binding molecules of the invention and the binding molecule to be screened may be another human binding molecule of the invention. In certain embodiments, the reference binding molecule may be the binding molecule comprising the CDR3 region comprising the amino acid sequence of SEQ ID NO:25 and the binding molecule to be screened may be one of the human binding molecules of the invention. In yet another embodiment, the reference binding molecule may be one of the human binding molecules of the invention and the binding molecule to be screened may be the binding molecule comprising the CDR3 region comprising the amino acid sequence of SEQ ID NO:25. Usually, the binding molecules to be screened are present in excess. Protocols based upon ELISAs are suitable for use in such simple competition studies. In certain embodiments, one may pre-mix the reference binding molecules with varying amounts of the binding molecules to be screened (e.g., 1:10, 1:20, 1:30, 1:40, 1:50, 1:60, 1:70, 1:80, 1:90 or 1:100) for a period of time prior to applying to the antigen composition. In other embodiments, the reference binding molecules and varying amounts of binding molecules to be screened can simply be admixed during exposure to the antigen composition. In any event, by using species or isotype secondary antibodies one will be able to detect only the bound reference binding molecules, the binding of which will be reduced by the presence of a binding molecule to be screened that recognizes substantially the same epitope. In conducting a binding molecule competition study between a reference binding molecule and any binding molecule to be screened (irrespective of species or isotype), one may first label the reference binding molecule with a detectable label, such as, e.g., biotin, an enzymatic, a radioactive or other label to enable subsequent identification. In these cases, one would pre-mix or incubate the labeled reference binding molecules with the binding molecules to be screened at various ratios (e.g., 1:10, 1:20, 1:30, 1:40, 1:50, 1:60, 1:70, 1:80, 1:90 or 1:100) and (optionally after a suitable period of time) then assay the reactivity of the labeled reference binding molecules and compare this with a control value in which no potentially competing binding molecule was included in the incubation. The assay may again be any one of a range of immunological assays based upon antibody hybridization, and the reference binding molecules would be detected by means of detecting their label, e.g., using streptavidin in the case of biotinylated reference binding molecules or by using a chromogenic substrate in connection with an enzymatic label (such as 3,3'5,5'-tetramethylbenzidine (TMB) substrate with peroxidase enzyme) or by simply detecting a radioactive label. A binding molecule to be screened that binds to the same epitope as the reference binding molecule will be able to effectively compete for binding and thus will significantly reduce reference binding molecule binding, as evidenced by a reduction in bound label. Binding molecules binding different non-competing epitopes will show no reduction. The reactivity of the (labeled) reference binding molecule in the absence of a completely irrelevant binding molecule would be the control high value. The control low value would be obtained by incubating the labeled reference binding molecule with unlabelled reference binding molecules of exactly the same type, when competition would occur and reduce binding of the labeled reference binding molecule. In a test assay, a significant reduction in labeled reference binding molecule reactivity in the presence of a binding molecule to be screened is indicative of a binding molecule that recognizes the same epitope, i.e., one that "cross-reacts" with the labeled reference binding molecule. If no reduction is shown, the binding molecule may bind a different non-competing epitope.

Binding molecules identified by these competition assays ("competitive binding molecules") include, but are not limited to, antibodies, antibody fragments and other binding agents that bind to an epitope or binding site bound by the reference binding molecule as well as antibodies, antibody fragments and other binding agents that bind to an epitope or binding site sufficiently proximal to an epitope bound by the reference binding molecule for competitive binding between the binding molecules to be screened and the reference binding molecule to occur. In certain embodiments, competitive binding molecules of the invention will, when present in excess, inhibit specific binding of a reference binding molecule to a selected target species by at least 10%, preferably by at least 25%, more preferably by at least 50%, and most preferably by at least 75% to 90% or even greater. The identification of one or more competitive binding molecules that bind to about, substantially, essentially or at the same epitope as the binding molecules of the invention is a straightforward technical matter. As the identification of competitive binding molecules is determined in comparison to a reference binding molecule, it will be understood that actually determining the epitope to which the reference binding molecule and the competitive binding molecule bind is not in any way required in order to identify a competitive binding molecule that binds to the same or substantially the same epitope as the reference binding molecule. Alternatively, binding molecules binding to different non-competing epitopes identified by these competition assays may also include, but are not limited to, antibodies, antibody fragments and other binding agents.

In another aspect, the invention provides a method of identifying a binding molecule potentially having neutralizing activity against an infectious agent causing disease in a living being or a nucleic acid molecule encoding a binding molecule potentially having neutralizing activity against an infectious agent causing disease in a living being, wherein the method comprises the steps of (a) contacting a collection of binding molecules on the surface of replicable genetic packages with at least a cell expressing a protein of the infectious agent causing disease in a living being on its surface under conditions conducive to binding, (b) separating and recovering binding molecules that bind to the cell expressing a protein of the infectious agent causing disease in a living being on its surface from binding molecules that do not bind the cell, (c) isolating at least one recovered binding molecule, (d) verifying if the binding molecule isolated has neutralizing activity against the infectious agent causing disease in a living being. The cell expressing a protein of the infectious agent causing disease in a living being on its surface can be a cell transfected with the protein. A person skilled in the art is aware that antigens of the infectious agent other than proteins can also be successfully used in the method. In a specific embodiment, the cell is a PER.C6® cell. However, other (E1-immortalized) cell lines could also be used to express the proteins such as BHK, CHO, NSO, HEK293, or 911 cells. In certain embodiments, the binding molecule is human. The infectious agent can be a virus, a bacterium, a yeast, a fungus or a parasite. In certain embodiments, the protein is a protein normally expressed on the surface of the infectious agent or comprises at least a part of a protein that is surface accessible. In a specific embodiment, the collection of binding molecules on the surface of replicable genetic packages are subtracted/counterselected with the cells used for expressing of the protein of the infectious agent, i.e., the cells are identical to the cells used in step (a) with the proviso that they do not express the protein of the infectious agent on their surface. The cells used for subtraction/counterselection can be untransfected cells. Alternatively, the cells can be transfected with a protein or (extracellular) part thereof that is similar and/or highly homologous in sequence or structure with the respective protein of the infectious agent and/or that is derived from an infectious agent of the same family or even genus.

Another aspect of the invention pertains to a binding molecule as defined herein having rabies virus-neutralizing activity, wherein the human binding molecule comprises at least a heavy chain CDR3 region comprising the amino acid sequence comprising SEQ ID NO:25 and further wherein the human binding molecule has a rabies virus-neutralizing activity of at least 2500 IU/mg protein. More preferably, the human binding molecule has a rabies virus-neutralizing activity of at least 2800 IU/mg protein, at least 3000 IU/mg protein, at least 3200 IU/mg protein, at least 3400 IU/mg protein, at least 3600 IU/mg protein, at least 3800 IU/mg protein, at least 4000 IU/mg protein, at least 4200 IU/mg protein, at least 4400 IU/mg protein, at least 4600 IU/mg protein, at least 4800 IU/mg protein, at least 5000 IU/mg protein, at least 5200 IU/mg protein, at least 5400 IU/mg protein. The neutralizing activity of the binding molecule was measured by an in vitro neutralization assay (modified RFFIT (rapid fluorescent focus inhibition test)). The assay is described in detail in the example section infra.

In certain embodiments, the binding molecule comprises a variable heavy chain comprising the amino acid sequence comprising SEQ ID NO:273. In certain embodiments, the binding molecule comprises a heavy chain comprising the amino acid sequence comprising SEQ ID NO:123. The variable light chain of the binding molecule may comprise the amino acid sequence comprising SEQ ID NO:275. The light chain of the binding molecule may comprise the amino acid sequence comprising SEQ ID NO:125.

A nucleic acid molecule encoding the binding molecules as described above is also a part of the invention. In certain embodiments, the nucleic acid molecule comprises the nucleotide sequence comprising SEQ ID NO:122. In addition, the nucleic acid molecule may also comprise the nucleotide sequence comprising SEQ ID NO:124. A vector comprising the nucleic acid molecules and a host cell comprising such a vector are also provided herein. In certain embodiments, the host cell is a mammalian cell such as a human cell. Examples of cells suitable for production of human binding molecules are inter alia HeLa, 911, AT1080, A549, 293 and HEK293T cells. Preferred mammalian cells are human retina cells such as 911 cells or the cell line deposited at the European Collection of Cell Cultures (ECACC), CAMR, Salisbury, Wiltshire SP4 OJG, Great Britain on 29 Feb. 1996 under number 96022940 and marketed under the trademark PER.C6® (PER.C6® is a registered trademark of Crucell Holland B.V.). For the purposes of this application "PER.C6®" refers to cells deposited under number 96022940 or ancestors, passages up stream or downstream as well as descendants from ancestors of deposited cells, as well as derivatives of any of the foregoing.

EXAMPLES

To illustrate the invention, the following examples are provided. The examples are not intended to limit the scope of the invention in any way.

Example 1

Epitope Recognition of Human Anti-Rabies Antibodies CR-57 and CR-JB

To address whether the human monoclonal antibodies called CR-57 and CR-JB recognize non-overlapping, non-competing epitopes, escape viruses of the human monoclonal antibodies called CR-57 and CR-JB were generated. CR-57 and CR-JB were generated essentially as described (see, Jones et al., 2003), via introduction of the variable heavy and light chain coding regions of the corresponding antibody genes into a single human IgG1 expression vector named pcDNA3002(Neo). The resulting vectors pgSO57C11 and pgSOJBC11 were used for transient expression in cells from the cell line deposited at the European Collection of Cell Cultures (ECACC), CAMR, Salisbury, Wiltshire SP4 OJG, Great Britain on 29 Feb. 1996 under number 96022940 and marketed under the trademark PER.C6®. The nucleotide and amino acid sequences of the heavy and light chains of these antibodies are shown in SEQ ID NOS:122 through 129, respectively. Serial dilutions (0.5 ml) of rabies virus strain CVS-11 (dilutions ranging from $10^{-1}$ to $10^{-8}$) were incubated with a constant amount (~4 IU/ml) of antibody CR-57 or CR-JB (0.5 ml) for one hour at 37° C./5% $CO_2$ before addition to wells containing mouse neuroblastoma cells (MNA cells) or BSR cells (Baby Hamster Kidney-like cell line). After three days of selection in the presence of either human monoclonal antibody CR-57 or CR-JB, medium (1 ml) containing potential escape viruses was harvested and stored at 4° C. until further use. Subsequently, the cells were acetone-fixed for 20 minutes at 4° C., and stained overnight at 37° C./5% $CO_2$ with an anti-rabies N-FITC antibody conjugate (Centocor). The number of foci per well were scored by immunofluorescence and medium of wells containing one to six foci were chosen for virus amplification. All E57 escape viruses were generated from one single focus with the exception of E57B1 (three foci). EJB escape viruses were isolated from one focus (EJB3F), three foci (EJB2B), four foci (EJB2C), five foci (EJB2E, 2F), or six foci (EJB2D), respectively. Each escape virus was first amplified on a small scale on BSR or MNA cells depending on their growth characteristics. These small virus batches were then used to further amplify the virus on a large scale on MNA or BSR cells. Amplified virus was then titrated on MNA cells to determine the titer of each escape virus batch as well as the optimal dilution of the escape virus (giving 80% to 100% infection after 24 hours) for use in a virus neutralization assay.

Modified RFFIT (rapid fluorescent focus inhibition test) assays were performed to examine cross-protection of E57 (the escape viruses of CR-57) and EJB (the escape viruses of CR-JB) with CR-JB and CR-57, respectively. Therefore, CR-57 or CR-JB was diluted by serial threefold dilutions starting with a 1:5 dilution. Rabies virus (strain CVS-11) was added to each dilution at a concentration that gives 80% to 100% infection. Virus/IgG mix was incubated for one hour at 37° C./5% $CO_2$ before addition to MNA cells. Twenty-four hours post-infection (at 34° C./5% $CO_2$) the cells were acetone-fixed for 20 minutes at 4° C., and stained for minimally three hours with an anti-rabies virus N-FITC antibody conjugate (Centocor). The wells were then analyzed for rabies virus infection under a fluorescence microscope to determine the 50% endpoint dilution. This is the dilution at which the virus infection is blocked by 50% in this assay. To calculate the potency, an Internat'l standard (Rabies Immune Globulin Lot R3, Reference material from the laboratory of Standards and Testing DMPQ/CBER/FDA) was included in each modified RFFIT. The 50% endpoint dilution of this standard corresponds with a potency of 2 IU/ml. The neutralizing potency of the single human monoclonal antibodies CR-57 and CR-JB as well as the combination of these antibodies were tested.

EJB viruses were no longer neutralized by CR-JB or CR-57 (see, Table 1), suggesting both antibodies bound to and induced amino acid changes in similar regions of the rabies virus glycoprotein. E57 viruses were no longer neutralized by CR-57, whereas 4 out of 6 E57 viruses were still neutralized by CR-JB, although with a lower potency (see, Table 1). A mixture of the antibodies CR-57 and CR-JB (in a 1:1 IU/mg ratio) gave similar results as observed with the single antibodies (data not shown).

To identify possible mutations in the rabies virus glycoprotein the nucleotide sequence of the glycoprotein open reading frame (ORF) of each of the EJB and E57 escape viruses was determined. Viral RNA of each of the escape viruses and CVS-11 was isolated from virus-infected MNA cells and converted into cDNA by standard RT-PCR. Subsequently, cDNA was used for nucleotide sequencing of the rabies virus glycoprotein ORFs in order to identify mutations.

Both E57 and EJB escape viruses showed mutations in the same region of the glycoprotein (see, FIGS. 1 and 2, respectively; see for all the sequences described in FIGS. 1 and 2 SEQ ID NOS:130 through 151). This indicates that both antibodies recognize overlapping epitopes. From the above can be concluded that the combination of CR-57 and CR-JB in a cocktail does not prevent the escape of neutralization-resistant variants and is therefore not an ideal immunoglobulin preparation for rabies post exposure prophylaxis.

Example 2

Construction of a ScFv Phage Display Library Using Peripheral Blood Lymphocytes of Rabies-Vaccinated Donors From four rabies-vaccinated human subjects, 50 ml blood was drawn from a vein one week after the last boost. Peripheral blood lymphocytes (PBL) were isolated from these blood samples using Ficoll cell density fractionation. The blood serum was saved and frozen at −20° C. The presence of anti-rabies antibodies in the sera was tested positive using a FACS staining on rabies virus glycoprotein transfected 293T cells. Total RNA was prepared from the PBL using organic phase separation (TRIZOL™) and subsequent ethanol precipitation. The obtained RNA was dissolved in DEPC-treated ultrapure water and the concentration was determined by OD 260 nm measurement. Thereafter, the RNA was diluted to a concentration of 100 ng/µl. Next, 1 µg of RNA was converted into cDNA as follows: To 10 µl total RNA, 13 µl DEPC-treated ultrapure water and 1 µl random hexamers (500 ng/µl) were added and the obtained mixture was heated at 65° C. for five minutes and quickly cooled on wet-ice. Then, 8 µl 5× First-Strand buffer, 2 µl dNTP (10 mM each), 2 µl DTT (0.1 M), 2 µl Rnase-inhibitor (40 U/µl) and 2 µl Superscript™III MMLV reverse transcriptase (200 U/µl) were added to the mixture, incubated at room temperature for five minutes and incubated for one hour at 50° C. The reaction was terminated by heat inactivation, i.e., by incubating the mixture for 15 minutes at 75° C.

The obtained cDNA products were diluted to a final volume of 200 µl with DEPC-treated ultrapure water. The OD 260 nm of a 50 times diluted solution (in 10 mM Tris buffer) of the dilution of the obtained cDNA products gave a value of 0.1.

For each donor 5 to 10 µl of the diluted cDNA products were used as template for PCR amplification of the immunoglobulin gamma heavy chain family and kappa or lambda light chain sequences using specific oligonucleotide primers (see, Tables 2 through 7). PCR reaction mixtures contained, besides the diluted cDNA products, 25 pmol sense primer and 25 pmol anti-sense primer in a final volume of 50 µl of 20 mM Tris-HCl (pH 8.4), 50 mM KCl, 2.5 mM MgCl$_2$, 250 µM dNTPs and 1.25 units Taq polymerase. In a heated-lid thermal cycler having a temperature of 96° C., the mixtures obtained were quickly melted for two minutes, followed by 30 cycles of: 30 seconds at 96° C., 30 seconds at 60° C. and 60 seconds at 72° C.

In a first round amplification, each of seventeen light chain variable region sense primers (eleven for the lambda light chain (see, Table 2) and six for the kappa light chain (see, Table 3) were combined with an anti-sense primer recognizing the C-kappa called HuCk 5'-ACACTCTCCCCTGT-TGAAGCTCTT-3' (see, SEQ ID NO:152) or C-lambda constant region HuCλ2 5'-TGAACATTCTGTAGGGGCCACTG-3' (see, SEQ ID NO:153) and HuCλ7 5'-AGAGCATTCTGCAGGGGC-CACTG-3' (see, SEQ ID NO:154) (the HuCλ2 and HuCλ7 anti-sense primers were mixed to equimolarity before use), yielding four times 17 products of about 600 base pairs. These products were purified on a 2% agarose gel and isolated from the gel using Qiagen® gel-extraction columns. One-tenth of each of the isolated products was used in an identical PCR reaction as described above using the same seventeen sense primers, whereby each lambda light chain sense primer was combined with one of the three Jlambda-region-specific anti-sense primers and each kappa light chain sense primer was combined with one of the five Jkappa-region-specific anti-sense primers. The primers used in the second amplification were extended with restriction sites (see, Table 4) to enable directed cloning in the phage display vector PDV-006 (see, FIG. 3 and SEQ ID NO:155). This resulted in four times 63 products of approximately 350 base pairs that were pooled to a total of ten fractions. This number of fractions was chosen to maintain the natural distribution of the different light chain families within the library and not to over or under represent certain families. The number of alleles within a family was used to determine the percentage of representation within a library (see, Table 5). In the next step, 2.5 µg of pooled fraction and 100 PDV-C06 vector were digested with SalI and NotI and purified from gel. Thereafter, a ligation was performed overnight at 16° C. as follows. To 500 ng PDV-006 vector 70 ng pooled fraction was added in a total volume of 50 µl ligation mix containing 50 mM Tris-HCl (pH 7.5), 10 mM MgCl$_2$, 10 mM DTT, 1 mM ATP, 25 µg/ml BSA and 2.5 µl T4 DNA Ligase (400 U/µl). This procedure was followed for each pooled fraction. The ligation mixes were purified by phenol/chloroform, followed by a chloroform extraction and ethanol precipitation, methods well known to the skilled artisan. The DNA obtained was dissolved in 50 µl ultrapure water and per ligation mix two times 2.5 µl aliquots were electroporated into 40 µl of TG1 competent *E. coli* bacteria according to the manufacturer's protocol (Stratagene). Transformants were grown overnight at 37° C. in a total of 30 dishes (three dishes per pooled fraction; dimension of dish: 240 mm×240 mm) containing 2TY agar supplemented with 50 µg/ml ampicillin and 4.5% glucose. A (sub)library of variable light chain regions was obtained by scraping the transformants from the agar plates. This (sub)library was directly used for plasmid DNA preparation using a QIAGEN®QIAFilter MAXI prep kit.

For each donor the heavy chain immunoglobulin sequences were amplified from the same cDNA preparations in a similar two round PCR procedure and identical reaction parameters as described above for the light chain regions with the proviso that the primers depicted in Tables 6 and 7 were used. The first amplification was performed using a set of nine sense directed primers (see, Table 6; covering all families of heavy chain variable regions) each combined with an IgG-specific constant region anti-sense primer called HuCIgG 5'-GTC CAC CTT GGT GTT GCT GGG CTT-3' (SEQ ID NO:156) yielding four times nine products of about 650 base pairs. These products were purified on a 2% agarose gel and isolated from the gel using QIAGEN® gel-extraction columns. One-tenth of each of the isolated products was used in an identical PCR reaction as described above using the same nine sense primers, whereby each heavy chain sense primer was combined with one of the four JH-region-specific antisense primers. The primers used in the second round were extended with restriction sites (see, Table 7) to enable directed cloning in the light chain (sub)library vector. This resulted per donor in 36 products of approximately 350 base pairs. These products were pooled for each donor per used (VH) sense primer into nine fractions. The products obtained were purified using QIAGEN® PCR Purification columns. Next, the fractions were digested with SfiI and XhoI and ligated in the light chain (sub)library vector, which was cut with the same restriction enzymes, using the same ligation procedure and volumes as described above for the light chain (sub)library. Alternatively, the fractions were digested with NcoI and XhoI and ligated in the light chain vector, which was cut with the same restriction enzymes, using the same ligation procedure and volumes as described above for the light chain (sub)library. Ligation purification and subsequent transformation of the resulting definitive library was also performed as described above for the light chain (sub)library and at this point, the ligation mixes of each donor were combined per VH pool. The transformants were grown in 27 dishes (three dishes per pooled fraction; dimension of dish: 240 mm×240 mm) containing 2TY agar supplemented with 50 µg/ml ampicillin and 4.5% glucose. All bacteria were harvested in 2TY culture medium containing 50 µg/ml ampicillin and 4.5% glucose, mixed with glycerol to 15% (v/v) and frozen in 1.5 ml aliquots at −80° C. Rescue and selection of each library were performed as described below.

Example 3

Selection of Phages Carrying Single Chain Fv Fragments Specifically Recognizing Rabies Virus Glycoprotein Antibody fragments were selected using antibody phage display libraries, general phage display technology and MABSTRACT® technology, essentially as described in U.S. Pat. No. 6,265,150 and in WO 98/15833 (both of which are incorporated by reference herein). The antibody phage libraries used were two different semi-synthetic scFv phage libraries (JK1994 and WT2000) and the immune scFv phage libraries (RAB-03-G01 and RAB-04-G01) prepared as described in Example 2 above. The first semi-synthetic scFv phage library (JK1994) has been described in de Kruif et al. (1995b), the second one (WT2000) was built essentially as described in de Kruif et al. (1995b). Briefly, the library has a semi-synthetic format whereby variation was incorporated in the heavy and light chain V genes using degenerated oligonucleotides that incorporate variation within CDR regions. Only VH3 heavy chain genes were used, in combination with kappa and lambda light chain genes. CDR1 and CDR3 of the heavy chain and CDR3 of the light chain were recreated synthetically in a PCR-based approach similar as described in de Kruif et al. (1995b). The thus created V region genes were cloned sequentially in scFv format in a phagemid vector and amplified to generate a phage library as described before. Furthermore, the methods and helper phages as described in WO 02/103012 (incorporated by reference herein) were used in the invention. For identifying phage antibodies recognizing rabies virus glycoprotein phage selection experiments were performed using whole rabies virus (rabies virus Pitman-Moore strain) inactivated by treatment with beta-propiolactone, purified rabies virus glycoprotein (rabies virus ERA strain), and/or transfected cells expressing rabies virus G protein (rabies virus ERA strain).

The G protein was purified from the rabies virus ERA strain as follows. To a virus solution, 1/10 volume of 10% octyl-beta-glucopyranoside was added and mixed gently. Upon a 30-minute incubation at 4° C., the virus sample was centrifuged (36,000 rpm, 4° C.) in a SW51 rotor. The supernatant was collected and dialyzed overnight at 4° C. against 0.1 M Tris/EDTA. Subsequently, the glycoprotein was collected from the dialysis chamber, aliquoted, and stored at −80° C. until further use. The protein concentration was determined by OD 280 nm and the integrity of the G protein was analyzed by SDS-PAGE.

Whole inactivated rabies virus or rabies virus G protein were diluted in phosphate buffered saline (PBS), 2 to 3 ml was added to MaxiSorp Nunc-Immuno Tubes (Nunc) and incubated overnight at 4° C. on a rotating wheel. An aliquot of a phage library (500 μl, approximately $10^{13}$ cfu, amplified using CT helper phage (see, WO 02/103012)) was blocked in blocking buffer (2% Protifar in PBS) for one to two hours at room temperature. The blocked phage library was added to the immunotube (either preincubated with or without CR-57 scFv to block the epitope recognized by CR-57), incubated for two hours at room temperature, and washed with wash buffer (0.1% Tween-20 (Serva) in PBS) to remove unbound phages. Bound phages were then eluted from the antigen by incubation for ten minutes at room temperature with 1 ml of 50 mM Glycine-HCl pH 2.2. Subsequently, the eluted phages were mixed with 0.5 ml of 1 M Tris-HCl pH 7.5 to neutralize the pH. This mixture was used to infect 5 ml of an XL1-Blue *E. coli* culture that had been grown at 37° C. to an OD 600 nm of approximately 0.3. The phages were allowed to infect the XL1-Blue bacteria for 30 minutes at 37° C. Then, the mixture was centrifuged for ten minutes, at 3200*g at room temperature and the bacterial pellet was resuspended in 0.5 ml 2-trypton yeast extract (2TY) medium. The obtained bacterial suspension was divided over two 2TY agar plates supplemented with tetracycline, ampicillin and glucose. After incubation overnight of the plates at 37° C., the colonies were scraped from the plates and used to prepare an enriched phage library, essentially as described by de Kruif et al. (1995a) and WO 02/103012. Briefly, scraped bacteria were used to inoculate 2TY medium containing ampicillin, tetracycline and glucose and grown at a temperature of 37° C. to an OD 600 nm of ~0.3. CT helper phages were added and allowed to infect the bacteria after which the medium was changed to 2TY containing ampicillin, tetracycline and kanamycin. Incubation was continued overnight at 30° C. The next day, the bacteria were removed from the 2TY medium by centrifugation after which the phages in the medium were precipitated using polyethylene glycol (PEG) 6000/NaCl. Finally, the phages were dissolved in 2 ml of PBS with 1% bovine serum albumin (BSA), filter-sterilized and used for the next round of selection.

Phage selections were also performed with rabies virus glycoprotein transfected cells. The cells used were cells from the cell line deposited at the European Collection of Cell Cultures (ECACC), CAMR, Salisbury, Wiltshire SP4 OJG, Great Britain on 29 Feb. 1996, under number 96022940 and marketed under the trademark PER.C6®. They are hereinafter referred to as PER.C6® cells. Here, the blocked phage library (2 ml) was first added to $1*10^7$ subtractor cells (in DMEM/10% FBS) and incubated for one hour at 4° C. on a rotating wheel. The subtractor cells were PER.C6® cells that expressed the Vesicular Stomatitis Virus (VSV) glycoprotein ecto domain on their surface fused to the rabies virus transmembrane and cytoplasmic domain. With this subtraction step phages recognizing either VSV glycoprotein or antigens specific for PER.C6® cells were removed from the phage library. The phage/cell mixture was centrifuged (five minutes at 4° C. at 500×g) to remove cell-bound phages, and the supernatant was added to a new tube containing 3 ml of $1*10^7$ subtractor cells. The subtraction step was repeated twice with the respective supernatant. Subsequently, the subtracted phages were incubated for 1.5 hours at 4° C. on a rotating wheel with the rabies virus glycoprotein expressing transfected cells (PER.C6® cells ($3*10^6$ cells)). Before that, the transfected cells were preincubated, either with or without CR-57 scFv, to block the epitope recognized by CR-57. After incubation, the cells were washed five times with 1 ml of DMEM/10% FBS (for each wash, the cells were resuspended and transferred to new tube), phages were eluted and processed as described above.

Typically, two rounds of selections were performed before isolation of individual phage antibodies. After the second round of selection, individual E. coli colonies were used to prepare monoclonal phage antibodies. Essentially, individual colonies were grown to log-phase in 96-well plate format and infected with VCSM13 helper phages after which phage antibody production was allowed to proceed overnight. The produced phage antibodies were PEG/NaCl-precipitated and filter-sterilized and tested in ELISA for binding to both whole inactivated rabies virus and purified rabies virus G protein. From the selection, a large panel of phage antibodies was obtained that demonstrated binding to both whole inactivated rabies virus and rabies virus G protein (see, example below). Two selection strategies were followed with the above-described immune libraries. In the first strategy 736 phage antibodies were selected after two selection rounds using in the first and second selection round inactivated virus or purified G protein. In the second strategy, 736 phage antibodies were selected after two selection rounds using in the first selection round cell surface expressed recombinant G protein and in the second selection round inactivated virus or purified G protein. The number of unique phage antibodies obtained by the first strategy was 97, while the second strategy yielded 70 unique ones. The 97 unique phage antibodies found by means of the first strategy gave rise to 18 neutralizing antibodies and the 70 unique clones identified by means of the second strategy yielded 33 neutralizing antibodies. This clearly demonstrates that selections that included rabies virus glycoprotein transfected cells, i.e., cell surface expressed recombinant G protein, as antigen appeared to yield more neutralizing antibodies compared to selections using only purified G protein and/or inactivated virus.

Example 4

Validation of the Rabies Virus Glycoprotein-Specific Single-Chain Phage Antibodies Selected single-chain phage antibodies that were obtained in the screens described above, were validated in ELISA for specificity, i.e., binding to rabies virus G protein, purified as described supra. Additionally, the single-chain phage antibodies were also tested for binding to 5% FBS. For this purpose, the rabies virus G protein or 5% FBS preparation was coated to Maxisorp™ ELISA plates. After coating, the plates were blocked in PBS/1% Protifar for one hour at room temperature. The selected single-chain phage antibodies were incubated for 15 minutes in an equal volume of PBS/1% Protifar to obtain blocked phage antibodies. The plates were emptied, and the blocked phage antibodies were added to the wells. Incubation was allowed to proceed for one hour, the plates were washed in PBS containing 0.1% Tween-20 and bound phage antibodies were detected (using OD 492 nm measurement) using an anti-M13 antibody conjugated to peroxidase. As a control, the procedure was performed simultaneously using no single-chain phage antibody, a negative control single chain phage antibody directed against CD8 (SC02-007) or a positive control single chain phage antibody directed against rabies virus glycoprotein (scFv SO57). As shown in Table 8, the selected phage antibodies called SC04-001, SC04-004, SC04-008, SC04-010, SC04-018, SC04-021, SC04-026, 5C04-031, SC04-038, SC04-040, SC04-060, SC04-073, SC04-097, SC04-098, SC04-103, SC04-104, SC04-108, SC04-120, SC04-125, SC04-126, SC04-140, SC04-144, SC04-146, and SC04-164 displayed significant binding to the immobilized purified rabies virus G protein, while no binding to FBS was observed. Identical results were obtained in ELISA using the whole inactivated rabies virus prepared as described supra (data not shown).

Example 5

Characterization of the Rabies Virus-Specific scFvs

From the selected specific single chain phage antibody (scFv) clones plasmid DNA was obtained and nucleotide sequences were determined according to standard techniques. The nucleotide sequences of the scFvs (including restriction sites for cloning) called SC04-001, SC04-004, SC04-008, SC04-010, SC04-018, SC04-021, SC04-026, SC04-031, 5C04-038, SC04-040, 5C04-060, SC04-073, SC04-097, SC04-098, SC04-103, SC04-104, SC04-108, SC04-120, SC04-125, SC04-126, SC04-140, SC04-144, SC04-146, and SC04-164 are shown in SEQ ID NO:157, SEQ ID NO:159, SEQ ID NO:161, SEQ ID NO:163, SEQ ID NO:165, SEQ ID NO:167, SEQ ID NO:169, SEQ ID NO:171, SEQ ID NO:173, SEQ ID NO:175, SEQ ID NO:177, SEQ ID NO:179, SEQ ID NO:181, SEQ ID NO:183, SEQ ID NO:185, SEQ ID NO:187, SEQ ID NO:189, SEQ ID NO:191, SEQ ID NO:193, SEQ ID NO:195, SEQ ID NO:197, SEQ ID NO:199, SEQ ID NO:201 and SEQ ID NO:203, respectively. The amino acid sequences of the scFvs called SC04-001, 5C04-004, 5C04-008, SC04-010, SC04-018, 5C04-021, SC04-026, SC04-031, SC04-038, SC04-040, SC04-060, SC04-073, SC04-097, SC04-098, SC04-103, SC04-104, SC04-108, SC04-120, SC04-125, SC04-126, SC04-140, SC04-144, SC04-146, and SC04-164 are shown in SEQ ID NO:158, SEQ ID NO:160, SEQ ID NO:162, SEQ ID NO:164, SEQ ID NO:166, SEQ ID NO:168, SEQ ID NO:170, SEQ ID NO:172, SEQ ID NO:174, SEQ ID NO:176, SEQ ID NO:178, SEQ ID NO:180, SEQ ID NO:182, SEQ ID NO:184, SEQ ID NO:186, SEQ ID NO:188, SEQ ID NO:190, SEQ ID NO:192, SEQ ID NO:194, SEQ ID NO:196, SEQ ID NO:198, SEQ ID NO:200, SEQ ID NO:202 and SEQ ID NO:204, respectively.

The VH and VL gene identity (see, I. M. Tomlinson, S. C. Williams, O. Ignatovitch, S. J. Corbett, G. Winter, "V-BASE Sequence Directory," Cambridge United Kingdom: MRC Centre for Protein Engineering (1997)) and heavy chain CDR3 compositions of the scFvs specifically binding the rabies virus G protein are depicted in Table 9.

Example 6

In Vitro Neutralization of Rabies Virus by Rabies Virus-Specific scFvs (Modified RFFIT)

In order to determine whether the selected scFvs were capable of blocking rabies virus infection, in vitro neutralization assays (modified RFFIT) were performed. The scFv preparations were diluted by serial threefold dilutions starting with a 1:5 dilution. Rabies virus (strain CVS-11) was added to each dilution at a concentration that gives 80% to 100% infection. Virus/scFv mix was incubated for one hour at 37° C./5% $CO_2$ before addition to MNA cells. Twenty-four hours post-infection (at 34° C./5% $CO_2$), the cells were acetone-fixed for 20 minutes at 4° C., and stained for minimally three hours with an anti-rabies N-FITC antibody conjugate (Centocor). The cells were then analyzed for rabies virus infection under a fluorescence microscope to determine the 50% end-point dilution. This is the dilution at which the virus infection is blocked by 50% in this assay (see, Example 1). Several scFvs were identified that showed neutralizing activity against rabies virus (see, Table 10).

Additionally, it was investigated by means of the in vitro neutralization assay (modified RFFIT) as described above, if the selected scFvs were capable of neutralizing the E57 escape viruses as prepared in Example 1 (E57A2, E57A3, E57B1, E57B2, E57B3 and E57C3). Several scFvs were identified that showed neutralizing activity against the E57 escape viruses (see, Tables 11A and 11B).

Example 7

Rabies Virus G Protein Competition ELISA with scFvs

To identify antibodies that bind to non-overlapping, non-competing epitopes, a rabies glycoprotein competition ELISA was performed. Nunc-Immuno™ Maxisorp F96 plates (Nunc) were coated overnight at 4° C. with a 1:1000 dilution of purified rabies virus glycoprotein (1 mg/ml; rabies virus ERA strain) in PBS (50 µl). Uncoated protein was washed away before the wells were blocked with 100 µl PBS/1% Protifar for one hour at room temperature. Subsequently, the blocking solution was discarded and 50 µl of the non-purified anti-rabies virus scFvs in PBS/1% Protifar (2× diluted) was added. Wells were washed five times with 100 µA of PBS/0.05% Tween-20. Then, 50 µl biotinylated anti-rabies virus competitor IgG, CR-57bio, was added to each well, incubated for five minutes at room temperature, and the wells were washed five times with 100 µl of PBS/0.05% Tween-20. To detect the binding of CR-57bio, 50 µl of a 1:2000 dilution of streptavidin-HRP antibody (Becton Dickinson) was added to the wells and incubated for one hour at room temperature. Wells were washed again as above and the ELISA was further developed by addition of 100 µl of OPD reagens (Sigma). The reaction was stopped by adding 50 µl 1 M $H_2SO_4$ before measuring the OD at 492 nm.

Figure 4:
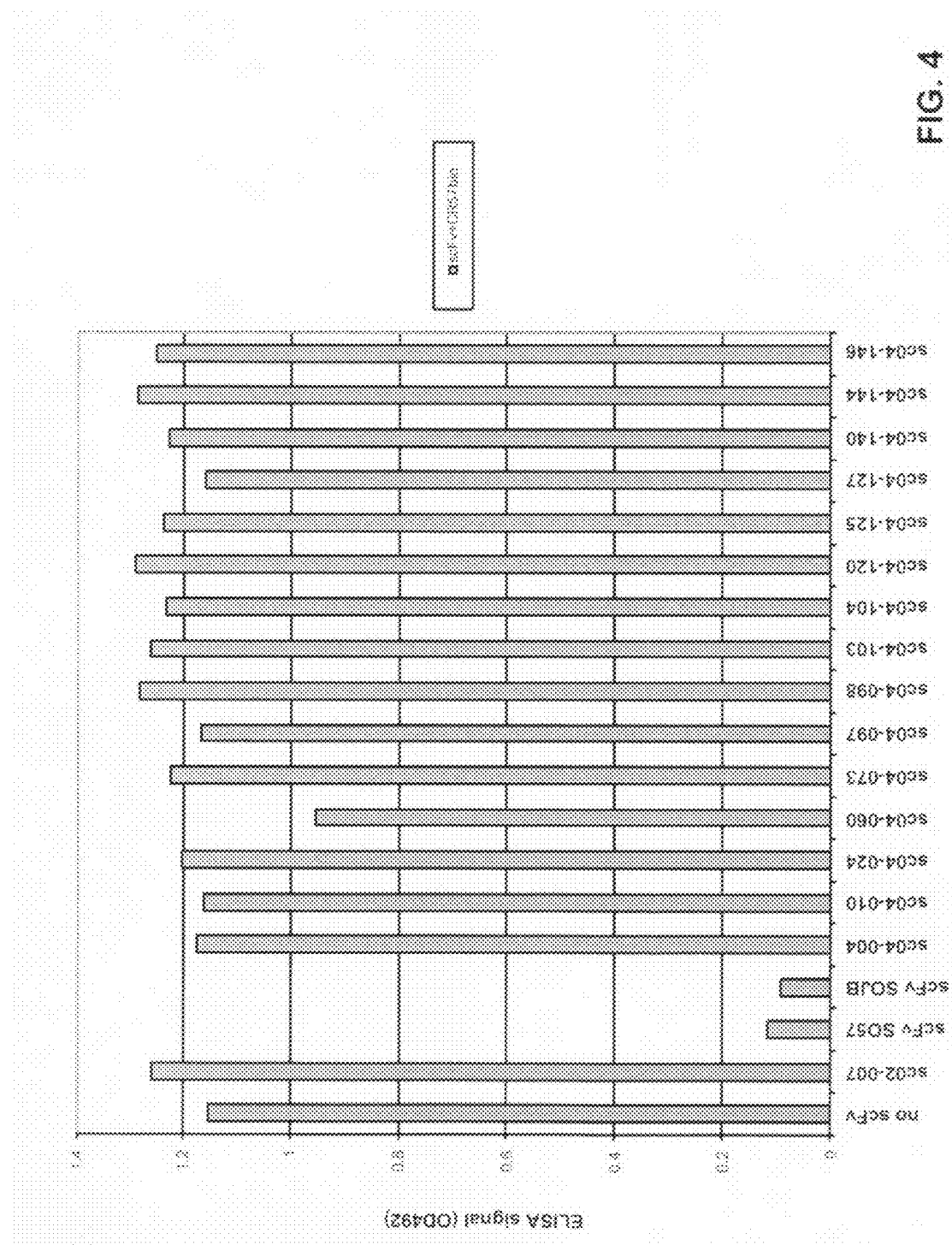
FIG. 4 shows a competition ELISA of anti-rabies virus scFvs and the biotinylated anti-rabies virus antibody called CR-57. ELISA plates coated with purified rabies virus G protein were incubated with the respective scFvs before addition of CR-57bio (0.5 µg/ml). Subsequently, CR-57bio binding was monitored in absence and presence of scFvs.

The signal obtained with CR-57bio alone could be reduced to background levels when co-incubated with scFv 5057, i.e., the scFv form of CR-57 (for nucleotide and amino acid sequence of SO57 see SEQ ID NOS:205 and 206, respectively) or scFv SOJB, i.e., the scFv form of CR-JB (for nucleotide and amino acid sequence of SOJB see SEQ ID NOS:312 and 313, respectively). This indicates that the scFvs SO57 and SOJB compete with the interaction of CR-57bio to rabies virus glycoprotein by binding to the same epitope or to an overlapping epitope as CR-57bio, respectively. In contrast, an irrelevant scFv called SC02-007, i.e., a scFv binding to CD8, did not compete for binding. The anti-rabies virus scFvs called SC04-004, SC04-010, SC04-024, SC04-060, SC04-073, SC04-097, SC04-098, SC04-103, SC04-104, SC04-120, SC04-125, SC04-127, SC04-140, SC04-144 and SC04-146 did also not compete with CR-57bio, indicating that these scFvs bind to a different epitope than the epitope recognized by CR-57 (see, FIG. 4).

Figure 5:
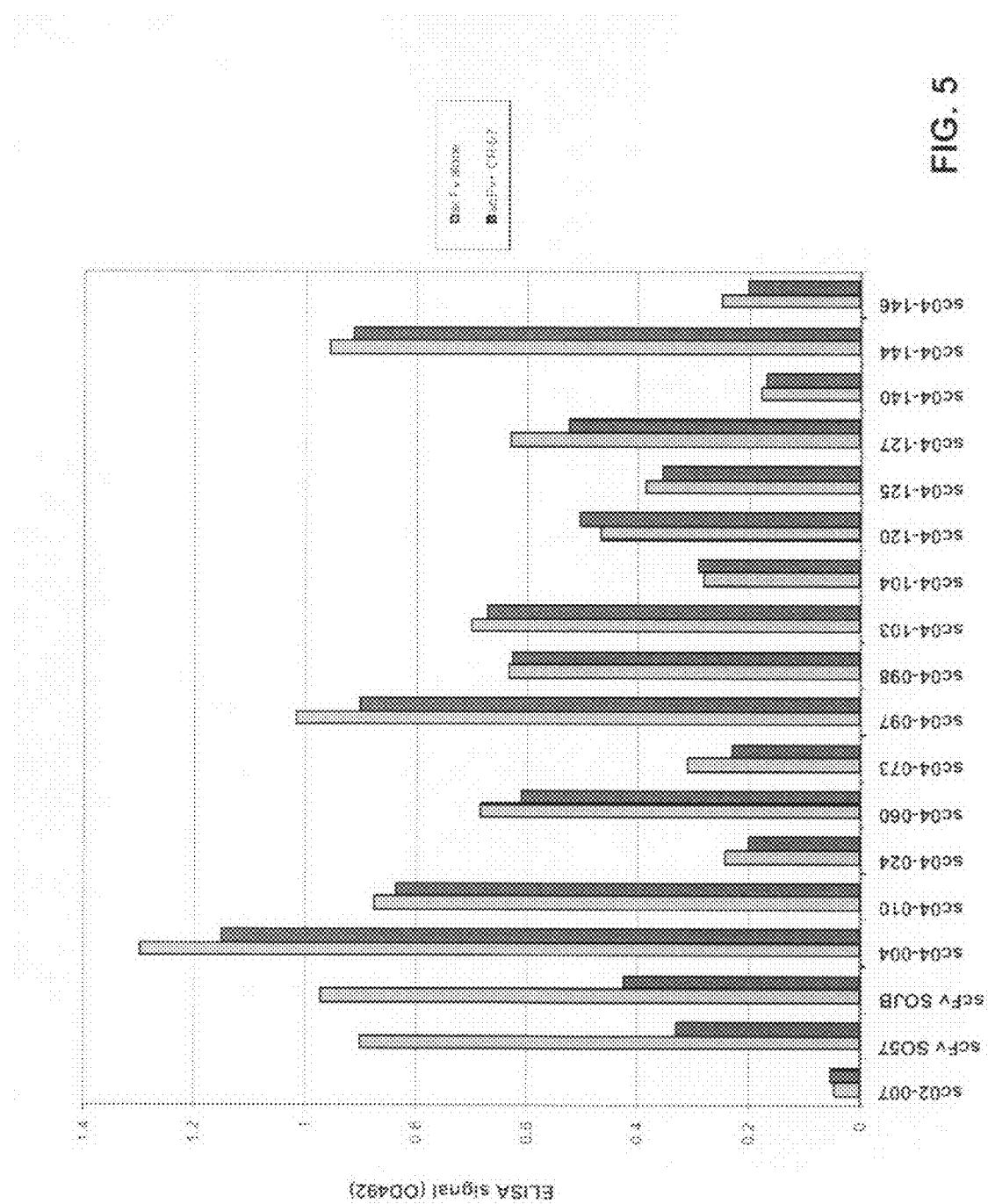
FIG. 5 shows a competition ELISA of anti-rabies virus scFvs and the anti-rabies virus antibody called CR-57. ELISA plates coated with purified rabies virus G protein were incubated with CR-57 (1 µg/ml) before addition of excess scFvs. Subsequently, scFv binding was monitored in absence and presence of CR-57.

Similar results were obtained with the following experiment. First, the rabies virus antibody CR-57 was added to wells coated with rabies virus G protein. Next, the competing scFvs were added. In this set-up the anti-rabies virus scFvs were detected with anti-VSV-HRP by virtue of the presence of a VSV-tag in the scFv amino acid sequences (see, FIG. 5).

Example 8

Construction of Fully Human Immunoglobulin Molecules (Human Monoclonal Anti-Rabies Virus Antibodies) from the Selected Anti-Rabies Virus Single Chain Fvs Heavy and light chain variable regions of the scFvs called SC04-001, SC04-008, SC04-018, SC04-040 and SC04-126 were PCR-amplified using oligonucleotides to append restriction sites and/or sequences for expression in the IgG expression vectors pSyn-C03-HCγ1 (see, SEQ ID NO:277) and pSyn-C04-Cλ (see, SEQ ID NO:278), respectively. The $V_H$ and $V_L$ genes were amplified using the oligonucleotides as shown in Table 12 and 13, respectively, and the PCR products were cloned into the vectors pSyn-C03-HCγ1 and pSyn-C04-Cλ, respectively.

Heavy and light chain variable regions of the scFvs called SC04-004, SC04-010, SC04-021, 5C04-026, SC04-031, SC04-038, SC04-060, SC04-073, SC04-097, SC04-098, SC04-103, SC04-104, SC04-108, SC04-120, SC04-125, SC04-140, SC04-144, SC04-146 and SC04-164 were also PCR-amplified using oligonucleotides to append restriction sites and/or sequences for expression in the IgG expression vectors pSyn-C03-HCγ1 and pSyn-C05-Cκ (see, SEQ ID NO:279), respectively. The $V_H$ and $V_L$ genes were amplified using the oligonucleotides as given in Table 12 and 13, respectively, and the PCR products were cloned into the vectors pSyn-C03-HCγ1 and pSyn-C05-Ck, respectively. The oligonucleotides are designed such that they correct any deviations from the germline sequence that have been introduced during library construction, due to the limited set of oligonucleotides that have been used to amplify the large repertoire of antibody genes. Nucleotide sequences for all constructs were verified according to standard techniques known to the skilled artisan.

The resulting expression constructs pgG104-001C03, pgG104-008C03, pgG104-018C03, pgG104-040C03 and pgG104-126C03 encoding the anti-rabies virus human IgG1 heavy chains in combination with the relevant pSyn-004-Vλ construct encoding the corresponding light chain were transiently expressed in 293T cells and supernatants containing IgG1 antibodies were obtained. The expression constructs pgG104-004C03, pgG104-010C03, pgG104-021C03, pgG104-026C03, pgG104-031C03, pgG104-038C03, pgG104-060C03, pgG104-073C03, pgG104-097C03, pgG104-098C03, pgG104-103C03, pgG104-104C03, pgG104-108C03, pgG104-120C03, pgG104-125C03, pgG104-140C03, pgG104-144C03, pgG104-146C03 and pgG104-164C03 encoding the anti-rabies virus human IgG1 heavy chains in combination with the relevant pSyn-C05-Vκ construct encoding the corresponding light chain were transiently expressed in 293T cells and supernatants containing IgG1 antibodies were obtained.

The nucleotide and amino acid sequences of the heavy and light chains of the antibodies called CR04-001, CR04-004, CR04-008, CR04-010, CR04-018, CR04-021, CR04-026, CR04-031, CR04-038, CR04-040, CR04-060, CR04-073, CR04-097, CR04-098, CR04-103, CR04-104, CR04-108, CR04-120, CR04-125, CR04-126, CR04-140, CR04-144, CR04-146 and CR04-164 were determined according to standard techniques. Subsequently, the recombinant human monoclonal antibodies were purified over a protein-A column followed by a buffer exchange on a desalting column using standard purification methods used generally for immunoglobulins (see, for instance WO 00/63403 which is incorporated by reference herein).

Additionally, for CR04-098, a single human IgG1 expression vector named pgG104-098C10 was generated as described above for vectors pgSO57C11 and pgSOJBC11 encoding CR-57 and CR-JB, respectively (see, Example 1). The nucleotide and amino acid sequences of the heavy and light chains of antibody CR04-098 encoded by vector pgG104-098C10 are shown in SEQ ID NOS:334 through 337, respectively. Vectors pgSO57C11 (see, Example 1) and pgG104-098C10 were used for stable expression of CR-57 and CR04-098, respectively, in cells from the cell line deposited at the European Collection of Cell Cultures (ECACC), CAMR, Salisbury, Wiltshire SP4 OJG, Great Britain on 29 Feb. 1996 under number 96022940 and marketed under the trademark PER.C6®. The stably produced CR-57 and CR04-098 have a calculated isoelectric point of 8.22 and 8.46, respectively. The experimentally observed isoelectric points are between 8.1-8.3 for CR-57 and 9.0-9.2 for CR04-098. The recombinant human monoclonal antibodies were purified as described above. Unless otherwise stated, for CR04-001, CR04-004, CR04-008, CR04-010, CR04-018, CR04-021, CR04-026, CR04-031, CR04-038, CR04-040, CR04-060, CR04-073, CR04-097, CR04-098, CR04-103, CR04-104, CR04-108, CR04-120, CR04-125, CR04-126, CR04-140, CR04-144, CR04-146 and CR04-164 use was made of recombinant human monoclonal antibodies transiently expressed by the two vector system as described above and for CR57 use was made of recombinant human monoclonal antibody transiently expressed by the one vector system as described in Example 1.

Example 9

Rabies Virus G Protein Competition ELISA with IgGs

To address whether the human monoclonal anti-rabies virus G protein IgGs bind to non-overlapping, non-competing epitopes, competition experiments are performed. Wells with coated rabies virus G protein are incubated with increasing concentrations (0 to 50 µg/ml) of unlabeled anti-rabies virus G protein IgG for one hour at room temperature. Then, 50 µl of a different biotinylated anti-rabies virus IgG (1 µg/ml) is added to each well, incubated for five minutes at room temperature, and immediately washed five times with 100 µl of PBS/0.05% Tween-20. Subsequently, wells are incubated for one hour at room temperature with 50 µl of a 1:2000 dilution of streptavidin-HRP (Becton Dickinson), washed and developed as described above. A decrease in signal with increasing concentration of unlabeled IgG indicates that the two antibodies are competing with each other and recognize the same epitope or overlapping epitopes.

Figure 6:
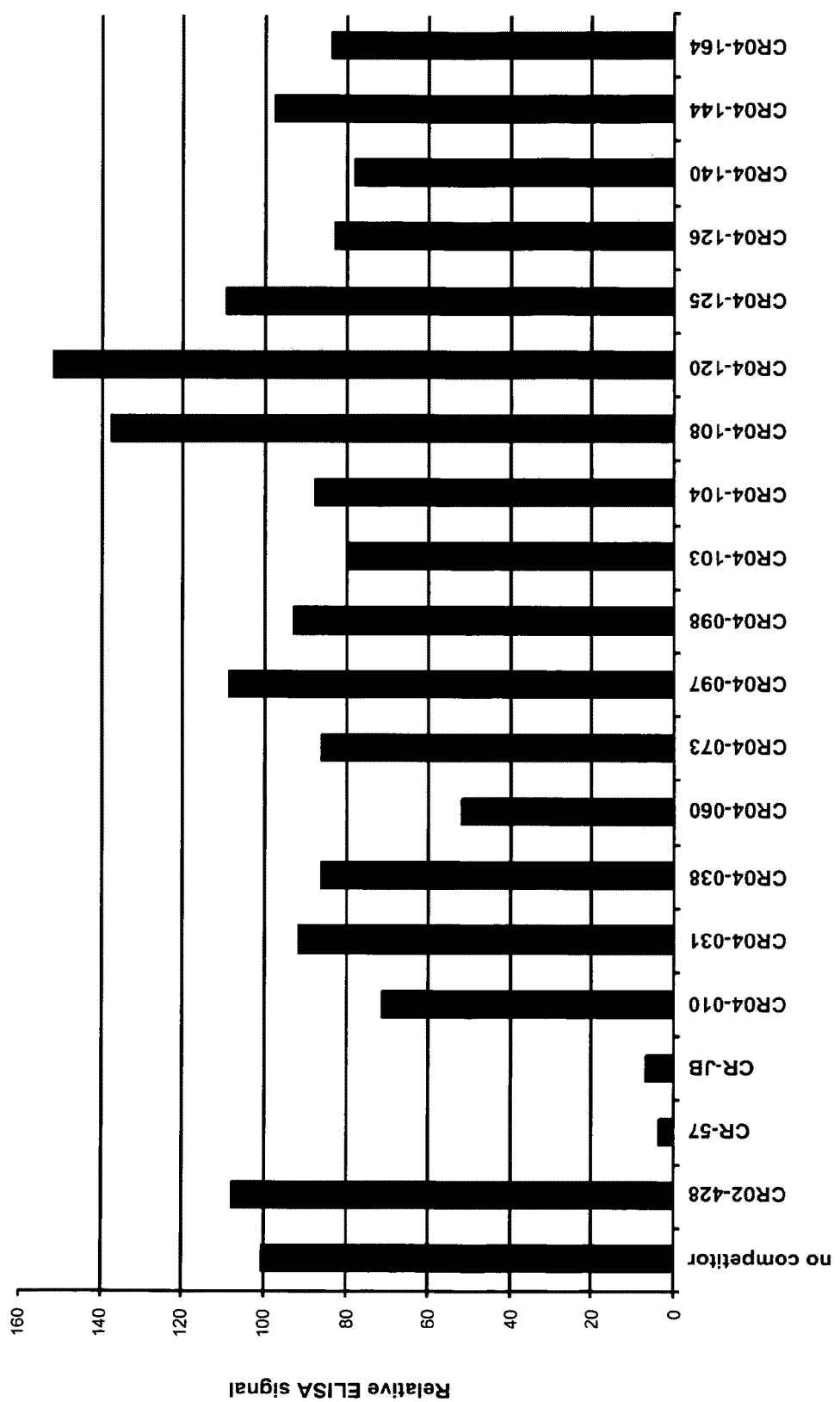
FIG. 6 shows a competition ELISA assay of anti-rabies virus G protein IgGs and the anti-rabies virus antibody called CR-57. G protein (ERA strain) was incubated with unlabeled IgGs (shown on the X-axis). Biotinylated CR57 (CR57bio) was added and allowed to bind to the G protein before visualization by means of streptavidin-HRP. ELISA signals are shown as percentage of CR57bio binding alone.

Alternatively, wells coated with rabies virus G protein (ERA strain) were incubated with 50 lag/ml of unlabeled anti-rabies virus G protein IgG for one hour at room temperature. Then, 50 µl of biotinylated CR57 (0.5 to 5 µg/ml; at subsaturated levels) was added to each well. The further steps were performed as described supra. The signals obtained were compared to the signal obtained with only biotinylated CR57 (see, FIG. 6; no competitor). From FIG. 6 can be deduced that the signal could not be reduced with the antibody called CR02-428 which served as a negative control. In contrast, competition with unlabeled CR57 (positive control) or CR-JB reduced the signal to background levels. From FIG. 6 can further be deduced that none of the anti-rabies virus G protein IgGs competed significantly with CR-57, which is in agreement with the scFv competition data as described in Example 7.

Figure 7:
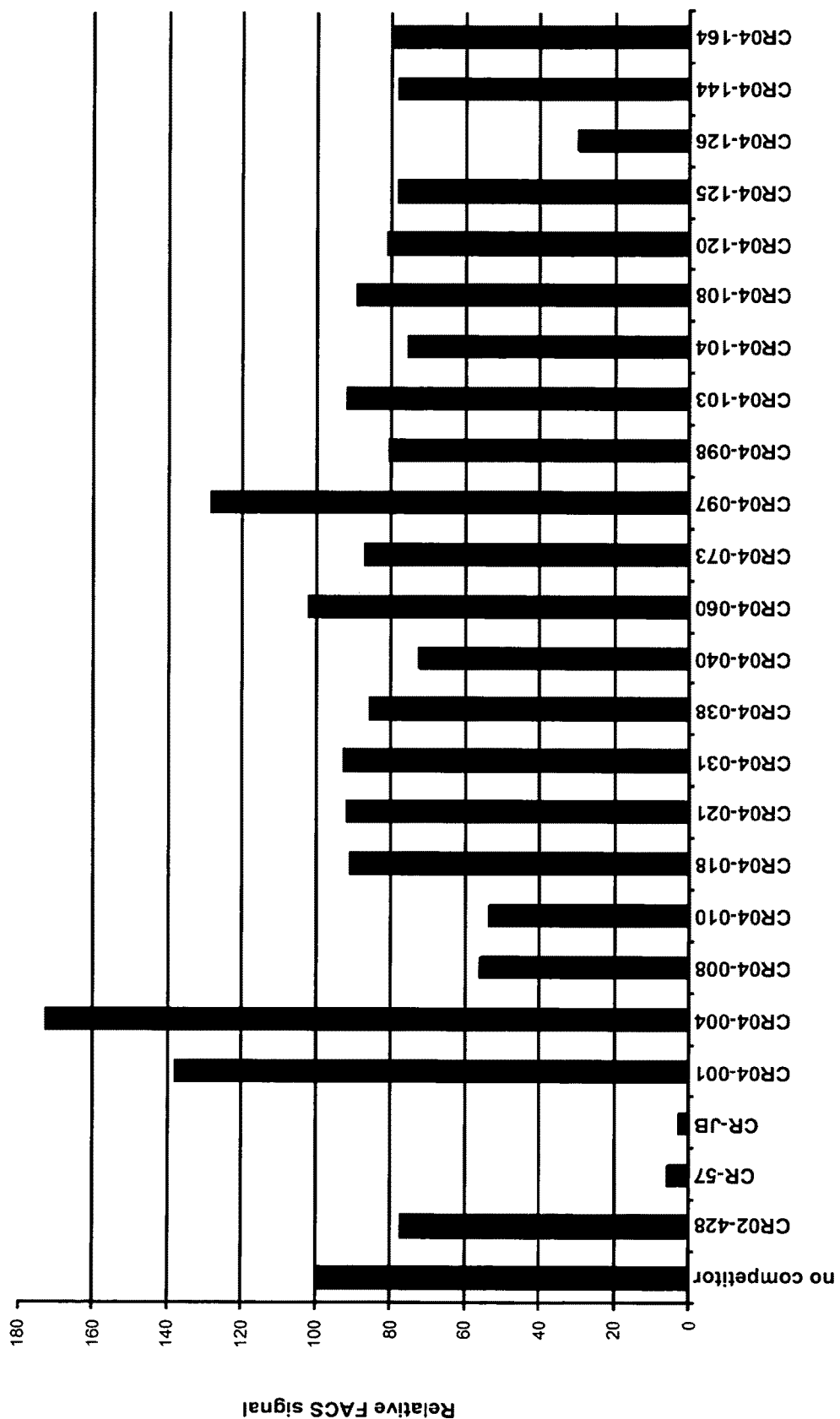
FIG. 7 shows a competition FACS assay of anti-rabies virus G protein IgGs and the anti-rabies virus antibody called CR-57. G protein (ERA strain) expressing PER.C6® cells were incubated with unlabeled IgGs (shown on the X-axis). Biotinylated CR57 (CR57bio) was added and allowed to bind to the G protein expressing cells before visualization by means of streptavidin-PE. FACS signals are shown as percentage of CR57bio binding alone.

In addition, competition experiments were performed on rabies virus G protein (ERA strain) transfected PER.C6® cells by means of flow cytometry. Transfected cells were incubated with 20 µA of unlabeled anti-rabies virus G protein IgG (50 µg/ml) for 20 minutes at 4° C. After washing of the cells with PBS containing 1% BSA, 20 µl of biotinylated CR57 (0.5 to 5 µg/ml; at subsaturated levels) were added to each well, incubated for five minutes at 4° C., and immediately washed twice with 100 µl of PBS containing 1% BSA. Subsequently, wells were incubated for 15 minutes at 4° C. with 20 µl of a 1:200 dilution of streptavidin-PE (Caltag), washed and developed as described above. The signal obtained with biotinylated CR57 could not be reduced significantly with the negative control antibody CR02-428 (see, FIG. 7). In contrast, competition with unlabeled CR57 (positive control) or CR-JB reduced the signal to background levels. None of the anti-rabies virus G protein IgGs competed significantly with CR-57, with the exception of CR04-126 which reduced the signal to approximately 30% (see, FIG. 7). The latter did not compete in ELISA (see, FIG. 6). This may be caused by the difference in the way the glycoprotein is presented to the antibody in FACS experiments compared to ELISA experiments. The binding of CR04-126 could be more dependent on the conformation of the glycoprotein, resulting in the competitive effect observed with CR04-126 in the FACS-based competition assay and not in the ELISA-based competition assay. Additionally, CR04-008 and CR04-010 reduced the signal to approximately 50% (see, FIG. 7) in the FACS-based competition assay indicating that they might compete with CR57. For CR04-010 this was however not confirmed by the scFv competition data or the ELISA-based competition assay. For the other IgGs, the FACS data were in agreement with the respective ELISA data of both the scFvs and the IgGs.

Example 10

Additive/Synergistic Effects of Anti-Rabies IgGs in In Vitro Neutralization of Rabies Virus (Modified RFFIT)

In order to determine whether the anti-rabies virus G protein IgGs have additive or synergistic effects in neutralization of rabies virus, different combinations of the IgGs are tested. First, the potency (in IU/mg) of each individual antibody is determined in a modified RFFIT (see, Example 1). Then, antibody combinations are prepared based on equal amounts of IU/mg and tested in the modified RFFIT. The potencies of each antibody combination can be determined and compared with the expected potencies. If the potency of the antibody combination is equal to the sum of the potencies of each individual antibody present in the combination, the antibodies have an additive effect. If the potency of the antibody combination is higher, the antibodies have a synergistic effect in neutralization of rabies virus.

Alternatively, additive or synergistic effects can be determined by the following experiment. First, the potency of the antibodies to be tested, e.g., CR-57 and CR04-098, is determined in a standard RFFIT (see, "Laboratory techniques in rabies," edited by F.-X. Meslin, M. M. Kaplan and H. Koprowski (1996), 4th edition, Chapter 15, World Health Organization, Geneva). Then, the antibodies are mixed in a 1:1 ratio based on IU/ml. This antibody mixture, along with the individual antibodies at the same concentration, are tested in six independent RFFIT experiments to determine the 50% neutralizing endpoint. Subsequently, the combination index (CI) is determined for the antibody mixture using the formula CI=(C1/Cx1)+(C2/Cx2)+(C1C2/Cx1Cx2) as described by Chou et al. (1984). C1 and C2 are the amount (in µg) of monoclonal antibody 1 and monoclonal antibody 2 that lead to 50% neutralization when used in combination and Cx1 and Cx2 are the amount (in µg) of monoclonal antibody 1 and monoclonal antibody 2 that lead to 50% neutralization when used alone. CI=1, indicates an additive effect, CI<1 indicates a synergistic effect and CI>1 indicates an antagonistic effect of the monoclonal antibodies.

Example 11

Identification of Epitopes Recognized by Recombinant Human Anti-Rabies Virus Antibodies by PEPSCAN-ELISA 15 mer linear and looped/cyclic peptides were synthesized from the extracellular domain of the G protein of the rabies virus strain ERA (see, SEQ ID NO:207 for the complete amino acid sequence of the glycoprotein G of the rabies virus strain ERA, the extracellular domain consists of amino acids 20 458; the protein id of the glycoprotein of rabies virus strain ERA in the EMBL database is J02293) and screened using credit card format mini PEPSCAN® cards (455 peptide formats/card) as described previously (Slootstra et al., 1996; WO 93/09872). All peptides were acetylated at the amino terminus. In all looped peptides, position 2 and position 14 were replaced by a cysteine (acetyl XCXXXXXXXXXXXCX minicard). If other cysteines besides the cysteines at position 2 and position 14 were present in a prepared peptide, the other cysteines were replaced by an alanine. The looped peptides were synthesized using standard Fmoc chemistry and deprotected using trifluoric acid with scavengers. Subsequently, the deprotected peptides were reacted on the cards with an 0.5 mM solution of 1,3 bis(bromomethyl)benzene in ammonium bicarbonate (20 mM, pH 7.9/acetonitrile (1:1 (v/v)). The cards were gently shaken in the solution for 30 to 60 minutes, while completely covered in the solution. Finally, the cards were washed extensively with excess of H2O and sonicated in disrupt buffer containing 1% SDS/0.1% beta mercaptoethanol in PBS (pH 7.2) at 70° C. for 30 minutes, followed by sonication in H$_2$O for another 45 minutes.

The human monoclonal antibodies were prepared as described above. Binding of these antibodies to each linear and looped peptide was tested in a PEPSCAN® system-based enzyme-linked immunosorbent assay (ELISA). The 455-well credit card format polypropylene cards, containing the covalently linked peptides, were incubated with the antibodies (10 µg/ml; diluted in blocking solution, which contained 5% horse-serum (v/v) and 5% ovalbumin (w/v)) (4° C., overnight). After washing, the peptides were incubated with anti-human antibody peroxidase (dilution 1/1000) (one hour, 25° C.), and subsequently, after washing, the peroxidase substrate 2,2'-azino-di-3-ethylbenzthiazoline sulfonate (ABTS) and 2 µl/ml 3% H$_2$O$_2$ were added. Controls (for linear and looped) were incubated with anti-human antibody peroxidase only.

After one hour, the color development was measured. The color development of the ELISA was quantified with a CCD-camera and an image processing system. The set-up consisted of a CCD-camera and a 55 mm lens (SONY® CCD Video Camera XC-77RR, NIKON® MICRO-NIKKOR® 55 mm f/2.8 lens), a camera adaptor (SONY® Camera adaptor DC-77RR) and the Image Processing Software package OPTIMAS™, version 6.5 (Media Cybernetics, Silver Spring, Md. 20910, U.S.A.). The OPTIMAS™ software ran on a Pentium II computer system.

The human anti-rabies virus G protein monoclonal antibodies were tested for binding to the 15-mer linear and looped/cyclic peptides synthesized as described supra. A peptide is considered to relevantly bind to an antibody when OD values are equal to or higher than two times the average OD-value of all peptides (per antibody). See Table 14 for results of the binding of the human monoclonal antibodies called CR57, CRJB and CR04-010 to the linear peptides of the extracellular domain of glycoprotein G of rabies virus strain ERA. Regions showing significant binding to the respective antibodies are highlighted in grey.

Antibody CR57 bound to the linear peptides having an amino acid sequence selected from the group consisting of SLKGACKLKLCGVLG (SEQ ID NO:314), LKGACK-LKLCGVLGL (SEQ ID NO:315), KGACKLKLCGVLGLR (SEQ ID NO:316), GACKLKLCGVLGLRL (SEQ ID NO:317), ACKLKLCGVLGLRLM (SEQ ID NO:318), CKLKLCGVLGLRLMD (SEQ ID NO:319), KLKLCGV-LGLRLMDG (SEQ ID NO:320), LKLCGVLGLRLMDGT (SEQ ID NO:321) and KLCGVLGLRLMDGTW (SEQ ID NO:322) (see, Table 14). The peptides having the amino acid sequences GACKLKLCGVLGLRL (SEQ ID NO:317) and ACKLKLCGVLGLRLM (SEQ ID NO:318) have an OD-value that is lower than twice the average value. Nevertheless these peptides were claimed, because they are in the near proximity of a region of antigenic peptides recognized by antibody CR57. Binding was most prominent to the peptide with the amino acid sequence KLCGVLGLRLMDGTW (SEQ ID NO:322).

Antibody CR04-010 bound to the linear peptides having an amino acid sequence selected from the group consisting of GFGKAYTIFNKTLME (SEQ ID NO:323), FGKAY-TIFNKTLMEA (SEQ ID NO:324), GKAYTIFNKTLMEAD (SEQ ID NO:325), KAYTIFNKTLMEADA (SEQ ID NO:326), AYTIFNKTLMEADAH (SEQ ID NO:327), YTIFNKTLMEADAHY (SEQ ID NO:328), TIFNK-TLMEADAHYK (SEQ ID NO:329), IFNK-TLMEADAHYKS (SEQ ID NO:330) and FNK-TLMEADAHYKSV (SEQ ID NO:331). The peptides having the amino acid sequences AYTIFNKTLMEADAH (SEQ ID NO:327) and YTIFNKTLMEADAHY (SEQ ID NO:328) have an OD-value that is lower than twice the average value. Nevertheless these peptides were claimed, because they are in the near proximity of a region of antigenic peptides recognized by antibody CR04-010. Binding was most prominent to the peptides with the amino acid sequences TIFNK-TLMEADAHYK (SEQ ID NO:329), IFNK-TLMEADAHYKS (SEQ ID NO:330) and FNK-TLMEADAHYKSV (SEQ ID NO:331).

CRJB and the antibodies called CR04-040, CR04-098 and CR04-103 (data not shown) did not recognize a region of linear antigenic peptides.

Any of the above peptides or parts thereof represents good candidates of a neutralizing epitope of rabies virus and could form the basis for a vaccine or for raising neutralizing antibodies to treat and/or prevent a rabies virus infection.

SLKGACKLKLCGVLGRLMDGTW (SEQ ID NO:332) and GFGKAYTIFNKTLMEADAHYKSV (SEQ ID NO:333) are particularly interesting regions of the glycoprotein based on their high reactivity in PEPSCAN®.

From the above PEPSCAN® data can further be deduced that the human monoclonal antibodies called CR57 and CR04-010 bind to different regions of the rabies virus G protein indicating that they recognize non-competing epitopes.

Example 12

Determination of Neutralizing Potency of Anti-Rabies G Protein IgGs Using an In Vitro Neutralization Assay (Modified RFFIT)

The neutralizing potency of each of the produced human monoclonal antibodies was determined in a modified RFFIT as described in Example 1. Sixteen IgGs neutralized rabies strain CVS-11 with a potency higher than 1000 IU/mg, whereas only two IgGs had a potency lower than 2 IU/mg (see, Table 15). Eight of the sixteen antibodies outperformed transiently produced CR-57 with regard to potency, suggesting a higher efficiency in post exposure prophylaxis of rabies virus than CR-57. The potency of transiently produced CR-57 was approximately 3800 IU/mg protein (see, Tables 1 and 15), whereas stably produced CR-57 displayed a potency of 5400 IU/mg protein (data not shown). Interestingly, the majority of the neutralizing human monoclonal antibodies identified contain a variable heavy 3-30 germline gene (see, Table 9).

Based on the affinity of the antibodies for rabies virus (data not shown) and 100% endpoint dilution of the antibodies in a modified RFFIT assay (data not shown), a panel of six unique IgGs, i.e., CR04-010, CR04-040, CR04-098, CR04-103, CR04-104, and CR04-144, were chosen for further development. Within this panel, antibody CR04-098 was particularly interesting as it displayed the highest potency, i.e., approximately 7300 IU/mg protein (see, Table 15). A similar potency was also found for stably produced CR04-098 (data not shown).

Example 13

In Vitro Neutralization of E57 Escape Viruses by Anti-Rabies Virus IgGs

To further characterize the novel human monoclonal anti-rabies antibodies the neutralizing activity of the IgGs against E57 escape viruses was tested in a modified RFFIT as described above. The majority of the anti-rabies virus IgGs had good neutralizing activity against all six E57 escape viruses (see, Table 16). In contrast, CR04-008, CR04-018 and CR04-126 did not neutralize 6/6, 2/6 and 3/6 E57 escape viruses, respectively. No neutralization means that no 50% endpoint was reached at an antibody dilution of 1:100. CR04-021, CR04-108, CR04-120, CR04-125, and CR04-164 showed a significant decrease in neutralizing activity against a number of escape viruses. This suggests that the epitope of these antibodies has been affected either directly or indirectly in the E57 escape virus glycoprotein. On the basis of the above several anti-rabies virus IgGs may be compatible with CR-57 in an anti-rabies cocktail for post exposure prophylaxis treatment. In particular, the panel of six unique IgGs as identified above, i.e., antibodies CR04-010, CR04-040, CR04-098, CR04-103, CR04-104, and CR04-144, displayed good neutralizing potency towards the E57 escape viruses suggesting that epitope(s) recognized by these antibodies was/were not affected by the amino acid mutations induced by CR-57. Antibody CR04-098 appeared most promising since it had a potency higher than 3000 IU/mg for each of the escape viruses.

Example 14

Epitope Recognition of Anti-Rabies Antibodies CR-57 and CR04-098

To confirm that the human monoclonal antibodies called CR-57 and CR04-098 recognize non-overlapping, non-competing epitopes, escape viruses of the human monoclonal antibody called CR04-098 were generated essentially as described for escape viruses of CR57 (see, Example 1). In short, the number of foci per well was scored by immunofluorescence and medium of wells containing preferably one focus were chosen for virus amplification. All E98 escape viruses were generated from one single focus with the exception of E98-2 (two foci) and E98-4 (four foci). A virus was defined as an escape variant if the neutralization index was <2.5 logs. The neutralization index was determined by subtracting the number of infectious virus particles/ml produced in BSR cell cultures infected with virus plus monoclonal antibody (~4 IU/ml) from the number of infectious virus particles/ml produced in BSR or MNA cell cultures infected with virus alone (log focus forming units/ml virus in absence of monoclonal antibody minus log ffu/ml virus in presence of monoclonal antibody). An index lower than 2.5 logs was considered as evidence of escape.

To further investigate that CR04-098 binds to a different non-overlapping, non-competing epitope compared to CR-57, CR-57 was tested against E98 escape viruses in a modified RFFIT assay as described above. As shown in Table 17, CR-57 had good neutralizing activity against all five E98 escape viruses. Additionally, antibodies CR04-010 and CR04-144 were tested for neutralizing activity against the E98 escape viruses. Both antibodies did not neutralize the E98 escape viruses (data not shown) suggesting that the epitope recognized by both antibodies is either directly or indirectly affected by the amino acid mutation induced by antibody CR04-098. The antibodies CR04-018 and CR04-126 were tested for neutralizing activity against only one of the E98 escape viruses, i.e., E98-4. CR04-018 was capable of neutralizing the escape virus, while CR04-126 only had a weak neutralizing potency towards the escape virus. This suggests that the epitope recognized by CR04-018 is not affected by the mutation induced by antibody CR04-098. Additionally, the antibodies CR04-010, CR04-038, CR04-040, CR04-073, CR04-103, CR04-104, CR04-108, CR04-120, CR04-125, CR04-164 did not neutralize E98-4 suggesting that they recognize the same epitope as CR04-098 (data not shown).

To identify possible mutations in the rabies glycoprotein of each of the E98 escape viruses, the nucleotide sequence of the glycoprotein open reading frame (ORF) was determined as described before for the E57 and EJB escape viruses. All E98 escape viruses showed the mutation N to D at amino acid position 336 of the rabies glycoprotein (see, FIG. 8). This region of the glycoprotein has been defined as antigenic site III comprising of amino acids 330-338 (numbering without signal peptide). In contrast, CR-57 recognized an epitope located at amino acids 226-231 (numbering without signal peptide), which overlaps with antigenic site I. In addition to the N336D mutation the E98 escape virus called E98-5 showed the mutation H to Q at amino acid position 354 (codon change CAT to CAG) of the rabies glycoprotein (data not shown).

Moreover, PEPSCAN® analysis of binding of CR57 to peptides harboring a mutated CR57 epitope (as observed in E57 escape viruses) did show that interaction of CR57 was abolished (data not shown). Strikingly, CR04-098 was still capable of binding to the mutated glycoprotein (comprising the N336D mutation) expressed on PER.C6® cells, as measured by flow cytometry (data not shown), even though viruses containing this mutation were no longer neutralized.

Furthermore, epitope mapping studies and affinity ranking studies were performed using surface plasmon resonance analysis using a BIACORE 3000™ analytical system. Purified rabies glycoprotein (ERA strain) was immobilized as a ligand on a research grade CM5 four flow channel (Fc) sensor chip (Biacore AB, Sweden) using amine coupling. Ranking was performed at 25° C. with HBS EP (Biacore AB, Sweden) as running buffer. 50 µl of each antibody was injected at a constant flow rate of 20 µl/minute. Then, running buffer was applied for 750 seconds followed by regeneration of the CM5 chip with 5 µl 2M NaOH, 5 µl 45 mM HCl and 5 µl 2 mM NaOH. The resonance signals expressed as resonance units (RU) were plotted as a function of time and the increase and decrease in RU as a measure of association and dissociation, respectively, were determined and used for ranking of the antibodies. The actual KD values for CR57 and CR04 098 as determined by surface plasmon resonance analysis were 2.4 nM and 4.5 nM, respectively. The epitope mapping studies further confirmed that CR57 and CR04 098 bind to different epitopes on rabies glycoprotein. Injection of CR57 resulted in a response of 58 RU (data not shown). After injection of CR04 098 an additional increase in response level (24 RU) was obtained, suggesting that binding sites for CR04 098 were not occupied (data not shown). Similar results were observed when the reverse order was applied showing that each antibody reached similar RU levels regardless of the order of injection (data not shown). These results further demonstrate that CR57 and CR04 098 can bind simultaneously and recognize different epitopes on the rabies virus glycoprotein.

Overall, the above data further confirm that the antibodies CR-57 and CR04-098 recognize distinct non-overlapping epitopes, i.e., epitopes in antigenic site I and III, respectively. The data are in good agreement with the ELISA/FACS competition data indicating that CR-57 and CR04-098 do not compete for binding to ERA G and the good neutralizing activity of antibody CR04-098 against all E57 escape viruses. On the basis of these results and the fact that in vitro exposure of rabies virus to the combination of CR57 and CR04-098 (selection in the presence of 4 IU/ml of either antibody) yielded no escape viruses (data not shown), it was concluded that the antibodies CR-57 and CR04-098 recognize non-overlapping, non-competing epitopes and can advantageously be used in an anti-rabies virus antibody cocktail for post-exposure prophylaxis treatment.

Example 15

Assessment of Conservation of the Epitope Recognized by CR57 and CR04-098

The minimal binding region of CR 57 (amino acids KLCGVL within SEQ ID NO:332, the region of the glycoprotein of rabies virus recognized by CR57 as determined by means of PEPSCAN® and alanine scanning technology) was aligned with nucleotide sequences of 229 genotype 1 rabies virus isolates to assess the conservation of the epitope (see, Table 18). The sample set contained human isolates, bat isolates and isolates from canines or from domestic animals most likely bitten by rabid canines. Frequency analysis of the amino acids at each position within the minimal binding region revealed that the critical residues constituting the epitope were highly conserved. The lysine at position one was conserved in 99.6% of the isolates, while in only 1/229 isolates a conservative K>R mutation was observed. Positions two and three (L and C) were completely conserved. It is believed that the central cysteine residue is structurally involved in the glycoprotein folding and is conserved among all lyssa viruses (see, Badrane and Tordo, 2001). The glycine at position four was conserved in 98.7% of the isolates, while in 3/229 isolates mutations towards charged amino acids (G>R in 1/229; G>E in 2/229) were observed. The fifth position was also conserved with the exception of one isolate where a conservative V>I mutation was observed. At the sixth position, which is not a critical residue as determined by an alanine replacement scan, significant heterogeneity was observed in the street isolates: L in 70.7%, P in 26.7% and S in 2.6% of the strains, respectively. Taken together, approximately 99 percent of the rabies viruses that can be encountered are predicted to be recognized by the CR 57 antibody.

Figure 9:
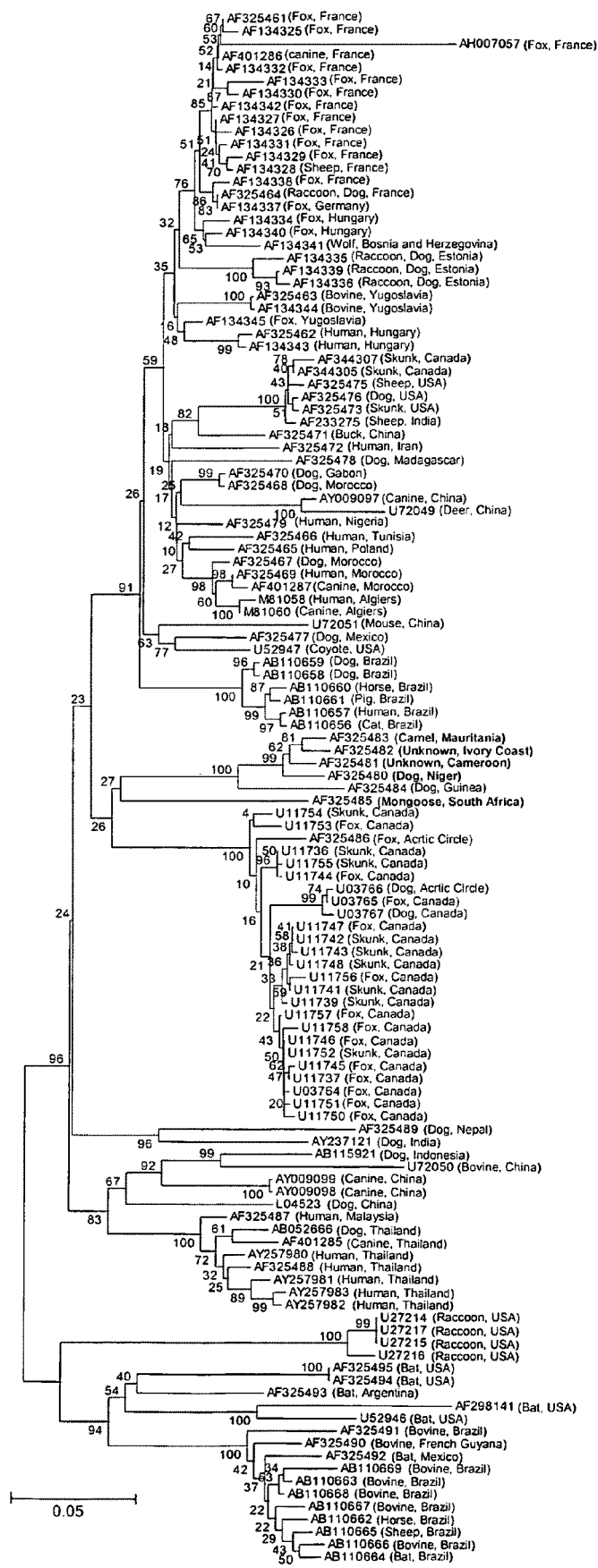
FIG. 9 shows a phylogenetic tree of 123 rabies street viruses (123 rabies virus G glycoprotein sequences, Neighbor joining, Kimura-2-parameter method, 500 bootstraps). Bold indicates viruses harboring the N>D mutation as observed in E98 escape viruses.

One hundred twenty-three of these 229 virus isolates were analyzed for the presence of mutations in both the CR-57 and CR04-098 epitope. None of these 123 street viruses did contain mutations in both epitopes. The N>D mutation as observed in the E98 escape viruses was present in only five virus isolates. These viruses were geographically distinct and isolated from animals in Africa (see, FIG. 9 for phylogenetic tree; the five virus isolates, i.e., AF325483, AF325482, AF325481, AF325480 and AF325485, are indicated in bold). The phylogenetic analysis of glycoprotein sequences revealed that rabies viruses with mutated CR57 epitopes are only distantly related to rabies viruses bearing a mutated CR04-098 epitope. Therefore, the likelihood of encountering a rabies virus resistant to neutralization by a cocktail of CR-57 and CR04-098 is virtually absent.

TABLE 1

Neutralizing potency of CR-57 and CR-JB against wild-type and escape viruses.

| Virus | Potency CR-57 (IU/mg) | Potency CR-JB (IU/mg) | Virus | Potency CR-57 (IU/mg) | Potency CR-JB (IU/mg) |
|---|---|---|---|---|---|
| CVS-11 | 3797 | 605 | CVS-11 | 3797 | 605 |
| E57A2 | 0 | <0.2 | EJB2B | 0.004 | 0.6 |
| E57A3 | 0 | 419 | EJB2C | <0.004 | 2 |
| E57B1 | 0 | 93 | EJB2D | <0.004 | 3 |
| E57B2 | 0 | <0.3 | EJB2E | <0.2 | <0.3 |
| E57B3 | 0 | 419 | EJB2F | <0.06 | 3 |
| E57C3 | 0 | 31 | EJB3F | <0.04 | 0.06 |

TABLE 2

Human lambda chain variable region primers (sense).

| Primer name | Primer nucleotide sequence | SEQ ID NO |
|---|---|---|
| HuVλ1A | 5'-CAGTCTGTGCTGACTCAGCCACC-3' | SEQ ID NO: 208 |
| HuVλ1B | 5'-CAGTCTGTGYTGACGCAGCCGCC-3' | SEQ ID NO: 209 |
| HuVλ1C | 5'-CAGTCTGTCGTGACGCAGCCGCC-3' | SEQ ID NO: 210 |
| HuVλ2 | 5'-CARTCTGCCCTGACTCAGCCT-3' | SEQ ID NO: 211 |
| HuVλ3A | 5'-TCCTATGWGCTGACTCAGCCACC-3' | SEQ ID NO: 212 |

TABLE 2-continued

Human lambda chain variable region primers (sense).

| Primer name | Primer nucleotide sequence | SEQ ID NO |
|---|---|---|
| HuVλ3B | 5'-TCTTCTGAGCTGACTCAGGACCC-3' | SEQ ID NO: 213 |
| HuVλ4 | 5'-CACGTTATACTGACTCAACCGCC-3' | SEQ ID NO: 214 |
| HuVλ5 | 5'-CAGGCTGTGCTGACTCAGCCGTC-3' | SEQ ID NO: 215 |
| HuVλ6 | 5'-AATTTTATGCTGACTCAGCCCCA-3' | SEQ ID NO: 216 |
| HuVλ7/8 | 5'-CAGRCTGTGGTGACYCAGGAGCC-3' | SEQ ID NO: 217 |
| HuVλ9 | 5'-CWGCCTGTGCTGACTCAGCCMCC-3' | SEQ ID NO: 218 |

TABLE 3

Human kappa chain variable region primers (sense).

| Primer name | Primer nucleotide sequence | SEQ ID NO |
|---|---|---|
| HuVκ1B | 5'-GACATCCAGWTGACCCAGTCTCC-3' | SEQ ID NO: 219 |
| HuVκ2 | 5'-GATGTTGTGATGACTCAGTCTCC-3' | SEQ ID NO: 220 |
| HuVκ3 | 5'-GAAATTGTGWTGACRCAGTCTCC-3' | SEQ ID NO: 221 |
| HuVκ4 | 5'-GATATTGTGATGACCCACACTCC-3' | SEQ ID NO: 222 |
| HuVκ5 | 5'-GAAACGACACTCACGCAGTCTCC-3' | SEQ ID NO: 223 |
| HuVκ6 | 5'-GAAATTGTGCTGACTCAGTCTCC-3' | SEQ ID NO: 224 |

TABLE 4

Human kappa chain variable region primers extended with SalI restriction sites (sense), human kappa chain J-region primers extended with NotI restriction sites (anti-sense), human lambda chain variable region primers extended with SalI restriction sites (sense) and human lambda chain J-region primers extended with NotI restriction sites (anti-sense).

| Primer name | Primer nucleotide sequence | SEQ ID NO |
|---|---|---|
| HuVκ1B-SalI | 5'-TGAGCACACAGGTCGACGGACATCCAGWTGACCCAGTCTCC-3' | SEQ ID NO: 225 |
| HuVκ2-SalI | 5'-TGAGCACACAGGTCGACGGATGTTGTGATGACTCAGTCTCC-3' | SEQ ID NO: 226 |
| HuVκ3B-SalI | 5'-TGAGCACACAGGTCGACGGAAATTGTGWTGACRCAGTCTCC-3' | SEQ ID NO: 227 |
| HuVκ4B-SalI | 5'-TGAGCACACAGGTCGACGGATATTGTGATGACCCACACTCC-3' | SEQ ID NO: 228 |
| HuVκ5-SalI | 5'-TGAGCACACAGGTCGACGGAAACGACACTCACGCAGTCTCC-3' | SEQ ID NO: 229 |
| HuVκ6-SalI | 5'-TGAGCACACAGGTCGACGGAAATTGTGCTGACTCAGTCTCC-3' | SEQ ID NO: 230 |
| HuJκ1-NotI | 5'-GAGTCATTCTCGACTTGCGGCCGCACGTTTGATTTCCACCTTGGTCCC-3' | SEQ ID NO: 231 |
| HuJκ2-NotI | 5'-GAGTCATTCTCGACTTGCGGCCGCACGTTTGATCTCCAGCTTGGTCCC-3' | SEQ ID NO: 232 |
| HuJκ3-NotI | 5'-GAGTCATTCTCGACTTGCGGCCGCACGTTTGATATCCACTTTGGTCCC-3' | SEQ ID NO: 233 |
| HuJκ4-NotI | 5'-GAGTCATTCTCGACTTGCGGCCGCACGTTTGATCTCCACCTTGGTCCC-3' | SEQ ID NO: 234 |
| HuJκ5-NotI | 5'-GAGTCATTCTCGACTTGCGGCCGCACGTTTAATCTCCAGTCGTGTCCC-3' | SEQ ID NO: 235 |
| HuVλ1A-SalI | 5'-TGAGCACACAGGTCGACGCAGTCTGTGCTGACTCAGCCACC-3' | SEQ ID NO: 236 |
| HuVλ1B-SalI | 5'-TGAGCACACAGGTCGACGCAGTCTGTGYTGACGCAGCCGCC-3' | SEQ ID NO: 237 |
| HuVλ1C-SalI | 5'-TGAGCACACAGGTCGACGCAGTCTGTCGTGACGCAGCCGCC-3' | SEQ ID NO: 238 |
| HuVλ2-SalI | 5'-TGAGCACACAGGTCGACGCARTCTGCCCTGACTCAGCCT-3' | SEQ ID NO: 239 |
| HuVλ3A-SalI | 5'-TGAGCACACAGGTCGACGTCCTATGWGCTGACTCAGCCACC-3' | SEQ ID NO: 240 |
| HuVλ3B-SalI | 5'-TGAGCACACAGGTCGACGTCTTCTGAGCTGACTCAGGACCC-3' | SEQ ID NO: 241 |
| HuVλ4-SalI | 5'-TGAGCACACAGGTCGACGCACGTTATACTGACTCAACCGCC-3' | SEQ ID NO: 242 |
| HuVλ5-SalI | 5'-TGAGCACACAGGTCGACGCAGGCTGTGCTGACTCAGCCGTC-3' | SEQ ID NO: 243 |
| HuVλ6-SalI | 5'-TGAGCACACAGGTCGACGAATTTTATGCTGACTCAGCCCCA-3' | SEQ ID NO: 244 |
| HuVλ7/8-SalI | 5'-TGAGCACACAGGTCGACGCAGRCTGTGGTGACYCAGGAGCC-3' | SEQ ID NO: 245 |

TABLE 4-continued

Human kappa chain variable region primers extended with SalI restriction sites (sense), human kappa chain J-region primers extended with NotI restriction sites (anti-sense), human lambda chain variable region primers extended with SalI restriction sites (sense) and human lambda chain J-region primers extended with NotI restriction sites (anti-sense).

| Primer name | Primer nucleotide sequence | SEQ ID NO |
|---|---|---|
| HuVλ9-SalI | 5'-TGAGCACACAGGTCGACGCWGCCTGTGCTGACTCAGCCMCC-3' | SEQ ID NO: 246 |
| HuJλ1-NotI | 5'-GAGTCATTCTCGACTTGCGGCCGCACCTAGGACGGTGACCTTGGTCCC-3' | SEQ ID NO: 247 |
| HuJλ2/3-NotI | 5'-GAGTCATTCTCGACTTGCGGCCGCACCTAGGACGGTCAGCTTGGTCCC-3' | SEQ ID NO: 248 |
| HuJλ4/5-NotI | 5'-GAGTCATTCTCGACTTGCGGCCGCACYTAAAACGGTGAGCTGGGTCCC-3' | SEQ ID NO: 249 |

TABLE 5

Distribution of the different light chain products over the ten fractions.

| Light chain products | Number of alleles | Fraction number | alleles/fraction |
|---|---|---|---|
| Vk1B/Jk1-5 | 19 | 1 and 2 | 9.5 |
| Vk2/Jk1-5 | 9 | 3 | 9 |
| Vk3B/Jk1-5 | 7 | 4 | 7 |
| Vk4B/Jk1-5 | 1 | 5 | 5 |
| Vk5/Jk1-5 | 1 | | |
| Vk6/Jk1-5 | 3 | | |
| Vλ1A/Jl1-3 | 5 | 6 | 5 |
| Vλ1B/Jl1-3 | | | |
| Vλ1C/Jl1-3 | | | |
| Vλ2/Jl1-3 | 5 | 7 | 5 |
| Vλ3A/Jl1-3 | 9 | 8 | 9 |
| Vλ3B/Jl1-3 | | | |
| Vλ4/Jl1-3 | 3 | 9 | 5 |
| Vλ5/Jl1-3 | 1 | | |
| Vλ6/Jl1-3 | 1 | | |
| Vλ7/8/Jl1-3 | 3 | 10 | 6 |
| Vλ9/Jl1-3 | 3 | | |

TABLE 6

Human IgG heavy chain variable region primers (sense).

| Primer name | Primer nucleotide sequence | SEQ ID NO |
|---|---|---|
| HuVH1B/7A | 5'-CAGRTGCAGCTGGTGCARTCTGG-3' | SEQ ID NO: 250 |
| HuVH1C | 5'-SAGGTCCAGCTGGTRCAGTCTGG-3' | SEQ ID NO: 251 |
| HuVH2B | 5'-SAGGTGCAGCTGGTGGAGTCTGG-3' | SEQ ID NO: 252 |
| HuVH3B | 5'-SAGGTGCAGCTGGTGGAGTCTGG-3' | SEQ ID NO: 253 |
| HuVH3C | 5'-GAGGTGCAGCTGGTGGAGWCYGG-3' | SEQ ID NO: 254 |
| HuVH4B | 5'-CAGGTGCAGCTACAGCAGTGGGG-3' | SEQ ID NO: 255 |
| HuVH4C | 5'-CAGSTGCAGCTGCAGGAGTCSGG-3' | SEQ ID NO: 256 |
| HuVH5B | 5'-GARGTGCAGCTGGTGCAGTCTGG-3' | SEQ ID NO: 257 |
| HuVH6A | 5'-CAGGTACAGCTGCAGCAGTCAGG-3' | SEQ ID NO: 258 |

TABLE 7

Human IgG heavy chain variable region primers extended with SfiI/NcoI restriction sites (sense) and human IgG heavy chain J-region primers extended with XhoI/BstEII restriction sites (anti-sense).

| Primer name | Primer nucleotide sequence | SEQ ID NO |
|---|---|---|
| HuVH1B/7A-SfiI | 5'-GTCCTCGCAACTGCGGCCCAGCCGGCCATGGCCCAGRTGCAGCTGGTGCARTCTGG-3' | SEQ ID NO: 259 |
| HuVH1C-SfiI | 5'-GTCCTCGCAACTGCGGCCCAGCCGGCCATGGCCSAGGTCCAGCTGGTRCAGTCTGG-3' | SEQ ID NO: 260 |
| HuVH2B-SfiI | 5'-GTCCTCGCAACTGCGGCCCAGCCGGCCATGGCCCAGRTCACCTTGAAGGAGTCTGG-3' | SEQ ID NO: 261 |
| HuVH3B-SfiI | 5'-GTCCTCGCAACTGCGGCCCAGCCGGCCATGGCCSAGGTGCAGCTGGTGGAGTCTGG-3' | SEQ ID NO: 262 |
| HuVH3C-SfiI | 5'-GTCCTCGCAACTGCGGCCCAGCCGGCCATGGCCGAGGTGCAGCTGGTGGAGWCYGG-3' | SEQ ID NO: 263 |
| HuVH4B-SfiI | 5'-GTCCTCGCAACTGCGGCCCAGCCGGCCATGGCCCAGGTGCAGCTACAGCAG TGGGG-3' | SEQ ID NO: 264 |
| HuVH4C-SfiI | 5'-GTCCTCGCAACTGCGGCCCAGCCGGCCATGGCCCAGSTGCAGCTGCAGGAGTCSGG-3' | SEQ ID NO: 265 |
| HuVH5B-SfiI | 5'-GTCCTCGCAACTGCGGCCCAGCCGGCCATGGCCGARGTGCAGCTGGTGCAGTCTGG-3' | SEQ ID NO: 266 |

TABLE 7-continued

Human IgG heavy chain variable region primers extended with SfiI/NcoI restriction sites (sense) and human IgG heavy chain J-region primers extended with XhoI/BstEII restriction sites (anti-sense).

| Primer name | Primer nucleotide sequence | SEQ ID NO |
| --- | --- | --- |
| HuVH6A-SfiI | 5'-GTCCTCGCAACTGCGGCCCAGCCGGCCATGGCCCAGGTACAGCTGCAGCAGTCAGG-3' | SEQ ID NO: 267 |
| HuJH1/2-XhoI | 5'-GAGTCATTCTCGACTCGAGACGGTGACCAGGGTGCC-3' | SEQ ID NO: 268 |
| HuJH3-XhoI | 5'-GAGTCATTCTCGACTCGAGACGGTGACCATTGTCCC-3' | SEQ ID NO: 269 |
| HuJH4/5-XhoI | 5'-GAGTCATTCTCGACTCGAGACGGTGACCAGGGTTCC-3' | SEQ ID NO: 270 |
| HuJH6-XhoI | 5'-GAGTCATTCTCGACTCGAGACGGTGACCGTGGTCCC-3' | SEQ ID NO: 271 |

TABLE 8

Binding of single-chain (scFv) phage antibodies to rabies virus G protein (ERA strain) and to FBS as measured by ELISA.

| Name phage antibody | Rabies virus G protein (OD 492 nm) | FBS (OD 492 nm) |
| --- | --- | --- |
| SC04-001 | 0.828 | 0.053 |
| SC04-004 | 0.550 | 0.054 |
| SC04-008 | 0.582 | 0.058 |
| SC04-010 | 0.915 | 0.043 |
| SC04-018 | 0.247 | 0.052 |
| SC04-021 | 0.278 | 0.052 |
| SC04-026 | 0.212 | 0.054 |
| SC04-031 | 0.721 | 0.065 |
| SC04-038 | 0.653 | 0.061 |
| SC04-040 | 0.740 | 0.053 |
| SC04-060 | 0.923 | 0.056 |
| SC04-073 | 0.657 | 0.054 |
| SC04-097 | 0.835 | 0.056 |
| SC04-098 | 0.798 | 0.060 |
| SC04-103 | 0.606 | 0.059 |
| SC04-104 | 0.566 | 0.063 |
| SC04-108 | 0.363 | 0.052 |
| SC04-120 | 0.571 | 0.052 |
| SC04-125 | 0.735 | 0.049 |
| SC04-126 | 0.232 | 0.051 |
| SC04-140 | 0.865 | 0.057 |
| SC04-144 | 0.775 | 0.054 |
| SC04-146 | 0.484 | 0.057 |
| SC04-164 | 0.547 | 0.057 |
| control (SO57) | 0.650 | 0.055 |
| control (02-007) | 0.063 | 0.052 |

TABLE 9

Data of the single-chain Fvs capable of binding rabies virus G protein.

| Name scFv (libr.) | SEQ ID NO of nucl. sequence | SEQ ID NO of amino acid sequence | HCDR3 (SEQ ID NO:) | $V_H$-locus | $V_L$-locus |
| --- | --- | --- | --- | --- | --- |
| sc04-001 (JK1994) | 157 | 158 | GLYGELFDY (SEQ ID NO: 1) | 3-20 (DP32) | Vl3 (31-V2-13) |
| sc04-004 (WT2000) | 159 | 160 | DYLYPTTDFDY (SEQ ID NO: 2) | 3-23 (DP47) | VkI (O12/O2-DPK9) |
| sc04-008 (RAB-03-G01) | 161 | 162 | MGFTGTYFDY (SEQ ID NO: 3) | 2-70 (DP28) | Vl3 (3h-V2-14) |
| sc04-010 (RAB-03-G01) | 163 | 164 | DGLDLTGTIQPFGY (SEQ ID NO: 4) | 3-30 (DP49) | VkI (L11-DPK3) |
| sc04-018 (RAB-03-G01) | 165 | 166 | VSVTTGAFNI (SEQ ID NO: 5) | 4-04 (DP70) | Vl1 (1c-V1-16) |
| sc04-021 (RAB-03-G01) | 167 | 168 | GSVLGDAFDI (SEQ ID NO: 6) | 3-30 (DP49) | VkI (L8) |
| sc04-026 (RAB-03-G01) | 169 | 170 | TSNWNYLDRFDP (SEQ ID NO: 7) | 5-51 (DP73) | VkII (A19/O3-DPK15) |
| sc04-031 (RAB-03-G01) | 171 | 172 | GSVLGDAFDI (SEQ ID NO: 8) | 3-30 (DP49) | VkI (L5-DPK5) |
| sc04-038 (RAB-03-G01) | 173 | 174 | GSVLGDAFDI (SEQ ID NO: 9) | 3-30 (DP49) | VkI (L5-DPK5) |
| sc04-040 (RAB-03-G01) | 175 | 176 | GSKVGDFDY (SEQ ID NO: 10) | 3-30 (DP49) | Vl3 (3h-V2-14) |
| sc04-060 (RAB-04-G01) | 177 | 178 | EKEKYSDRSGYSYYYYYMDV (SEQ ID NO: 11) | 4-59 (DP71) | VkI (O12/O2-DPK9) |
| sc04-073 (RAB-04-G01) | 179 | 180 | DGLDLTGTIQPFGY (SEQ ID NO: 12) | 3-30 (DP49) | VkI (L12) |

TABLE 9-continued

Data of the single-chain Fvs capable of binding rabies virus G protein.

| Name scFv (libr.) | SEQ ID NO of nucl. sequence | SEQ ID NO of amino acid sequence | HCDR3 (SEQ ID NO:) | $V_H$-locus | $V_L$-locus |
|---|---|---|---|---|---|
| sc04-097 (RAB-04-G01) | 181 | 182 | TASNLGRGGMDV (SEQ ID NO: 13) | 3-23 (DP47) | VkI (L8) |
| sc04-098 (RAB-04-G01) | 183 | 184 | VAVAGTHFDY (SEQ ID NO: 14) | 3-30 (DP49) | VkI (A30) |
| sc04-103 (RAB-04-G01) | 185 | 186 | VAVAGESFDS (SEQ ID NO: 15) | 3-30 (DP49) | VkI (L5-DPK5) |
| sc04-104 (RAB-04-G01) | 187 | 188 | IVVVTALDAFDI (SEQ ID NO: 16) | 3-30 (DP49) | VkI (L12) |
| sc04-108 (RAB-04-G01) | 189 | 190 | FMIVADDAFDI (SEQ ID N0: 17) | 3-30 (DP49) | VkI (L1) |
| sc04-120 (RAB-04-G01) | 191 | 192 | GGKTGEFDY (SEQ ID NO: 18) | 3-30 (DP49) | VkI (L8) |
| sc04-125 (RAB-04-G01) | 193 | 194 | IATAGTGFDY (SEQ ID NO: 19) | 3-30 (DP49) | VkI (L8) |
| sc04-126 (RAB-04-G01) | 195 | 196 | MGFTGTYFDY (SEQ ID NO: 20) | 2-70 (DP28) | Vl3 (3h-V2-14) |
| sc04-14 (RAB-04-G01) | 197 | 198 | VTNPGDAFDI (SEQ ID NO: 21) | 3-30 (DP49) | VkI (L4/18a) |
| sc04-144 (RAB-04-G01) | 199 | 200 | GGKTGEFDY (SEQ ID NO: 22) | 3-30 (DP49) | VkI (L8) |
| sc04-146 (RAB-04-G01) | 201 | 202 | GGKTGEFDY (SEQ ID NO: 23) | 3-30 (DP49) | VkIII (L2-DPK21) |
| sc04-164 (RAB-04-G01) | 203 | 204 | GSVLGDAFDI (SEQ ID NO: 24) | 3-30 (DP49) | VkI (L19-DPK6) |
| SO57 | 205 | 206 | ENLDNSGTYYYFSGWFDP (SEQ ID NO: 25) | 1-69 (DP10) | Vl2 (2e-V1-3) |
| SOJB | 312 | 313 | RQHISSFPWFDS (SEQ ID NO: 276) | 2-05 | Vl3 (3h-V2-14) |

TABLE 10

Data of assay for rabies virus-neutralizing activity of scFvs.

| Name scFv | 50% endpoint dilution | 50% endpoint dilution WHO standard (2 IU/ml) | Potency (IU/ml) |
|---|---|---|---|
| SC04-001 | 270 | 405 | 1.3 |
| SC04-004 | 3645 | 405 | 18 |
| SC04-008 | >10935 | 405 | >54 |
| SC04-010 | 810 | 405 | 4 |
| SC04-018 | 15 | 405 | 0.1 |
| SC04-021 | 270 | 405 | 1.3 |
| SC04-026 | 45 | 270 | 0.3 |
| SC04-031 | 90 | 270 | 0.7 |
| SC04-038 | 270 | 270 | 2 |
| SC04-040 | 45 | 270 | 0.3 |
| SC04-060 | 30 | 270 | 0.2 |
| SC04-073 | 405 | 270 | 3 |
| SC04-097 | 30 | 270 | 0.2 |
| SC04-098 | 1215 | 270 | 9 |
| SC04-103 | 45 | 270 | 0.3 |
| SC04-104 | 135 | 270 | 1 |
| SC04-108 | 135 | 270 | 1 |
| SC04-120 | 810 | 270 | 6 |
| SC04-125 | 405 | 270 | 3 |
| SC04-126 | 10 | 270 | 0.1 |
| SC04-140 | 135 | 270 | 1 |
| SC04-144 | 810 | 270 | 6 |
| SC04-146 | 405 | 270 | 3 |
| SC04-164 | 45 | 270 | 0.3 |

TABLE 11A

Data of assay for measuring neutralizing activity of scFvs for E57 escape viruses E57A2, E57A3 and E57B1.

| Name scFv | E57A2 | | | E57A3 | | | E57B1 | | |
|---|---|---|---|---|---|---|---|---|---|
| | 1* | 2* | 3* | 1* | 2* | 3* | 1* | 2* | 3* |
| SC04-001 | 10 | 90 | 0.2 | 10 | 90 | 0.2 | 30 | 45 | 1.3 |
| SC04-004 | 810 | 90 | 18.0 | 1215 | 90 | 27.0 | 810 | 45 | 36.0 |
| SC04-008 | 10 | 90 | 0.2 | 15 | 90 | 0.3 | 270 | 45 | 12.0 |
| SC04-010 | 270 | 90 | 6.0 | 270 | 90 | 6.0 | 270 | 45 | 12.0 |
| SC04-018 | 5 | 90 | 0.1 | 15 | 90 | 0.3 | 15 | 45 | 0.7 |
| SC04-021 | 10 | 90 | 0.2 | 30 | 90 | 0.7 | 10 | 90 | 0.2 |
| SC04-026 | <5 | 90 | 0.0 | <5 | 45 | 0.0 | <5 | 90 | 0.0 |
| SC04-031 | 10 | 90 | 0.2 | 30 | 90 | 0.7 | 10 | 90 | 0.2 |
| SC04-038 | 90 | 90 | 2.0 | 90 | 90 | 2.0 | 45 | 90 | 1.0 |
| SC04-040 | 15 | 90 | 0.3 | 5 | 90 | 0.1 | 5 | 90 | 0.1 |
| SC04-060 | 5 | 90 | 0.1 | 5 | 90 | 0.1 | <5 | 90 | 0.0 |
| SC04-073 | 135 | 90 | 3.0 | 90 | 30 | 6.0 | 30 | 90 | 2.0 |
| SC04-097 | <5 | 90 | 0.0 | <5 | 90 | 0.0 | <5 | 90 | 0.0 |
| SC04-098 | 810 | 90 | 18.0 | 270 | 30 | 18.0 | 270 | 30 | 18.0 |
| SC04-103 | <5 | 90 | 0.0 | 10 | 90 | 0.2 | 5 | 90 | 0.1 |
| SC04-104 | 90 | 90 | 2.0 | 30 | 30 | 2.0 | 30 | 30 | 2.0 |
| SC04-108 | 15 | 90 | 0.3 | <5 | 90 | 0.0 | <5 | 90 | 0.0 |
| SC04-120 | 45 | 90 | 1.0 | 30 | 30 | 2.0 | 10 | 30 | 0.7 |
| SC04-125 | 135 | 90 | 3.0 | 135 | 30 | 9.0 | 90 | 30 | 6.0 |
| SC04-126 | <5 | 90 | 0.0 | <5 | 45 | 0.0 | <5 | 90 | 0.0 |
| SC04-140 | 30 | 45 | 1.3 | 90 | 30 | 6.0 | 45 | 90 | 1.0 |
| SC04-144 | 270 | 45 | 12.0 | 270 | 30 | 18.0 | 135 | 90 | 3.0 |
| SC04-146 | 90 | 45 | 4.0 | 90 | 30 | 6.0 | 90 | 90 | 2.0 |
| SC04-164 | 15 | 45 | 0.7 | 30 | 30 | 2.0 | 15 | 90 | 0.3 |

1* is 50% endpoint dilution
2* is 50% endpoint dilution WHO standard (2 IU/ml)
3* is Potency (IU/ml)

TABLE 11B

Data of assay for measuring neutralizing activity of scFvs for E57 escape viruses E57B2, E57B3 and E57C3.

| Name scFv | E57B2 1* | E57B2 2* | E57B2 3* | E57B3 1* | E57B3 2* | E57B3 3* | E57C3 1* | E57C3 2* | E57C3 3* |
|---|---|---|---|---|---|---|---|---|---|
| SC04-001 | 30 | 45 | 1.3 | 90 | 270 | 0.7 | 5 | 90 | 0.1 |
| SC04-004 | 5 | 45 | 0.2 | 2430 | 270 | 18.0 | 270 | 90 | 6.0 |
| SC04-008 | 5 | 45 | 0.2 | 45 | 270 | 0.3 | 10 | 90 | 0.2 |
| SC04-010 | 45 | 45 | 2.0 | 405 | 270 | 3.0 | 270 | 90 | 6.0 |
| SC04-018 | 15 | 45 | 0.7 | 15 | 270 | 0.1 | 30 | 90 | 0.7 |
| SC04-021 | 10 | 90 | 0.2 | 30 | 270 | 0.2 | 10 | 90 | 0.2 |
| SC04-026 | <5 | 45 | 0.0 | <5 | 45 | 0.0 | <5 | 30 | 0.0 |
| SC04-031 | 10 | 90 | 0.2 | 30 | 270 | 0.2 | 30 | 90 | 0.7 |
| SC04-038 | 30 | 90 | 0.7 | 90 | 270 | 0.7 | 90 | 90 | 2.0 |
| SC04-040 | 5 | 90 | 0.1 | 15 | 135 | 0.2 | 10 | 90 | 0.2 |
| SC04-060 | <5 | 90 | 0.0 | 10 | 135 | 0.1 | 5 | 90 | 0.1 |
| SC04-073 | 30 | 90 | 0.7 | 90 | 270 | 0.7 | 90 | 90 | 2.0 |
| SC04-097 | <5 | 90 | 0.0 | <5 | 135 | 0.0 | <5 | 90 | 0.0 |
| SC04-098 | 90 | 90 | 2.0 | 810 | 270 | 6.0 | 270 | 90 | 6.0 |
| SC04-103 | <5 | 90 | 0.0 | 10 | 135 | 0.1 | 10 | 90 | 0.2 |
| SC04-104 | 45 | 90 | 1.0 | 45 | 270 | 0.3 | 90 | 90 | 2.0 |
| SC04-108 | 10 | 90 | 0.2 | <5 | 135 | 0.0 | 15 | 90 | 0.3 |
| SC04-120 | 15 | 90 | 0.3 | 45 | 270 | 0.3 | 30 | 90 | 0.7 |
| SC04-125 | 90 | 90 | 2.0 | 270 | 270 | 2.0 | 270 | 90 | 6.0 |
| SC04-126 | <5 | 45 | 0.0 | <5 | 45 | 0.0 | <5 | 30 | 0.0 |
| SC04-140 | 30 | 90 | 0.7 | 90 | 90 | 2.0 | 270 | 90 | 6.0 |
| SC04-144 | 90 | 90 | 2.0 | 270 | 90 | 6.0 | 405 | 90 | 9.0 |
| SC04-146 | 30 | 90 | 0.7 | 90 | 90 | 2.0 | 90 | 90 | 2.0 |
| SC04-164 | 15 | 90 | 0.3 | 15 | 90 | 0.3 | 30 | 90 | 0.7 |

1* is 50% endpoint dilution
2* is 50% endpoint dilution WHO standard (2 IU/ml)
3* is Potency (IU/ml)

TABLE 12

Oligonucleotides used for PCR amplification of $V_H$ genes.

| Name and nucleotide sequence | $V_H$ gene | SEQ ID NO: |
|---|---|---|
| 5H-B: acctgtcttgaattctccatggccgaggtgcagctggtggagtctg | SC04-001 | 280 |
| 5H-C: acctgtcttgaattctccatggcccaggtgcagctggtggagtctgg | SC04-021<br>SC04-031<br>SC04-125<br>SC04-164 | 281 |
| 5H-C-long: acctgtcttgaattctccatggcccaggtgcagctggtggagtctgggg | SC04-010<br>SC04-038<br>SC04-040<br>SC04-073<br>SC04-098<br>SC04-103<br>SC04-104<br>SC04-108<br>SC04-120<br>SC04-140<br>SC04-144<br>SC04-146 | 282 |
| 5H-F: acctgtcttgaattctccatggcccaggtgcagctgcaggagtccggccc | SC04-018<br>SC04-060 | 283 |
| 5H-H: acctgtcttgaattctccatggccgaggtgcagctggtgcagtctgg | SC04-026 | 284 |
| 5H-I: acctgtcttgaattctccatggccgaggtgcagctgctggagtctgg | SC04-004<br>SC04-097 | 285 |
| 5H-M: acctgtcttgaattctccatggcccaggtgaccttgaaggagtctgg | SC04-008<br>SC04-126 | 286 |
| sy3H-A: gcccttggtgctagcgctggagacggtcaccagggtgccctggcccc | SC04-001<br>SC04-004<br>SC04-008<br>SC04-010<br>SC04-026<br>SC04-040<br>SC04-073<br>SC04-098<br>SC04-120<br>SC04-125<br>SC04-126<br>SC04-144<br>SC04-146 | 287 |
| sy3H-C: gcccttggtgctagcgctggagacggtcacggtggtgccctggcccc | SC04-097 | 288 |
| sy3H-C-long: gcccttggtgctagcgctggagacggtcacggtggtgcccttgccccagacgtc | SC04-060 | 289 |

TABLE 12-continued

Oligonucleotides used for PCR amplification of $V_H$ genes.

| Name and nucleotide sequence | $V_H$ gene | SEQ ID NO: |
|---|---|---|
| sy3H-D: gcccttggtgctagcgctggacacggtcaccatggtgccctggcccc | SC04-018<br>SC04-021<br>SC04-031<br>SC04-038<br>SC04-104<br>SC04-108<br>SC04-140<br>SC04-164 | 290 |
| sy3H-E: gcccttggtgctagcgctggacacggtcaccagggtgccccggcccc | SC04-103 | 291 |

TABLE 13

Oligonucleotides used for PCR amplification of $V_L$ genes.

| Name and nucleotide sequence | $V_L$ gene | SEQ ID NO: |
|---|---|---|
| 3L-B: ttttccttagcggccgcgactcacctaggacggtcagcttggtc | SC04-001 | 292 |
| 5K-B: acctgtctcgagttttccatggctgacatccagatgacccagtc | SC04-031<br>SC04-060<br>SC04-073<br>SC04-098<br>SC04-103<br>SC04-104<br>SC04-108<br>SC04-164 | 293 |
| 5K-C: acctgtctcgagttttccatggctgacatccagatgacccagtctccatcctccc | SC04-004 | 294 |
| 5K-G: acctgtctcgagttttccatggctgacatcgtgatgacccagtctcc | SC04-026 | 295 |
| 5K-K: acctgtctcgagttttccatggctgccatccagatgacccagtctcc | SC04-010 | 296 |
| 5K-M: acctgtctcgagttttccatggctgacatccagctgacccagtc | SC04-021<br>SC04-097<br>SC04-120<br>SC04-125<br>SC04-144 | 297 |
| 5K-N: acctgtctcgagttttccatggctgacatccagatgactcagtc | SC04-038 | 298 |
| 5K-O: acctgtctcgagttttccatggctgccatccagctgacccagtc | SC04-140 | 299 |
| 5K-Q: acctgtctcgagttttccatggctgagatcgtgatgactcagtc | SC04-146 | 300 |
| 5L-E: acctgtctcgagttttccatggcttcctacgtgctgactcagccg | SC04-008 | 301 |
| 5L-F: acctgtctcgagttttccatggctcagtccgtgctgactcagcc | SC04-018 | 302 |
| 5L-G: acctgtctcgagttttccatggcttcctacgtgctgactcagcc | SC04-040<br>SC04-126 | 303 |
| sy3K-F: gctggggcggccacggtccgcttgatctccaccttggtccc | SC04-004<br>SC04-010<br>SC04-021<br>SC04-031<br>SC04-098<br>SC04-104<br>SC04-125<br>SC04-140<br>SC04-144<br>SC04-164 | 304 |
| sy3K-I: gctggggcggccacggtccgcttgatctccagccgtgtccc | SC04-038<br>SC04-097<br>SC04-103<br>SC04-108<br>SC04-146 | 305 |
| sy3K-J: gctggggcggccacggtccgcttgatctccagcttggtccc | SC04-026<br>SC04-060<br>SC04-073 | 306 |

TABLE 13-continued

Oligonucleotides used for PCR amplification of $V_L$ genes.

| Name and nucleotide sequence | $V_L$ gene | SEQ ID NO: |
|---|---|---|
| sy3K-K: gctgggggcggccacggtccgcttgatgtccaccttggtccc | SC04-120 | 307 |
| sy3L-A: ccagcacggtaagcttcagcacggtcaccttggtgccagttcc | SC04-018<br>SC04-126 | 308 |
| sy3L-C: ccagcacggtaagcttcagcacggtcagcttggtgcctccgcc | SC04-040 | 309 |
| sy3L-D: ccagcacggtaagcttcaacacggtcagctgggtccc | SC04-008 | 310 |
| sy5L-A: acctgtctcgagttttccatggcttcctccgagctgacccaggaccctgctg | SC04-001 | 311 |

TABLE 14

Binding of the human monoclonal antibodies CR57, CRJB and CR04-010 (10 µg/ml) to linear peptides of the extracellular domain of glycoprotein G of rabies virus strain ERA.

| Amino acid sequence of linear peptide | CR57 | CRJB | CR04-010 | SEQ ID NO: |
|---|---|---|---|---|
| KFPIYTILDKLGPWS | 71 | 97 | 1 | 338 |
| FPIYTILDKLGPWSP | 42 | 105 | 39 | 339 |
| PIYTILDKLGPWSPI | 36 | 89 | 87 | 340 |
| IYTILDKLGPWSPID | 44 | 97 | 104 | 341 |
| YTILDKLGPWSPIDI | 48 | 114 | 91 | 342 |
| TILDKLGPWSPIDIH | 76 | 96 | 88 | 343 |
| ILDKLGPWSPIDIHH | 54 | 104 | 69 | 344 |
| LDKLGPWSPIDIHHL | 55 | 99 | 107 | 345 |
| DKLGPWSPIDIHHLS | 62 | 103 | 93 | 346 |
| KLGPWSPIDIHHLSC | 72 | 105 | 45 | 347 |
| LGPWSPIDIHHLSCP | 69 | 112 | 19 | 348 |
| GPWSPIDIHHLSCPN | 68 | 114 | 33 | 349 |
| PWSPIDIHHLSCPNN | 62 | 104 | 47 | 350 |
| WSPIDIHHLSCPNNL | 80 | 106 | 11 | 351 |
| SPIDIHHLSCPNNLV | 74 | 85 | 1 | 352 |
| PIDIHHLSCPNNLVV | 46 | 93 | 90 | 353 |
| IDLHHLSCPNNLVVE | 69 | 102 | 55 | 354 |
| DIHHLSCPNNLVVED | 38 | 96 | 78 | 355 |
| IHHLSCPNNLVVEDE | 37 | 85 | 113 | 356 |
| HHLSCPNNLVVEDEG | 56 | 76 | 117 | 357 |
| HLSCPNNLVVEDEGC | 65 | 119 | 111 | 358 |
| LSCPNNLVVEDEGCT | 69 | 117 | 127 | 359 |
| SCPNNLVVEDEGCTN | 83 | 114 | 91 | 360 |
| CPNNLVVEDEGCTNL | 77 | 97 | 49 | 361 |
| PNNLVVEDEGCTNLS | 78 | 107 | 97 | 362 |
| NNLVVEDEGCTNLSG | 72 | 99 | 97 | 363 |
| NLVVEDEGCTNLSGF | 75 | 119 | 55 | 364 |

TABLE 14-continued

Binding of the human monoclonal antibodies CR57, CRJB and CR04-010 (10 µg/ml) to linear peptides of the extracellular domain of glycoprotein G of rabies virus strain ERA.

| Amino acid sequence of linear peptide | CR57 | CRJB | CR04-010 | SEQ ID NO: |
|---|---|---|---|---|
| LVVEDEGCTNLSGFS | 76 | 103 | 52 | 365 |
| VVEDEGCTNLSGFSY | 73 | 107 | 91 | 366 |
| VEDEGCTNLSGFSYM | 74 | 103 | 31 | 367 |
| EDEGCTNLSGFSYME | 54 | 90 | 7 | 368 |
| DEGCTNLSGFSYMEL | 1 | 23 | 1 | 369 |
| EGCTNLSGFSYMELK | 51 | 114 | 129 | 370 |
| GCTNLSGFSYMELKV | 55 | 114 | 118 | 371 |
| CTNLSGFSYMELKVG | 47 | 110 | 137 | 372 |
| TNLSGFSYMELKVGY | 43 | 106 | 161 | 373 |
| NLSGFSYMELKVGYI | 61 | 115 | 170 | 374 |
| LSGFSYMELKVGYIL | 71 | 132 | 169 | 375 |
| SGFSYMELKVGYILA | 79 | 132 | 161 | 376 |
| GFSYMELKVGYILAI | 65 | 111 | 141 | 377 |
| FSYMELKVGYILAIK | 89 | 112 | 192 | 378 |
| SYMELKVGYILAIKM | 65 | 123 | 152 | 379 |
| YMELKVGYILAIKMN | 78 | 114 | 150 | 380 |
| MELKVGYILAIKMNG | 76 | 141 | 107 | 381 |
| ELKVGYILAIKMNGF | 87 | 132 | 76 | 382 |
| LKVGYILAIKMNGFT | 78 | 112 | 118 | 383 |
| KVGYILAIKMNGFTC | 78 | 118 | 68 | 384 |
| VGYILAIKMNGFTCT | 77 | 93 | 1 | 385 |
| GYILAIKMNGFTCTG | 75 | 90 | 1 | 386 |
| YILAIKMNGFTCTGV | 47 | 107 | 107 | 387 |
| ILAIKMNGFTCTGVV | 79 | 103 | 104 | 388 |
| LAIKMNGFTCTGVVT | 68 | 130 | 159 | 389 |
| AIKMNGFTCTGVVTE | 47 | 103 | 152 | 390 |
| IKMNGFTCTGVVTEA | 68 | 108 | 138 | 391 |
| KMNGFTCTGVVTEAE | 76 | 104 | 133 | 392 |
| MNGFTCTGVVTEAEN | 69 | 99 | 148 | 393 |
| NGFTCTGVVTEAENY | 69 | 101 | 138 | 394 |
| GFTCTGVVTEAENYT | 71 | 86 | 129 | 395 |
| FTCTGVVTEAENYTN | 83 | 125 | 154 | 396 |
| TCTGVVTEAENYTNF | 92 | 112 | 129 | 397 |
| CTGVVTEAENYTNFV | 76 | 123 | 150 | 398 |
| TGVVTEAENYTNFVG | 85 | 110 | 154 | 399 |
| GVVTEAENYTNFVGY | 86 | 111 | 110 | 400 |
| VVTEAENYTNFVGYV | 87 | 106 | 114 | 401 |

TABLE 14-continued

Binding of the human monoclonal antibodies CR57, CRJB and CR04-010 (10 µg/ml) to linear peptides of the extracellular domain of glycoprotein G of rabies virus strain ERA.

| Amino acid sequence of linear peptide | CR57 | CRJB | CR04-010 | SEQ ID NO: |
|---|---|---|---|---|
| VTEAENYTNFVGYVT | 79 | 90 | 73 | 402 |
| TEAENYTNFVGYVTT | 68 | 84 | 8 | 403 |
| EAENYTNFVGYVTTT | 69 | 117 | 142 | 404 |
| AENYINFVGYVTTTF | 66 | 106 | 110 | 405 |
| ENYTNFVGYVTTTFK | 44 | 112 | 183 | 406 |
| NYTNFVGYVTTTFKR | 49 | 114 | 174 | 407 |
| YTNFVGYVTTTFKRK | 51 | 104 | 138 | 408 |
| TNFVGYVTTTFKRKH | 71 | 125 | 165 | 409 |
| NFVGYVTTTFKRKHF | 65 | 107 | 154 | 410 |
| FVGYVTTTFKRKHFR | 70 | 111 | 152 | 411 |
| VGYVTTTFKRKHFRP | 75 | 113 | 155 | 412 |
| GYVTTTFKRKHFRPT | 70 | 123 | 160 | 413 |
| YVTTTFKRKHFRPTP | 85 | 106 | 160 | 414 |
| VTTTFKRKHFRPTPD | 79 | 105 | 119 | 415 |
| TTTFKRKHFRPTPDA | 80 | 108 | 137 | 416 |
| TTFKRKHFRPTPDAC | 74 | 99 | 110 | 417 |
| TFKRKHFRPTPDACR | 96 | 111 | 108 | 418 |
| FKRKHFRPTPDACRA | 64 | 92 | 62 | 419 |
| KRKHFRPTPDACRAA | 65 | 93 | 1 | 420 |
| RKHFRPTPDACRAAY | 64 | 107 | 99 | 421 |
| KHFRPTPDACRAAYN | 73 | 112 | 124 | 422 |
| HFRPTPDACRAAYNW | 46 | 113 | 118 | 423 |
| FRPTPDACRAAYNWK | 43 | 112 | 148 | 424 |
| RPTPDACRAAYNWKM | 77 | 101 | 129 | 425 |
| PTPDACRAAYNWKMA | 99 | 125 | 143 | 426 |
| TPDACRAAYNWKMAG | 92 | 132 | 160 | 427 |
| PDACRAAYNWKMAGD | 61 | 124 | 147 | 428 |
| DACRAAYNWKMAGDP | 84 | 113 | 136 | 429 |
| ACRAAYNWKMAGDPR | 82 | 116 | 138 | 430 |
| CRAAYNWKMAGDPRY | 87 | 118 | 137 | 431 |
| RAAYNWKMAGDPRYE | 90 | 130 | 120 | 432 |
| AAYNWKMAGDPRYEE | 68 | 106 | 120 | 433 |
| AYNWKMAGDPRYEES | 96 | 94 | 77 | 434 |
| YNWKMAGDPRYEESL | 83 | 118 | 116 | 435 |
| NWKMAGDPRYEESLH | 58 | 101 | 69 | 436 |
| WKMAGDPRYEESLHN | 69 | 101 | 1 | 437 |
| KMAGDPRYEESLHNP | 62 | 102 | 84 | 438 |

TABLE 14-continued

Binding of the human monoclonal antibodies CR57, CRJB and CR04-010 (10 µg/ml) to linear peptides of the extracellular domain of glycoprotein G of rabies virus strain ERA.

| Amino acid sequence of linear peptide | CR57 | CRJB | CR04-010 | SEQ ID NO: |
|---|---|---|---|---|
| MAGDPRYEESLHNPY | 64 | 116 | 112 | 439 |
| AGDPRYEESLHNPYP | 40 | 101 | 125 | 440 |
| GDPRYEESLHNPYPD | 36 | 98 | 123 | 441 |
| DPRYEESLHNPYPDY | 57 | 110 | 118 | 442 |
| PRYEESLHNPYPDYR | 73 | 115 | 129 | 443 |
| RYEESLHNPYPDYRW | 69 | 112 | 125 | 444 |
| YEESLHNPYPDYRWL | 58 | 106 | 120 | 445 |
| EESLHNPYPDYRWLR | 76 | 123 | 141 | 446 |
| ESLHNPYPDYRWLRT | 92 | 132 | 125 | 447 |
| SLHNPYPDYRWLRTV | 78 | 111 | 137 | 448 |
| LHNPYPDYRWLRTVK | 79 | 106 | 142 | 449 |
| HNPYPDYRWLRTVKT | 86 | 108 | 146 | 450 |
| NPYPDYRWLRTVKTT | 85 | 102 | 151 | 451 |
| PYPDYRWLRTVKTTK | 65 | 93 | 103 | 452 |
| YPDYRWLRTVKTTKE | 72 | 97 | 97 | 453 |
| PDYRWLRTVKTTKES | 76 | 85 | 27 | 454 |
| DYRWLRTVKTTKESL | 54 | 111 | 105 | 455 |
| YRWLRTVKTTKESLV | 46 | 117 | 125 | 456 |
| RWLRTVKTTKESLVI | 40 | 110 | 120 | 457 |
| WLRTVKTTKESLVII | 41 | 104 | 125 | 458 |
| LRTVKTTKESLVIIS | 65 | 104 | 161 | 459 |
| RTVKTTKESLVIISP | 82 | 120 | 150 | 460 |
| TVKTTKESLVIISPS | 76 | 116 | 150 | 461 |
| VKTTKESLVIISPSV | 71 | 120 | 154 | 462 |
| KTTKESLVIISPSVA | 101 | 112 | 147 | 463 |
| TTKESLVIISPSVAD | 78 | 121 | 141 | 464 |
| TKESLVIISPSVADL | 86 | 112 | 132 | 465 |
| KESLVIISPSVADLD | 86 | 117 | 111 | 466 |
| ESLVIISPSVADLDP | 88 | 125 | 143 | 467 |
| SLVIISPSVADLDPY | 68 | 105 | 125 | 468 |
| LVIISPSVADLDPYD | 85 | 107 | 93 | 469 |
| VIISPSVADLDPYDR | 59 | 98 | 50 | 470 |
| IISPSVADLDPYDRS | 83 | 125 | 14 | 471 |
| ISPSVADLDPYDRSL | 50 | 119 | 91 | 472 |
| SPSVADLDPYDRSLH | 59 | 114 | 118 | 473 |
| PSVADLDPYDRSLHS | 44 | 114 | 118 | 474 |
| SVADLDPYDRSLHSR | 49 | 106 | 129 | 475 |

TABLE 14-continued

Binding of the human monoclonal antibodies CR57, CRJB and CR04-010 (10 μg/ml) to linear peptides of the extracellular domain of glycoprotein G of rabies virus strain ERA.

| Amino acid sequence of linear peptide | CR57 | CRJB | CR04-010 | SEQ ID NO: |
|---|---|---|---|---|
| VADLDPYDRSLHSRV | 71 | 113 | 141 | 476 |
| ADLDPYDRSLHSRVF | 70 | 121 | 141 | 477 |
| DLDPYDRSLHSRVFP | 111 | 152 | 127 | 478 |
| LDPYDRSLHSRVFPS | 99 | 142 | 106 | 479 |
| DPYDRSLHSRVFPSG | 90 | 120 | 134 | 480 |
| *PYDRSLHSRVFPSGK* | 86 | 120 | 130 | 481 |
| *YDRSLHSRVFPSGKC* | 364 | 818 | 127 | 482 |
| DRSLHSRVFPSGKCS | 98 | 142 | 141 | 483 |
| *RSLHSRVFPSGKCSG* | 87 | 141 | 156 | 484 |
| SLHSRVFPSGKCSGV | 69 | 111 | 141 | 485 |
| LHSRVFPSGKCSGVA | 78 | 114 | 129 | 486 |
| HSRVFPSGKCSGVAV | 97 | 118 | 111 | 487 |
| SRVFPSGKCSGVAVS | 100 | 125 | 24 | 488 |
| RVFPSGKCSGVAVSS | 69 | 110 | 106 | 489 |
| VFPSGKCSGVAVSST | 74 | 114 | 142 | 490 |
| FPSGKCSGVAVSSTY | 64 | 134 | 146 | 491 |
| PSGKCSGVAVSSTYC | 56 | 112 | 132 | 492 |
| SGKCSGVAVSSTYCS | 64 | 121 | 120 | 493 |
| GKCSGVAVSSTYCST | 92 | 143 | 145 | 494 |
| KCSGVAVSSTYCSTN | 88 | 130 | 130 | 495 |
| CSGVAVSSTYCSTNH | 110 | 165 | 143 | 496 |
| SGVAVSSTYCSTNHD | 79 | 110 | 115 | 497 |
| GVAVSSTYCSTNHDY | 79 | 114 | 108 | 498 |
| VAVSSTYCSTNHDYT | 85 | 114 | 118 | 499 |
| AVSSTYCSTNHDYTI | 71 | 105 | 102 | 500 |
| VSSTYCSTNHDYTIW | 78 | 107 | 121 | 501 |
| SSTYCSTNHDYTIWM | 76 | 107 | 121 | 502 |
| STYCSTNHDYTIWMP | 86 | 99 | 119 | 503 |
| TYCSTNHDYTIWMPE | 96 | 107 | 74 | 504 |
| YCSTNHDYTIWMPEN | 47 | 92 | 29 | 505 |
| CSTNHDYTIWMPENP | 52 | 106 | 86 | 506 |
| STNHDYTIWMPENPR | 60 | 112 | 107 | 507 |
| TNHDYTIWMPENPRL | 69 | 129 | 119 | 508 |
| NHDYTIWMPENPRLG | 71 | 119 | 130 | 509 |
| HDYTIWMPENPRLGM | 82 | 125 | 123 | 510 |
| DYTIWMPENPRLGMS | 93 | 127 | 123 | 511 |
| YTIWMPENPRLGMSC | 97 | 132 | 143 | 512 |

TABLE 14-continued

Binding of the human monoclonal antibodies CR57, CRJB and CR04-010 (10 µg/ml) to linear peptides of the extracellular domain of glycoprotein G of rabies virus strain ERA.

| Amino acid sequence of linear peptide | CR57 | CRJB | CR04-010 | SEQ ID NO: |
|---|---|---|---|---|
| TIWMPENPRLGMSCD | 69 | 106 | 134 | 513 |
| IWMPENPRLGMSCDI | 98 | 110 | 101 | 514 |
| WMPENPRLGMSCDIF | 88 | 113 | 120 | 515 |
| MPENPRLGMSCDIFT | 105 | 121 | 143 | 516 |
| PENPRLGMSCDIFTN | 83 | 111 | 104 | 517 |
| ENPRLGMSCDIFTNS | 71 | 118 | 111 | 518 |
| NPRLGMSCDIFTNSR | 90 | 113 | 138 | 519 |
| PRLGMSCDIFTNSRG | 72 | 112 | 105 | 520 |
| RLGMSCDIFTNSRGK | 88 | 106 | 113 | 521 |
| LGMSCDIFTNSRGKR | 76 | 110 | 114 | 522 |
| GMSCDIFTNSRGKRA | 54 | 120 | 101 | 523 |
| MSCDIFTNSRGKRAS | 46 | 110 | 106 | 524 |
| SCDIFTNSRGKRASK | 44 | 111 | 98 | 525 |
| CDIFTNSRGKRASKG | 42 | 104 | 117 | 526 |
| DIFTNSRGKRASKGS | 70 | 107 | 111 | 527 |
| IFTNSRGKRASKGSE | 77 | 125 | 87 | 528 |
| FTNSRGKRASKGSET | 83 | 111 | 119 | 529 |
| TNSRGKRASKGSETC | 68 | 108 | 110 | 530 |
| NSRGKRASKGSETCG | 92 | 100 | 119 | 531 |
| SRGKRASKGSETCGF | 64 | 93 | 90 | 532 |
| RGKRASKGSETCGFV | 75 | 104 | 115 | 533 |
| GKRASKGSETCGFVD | 92 | 124 | 118 | 534 |
| KRASKGSETCGFVDE | 92 | 106 | 129 | 535 |
| RASKGSETCGFVDER | 86 | 110 | 134 | 536 |
| ASKGSETCGFVDERG | 97 | 108 | 103 | 537 |
| SKGSETCGFVDERGL | 92 | 102 | 76 | 538 |
| KGSETCGFVDERGLY | 90 | 97 | 44 | 539 |
| GSETCGFVDERGLYK | 57 | 115 | 92 | 540 |
| SETCGFVDERGLYKS | 33 | 116 | 86 | 541 |
| ETCGFVDERGLYKSL | 64 | 120 | 138 | 542 |
| TCGFVDERGLYKSLK | 47 | 120 | 125 | 543 |
| CGFVDERGLYKSLKG | 72 | 115 | 120 | 544 |
| GFVDERGLYKSLKGA | 84 | 120 | 129 | 545 |
| FVDERGLYKSLKGAC | 86 | 121 | 124 | 546 |
| VDERGLYKSLKGACK | 50 | 108 | 110 | 547 |
| DERGLYKSLKGACKL | 90 | 119 | 54 | 548 |
| ERGLYKSLKGACKLK | 90 | 118 | 106 | 549 |

TABLE 14-continued

Binding of the human monoclonal antibodies CR57, CRJB and CR04-010 (10 µg/ml) to linear peptides of the extracellular domain of glycoprotein G of rabies virus strain ERA.

| Amino acid sequence of linear peptide | CR57 | CRJB | CR04-010 | SEQ ID NO: |
|---|---|---|---|---|
| RGLYKSLKGACKLKL | 90 | 121 | 121 | 550 |
| GLYKSLKGACKLKLC | 94 | 129 | 92 | 551 |
| LYKSLKGACKLKLCG | 93 | 136 | 141 | 552 |
| YKSLKGACKLKLCGV | 80 | 112 | 110 | 553 |
| KSLKGACKLKLCGVL | 129 | 113 | 110 | 554 |
| SLKGACKLKLCGVLG | ▒▒▒ | 111 | 124 | 314 |
| LKGACKLKLCGVLGL | ▒▒▒ | 90 | 23 | 315 |
| KGACKLKLCGVLGLR | ▒▒▒ | 111 | 100 | 316 |
| GACKLKLCGVLGLRL | ▒▒▒ | 134 | 129 | 317 |
| ACKLKLCGVLGLRLM | ▒▒▒ | 117 | 142 | 318 |
| CKLKLCGVLGLRLMD | ▒▒▒ | 111 | 147 | 319 |
| KLKLCGVLGLRLMDG | ▒▒▒ | 120 | 114 | 320 |
| LKLCGVLGLRLMDGT | ▒▒▒ | 145 | 148 | 321 |
| KLCGVLGLRLMDGTW | ▒▒▒ | 132 | 86 | 322 |
| LCGVLGLRLMDGTWV | 83 | 138 | 129 | 555 |
| CGVLGLRLMDGTWVA | 99 | 117 | 104 | 556 |
| GVLGLRLMDGTWVAM | 89 | 148 | 117 | 557 |
| VLGLRLMDGTWVAMQ | 90 | 141 | 127 | 558 |
| LGLRLMDGTWVAMQT | 102 | 115 | 97 | 559 |
| GLRLMDGTWVAMQTS | 104 | 138 | 120 | 560 |
| LRLMDGTWVAMQTSN | 103 | 114 | 118 | 561 |
| RLMDGTWVAMQTSNE | 100 | 113 | 130 | 562 |
| LMDGTWVAMQTSNET | 96 | 106 | 106 | 563 |
| MDGTWVAMQTSNETK | 97 | 97 | 110 | 564 |
| DGTWVAMQTSNETKW | 69 | 114 | 92 | 565 |
| GTWVAMQTSNETKWC | 58 | 113 | 82 | 566 |
| TWVAMQTSNETKWCP | 78 | 118 | 107 | 567 |
| WVAMQTSNETKWCPP | 50 | 114 | 116 | 568 |
| VAMQTSNETKWCPPD | 86 | 104 | 151 | 569 |
| AMQTSNETKWCPPDQ | 104 | 114 | 128 | 570 |
| MQTSNETKWCPPDQL | 104 | 132 | 125 | 571 |
| QTSNETKWCPPDQLV | 92 | 120 | 155 | 572 |
| TSNETKWCPPDQLVN | 97 | 111 | 90 | 573 |
| SNETKWCPPDQLVNL | 99 | 129 | 110 | 574 |
| NETKWCPPDQLVNLH | 90 | 128 | 107 | 575 |
| ETKWCPPDQLVNLHD | 105 | 120 | 118 | 576 |

TABLE 14-continued

Binding of the human monoclonal antibodies CR57, CRJB and CR04-010 (10 μg/ml) to linear peptides of the extracellular domain of glycoprotein G of rabies virus strain ERA.

| Amino acid sequence of linear peptide | CR57 | CRJB | CR04-010 | SEQ ID NO: |
|---|---|---|---|---|
| TKWCPPDQLVNLHDF | 85 | 125 | 125 | 577 |
| KWCPPDQLVNLHDFR | 89 | 113 | 121 | 578 |
| WCPPDQLVNLHDFRS | 101 | 119 | 99 | 579 |
| CPPDQLVNLHDFRSD | 93 | 137 | 127 | 580 |
| PPDQLVNLHDFRSDE | 107 | 120 | 56 | 581 |
| PDQLVNLHDFRSDEI | 35 | 106 | 63 | 582 |
| DQLVNLHDFRSDEIE | 54 | 117 | 97 | 583 |
| QLVNLHDFRSDEIEH | 60 | 113 | 106 | 584 |
| LVNLHDFRSDEIEHL | 47 | 104 | 100 | 585 |
| VNLHDFRSDEIEHLV | 83 | 129 | 98 | 586 |
| NLHDFRSDEIEHLVV | 83 | 113 | 110 | 587 |
| LHDFRSDEIEHLVVE | 93 | 115 | 121 | 588 |
| HDFRSDEIEHLVVEE | 69 | 107 | 150 | 589 |
| DFRSDEIEHLVVEEL | 99 | 103 | 110 | 590 |
| FRSDEIEHLVVEELV | 86 | 114 | 116 | 591 |
| RSDEIEHLVVEELVR | 100 | 138 | 104 | 592 |
| SDEIEHLVVEELVRK | 101 | 117 | 118 | 593 |
| DEIEHLVVEELVRKR | 94 | 123 | 143 | 594 |
| EIEHLVVEELVRKRE | 82 | 113 | 121 | 595 |
| IEHLVVEELVRKREE | 90 | 129 | 118 | 596 |
| EHLVVEELVRKREEC | 82 | 114 | 106 | 597 |
| HLVVEELVRKREECL | 82 | 123 | 46 | 598 |
| LVVEELVRKREECLD | 64 | 100 | 79 | 599 |
| VVEELVRKREECLDA | 62 | 108 | 97 | 600 |
| VEELVRKREECLDAL | 58 | 111 | 101 | 601 |
| EELVRKREECLDALE | 69 | 112 | 123 | 602 |
| ELVRKREECLDALES | 82 | 113 | 117 | 603 |
| LVRKREECLDALESI | 86 | 130 | 124 | 604 |
| VRKREECLDALESIM | 58 | 181 | 151 | 605 |
| RKREECLDALESIMT | 73 | 110 | 137 | 606 |
| KREECLDALESIMTT | 102 | 113 | 97 | 607 |
| REECLDALESIMTTK | 94 | 110 | 106 | 608 |
| EECLDALESIMTTKS | 82 | 120 | 133 | 609 |
| ECLDALESIMTTKSV | 91 | 112 | 125 | 610 |
| CLDALESIMTTKSVS | 101 | 146 | 155 | 611 |
| LDALESIMTTKSVSF | 97 | 116 | 152 | 612 |
| DALESIMTTKSVSFR | 104 | 120 | 188 | 613 |

TABLE 14-continued

Binding of the human monoclonal antibodies CR57, CRJB and CR04-010 (10 μg/ml) to linear peptides of the extracellular domain of glycoprotein G of rabies virus strain ERA.

| Amino acid sequence of linear peptide | CR57 | CRJB | CR04-010 | SEQ ID NO: |
|---|---|---|---|---|
| ALESIMTTKSVSFRR | 97 | 132 | 137 | 614 |
| LESIMTTKSVSFRRL | 48 | 114 | 130 | 615 |
| ESIMTTKSVSFRRLS | 62 | 111 | 114 | 616 |
| SIMTTKSVSFRRLSH | 54 | 130 | 97 | 617 |
| IMTTKSVSFRRLSHL | 43 | 101 | 111 | 618 |
| MTTKSVSFRRLSHLR | 59 | 116 | 125 | 619 |
| TTKSVSFRRLSHLRK | 66 | 118 | 111 | 620 |
| TKSVSFRRLSHLRKL | 83 | 125 | 123 | 621 |
| KSVSFRRLSHLRKLV | 108 | 124 | 129 | 622 |
| SVSFRRLSHLRKLVP | 64 | 123 | 117 | 623 |
| VSFRRLSHLRKLVPG | 90 | 111 | 105 | 624 |
| SFRRLSHLRKLVPGF | 92 | 110 | 96 | 625 |
| FRRLSHLRKLVPGFG | 90 | 108 | 111 | 626 |
| RRLSHLRKLVPGFGK | 92 | 143 | 118 | 627 |
| RLSHLRKLVPGFGKA | 93 | 123 | 148 | 628 |
| LSHLRKLVPGFGKAY | 96 | 139 | 150 | 629 |
| SHLRKLVPGFGKAYT | 113 | 132 | 132 | 630 |
| HLRKLVPGFGKAYTI | 99 | 111 | 102 | 631 |
| LRKLVPGFGKAYTIF | 83 | 118 | 82 | 632 |
| RKLVPGFGKAYTIFN | 47 | 115 | 86 | 633 |
| KLVPGFGKAYTIFNK | 47 | 114 | 123 | 634 |
| LVPGFGKAYTIFNKT | 54 | 112 | 139 | 635 |
| VPGFGKAYTIFNKTL | 58 | 114 | 138 | 636 |
| PGFGKAYTIFNKTLM | 78 | 113 | 157 | 637 |
| GFGKAYTIFNKTLME | 78 | 123 | ▒▒▒ | 323 |
| FGKAYTIFNKTLMEA | 90 | 151 | ▒▒▒ | 324 |
| GKAYTIFNKTLMEAD | 76 | 127 | ▒▒▒ | 325 |
| KAYTIFNKTLMEADA | 101 | 123 | ▒▒▒ | 326 |
| AYTIFNKTLMEADAH | 86 | 121 | ▒▒▒ | 327 |
| YTIFNKTLMEADAHY | 104 | 147 | ▒▒▒ | 328 |
| TIFNKTLMEADAHYK | 107 | 123 | ▒▒▒ | 329 |
| IFNKTLMEADAHYKS | 100 | 118 | ▒▒▒ | 330 |
| FNKTLMEADAHYKSV | 111 | 141 | ▒▒▒ | 331 |
| NKTLMEADAHYKSVR | 104 | 116 | 141 | 638 |
| KTLMEADAHYKSVRT | 91 | 98 | 123 | 639 |
| TLMEADAHYKSVRTW | 100 | 114 | 90 | 640 |
| LMEADAHYKSVRTWN | 73 | 107 | 97 | 641 |

TABLE 14-continued

Binding of the human monoclonal antibodies CR57, CRJB and CR04-010 (10 μg/ml) to linear peptides of the extracellular domain of glycoprotein G of rabies virus strain ERA.

| Amino acid sequence of linear peptide | CR57 | CRJB | CR04-010 | SEQ ID NO: |
|---|---|---|---|---|
| MEADAHYKSVRTWNE | 62 | 129 | 83 | 642 |
| EADAHYKSVRTWNEI | 58 | 97 | 106 | 643 |
| ADAHYKSVRTWNEIL | 56 | 100 | 100 | 644 |
| DAHYKSVRTWNEILP | 59 | 121 | 112 | 645 |
| AHYKSVRTWNEILPS | 112 | 160 | 125 | 646 |
| HYKSVRTWNEILPSK | 80 | 130 | 123 | 647 |
| YKSVRTWNEILPSKG | 66 | 137 | 116 | 648 |
| KSVRTWNEILPSKGC | 115 | 125 | 114 | 649 |
| SVRTWNEILPSKGCL | 106 | 138 | 118 | 650 |
| VRTWNEILPSKGCLR | 90 | 124 | 133 | 651 |
| RTWNEILPSKGCLRV | 120 | 127 | 120 | 652 |
| TWNEILPSKGCLRVG | 97 | 146 | 127 | 653 |
| WNEILPSKGCLRVGG | 102 | 136 | 117 | 654 |
| NEILPSKGCLRVGGR | 104 | 130 | 163 | 655 |
| EILPSKGCLRVGGRC | 104 | 112 | 128 | 656 |
| ILPSKGCLRVGGRCH | 79 | 113 | 107 | 657 |
| LPSKGCLRVGGRCHP | 77 | 119 | 100 | 658 |
| PSKGCLRVGGRCHPH | 69 | 138 | 91 | 659 |
| SKGCLRVGGRCHPHV | 72 | 121 | 103 | 660 |
| KGCLRVGGRCHPHVN | 68 | 130 | 115 | 661 |
| GCLRVGGRCHPHVNG | 85 | 125 | 123 | 662 |
| CLRVGGRCHPHVNGV | 102 | 132 | 134 | 663 |
| LRVGGRCHPHVNGVF | 104 | 143 | 133 | 664 |
| RVGGRCHPHVNGVFF | 86 | 143 | 99 | 665 |
| VGGRCHPHVNGVFFN | 120 | 136 | 120 | 666 |
| GGRCHPHVNGVFFNG | 86 | 119 | 119 | 667 |
| GRCHPHVNGVFFNGI | 117 | 113 | 117 | 668 |
| RCHPHVNGVFFNGII | 98 | 141 | 143 | 669 |
| CHPHVNGVFFNGIIL | 97 | 150 | 151 | 670 |
| HPHVNGVFFNGIILG | 104 | 138 | 164 | 671 |
| PHVNGVFFNGIILGP | 93 | 173 | 146 | 672 |
| HVNGVFFNGIILGPD | 97 | 123 | 114 | 673 |
| VNGVFFNGIILGPDG | 68 | 116 | 85 | 674 |
| NGVFFNGIILGPDGN | 66 | 117 | 97 | 675 |
| GVFFNGIILGPDGNV | 58 | 116 | 100 | 676 |
| VFFNGIILGPDGNVL | 55 | 132 | 108 | 677 |
| FFNGIILGPDGNVLI | 92 | 143 | 105 | 678 |

TABLE 14-continued

Binding of the human monoclonal antibodies CR57, CRJB and CR04-010 (10 µg/ml) to linear peptides of the extracellular domain of glycoprotein G of rabies virus strain ERA.

| Amino acid sequence of linear peptide | CR57 | CRJB | CR04-010 | SEQ ID NO: |
|---|---|---|---|---|
| FNGIILGPDGNVLIP | 61 | 139 | 130 | 679 |
| NGIILGPDGNVLIPE | 102 | 146 | 141 | 680 |
| GIILGPDGNVLIPEM | 107 | 132 | 123 | 681 |
| IILGPDGNVLIPEMQ | 85 | 118 | 93 | 682 |
| ILGPDGNVLIPEMQS | 125 | 134 | 119 | 683 |
| LGPDGNVLIPEMQSS | 100 | 134 | 150 | 684 |
| GPDGNVLIPEMQSSL | 86 | 154 | 157 | 685 |
| PDGNVLIPEMQSSLL | 87 | 129 | 139 | 686 |
| DGNVLIPEMQSSLLQ | 123 | 134 | 169 | 687 |
| GNVLIPEMQSSLLQQ | 96 | 120 | 168 | 688 |
| NVLIPEMQSSLLQQH | 72 | 120 | 150 | 689 |
| VLIPEMQSSLLQQHM | 92 | 104 | 142 | 690 |
| LIPEMQSSLLQQHME | 89 | 111 | 85 | 691 |
| IPEMQSSLLQQHMEL | 89 | 128 | 129 | 692 |
| PEMQSSLLQQHMELL | 62 | 133 | 93 | 693 |
| EMQSSLLQQHMELLE | 58 | 129 | 142 | 694 |
| MQSSLLQQHMELLES | 65 | 113 | 117 | 695 |
| QSSLLQQHMELLESS | 82 | 114 | 132 | 696 |
| SSLLQQHMELLESSV | 90 | 128 | 132 | 697 |
| SLLQQHMELLESSVI | 124 | 163 | 133 | 698 |
| LLQQHMELLESSVIP | 78 | 111 | 121 | 699 |
| LQQHMELLESSVIPL | 106 | 134 | 128 | 700 |
| QQHMELLESSVIPLV | 103 | 134 | 133 | 701 |
| QHMELLESSVIPLVH | 98 | 146 | 139 | 702 |
| HMELLESSVIPLVHP | 110 | 129 | 134 | 703 |
| MELLESSVIPLVHPL | 90 | 125 | 152 | 704 |
| ELLESSVIPLVHPLA | 90 | 133 | 155 | 705 |
| LLESSVIPLVHPLAD | 72 | 117 | 118 | 706 |
| LESSVIPLVHPLADP | 90 | 128 | 128 | 707 |
| ESSVIPLVHPLADPS | 104 | 138 | 143 | 708 |
| SSVIPLVHPLADPST | 73 | 104 | 93 | 709 |
| SVIPLVHPLADPSTV | 72 | 137 | 107 | 710 |
| VIPLVHPLADPSTVF | 69 | 141 | 123 | 711 |
| IPLVHPLADPSTVFK | 96 | 156 | 188 | 712 |
| PLVHPLADPSTVFKD | 93 | 112 | 138 | 713 |
| LVHPLADPSTVFKDG | 164 | 174 | 188 | 714 |
| VHPLADPSTVFKDGD | 98 | 138 | 125 | 715 |

TABLE 14-continued

Binding of the human monoclonal antibodies CR57, CRJB and CR04-010 (10 μg/ml) to linear peptides of the extracellular domain of glycoprotein G of rabies virus strain ERA.

| Amino acid sequence of linear peptide | CR57 | CRJB | CR04-010 | SEQ ID NO: |
|---|---|---|---|---|
| HPLADPSTVFKDGDE | 74 | 141 | 117 | 716 |
| PLADPSTVFKDGDEA | 99 | 125 | 90 | 717 |
| LADPSTVFKDGDEAE | 68 | 116 | 113 | 718 |
| ADPSTVFKDGDEAED | 147 | 152 | 110 | 719 |
| DPSTVFKDGDEAEDF | 98 | 147 | 137 | 720 |
| PSTVFKDGDEAEDFV | 104 | 143 | 141 | 721 |
| STVFKDGDEAEDFVE | 104 | 120 | 125 | 722 |
| TVFKDGDEAEDFVEV | 107 | 124 | 96 | 723 |
| VFKDGDEAEDFVEVH | 100 | 106 | 93 | 724 |
| FKDGDEAEDFVEVHL | 65 | 76 | 119 | 725 |
| KDGDEAEDFVEVHLP | 72 | 93 | 76 | 726 |
| DGDEAEDFVEVHLPD | 85 | 123 | 91 | 727 |
| GDEAEDFVEVHLPDV | 46 | 124 | 113 | 728 |
| DEAEDFVEVHLPDVH | 68 | 136 | 123 | 729 |
| EAEDFVEVHLPDVHN | 76 | 117 | 114 | 730 |
| AEDFVEVHLPDVHNQ | 123 | 138 | 123 | 731 |
| EDFVEVHLPDVHNQV | 90 | 141 | 123 | 732 |
| DFVEVHLPDVHNQVS | 96 | 141 | 118 | 733 |
| FVEVHLPDVHNQVSG | 92 | 143 | 102 | 734 |
| VEVHLPDVHNQVSGV | 106 | 141 | 123 | 735 |
| EVHLPDVHNQVSGVD | 91 | 150 | 139 | 736 |
| VHLPDVHNQVSGVDL | 110 | 114 | 137 | 737 |
| HLPDVHNQVSGVDLG | 104 | 150 | 129 | 738 |
| LPDVHNQVSGVDLGL | 104 | 154 | 154 | 739 |
| PDVHNQVSGVDLGLP | 106 | 129 | 115 | 740 |
| DVHNQVSGVDLGLPN | 117 | 133 | 113 | 741 |
| VHNQVSGVDLGLPNW | 100 | 119 | 38 | 742 |
| HNQVSGVDLGLPNWG | 76 | 106 | 38 | 743 |
| NQVSGVDLGLPNWGK | 78 | 138 | 98 | 744 |
| Average | 91.9 | 119.5 | 130.9 | |
| StDV | 157.9 | 37.6 | 169.8 | |

TABLE 15

Neutralizing potencies of anti-rabies virus G protein IgGs.

| Name IgG | IU/mg |
|---|---|
| CR04-001 | 89 |
| CR04-004 | 5 |
| CR04-008 | 1176 |
| CR04-010 | 3000 |

TABLE 15-continued

Neutralizing potencies of anti-rabies virus G protein IgGs.

| Name IgG | IU/mg |
|---|---|
| CR04-018 | 1604 |
| CR04-021 | 1500 |
| CR04-026 | <2 |
| CR04-031 | 272 |
| CR04-038 | 2330 |
| CR04-040 | 3041 |
| CR04-060 | 89 |
| CR04-073 | 6116 |
| CR04-097 | <1 |
| CR04-098 | 7317 |
| CR04-103 | 3303 |
| CR04-104 | 4871 |

TABLE 15-continued

Neutralizing potencies of anti-rabies virus G protein IgGs.

| Name IgG | IU/mg |
|---|---|
| CR04-108 | 4871 |
| CR04-120 | 4938 |
| CR04-125 | 4718 |
| CR04-126 | 2655 |
| CR04-140 | 478 |
| CR04-144 | 6250 |
| CR04-146 | ND |
| CR04-164 | 4724 |
| CR57 | 3800 |
| CRJB | 605 |

ND = not determined

TABLE 16

Neutralizing potencies of anti-rabies virus G protein IgGs against E57 escape viruses.

| Name IgG | E57A2 (IU/mg) | E57A3 (IU/mg) | E57B1 (IU/mg) | E57B2 (IU/mg) | de Kruif J., L. Terstappen, E. Boel and T. Logtenberg (1995a). Rapid selection of cell subpopulation-specific human monoclonal antibodies from a synthetic phage antibody library. *Proc. Natl. Acad. Sci. USA* 92:3938.

de Kruif J., E. Boel and T. Logtenberg (1995b). Selection and application of human single-chain Fv antibody fragments from a semi-synthetic phage antibody display library with designed CDR3 regions. *J. Mol. Biol.* 248:97-105.

Dietzschold B., W. H. Wunner, T. J. Wiktor, A. D. Lopes, M. Lafon, C. L. Smith and H. Koprowski (1983). Characterization of an antigenic determinant of the glycoprotein that correlates with pathogenicity of rabies virus. *Proc. Natl. Acad. Sci. USA* 80:70-74.

Dietzschold B., M. Gore, P. Casali, Y. Ueki, C. E. Rupprecht, A. L. Notkins and H. Koprowski (1990). Biological characterization of human monoclonal antibodies to rabies virus. *J. Virol.* 64:3087-3090.

Hanlon C. A., C. A. DeMattos, C. C. DeMattos, M. Niezgoda, D. C. Hooper, H. Koprowski, A. Notkins and C. E. Rupprecht (2001). Experimental utility of rabies virus-neutralizing human monoclonal antibodies in post-exposure prophylaxis. *Vaccine* 19:3834-3842.

Huls G., I. J. Heijnen, E. Cuomo, J. van der Linden, E. Boel, J. van de Winkel and T. Logtenberg (1999). Antitumor immune effector mechanisms recruited by phage display-derived fully human IgG1 and IgA1 monoclonal antibodies. *Cancer Res.* 59:5778-5784.

Jones D., N. Kroos, R. Anema, B. van Montfort, A. Vooys, S. van der Kraats, E. van der Helm, S. Smits, J. Schouten, K. Brouwer, F. Lagerwerf, P. van Berkel, D. J. Opstelten, T. Logtenberg and A. Bout (2003). High-level expression of recombinant IgG in the human cell line PER.C6. *Biotechnol. Prog.* 19:163-168.

Lafon M., T. J. Wiktor and R. I. Macfarlan (1983). Antigenic sites on the CVS rabies virus glycoprotein: analysis with monoclonal antibodies. *J. Gen. Virol.* 64 (Pt 4):843-851.

Luo T. R., N. Minamoto, H. Ito, H. Goto, S. Hiraga, N. Ito, M. Sugiyama and T. Kinjo (1997). A virus-neutralizing epitope on the glycoprotein of rabies virus that contains Trp251 is a linear epitope. *Virus Res.* 51:35-41.

Madhusudana S. N., R. Shamsundar and S. Seetharaman (2004). In vitro inactivation of the rabies virus by ascorbic acid. *Int. J. Infect. Dis.* 8:21-25.

Ni Y., Y. Tominaga, Y. Honda, K. Morimoto, S. Sakamoto and A. Kawai (1995). Mapping and characterization of a sequential epitope on the rabies virus glycoprotein which is recognized by a neutralizing monoclonal antibody, RG719. *Microbiol. Immunol.* 39:693-702.

Prehaud C., P. Coulon, F. LaFay, C. Thiers and A. Flamand (1988). Antigenic site II of the rabies virus glycoprotein: structure and role in viral virulence. *J. Virol.* 62:1-7.

Schumacher C. L., B. Dietzschold, H. C. Ertl, H. S, Niu, C. E. Rupprecht and H. Koprowski (1989). Use of mouse anti-rabies monoclonal antibodies in post-exposure treatment of rabies. *J. Clin. Invest.* 84:971-975.

Seif I., P. Coulon, E. Rollin and A. Flamand (1985). Rabies virulence: effect on pathogenicity and sequence characterization of rabies virus mutations affecting antigenic site III of the glycoprotein. *J. Virol.* 53:926-934.

Slootstra J. W., W. C. Puijk, G. J. Ligtvoet, J. P. Langeveld and R. H. Meloen (1996). Structural aspects of antibody-antigen interaction revealed through small random peptide libraries. *Mol. Divers.* 1:87-96.

Tordo N. (1996). Characteristics and molecular biology of rabies virus. In F.-X. Meslin, M. M. Kaplan, H. Koprowski, editors, *Laboratory Techniques in rabies*, 4th edition Geneva, Switzerland: World Health Organization.

White L. A. and W. A. Chappell (1982). Inactivation of rabies virus in reagents used for the fluorescent rabies antibody test. *J. Clin. Microbiol.* 16:253-256.

---

SEQUENCE LISTING

```
<160> NUMBER OF SEQ ID NOS: 748

<210> SEQ ID NO 1
<211> LENGTH: 9
<212> TYPE: PRT
<213> ORGANISM: Artificial sequence
<220> FEATURE:
<223> OTHER INFORMATION: CDR3 of SC04-001

<400> SEQUENCE: 1

Gly Leu Tyr Gly Glu Leu Phe Asp Tyr
1               5

<210> SEQ ID NO 2
<211> LENGTH: 11
<212> TYPE: PRT
<213> ORGANISM: Artificial sequence
<220> FEATURE:
<223> OTHER INFORMATION: CDR3 of SC04-004

<400> SEQUENCE: 2

Asp Tyr Leu Tyr Pro Thr Thr Asp Phe Asp Tyr
1               5                   10

<210> SEQ ID NO 3
<211> LENGTH: 10
<212> TYPE: PRT
<213> ORGANISM: Artificial sequence
<220> FEATURE:
```

<223> OTHER INFORMATION: CDR3 of SC04-008

<400> SEQUENCE: 3

Met Gly Phe Thr Gly Thr Tyr Phe Asp Tyr
1               5                   10

<210> SEQ ID NO 4
<211> LENGTH: 14
<212> TYPE: PRT
<213> ORGANISM: Artificial sequence
<220> FEATURE:
<223> OTHER INFORMATION: CDR3 of SC04-010

<400> SEQUENCE: 4

Asp Gly Leu Asp Leu Thr Gly Thr Ile Gln Pro Phe Gly Tyr
1               5                   10

<210> SEQ ID NO 5
<211> LENGTH: 10
<212> TYPE: PRT
<213> ORGANISM: Artificial sequence
<220> FEATURE:
<223> OTHER INFORMATION: CDR3 of SC04-018

<400> SEQUENCE: 5

Val Ser Val Thr Thr Gly Ala Phe Asn Ile
1               5                   10

<210> SEQ ID NO 6
<211> LENGTH: 10
<212> TYPE: PRT
<213> ORGANISM: Artificial sequence
<220> FEATURE:
<223> OTHER INFORMATION: CDR3 of SC04-021

<400> SEQUENCE: 6

Gly Ser Val Leu Gly Asp Ala Phe Asp Ile
1               5                   10

<210> SEQ ID NO 7
<211> LENGTH: 12
<212> TYPE: PRT
<213> ORGANISM: Artificial sequence
<220> FEATURE:
<223> OTHER INFORMATION: CDR3 of SC04-026

<400> SEQUENCE: 7

Thr Ser Asn Trp Asn Tyr Leu Asp Arg Phe Asp Pro
1               5                   10

<210> SEQ ID NO 8
<211> LENGTH: 10
<212> TYPE: PRT
<213> ORGANISM: Artificial sequence
<220> FEATURE:
<223> OTHER INFORMATION: CDR3 of SC04-031

<400> SEQUENCE: 8

Gly Ser Val Leu Gly Asp Ala Phe Asp Ile
1               5                   10

<210> SEQ ID NO 9
<211> LENGTH: 10
<212> TYPE: PRT
<213> ORGANISM: Artificial sequence
<220> FEATURE:
<223> OTHER INFORMATION: CDR3 of SC04-038

```
<400> SEQUENCE: 9

Gly Ser Val Leu Gly Asp Ala Phe Asp Ile
1               5                   10

<210> SEQ ID NO 10
<211> LENGTH: 9
<212> TYPE: PRT
<213> ORGANISM: Artificial sequence
<220> FEATURE:
<223> OTHER INFORMATION: CDR3 of SC04-040

<400> SEQUENCE: 10

Gly Ser Lys Val Gly Asp Phe Asp Tyr
1               5

<210> SEQ ID NO 11
<211> LENGTH: 20
<212> TYPE: PRT
<213> ORGANISM: Artificial sequence
<220> FEATURE:
<223> OTHER INFORMATION: CDR3 of SC04-060

<400> SEQUENCE: 11

Glu Lys Glu Lys Tyr Ser Asp Arg Ser Gly Tyr Ser Tyr Tyr Tyr
1               5                   10                  15

Tyr Met Asp Val
            20

<210> SEQ ID NO 12
<211> LENGTH: 14
<212> TYPE: PRT
<213> ORGANISM: Artificial sequence
<220> FEATURE:
<223> OTHER INFORMATION: CDR3 of SC04-073

<400> SEQUENCE: 12

Asp Gly Leu Asp Leu Thr Gly Thr Ile Gln Pro Phe Gly Tyr
1               5                   10

<210> SEQ ID NO 13
<211> LENGTH: 12
<212> TYPE: PRT
<213> ORGANISM: Artificial sequence
<220> FEATURE:
<223> OTHER INFORMATION: CDR3 of SC04-097

<400> SEQUENCE: 13

Thr Ala Ser Asn Leu Gly Arg Gly Gly Met Asp Val
1               5                   10

<210> SEQ ID NO 14
<211> LENGTH: 10
<212> TYPE: PRT
<213> ORGANISM: Artificial sequence
<220> FEATURE:
<223> OTHER INFORMATION: CDR3 of SC04-098

<400> SEQUENCE: 14

Val Ala Val Ala Gly Thr His Phe Asp Tyr
1               5                   10

<210> SEQ ID NO 15
<211> LENGTH: 10
<212> TYPE: PRT
<213> ORGANISM: Artificial sequence
```

```
<220> FEATURE:
<223> OTHER INFORMATION: CDR3 of SC04-103

<400> SEQUENCE: 15

Val Ala Val Ala Gly Glu Ser Phe Asp Ser
1               5                   10

<210> SEQ ID NO 16
<211> LENGTH: 12
<212> TYPE: PRT
<213> ORGANISM: Artificial sequence
<220> FEATURE:
<223> OTHER INFORMATION: CDR3 of SC04-104

<400> SEQUENCE: 16

Ile Val Val Val Thr Ala Leu Asp Ala Phe Asp Ile
1               5                   10

<210> SEQ ID NO 17
<211> LENGTH: 11
<212> TYPE: PRT
<213> ORGANISM: Artificial sequence
<220> FEATURE:
<223> OTHER INFORMATION: CDR3 of SC04-108

<400> SEQUENCE: 17

Phe Met Ile Val Ala Asp Asp Ala Phe Asp Ile
1               5                   10

<210> SEQ ID NO 18
<211> LENGTH: 9
<212> TYPE: PRT
<213> ORGANISM: Artificial sequence
<220> FEATURE:
<223> OTHER INFORMATION: CDR3 of SC04-120

<400> SEQUENCE: 18

Gly Gly Lys Thr Gly Glu Phe Asp Tyr
1               5

<210> SEQ ID NO 19
<211> LENGTH: 10
<212> TYPE: PRT
<213> ORGANISM: Artificial sequence
<220> FEATURE:
<223> OTHER INFORMATION: CDR3 of SC04-125

<400> SEQUENCE: 19

Ile Ala Thr Ala Gly Thr Gly Phe Asp Tyr
1               5                   10

<210> SEQ ID NO 20
<211> LENGTH: 10
<212> TYPE: PRT
<213> ORGANISM: Artificial sequence
<220> FEATURE:
<223> OTHER INFORMATION: CDR3 of SC04-126

<400> SEQUENCE: 20

Met Gly Phe Thr Gly Thr Tyr Phe Asp Tyr
1               5                   10

<210> SEQ ID NO 21
<211> LENGTH: 10
<212> TYPE: PRT
<213> ORGANISM: Artificial sequence
<220> FEATURE:
```

```
<223> OTHER INFORMATION: CDR3 of SC04-140

<400> SEQUENCE: 21

Val Thr Asn Pro Gly Asp Ala Phe Asp Ile
1               5                   10

<210> SEQ ID NO 22
<211> LENGTH: 9
<212> TYPE: PRT
<213> ORGANISM: Artificial sequence
<220> FEATURE:
<223> OTHER INFORMATION: CDR3 of SC04-144

<400> SEQUENCE: 22

Gly Gly Lys Thr Gly Glu Phe Asp Tyr
1               5

<210> SEQ ID NO 23
<211> LENGTH: 9
<212> TYPE: PRT
<213> ORGANISM: Artificial sequence
<220> FEATURE:
<223> OTHER INFORMATION: CDR3 of SC04-146

<400> SEQUENCE: 23

Gly Gly Lys Thr Gly Glu Phe Asp Tyr
1               5

<210> SEQ ID NO 24
<211> LENGTH: 10
<212> TYPE: PRT
<213> ORGANISM: Artificial sequence
<220> FEATURE:
<223> OTHER INFORMATION: CDR3 of SC04-164

<400> SEQUENCE: 24

Gly Ser Val Leu Gly Asp Ala Phe Asp Ile
1               5                   10

<210> SEQ ID NO 25
<211> LENGTH: 18
<212> TYPE: PRT
<213> ORGANISM: Artificial sequence
<220> FEATURE:
<223> OTHER INFORMATION: CDR3 of SO57

<400> SEQUENCE: 25

Glu Asn Leu Asp Asn Ser Gly Thr Tyr Tyr Tyr Phe Ser Gly Trp Phe
1               5                   10                  15

Asp Pro

<210> SEQ ID NO 26
<211> LENGTH: 117
<212> TYPE: PRT
<213> ORGANISM: Artificial sequence
<220> FEATURE:
<223> OTHER INFORMATION: Heavy chain variable region of SC04-001

<400> SEQUENCE: 26

Glu Val Gln Leu Val Glu Ser Gly Gly Val Val Arg Pro Gly Gly
1               5                   10                  15

Ser Leu Arg Leu Ser Cys Ala Ala Ser Gly Phe Thr Phe Asp Asp Tyr
                20                  25                  30

Gly Met Ser Trp Val Arg Gln Ala Pro Gly Lys Gly Leu Glu Trp Val
            35                  40                  45
```

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Leu Tyr Gly Glu Leu Phe Asp Tyr Trp Gly Gln Gly Thr
            100                 105                 110

Leu Val Thr Val Ser
            115

<210> SEQ ID NO 27
<211> LENGTH: 118
<212> TYPE: PRT
<213> ORGANISM: Artificial sequence
<220> FEATURE:
<223> OTHER INFORMATION: Heavy chain variable region of SC04-004

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Trp Met Asn Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Tyr Leu Tyr Pro Thr Thr Asp Phe Asp Tyr Trp Gly Gln
            100                 105                 110

Gly Thr Leu Val Thr Val
            115

<210> SEQ ID NO 28
<211> LENGTH: 120
<212> TYPE: PRT
<213> ORGANISM: Artificial sequence
<220> FEATURE:
<223> OTHER INFORMATION: Heavy chain variable region of SC04-008

<400> SEQUENCE: 28

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Val Gly Val Gly Trp Ile Arg Gln Pro Pro Gly Lys Ala Leu Glu
            35                  40                  45

Trp Leu Ala Arg Ile Asp Trp Asp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Met Gly Phe Thr Gly Thr Tyr Phe Asp Tyr Trp Gly Gln

```
                    100                 105                 110
Gly Thr Leu Val Thr Val Ser Ser
            115                 120

<210> SEQ ID NO 29
<211> LENGTH: 123
<212> TYPE: PRT
<213> ORGANISM: Artificial sequence
<220> FEATURE:
<223> OTHER INFORMATION: Heavy chain variable region of SC04-010

<400> SEQUENCE: 29

Gln Val Gln Leu Val Gln Ser Gly Gly Asp Leu Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Asp Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Leu Asp Leu Thr Gly Thr Ile Gln Pro Phe Gly Tyr
            100                 105                 110

Trp Gly Gln Gly Thr Leu Val Thr Val Ser Ser
        115                 120

<210> SEQ ID NO 30
<211> LENGTH: 119
<212> TYPE: PRT
<213> ORGANISM: Artificial sequence
<220> FEATURE:
<223> OTHER INFORMATION: Heavy chain variable region of SC04-018

<400> SEQUENCE: 30

Glu Val Gln Leu Val Glu Ser Gly Pro Gly Leu Val Arg Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Val Ser Val Thr Thr Gly Ala Phe Asn Ile Trp Gly Gln Gly
            100                 105                 110

Thr Met Val Thr Val Ser Ser
        115

<210> SEQ ID NO 31
<211> LENGTH: 119
<212> TYPE: PRT
<213> ORGANISM: Artificial sequence
<220> FEATURE:
```

<223> OTHER INFORMATION: Heavy chain variable region of SC04-021

<400> SEQUENCE: 31

```
Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Val Leu Gly Asp Ala Phe Asp Ile Trp Gly Gln Gly
            100                 105                 110

Thr Met Val Thr Val Ser Ser
            115
```

<210> SEQ ID NO 32
<211> LENGTH: 121
<212> TYPE: PRT
<213> ORGANISM: Artificial sequence
<220> FEATURE:
<223> OTHER INFORMATION: Heavy chain variable region of SC04-026

<400> SEQUENCE: 32

```
Glu Val Gln Leu Val Glu Ser Gly Ala Glu Val Lys Lys Pro Gly Glu
1               5                   10                  15

Ser Leu Lys Ile Ser Cys Lys Gly Ser Gly Tyr Asn Phe Pro Tyr Ser
            20                  25                  30

Trp Ile Ala Trp Val Arg Gln Met Pro Gly Lys Gly Leu Glu Trp Met
        35                  40                  45

Gly Ile Ile Phe Pro Gly Asp Ser Asp Thr Arg Tyr Ser Pro Pro Phe
    50                  55                  60

Gln Gly Gln Val Thr Ile Ser Ala Asp Asn Ser Lys Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Thr Ser Asn Trp Asn Tyr Leu Asp Arg Phe Asp Pro Trp Gly
            100                 105                 110

Gln Gly Thr Leu Val Thr Val Ser Ser
        115                 120
```

<210> SEQ ID NO 33
<211> LENGTH: 119
<212> TYPE: PRT
<213> ORGANISM: Artificial sequence
<220> FEATURE:
<223> OTHER INFORMATION: Heavy chain variable region of SC04-031

<400> SEQUENCE: 33

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
```

```
                35                  40                  45
Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Val Leu Gly Asp Ala Phe Asp Ile Trp Gly Gln Gly
            100                 105                 110

Thr Met Val Thr Val Ser Ser
        115

<210> SEQ ID NO 34
<211> LENGTH: 119
<212> TYPE: PRT
<213> ORGANISM: Artificial sequence
<220> FEATURE:
<223> OTHER INFORMATION: Heavy chain variable region of SC04-038

<400> SEQUENCE: 34

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Val Leu Gly Asp Ala Phe Asp Ile Trp Gly Gln Gly
            100                 105                 110

Thr Met Val Thr Val Ser Ser
        115

<210> SEQ ID NO 35
<211> LENGTH: 118
<212> TYPE: PRT
<213> ORGANISM: Artificial sequence
<220> FEATURE:
<223> OTHER INFORMATION: Heavy chain variable region of SC04-040

<400> SEQUENCE: 35

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Gly Ser Tyr
            20                  25                  30

Gly Met His Trp Val Arg Gln Ala Pro Gly Lys Gly Leu Glu Trp Val
        35                  40                  45

Ala Thr Ile Phe Tyr Asp Gly Ser Tyr Lys Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Lys Gly Ser Lys Val Gly Asp Phe Asp Tyr Trp Gly Gln Gly Thr
            100                 105                 110

Leu Val Thr Val Ser Ser
        115

<210> SEQ ID NO 36
<211> LENGTH: 128
<212> TYPE: PRT
<213> ORGANISM: Artificial sequence
<220> FEATURE:
<223> OTHER INFORMATION: Heavy chain variable region of SC04-060

<400> SEQUENCE: 36

Gln Val Gln Leu Val Glu Ser Gly Pro Gly Leu Val Lys Ala Ser Glu
1               5                   10                  15

Thr Leu Ser Leu Thr Cys Thr Val Ser Asp Gly Ser Ile Ser Ser Phe
            20                  25                  30

Tyr Trp Ser Trp Ile Arg Gln Pro Pro Gly Lys Gly Leu Glu Trp Val
        35                  40                  45

Gly Glu Ile Gln Asp Thr Gly Arg Thr Asn Tyr Asn Pro Ser Leu Lys
    50                  55                  60

Ser Arg Val Thr Ile Ser Leu Asp Thr Ser Lys Asn Gln Phe Ser Leu
65                  70                  75                  80

Thr Leu Ser Ser Val Thr Ala Ala Asp Thr Ala Val Tyr Tyr Cys Ala
                85                  90                  95

Arg Glu Lys Glu Lys Tyr Ser Asp Arg Ser Gly Tyr Ser Tyr Tyr Tyr
            100                 105                 110

Tyr Tyr Met Asp Val Trp Gly Lys Gly Thr Thr Val Thr Val Ser Ser
        115                 120                 125

<210> SEQ ID NO 37
<211> LENGTH: 123
<212> TYPE: PRT
<213> ORGANISM: Artificial sequence
<220> FEATURE:
<223> OTHER INFORMATION: Heavy chain variable region of SC04-073

<400> SEQUENCE: 37

Gln Val Gln Leu Val Gln Ser Gly Gly Gly Val Ala Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Asp Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Leu Asp Leu Thr Gly Thr Ile Gln Pro Phe Gly Tyr
            100                 105                 110

Trp Gly Gln Gly Thr Leu Val Thr Val Ser Ser
        115                 120

<210> SEQ ID NO 38
<211> LENGTH: 121
<212> TYPE: PRT
<213> ORGANISM: Artificial sequence
```

<220> FEATURE:
<223> OTHER INFORMATION: Heavy chain variable region of SC04-097

<400> SEQUENCE: 38

Glu Val Gln Leu Val Gln Ser Gly Gly His Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Leu Ile Ile Gly Ser Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Ala Ser Asn Leu Gly Arg Gly Gly Met Asp Val Trp Gly
            100                 105                 110

Gln Gly Thr Thr Val Thr Val Ser Ser
        115                 120

<210> SEQ ID NO 39
<211> LENGTH: 119
<212> TYPE: PRT
<213> ORGANISM: Artificial sequence
<220> FEATURE:
<223> OTHER INFORMATION: Heavy chain variable region of SC04-098

<400> SEQUENCE: 39

Glu Val Gln Leu Val Gln Ser Gly Gly Gly Ala Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Leu Tyr Asp Gly Ser Asp Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Ala Val Ala Gly Thr His Phe Asp Tyr Trp Gly Gln Gly
            100                 105                 110

Thr Leu Val Thr Val Ser Ser
        115

<210> SEQ ID NO 40
<211> LENGTH: 119
<212> TYPE: PRT
<213> ORGANISM: Artificial sequence
<220> FEATURE:
<223> OTHER INFORMATION: Heavy chain variable region of SC04-103

<400> SEQUENCE: 40

Gln Val Gln Leu Gln Glu Ser Gly Gly Gly Val Val Gln Pro Gly Arg
1               5                   10                  15

Ser Leu Arg Leu Ser Cys Ala Ser Gly Phe Thr Phe Ser Ser Tyr
            20                  25                  30

Gly Met His Trp Val Arg Gln Ala Pro Gly Lys Gly Leu Glu Trp Val
          35                  40                  45

Ala Val Ile Leu Tyr Asp Gly Ser Asp Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
              85                  90                  95

Ala Lys Val Ala Val Ala Gly Glu Ser Phe Asp Ser Trp Gly Arg Gly
             100                 105                 110

Thr Leu Val Thr Val Ser Ser
         115

<210> SEQ ID NO 41
<211> LENGTH: 121
<212> TYPE: PRT
<213> ORGANISM: Artificial sequence
<220> FEATURE:
<223> OTHER INFORMATION: Heavy chain variable region of SC04-104

<400> SEQUENCE: 41

Gln Val Gln Leu Gln Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
              20                  25                  30

Gly Met His Trp Val Arg Gln Ala Pro Gly Lys Gly Leu Glu Trp Val
          35                  40                  45

Ala Thr Ile Ser Tyr Asp Gly Asn Val Lys Asp Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Thr Glu Asp Thr Ala Val Tyr Tyr Cys
              85                  90                  95

Ala Lys Ile Val Val Val Thr Ala Leu Asp Ala Phe Asp Ile Trp Gly
             100                 105                 110

Gln Gly Thr Met Val Thr Val Ser Ser
         115                 120

<210> SEQ ID NO 42
<211> LENGTH: 120
<212> TYPE: PRT
<213> ORGANISM: Artificial sequence
<220> FEATURE:
<223> OTHER INFORMATION: Heavy chain varaible region of SC04-108

<400> SEQUENCE: 42

Glu Val Gln Leu Val Gln Ser Gly Gly Gly Leu Val Gln Pro Gly Gly
 1               5                  10                  15

Ser Leu Arg Leu Ser Cys Ala Ser Gly Phe Thr Phe Ser Ser Tyr
              20                  25                  30

Gly Met His Trp Val Arg Gln Ala Pro Gly Lys Gly Leu Glu Trp Val
          35                  40                  45

Ala Val Ile Leu Tyr Asp Gly Ser Asp Lys Phe Tyr Ala Asp Ser Val
 50                  55                  60

Lys Gly Arg Phe Thr Ile Ser Arg Asp Asn Ser Lys Asp Thr Leu Tyr
 65                  70                  75                  80

Leu Gln Met Asn Ser Leu Arg Ala Glu Asp Thr Ala Val Tyr Tyr Cys
              85                  90                  95

```
Ala Lys Phe Met Ile Val Ala Asp Asp Ala Phe Asp Ile Trp Gly Gln
            100                 105                 110

Gly Thr Met Val Thr Val Ser Ser
        115                 120

<210> SEQ ID NO 43
<211> LENGTH: 118
<212> TYPE: PRT
<213> ORGANISM: Artificial sequence
<220> FEATURE:
<223> OTHER INFORMATION: Heavy chain variable region of SC04-120

<400> SEQUENCE: 43

Glu Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Thr Ile Ser Tyr Asp Gly Ser Ile Lys Asp Tyr Ala Asp Ser Glu
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Lys Thr Gly Glu Phe Asp Tyr Trp Gly Gln Gly Thr
            100                 105                 110

Leu Val Thr Val Ser Ser
        115

<210> SEQ ID NO 44
<211> LENGTH: 119
<212> TYPE: PRT
<213> ORGANISM: Artificial sequence
<220> FEATURE:
<223> OTHER INFORMATION: Heavy chain variable region of SC04-125

<400> SEQUENCE: 44

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ala Thr Ala Gly Thr Gly Phe Asp Tyr Trp Gly Gln Gly
            100                 105                 110

Thr Leu Val Thr Val Ser Ser
        115

<210> SEQ ID NO 45
<211> LENGTH: 120
<212> TYPE: PRT
```

<213> ORGANISM: Artificial sequence
<220> FEATURE:
<223> OTHER INFORMATION: Heavy chain variable region of SC04-126

<400> SEQUENCE: 45

```
Gln Val Thr Leu Lys Glu Ser Gly Pro Thr Leu Val Asn Pro Thr Gln
1               5                   10                  15

Thr Leu Thr Leu Thr Cys Thr Phe Ser Gly Phe Ser Leu Ser Thr Gly
            20                  25                  30

Gly Val Gly Val Gly Trp Phe Arg Gln Pro Pro Gly Lys Ala Leu Glu
        35                  40                  45

Trp Leu Ala Arg Ile Asp Trp Asp Asp Asp Lys Tyr Tyr Ser Thr Ser
    50                  55                  60

Leu Lys Thr Arg Leu Thr Ile Ser Lys Asp Thr Ser Lys Ile Gln Val
65                  70                  75                  80

Val Leu Thr Met Thr Asn Met Asp Pro Val Asp Thr Ala Thr Tyr Tyr
                85                  90                  95

Cys Ala Arg Met Gly Phe Thr Gly Thr Tyr Phe Asp Tyr Trp Gly Gln
            100                 105                 110

Gly Thr Leu Val Thr Val Ser Ser
        115                 120
```

<210> SEQ ID NO 46
<211> LENGTH: 119
<212> TYPE: PRT
<213> ORGANISM: Artificial sequence
<220> FEATURE:
<223> OTHER INFORMATION: Heavy chain variable region of SC04-140

<400> SEQUENCE: 46

```
Gln Met Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Leu Tyr Asp Gly Ser Asn Lys Tyr Tyr Ala Asp Ser Val
    50                  55                  60

Lys Gly Arg Phe Thr Ile Ser Arg Asp Asn Ser Lys Asn Ala Leu Tyr
65                  70                  75                  80

Leu Gln Met Asn Ser Leu Arg Ala Glu Asp Thr Ala Val Tyr Tyr Cys
                85                  90                  95

Ala Lys Val Thr Asn Pro Gly Asp Ala Phe Asp Ile Trp Gly Gln Gly
            100                 105                 110

Thr Met Val Thr Val Ser Ser
        115
```

<210> SEQ ID NO 47
<211> LENGTH: 118
<212> TYPE: PRT
<213> ORGANISM: Artificial sequence
<220> FEATURE:
<223> OTHER INFORMATION: Heavy chain variable region of SC04-144

<400> SEQUENCE: 47

```
Gln Val Gln Leu Gln Glu Leu Gly Gly Gly Val Val Gln Pro Gly Arg
1               5                   10                  15

Ser Leu Arg Leu Ser Cys Ala Ala Ser Gly Phe Thr Phe Gly Ser Tyr
            20                  25                  30
```

```
Gly Met His Trp Val Arg Gln Ala Pro Gly Lys Gly Leu Glu Trp Val
            35                  40                  45

Ala Thr Ile Ser Tyr Asp Gly Ser Ile Lys Asp Tyr Ala Asp Ser Glu
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gly Gly Lys Thr Gly Glu Phe Asp Tyr Trp Gly Gln Gly Thr
            100                 105                 110

Leu Val Thr Val Ser Ser
            115

<210> SEQ ID NO 48
<211> LENGTH: 118
<212> TYPE: PRT
<213> ORGANISM: Artificial sequence
<220> FEATURE:
<223> OTHER INFORMATION: Heavy chain variable region of SC04-146

<400> SEQUENCE: 48

Glu Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Thr Ile Ser Tyr Asp Gly Ser Ile Lys Asp Tyr Ala Asp Ser Glu
        50                  55                  60

Glu Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gly Gly Lys Thr Gly Glu Phe Asp Tyr Trp Gly Gln Gly Thr
            100                 105                 110

Leu Val Thr Val Ser Ser
            115

<210> SEQ ID NO 49
<211> LENGTH: 119
<212> TYPE: PRT
<213> ORGANISM: Artificial sequence
<220> FEATURE:
<223> OTHER INFORMATION: Heavy chain variable region of SC04-164

<400> SEQUENCE: 49

Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
```

-continued

```
                85                  90                  95

Ala Lys Gly Ser Val Leu Gly Asp Ala Phe Asp Ile Trp Gly Gln Gly
               100                 105                 110

Thr Met Val Thr Val Ser Ser
        115

<210> SEQ ID NO 50
<211> LENGTH: 108
<212> TYPE: PRT
<213> ORGANISM: Artificial sequence
<220> FEATURE:
<223> OTHER INFORMATION: Light chain variable region of SC04-001

<400> SEQUENCE: 50

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu
            100                 105

<210> SEQ ID NO 51
<211> LENGTH: 103
<212> TYPE: PRT
<213> ORGANISM: Artificial sequence
<220> FEATURE:
<223> OTHER INFORMATION: Light chain variable region of SC04-004

<400> SEQUENCE: 51

Thr Gln Ser Pro Ser Ser Leu Ser Ala Ser Val Gly Asp Arg Val Thr
1               5                   10                  15

Ile Thr Cys Arg Ala Ser Gln Ser Ile Ser Ser Tyr Leu Asn Trp Tyr
                20                  25                  30

Gln Gln Lys Pro Gly Lys Ala Pro Lys Leu Leu Ile Tyr Ala Ala Ser
            35                  40                  45

Ser Leu Gln Ser Gly Val Pro Ser Arg Phe Ser Gly Ser Gly Ser Gly
        50                  55                  60

Thr Asp Phe Thr Leu Thr Ile Ser Ser Leu Gln Pro Glu Asp Phe Ala
65                  70                  75                  80

Thr Tyr Tyr Cys Gln Gln Ser Tyr Ser Thr Pro Pro Thr Phe Gly Gln
                85                  90                  95

Gly Thr Lys Val Glu Ile Lys
            100

<210> SEQ ID NO 52
<211> LENGTH: 109
<212> TYPE: PRT
<213> ORGANISM: Artificial sequence
<220> FEATURE:
<223> OTHER INFORMATION: Light chain variable region of SC04-008

<400> SEQUENCE: 52
```

Gln Ala Val Leu Thr Gln Pro Ser Ser Val Ser Val Ala Pro Gly Glu
1               5                   10                  15

Thr Ala Ser Val Thr Cys Gly Gly Asp Asn Ile Gly Ser Lys Ser Val
            20                  25                  30

His Trp Tyr Gln Lys Lys Pro Gly Gln Ala Pro Val Leu Val Val Phe
            35                  40                  45

Asp Asp Ser Asp Arg Pro Ser Gly Ile Pro Glu Arg Phe Ser Gly Ser
        50                  55                  60

Thr Ser Gly Asn Thr Ala Ala Leu Thr Ile Ser Arg Val Glu Ala Gly
65              70                  75                  80

Asp Glu Ala Asp Tyr Tyr Cys Gln Val Trp Asp Ser Ser Asn Asp His
                85                  90                  95

Leu Tyr Val Phe Gly Pro Gly Thr Gln Leu Thr Val Leu
            100                 105

<210> SEQ ID NO 53
<211> LENGTH: 107
<212> TYPE: PRT
<213> ORGANISM: Artificial sequence
<220> FEATURE:
<223> OTHER INFORMATION: Light chain variable region of SC04-010

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Leu Gln Asp Tyr Asn Tyr Pro Arg
                85                  90                  95

Thr Phe Gly Gln Gly Thr Lys Val Glu Ile Lys
            100                 105

<210> SEQ ID NO 54
<211> LENGTH: 110
<212> TYPE: PRT
<213> ORGANISM: Artificial sequence
<220> FEATURE:
<223> OTHER INFORMATION: Light chain variable region of SC04-018

<400> SEQUENCE: 54

Gln Pro Val Leu Thr Gln Pro Leu Ser Ala Ser Gly Thr Pro Gly Gln
1               5                   10                  15

Arg Val Thr Ile Ser Cys Ser Gly Asp Thr Ser Asn Ile Gly Ser Asn
            20                  25                  30

Thr Val His Trp Tyr Gln Arg Leu Pro Gly Thr Ala Pro Lys Leu Leu
            35                  40                  45

Ile His Asn Asn Asn Gln Arg Pro Ser Gly Val Pro Asp Arg Phe Ser
        50                  55                  60

Gly Ala Lys Ser Gly Thr Ser Ala Ser Leu Ala Ile Ser Gly Leu Gln
65              70                  75                  80

Ser Glu Asp Glu Ala Asp Tyr Phe Cys Ala Ala Trp Asp Asp Asn Leu

```
                85                  90                  95
Asn Gly Tyr Val Phe Gly Thr Gly Thr Lys Val Thr Val Leu
            100                 105                 110

<210> SEQ ID NO 55
<211> LENGTH: 107
<212> TYPE: PRT
<213> ORGANISM: Artificial sequence
<220> FEATURE:
<223> OTHER INFORMATION: Light chain variable region of SC04-021

<400> SEQUENCE: 55

Asp Ile Gln Met Thr Gln Ser Pro Phe Ser Leu Ser Ala Ser Val Gly
1               5                   10                  15

Asp Arg Val Thr Ile Thr Cys Arg Ala Ser Gln Gly Ile Gly Ser Ser
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Leu Gln His His Asp Tyr Pro Leu
                85                  90                  95

Thr Phe Gly Gly Gly Thr Lys Leu Glu Ile Lys
            100                 105

<210> SEQ ID NO 56
<211> LENGTH: 112
<212> TYPE: PRT
<213> ORGANISM: Artificial sequence
<220> FEATURE:
<223> OTHER INFORMATION: Light chain variable region of SC04-026

<400> SEQUENCE: 56

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly His Asp Tyr Leu Asp Trp Tyr Val Gln Lys Pro Gly Gln Ser
        35                  40                  45

Pro Gln Pro Leu Ile Tyr Leu Gly Ser Asp Arg Ala Ser Gly Val Pro
    50                  55                  60

Asp Arg Phe Ser Gly Ser Gly Ser Gly Thr His Phe Thr Leu Asn Ile
65                  70                  75                  80

Ser Arg Val Glu Ala Glu Asp Val Gly Val Tyr Tyr Cys Met Gln Ser
                85                  90                  95

Leu Gln Thr Pro Trp Thr Phe Gly Gln Gly Thr Lys Leu Glu Ile Lys
            100                 105                 110

<210> SEQ ID NO 57
<211> LENGTH: 107
<212> TYPE: PRT
<213> ORGANISM: Artificial sequence
<220> FEATURE:
<223> OTHER INFORMATION: Light chain variable region of SC04-031

<400> SEQUENCE: 57

Asp Ile Gln Met Thr Gln Ser Pro Ser Phe Val Ser Ala Ser Val Gly
1               5                   10                  15
```

```
Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 58
<211> LENGTH: 107
<212> TYPE: PRT
<213> ORGANISM: Artificial sequence
<220> FEATURE:
<223> OTHER INFORMATION: Light chain variable region of SC04-038

<400> SEQUENCE: 58

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Gly Ile Ser Gly Trp
            20                  25                  30

Leu Ala Trp Tyr Gln Gln Lys Pro Glu Lys Ala Pro Lys Leu Leu Ile
        35                  40                  45

Tyr Ala Ala Ser Ser Leu Gln Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
                85                  90                  95

Thr Phe Gly Gln Gly Thr Arg Leu Glu Ile Lys
            100                 105

<210> SEQ ID NO 59
<211> LENGTH: 108
<212> TYPE: PRT
<213> ORGANISM: Artificial sequence
<220> FEATURE:
<223> OTHER INFORMATION: Light chain variable region of SC04-040

<400> SEQUENCE: 59

Gln Pro Val Leu Thr Gln Pro Pro Ser Val Ser Val Ala Pro Gly Gln
1               5                   10                  15

Thr Ala Arg Ile Ser Cys Gly Gly Asp Asn Ile Gly Thr Asn Thr Val
            20                  25                  30

Gln Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asp Thr Ala Thr Leu Thr Ile Ser Arg Val Glu Ala Gly
65                  70                  75                  80

Asp Glu Ala Asp Tyr Tyr Cys Gln Val Trp Asp Asp Ser Ser Asp Leu
                85                  90                  95

Val Val Phe Gly Gly Gly Thr Lys Val Thr Val Leu
```

<210> SEQ ID NO 60
<211> LENGTH: 107
<212> TYPE: PRT
<213> ORGANISM: Artificial sequence
<220> FEATURE:
<223> OTHER INFORMATION: Light chain variable region of SC04-060

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Thr Tyr
            20                  25                  30

Leu Asn Trp Tyr Gln Gln Lys Pro Gly Lys Ala Pro Asn Leu Leu Ile
        35                  40                  45

Tyr Gly Ala Ser Asn Leu Gln Ser Gly Val Pro Ser Arg Phe Ser Gly
    50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Thr Thr Pro Arg
                85                  90                  95

Thr Phe Gly Gln Gly Thr Lys Leu Glu Ile Lys
            100                 105

<210> SEQ ID NO 61
<211> LENGTH: 107
<212> TYPE: PRT
<213> ORGANISM: Artificial sequence
<220> FEATURE:
<223> OTHER INFORMATION: Light chain variable region of SC04-073

<400> SEQUENCE: 61

Asp Ile Gln Leu Thr Gln Ser Pro Ser Phe Leu Ser Ala Ser Val Gly
1               5                   10                  15

Asp Arg Val Thr Ile Thr Cys Arg Ala Ser His Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Arg
                85                  90                  95

Thr Phe Gly Gln Gly Thr Lys Leu Glu Ile Lys
            100                 105

<210> SEQ ID NO 62
<211> LENGTH: 107
<212> TYPE: PRT
<213> ORGANISM: Artificial sequence
<220> FEATURE:
<223> OTHER INFORMATION: Light chain variable region of SC04-097

<400> SEQUENCE: 62

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser His
            20                  25                  30

```
Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Ile
                85                  90                  95

Thr Phe Gly Gln Gly Thr Arg Leu Glu Ile Lys
            100                 105

<210> SEQ ID NO 63
<211> LENGTH: 107
<212> TYPE: PRT
<213> ORGANISM: Artificial sequence
<220> FEATURE:
<223> OTHER INFORMATION: Light chain variable region of SC04-098

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Pro
                85                  90                  95

Thr Phe Gly Gly Gly Thr Lys Val Glu Ile Lys
            100                 105

<210> SEQ ID NO 64
<211> LENGTH: 107
<212> TYPE: PRT
<213> ORGANISM: Artificial sequence
<220> FEATURE:
<223> OTHER INFORMATION: Light chain variable region of SC04-103

<400> SEQUENCE: 64

Asp Ile Gln Leu Thr Gln Ser Pro Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Arg Ser Leu Ile
            35                  40                  45

Tyr Asp Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asp Ser Phe Pro Ile
                85                  90                  95

Thr Phe Gly Gln Gly Thr Arg Leu Glu Ile Lys
            100                 105
```

-continued

<210> SEQ ID NO 65
<211> LENGTH: 109
<212> TYPE: PRT
<213> ORGANISM: Artificial sequence
<220> FEATURE:
<223> OTHER INFORMATION: Light chain variable region of SC04-104

<400> SEQUENCE: 65

Asp Ile Gln Leu Thr Gln Ser Pro Ser Thr Leu Ser Ala Ser Val Gly
1               5                   10                  15

Asp Arg Val Thr Ile Thr Cys Arg Ala Ser Gln Ile Leu Gly His Trp
            20                  25                  30

Leu Pro Leu Ser Trp Tyr Gln Gln Lys Pro Gly Lys Ala Pro Lys Leu
        35                  40                  45

Leu Ile Ser Lys Ala Ser Ser Leu Glu Ser Gly Val Pro Pro Arg Phe
    50                  55                  60

Ser Gly Ser Gly Ser Gly Ser Asp Phe Thr Leu Thr Ile Ser Ser Leu
65                  70                  75                  80

Gln Pro Asp Asp Phe Ala Thr Tyr Tyr Cys Leu Gln Tyr His Glu Tyr
                85                  90                  95

Pro Leu Thr Phe Gly Gly Gly Thr Lys Leu Glu Ile Lys
            100                 105

<210> SEQ ID NO 66
<211> LENGTH: 107
<212> TYPE: PRT
<213> ORGANISM: Artificial sequence
<220> FEATURE:
<223> OTHER INFORMATION: Light chain variable region of SC04-108

<400> SEQUENCE: 66

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser His
            20                  25                  30

Leu Val Trp Tyr Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Glu Ser Ala Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Ile
                85                  90                  95

Thr Phe Gly Gln Gly Thr Arg Leu Glu Ile Lys
            100                 105

<210> SEQ ID NO 67
<211> LENGTH: 107
<212> TYPE: PRT
<213> ORGANISM: Artificial sequence
<220> FEATURE:
<223> OTHER INFORMATION: Light chain variable region of SC04-120

<400> SEQUENCE: 67

Asp Ile Gln Leu Thr Gln Ser Pro Ser Thr Leu Ser Ala Ser Val Gly
1               5                   10                  15

Asp Arg Val Thr Ile Thr Cys Arg Ala Ser Gln Gly Ile Asn Ser Tyr
            20                  25                  30

Leu Ala Trp Tyr Gln Gln Glu Pro Gly Lys Ala Pro Lys Leu Leu Ile
        35                  40                  45

```
Tyr Ala Ala Ser Thr Leu Gln Ser Gly Val Pro Ser Arg Phe Ser Gly
            50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro Phe
                 85                  90                  95

Thr Phe Gly Pro Gly Thr Lys Val Asp Ile Lys
            100                 105

<210> SEQ ID NO 68
<211> LENGTH: 107
<212> TYPE: PRT
<213> ORGANISM: Artificial sequence
<220> FEATURE:
<223> OTHER INFORMATION: Light chain variable region of SC04-125

<400> SEQUENCE: 68

Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Gly Ile Ser Ser Tyr
                 20                  25                  30

Leu Ala Trp Tyr Gln Gln Lys Pro Gly Lys Ala Pro Lys Leu Leu Ile
             35                  40                  45

Tyr Asp Ala Ser Ser Leu Glu Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Leu Asn Ser Tyr Pro Leu
                 85                  90                  95

Thr Phe Gly Gly Gly Thr Lys Val Glu Ile Lys
            100                 105

<210> SEQ ID NO 69
<211> LENGTH: 109
<212> TYPE: PRT
<213> ORGANISM: Artificial sequence
<220> FEATURE:
<223> OTHER INFORMATION: Light chain variable region of SC04-126

<400> SEQUENCE: 69

Gln Ser Val Leu Thr Gln Pro Pro Ser Val Ser Val Ala Pro Gly Lys
  1               5                  10                  15

Thr Ala Arg Ile Thr Cys Gly Gly Asn Asn Ile Gly Ser Lys Ser Val
                 20                  25                  30

His Trp Tyr Gln Gln Lys Pro Gly Gln Ala Pro Val Leu Val Ile Tyr
             35                  40                  45

Tyr Asp Ser Asp Arg Pro Ser Gly Ile Pro Glu Arg Phe Ser Gly Ser
         50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Pro Tyr Val Phe Gly Thr Gly Thr Lys Leu Thr Val Leu
            100                 105

<210> SEQ ID NO 70
<211> LENGTH: 107
<212> TYPE: PRT
```

```
<213> ORGANISM: Artificial sequence
<220> FEATURE:
<223> OTHER INFORMATION: Light chain variable region of SC04-140

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 71
<211> LENGTH: 107
<212> TYPE: PRT
<213> ORGANISM: Artificial sequence
<220> FEATURE:
<223> OTHER INFORMATION: Light chain variable region of SC04-144

<400> SEQUENCE: 71

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Gly Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Leu Ala Thr Tyr Tyr Cys Gln Gln Tyr Asp Ser Tyr Pro Leu
                85                  90                  95

Thr Phe Gly Gly Gly Thr Lys Val Glu Ile Lys
            100                 105

<210> SEQ ID NO 72
<211> LENGTH: 107
<212> TYPE: PRT
<213> ORGANISM: Artificial sequence
<220> FEATURE:
<223> OTHER INFORMATION: Light chain variable region of SC04-146

<400> SEQUENCE: 72

Asp Val Val Met Thr Gln Ser Pro Ala Thr Leu Ser Val Ser Pro Gly
1               5                   10                  15

Glu Ser Ala Thr Leu Phe Cys Arg Ala Ser Glu Ser Val Tyr Ser Asn
            20                  25                  30

Leu Ala Trp Tyr Gln His Lys Pro Gly Arg Ala Pro Arg Leu Leu Ile
        35                  40                  45

Tyr Gly Ala Ser Thr Arg Ala Thr Gly Ile Pro Ala Arg Phe Asp Gly
    50                  55                  60
```

```
Thr Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asp Trp Pro Ile
                85                  90                  95

Thr Phe Gly Gln Gly Thr Arg Leu Glu Ile Lys
            100                 105

<210> SEQ ID NO 73
<211> LENGTH: 107
<212> TYPE: PRT
<213> ORGANISM: Artificial sequence
<220> FEATURE:
<223> OTHER INFORMATION: Light chain variable region of SC04-164

<400> SEQUENCE: 73

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Asp Ile Lys
            100                 105

<210> SEQ ID NO 74
<211> LENGTH: 351
<212> TYPE: DNA
<213> ORGANISM: Artificial sequence
<220> FEATURE:
<223> OTHER INFORMATION: Heavy chain variable region SC04-001

<400> SEQUENCE: 74
gaggtgcagc tggtggagtc tgggggaggt gtggtacggc ctgggggggtc cctgagactc      60 tcctgtgcag cctctggatt cacctttgat gattatggca tgagctgggt ccgccaagct     120
ccagggaagg ggctggagtg ggtctctggt attaattgga atggtggtag cacaggttat     180
gcagactctg tgaagggccg attcaccatc tccagagaca cgccaagaa ctccctgtat      240 ctgcaaatga acagtctgag agccgaggac acggccgtgt attactgtgc aaagggcctt     300
tatggggagc ttttttgacta ctggggccaa ggtaccctgg tcaccgtctc g              351

<210> SEQ ID NO 75
<211> LENGTH: 354
<212> TYPE: DNA
<213> ORGANISM: Artificial sequence
<220> FEATURE:
<223> OTHER INFORMATION: Heavy chain variable region of SC04-004

<400> SEQUENCE: 75
gaggtgcagc tggtggagtc tgggggaggc ttggtccagc ctgggggggtc cctgagactc     60 tcctgtgcag cctctggatt caccttcagc aactactgga tgaactgggt ccgccaggcg    120
cccgggaagg ggctggagtg ggtctcagct attagtggta gtggtggtag cacatactac    180
```

```
gcagactccg tgaagggccg gttcaccatc tccagagaca attccaagaa cacgctgtat    240
ctgcaaatga acagcctgag agccgaggac acggctgtgt attactgtgc caaagactac    300
ctctacccca ccaccgactt cgattactgg ggccagggca ccctggtgac cgtg          354
```

<210> SEQ ID NO 76
<211> LENGTH: 360
<212> TYPE: DNA
<213> ORGANISM: Artificial sequence
<220> FEATURE:
<223> OTHER INFORMATION: Heavy chain varaible region of SC04-008

<400> SEQUENCE: 76

```
caggtcacct tgaaggagtc tggtcctacg ctggtgaaac ccacacagac cctcacgctg    60
acctgcacct ctctctgggtt ctcactcagc actagtggag tgggtgtggg ctggatccgt   120
cagcccccag gaaaggccct ggagtggctt gcacgcattg attgggatga tgataaatac   180
tacagcacat ctctgaagac caggctcacc atctccaagg acacctccaa aaaccaggtg   240
gtccttacaa tgaccaacat ggaccctgtg acacagcca cgtattactg tgcacggatg    300
ggtttcactg gaacctactt tgactactgg ggccagggca cctggtcac cgtctcgagc    360
```

<210> SEQ ID NO 77
<211> LENGTH: 369
<212> TYPE: DNA
<213> ORGANISM: Artificial sequence
<220> FEATURE:
<223> OTHER INFORMATION: Heavy chain variable region of SC04-010

<400> SEQUENCE: 77

```
caggtgcagc tggtgcagtc tgggggagac ttggtccagc ctgggaggtc cctgagactc    60
tcctgtgcag cctctggatt caccttcagt agctatggca tgcactgggt ccgccaggct   120
ccaggcaagg ggctggagtg gtggcagat atatcatatg atggaagtaa taatactat   180 gcagactccg tgaagggccg attcaccatt tccagagaca attccaagaa cacgctgtat   240
ctgcaaatga acagcctgag agctgaggac acggctgtgt attactgtgc gaaagatggg   300
ctggatttaa ctggaacgat tcagccattt ggctactggg gccagggaac cctggtcacc   360
gtctcgagc                                                             369
```

<210> SEQ ID NO 78
<211> LENGTH: 357
<212> TYPE: DNA
<213> ORGANISM: Artificial sequence
<220> FEATURE:
<223> OTHER INFORMATION: Heavy chain variable region of SC04-018

<400> SEQUENCE: 78

```
gaggtgcagc tggtggagtc tggcccagga ctggtgaggc cttcgggac cctgtccctc     60 acctgcgctg tctctggtgg ctccatcagc agtagtaact ggtggagttg ggtccgccag   120
cccccaggga aggggctgga gtggattggg gaaatctatc atagtgggag caccaactac   180
aacccgtccc tcaagagtcg agtcaccata tcagtagaca gtccaagaa ccagttctcc    240 ctgaagctga gctctgtgac cgccgcggac acggccgtgt attactgtgc gagagtttct   300
gtgactacgg gtgctttaa tatctggggc aagggacaa tggtcaccgt ctcgagc        357
```

<210> SEQ ID NO 79
<211> LENGTH: 357
<212> TYPE: DNA
<213> ORGANISM: Artificial sequence

```
<220> FEATURE:
<223> OTHER INFORMATION: Heavy chain varaible region SC04-021

<400> SEQUENCE: 79
gaggtgcagc tggtggagtc tgggggaggc gtggtccagc ctggaggtc cctgagactc      60 tcctgtgcag cctctggatt caccttcagt agctatggca tgcactgggt ccgccaggct     120
ccaggcaagg ggctggagtg ggtggcagtt atatcatatg atggaagtag taaatattat    180
gcagactccg tgaagggccg attcaccatc tccagagaca attccaagaa cacgctgtat    240
ctgcaaatga acagcctgag agctgaggac acggctgtgt attactgtgc gaaagggtcc    300
gtcctcggtg atgcttttga tatctggggc caagggacaa tggtcaccgt ctcgagc      357

<210> SEQ ID NO 80
<211> LENGTH: 363
<212> TYPE: DNA
<213> ORGANISM: Artificial sequence
<220> FEATURE:
<223> OTHER INFORMATION: Heavy chain variable region of SC04-026

<400> SEQUENCE: 80
gaggtgcagc tggtggagtc tgagcagag gtgaagaagc cggggaatc tctgaagatc      60 tcctgtaagg gttctggata caactttccc tactcctgga tcgcctgggt gcgccagatg    120
cccgggaaag gcctggagtg gatggggatc atctttcctg gtgactctga caccagatat   180
agtccgccct tccaaggcca ggtcaccatc tcagccgaca actccaaaag cacggcctac    240
ctgcagtgga gtagcctgaa ggcctcggac accgccatgt attactgtgc gcggaccctcg   300 aactggaact atttggaccg gttcgacccc tggggccagg gcaccctggt caccgtctcg    360
agc                                                                   363

<210> SEQ ID NO 81
<211> LENGTH: 357
<212> TYPE: DNA
<213> ORGANISM: Artificial sequence
<220> FEATURE:
<223> OTHER INFORMATION: Heavy chain varaible region of SC04-031

<400> SEQUENCE: 81
gaggtgcagc tggtggagtc tgggggaggc gtggtccagc ctggaggtc cctgagactc      60 tcctgtgcag cctctggatt caccttcagt agctatggca tgcactgggt ccgccaggct    120
ccaggcaagg ggctggagtg ggtggcagtt atatcatatg atggaagtaa taaatactat    180
gcagactccg tgaagggccg attcaccatc tccagagaca attccaagaa cacgctgtat    240
ctgcaaatga acagcctgag agctgaggac acggctgtgt attactgtgc gaaagggtcc    300
gtcctcggtg atgcttttga tatctggggc caagggacaa tggtcaccgt ctcgagc      357

<210> SEQ ID NO 82
<211> LENGTH: 357
<212> TYPE: DNA
<213> ORGANISM: Artificial sequence
<220> FEATURE:
<223> OTHER INFORMATION: Heavy chain varaible region of SC04-038

<400> SEQUENCE: 82
caggtgcagc tggtgcaatc tgggggaggc gtggtccagc ctggaggtc cctgagactc      60 tcctgtgcag cctctggatt caccttcagt agctatggca tgcactgggt ccgccaggct    120
ccaggcaagg ggctggagtg ggtggcagtt atatcatatg atggaagtag taaatattat    180
```

```
gcagactccg tgaagggccg attcaccatc tccagagaca attccaagaa cacgctgtat    240
ctgcaaatga acagcctgag agctgaggac acggctgtgt attactgtgc gaaagggtcc    300
gtcctcggtg atgctttga tatctggggc caagggacaa tggtcaccgt ctcgagc       357
```

<210> SEQ ID NO 83
<211> LENGTH: 354
<212> TYPE: DNA
<213> ORGANISM: Artificial sequence
<220> FEATURE:
<223> OTHER INFORMATION: Heavy chain variable region of SC04-040

<400> SEQUENCE: 83

```
caggtgcagc tggtgcagtc tgggggaggc gtggtccagc ctggggaggtc cctgagactc    60 tcctgtgcag cctctggatt caccttcggt agctatggca tgcactgggt ccgccaggct   120
ccaggcaagg ggctggagtg ggtggcaact atattctatg atggaagtta aaagactat    180 gcagactccg tgaagggccg attcaccatc tccagagaca attccaagaa cacgctgtat   240
ctgcaaatga acagcctgag agctgaggac acggctgtgt attactgtgc gaaaggcagt   300
aaggtaggcg actttgacta ctggggccag ggaaccctgg tcaccgtctc gagc         354
```

<210> SEQ ID NO 84
<211> LENGTH: 384
<212> TYPE: DNA
<213> ORGANISM: Artificial sequence
<220> FEATURE:
<223> OTHER INFORMATION: Heavy chain variable region of SC04-060

<400> SEQUENCE: 84

```
caggtgcagc tggtggagtc tggcccagga ctggtgaagg cttcggagac cctgtccctc     60
acttgcacgg tctctgatgg ctccatcagt agtttctact ggagctggat ccggcagccc   120
cccgggaagg gactggagtg ggttggggaa atccaggaca ctgggaggac caattacaac   180
ccctccctca agagtcgagt cactatatca ctagacacg ccaagaacca gttctccctg    240
acgttgagct ctgtgaccgc tgcggacacg gccgtgtatt actgcgcgag agagaaggag   300
aaatactctg atagaagcgg ttattcgtac tactactatt acatggacgt ctggggcaaa   360
gggaccacgg tcaccgtctc gagc                                          384
```

<210> SEQ ID NO 85
<211> LENGTH: 369
<212> TYPE: DNA
<213> ORGANISM: Artificial sequence
<220> FEATURE:
<223> OTHER INFORMATION: Heavy chain variable region of SC04-073

<400> SEQUENCE: 85

```
caggtgcagc tggtgcagtc tgggggaggc gtggcccagc ctggggaggtc cctgagactc    60 tcctgtgcag cgtctggatt caccttcagt agttatggca tgcactgggt ccgccaggct   120
ccaggcaagg ggctggagtg ggtggcagat atatcatatg atggaagtaa taaatactat   180
gcagactccg tgaagggccg attcaccatt tccagagaca attccaagaa cacgctgtat   240
ctgcaaatga acagcctgag agctgaggac acggctgtgt attactgtgc gaaagatggg   300
ctggatttaa ctggaacgat tcagccattt ggctactggg gccagggcac cctggtcacc   360
gtctcgagc                                                           369
```

<210> SEQ ID NO 86
<211> LENGTH: 369

<212> TYPE: DNA
<213> ORGANISM: Artificial sequence
<220> FEATURE:
<223> OTHER INFORMATION: Heavy chain variable region of SC04-097

<400> SEQUENCE: 86

| | |
|---|---|
| caggtgcagc tggtgcagtc tgggggagac ttggtccagc ctggggaggtc cctgagactc | 60 |
| tcctgtgcag cctctggatt caccttcagt agctatggca tgcactgggt ccgccaggct | 120 |
| ccaggcaagg gctggagtg gtggcagat atatcatatg atggaagtaa taaatactat | 180 |
| gcagactccg tgaagggccg attcaccatt tccagagaca attccaagaa cacgctgtat | 240 |
| ctgcaaatga acagcctgag agctgaggac acggctgtgt attactgtgc gaaagatggg | 300 |
| ctggatttaa ctggaacgat tcagccattt ggctactggg gccagggaac cctggtcacc | 360 |
| gtctcgagc | 369 |

<210> SEQ ID NO 87
<211> LENGTH: 357
<212> TYPE: DNA
<213> ORGANISM: Artificial sequence
<220> FEATURE:
<223> OTHER INFORMATION: Heavy chain variable region of SC04-098

<400> SEQUENCE: 87

| | |
|---|---|
| gaagtgcagc tggtgcagtc tgggggaggc gcggtccagc ctggggaggtc cctgagactc | 60 |
| tcctgtgcag cctctggatt caccttcagt agctatggca tgcactgggt ccgccaggct | 120 |
| ccaggcaagg gctggagtg gtggctgtt atattatatg atggaagtga taaattctat | 180 |
| gcagactccg tgaagggccg attcaccatc tccagagaca attccaagaa cacgctgtat | 240 |
| ctgcagatga acagcctgag agctgaggac acggctgtgt attactgtgc gaaagtagca | 300 |
| gtggctggta cgcactttga ctactggggc cagggaaccc tggtcaccgt ctcgagc | 357 |

<210> SEQ ID NO 88
<211> LENGTH: 357
<212> TYPE: DNA
<213> ORGANISM: Artificial sequence
<220> FEATURE:
<223> OTHER INFORMATION: Heavy chain variable region of SC04-103

<400> SEQUENCE: 88

| | |
|---|---|
| caggtgcagc tgcaggagtc gggggaggc gtggtccagc ctggggaggtc cctgagactc | 60 |
| tcctgtgcag cctctggatt caccttcagt agctatggca tgcactgggt ccgccaggct | 120 |
| ccaggcaagg gctggagtg gtggcagtt atattatatg atggaagtga taaatactat | 180 |
| gcagactccg tgaagggccg attcaccatc tccagagaca attccaagaa cacgctgtat | 240 |
| ctgcaaatga acagcctgag agctgaggac acggctgtgt attactgtgc gaaagtcgct | 300 |
| gtggctgggg aaagctttga ctcctggggc cggggcaccc tggtcaccgt ctcgagc | 357 |

<210> SEQ ID NO 89
<211> LENGTH: 363
<212> TYPE: DNA
<213> ORGANISM: Artificial sequence
<220> FEATURE:
<223> OTHER INFORMATION: Heavy chain variable region of SC04-104

<400> SEQUENCE: 89

| | |
|---|---|
| caggtgcagc tgcaggagtc gggggaggc gtggtccagc ctggggaggtc cctgagactc | 60 |
| tcctgtgcag cctctggatt caccttcagt agctatggca tgcactgggt ccgccaggct | 120 |

```
ccaggcaagg ggctggagtg ggtggcaact atatcatatg atggaaatgt taaagactat    180
gcagactccg tgaagggccg attcaccatc tccagagaca attccaagaa cacgctgtat    240
ctgcaaatga acagcctgag aactgaggac acggctgtgt attactgtgc gaaaatagtg    300
gtggtgaccg ccctcgatgc ttttgatatc tggggccaag ggacaatggt caccgtctcg    360
agc                                                                  363
```

```
<210> SEQ ID NO 90
<211> LENGTH: 360
<212> TYPE: DNA
<213> ORGANISM: Artificial sequence
<220> FEATURE:
<223> OTHER INFORMATION: Heavy chain varaible region of SC04-108

<400> SEQUENCE: 90
gaagtgcagc tggtgcagtc tgggggaggc ttggtacagc ctggggggtc cctgagactc     60
tcctgtgcag cgtctggatt caccttcagt agctatggca tgcactgggt ccgccaggct    120
ccaggcaagg ggctggagtg ggtggcagtt atattatatg atggaagtga taagttctat    180
gcagactccg tgaagggccg attcaccatc tccagagaca attccaagga cacgctgtat    240
ctgcaaatga acagcctgag agctgaggac acggctgtgt attactgtgc gaaatttatg    300
atagtagcag atgatgcttt tgatatctgg ggccaaggga caatggtcac cgtctcgagc    360
```

```
<210> SEQ ID NO 91
<211> LENGTH: 354
<212> TYPE: DNA
<213> ORGANISM: Artificial sequence
<220> FEATURE:
<223> OTHER INFORMATION: Heavy chain variable region of SC04-120

<400> SEQUENCE: 91
gaggtgcagc tggtgcagtc tgggggaggc ttggtacagc ctggcaggtc cctgagactc     60
tcctgtgcag cctctggatt caccttcagt acctatggca tgcactgggt ccgccaggct    120
ccaggcaagg ggctggagtg ggtggcaact atatcatatg atggaagtat taaagactat    180
gcagactccg agaagggccg attcaccatc tccagagaca attccaagaa cacgctgtat    240
ctgcaaatga acagcctgag agctgaggac acggctgtgt attactgtgc gaaagggggg    300
aagactggag agtttgacta ctggggccag ggaaccctgg tcaccgtctc gagc           354
```

```
<210> SEQ ID NO 92
<211> LENGTH: 357
<212> TYPE: DNA
<213> ORGANISM: Artificial sequence
<220> FEATURE:
<223> OTHER INFORMATION: Heavy chain variable region of SC04-125

<400> SEQUENCE: 92
caggtgcagc tggtggagtc tgggggaggc gtggtccagc ctggggaggtc cctgagactc    60 tcctgtgcag cctctggatt caccttcagt agctatggca tgcactgggt ccgccaggct    120
ccaggcaagg ggctggagtg ggtggcagtt atatcatatg atggaagtga taaatactat    180
gcagactccg tgaagggccg attcaccatc tccagagaca attccaagaa cacgctctat    240
ctgcaaatga acagcttgag agctgaggac acggctgtgt attactgtgc gaagatagca    300
acagctggta ccgggtttga ctactggggc cagggaaccc tggtcaccgt ctcgagc       357
```

```
<210> SEQ ID NO 93
<211> LENGTH: 360
```

<212> TYPE: DNA
<213> ORGANISM: Artificial sequence
<220> FEATURE:
<223> OTHER INFORMATION: Heavy chain variable region of SC04-126

<400> SEQUENCE: 93

```
caggtcacct tgaaggagtc tggtcccacg ctggtgaacc ccacacagac cctcacgttg      60
acctgcacct tctctgggtt ctcgctcagc actggtggag tgggtgtggg ctggttccgt     120
cagcccccag ggaaggccct ggagtggctt gcacgcattg attgggatga tgataaatac     180
tacagcacat ctctgaagac caggctcacc atctccaagg acacctccaa aatccaggtg     240
gtccttacaa tgaccaacat ggaccctgtg acacagcca cgtattactg tgcacggatg      300
ggtttcactg gaacctactt tgactactgg ggccagggca ccctggtcac cgtctcgagc     360
```

<210> SEQ ID NO 94
<211> LENGTH: 357
<212> TYPE: DNA
<213> ORGANISM: Artificial sequence
<220> FEATURE:
<223> OTHER INFORMATION: Heavy chain variable region of SC04-140

<400> SEQUENCE: 94

```
cagatgcagc tggtgcagtc tgggggaggc gtggtccagc ctgggaggtc cctgagactc      60
tcctgtgcag cctctggatt caccttcagt agctatggca tgcactgggt ccgccaggct     120
ccaggcaagg ggctggagtg ggtggcagtt atattatatg atggaagtaa taaatactat     180
gcagactccg tgaagggccg attcaccatc tccagagaca attccaagaa cgcgttgtat     240
ctgcaaatga acagcctgag agctgaggac acggctgtgt attactgtgc gaaggtgacc     300
aaccccggag atgcttttga tatctggggc caagggacca tggtcaccgt ctcgagc      357
```

<210> SEQ ID NO 95
<211> LENGTH: 354
<212> TYPE: DNA
<213> ORGANISM: Artificial sequence
<220> FEATURE:
<223> OTHER INFORMATION: Heavy chain variable region of SC04-144

<400> SEQUENCE: 95

```
caggtgcagc tgcaggagtt gggggggaggc gtggtccagc ctgggaggtc cctgagactc      60
tcctgtgcag cctctggatt caccttcggt agctatggca tgcactgggt ccgccaggct     120
ccgggcaagg ggctggagtg ggtggcaact atatcatatg atggaagtat taaagactat     180
gcagactccg agaagggccg attcaccatc tccagagaca attccaagaa cacactgtat     240
ctgcaaatga acagcctgag agctgaggac acggctgtgt attactgtgc gaaaggggg      300
aagactggag agtttgacta ctggggccag ggaaccctgg tcaccgtctc gagc         354
```

<210> SEQ ID NO 96
<211> LENGTH: 354
<212> TYPE: DNA
<213> ORGANISM: Artificial sequence
<220> FEATURE:
<223> OTHER INFORMATION: Heavy chain variable region of SC04-146

<400> SEQUENCE: 96

```
gaagtgcagc tggtgcagtc tgggggaggc gtggtccagc ctgggaggtc cctgagactc      60
tcctgtgcag cctctggatt caccttcagt agctatggca tgcactgggt ccgccaggct     120
ccgggcaagg ggctggagtg ggtggcaact atatcatatg atggaagtat taaagactat     180
```

```
gcagactccg aggagggccg attcaccatc tccagagaca attccaagaa cacactgtat    240
ctgcaaatga acagcctgag agctgaggac acggctgtgt attactgtgc gaaagggggg    300
aagactggag agtttgacta ctggggccag ggcaccctgg tcaccgtctc gagc          354

<210> SEQ ID NO 97
<211> LENGTH: 357
<212> TYPE: DNA
<213> ORGANISM: Artificial sequence
<220> FEATURE:
<223> OTHER INFORMATION: Heavy chain variable region of SC04-164

<400> SEQUENCE: 97
gaggtgcagc tggtggagtc tggggggggc gtggtccagc ctggggaggtc cctgagactc    60 tcctgtgcag cctctggatt caccttcagt agctatggca tgcactgggt ccgccaggct   120
ccaggcaagg ggctggagtg ggtggcagtt atatcatatg atggaagcag taaatactac   180
gcagactccg tgaagggccg attcaccatc tccagagaca attccaagaa cacgctgtat   240
ctgcaaatga acagcctgag agctgaggac acggctgtgt attactgtgc gaaagggtcc   300
gtcctcggtg atgcttttga tatctggggc caagggacaa tggtcaccgt ctcgagc      357

<210> SEQ ID NO 98
<211> LENGTH: 324
<212> TYPE: DNA
<213> ORGANISM: Artificial sequence
<220> FEATURE:
<223> OTHER INFORMATION: Light chain varaible region of SC04-001

<400> SEQUENCE: 98
tcgtctgagc tgactcagga ccctgctgtg tctgtggcct tgggacagac agtcaggatc    60
acatgccaag agacagcct cagaagctat tatgcaagct ggtaccagca gaagccagga   120
caggcccctg tacttgtcat ctatggtaaa acaaccggc cctcagggat cccagaccga   180
ttctctggct ccagctcagg aaacacagct tccttgacca tcactgggc tcaggcggaa   240 gatgaggctg actattactg taactcccgg gacagcagtg taaccatgt ggtattcggc   300 ggagggacca agctgaccgt ccta                                          324

<210> SEQ ID NO 99
<211> LENGTH: 309
<212> TYPE: DNA
<213> ORGANISM: Artificial sequence
<220> FEATURE:
<223> OTHER INFORMATION: Light chain variable region of SC04-004

<400> SEQUENCE: 99
acccagtctc catcctccct gtctgcatct gtaggagaca gagtcaccat cacttgccgg    60
gcaagtcaga gcattagcag ctacttaaat tggtatcagc agaaaccagg gaaagcccct   120
aagctcctga tctatgctgc atccagtttg caaagtgggg tcccatcaag gttcagtggc   180
agtggatctg ggacagattt cactctcacc atcagcagtc tgcaacctga agattttgca   240
acttactact gtcaacagag ttacagtacc cctccaacgt tcggccaagg gaccaaggtg   300
gagatcaaa                                                           309

<210> SEQ ID NO 100
<211> LENGTH: 327
<212> TYPE: DNA
<213> ORGANISM: Artificial sequence
<220> FEATURE:
<223> OTHER INFORMATION: Light chain variable region of SC04-008
```

<400> SEQUENCE: 100

```
caggctgtgc tgactcagcc gtcctcggtg tcagtggccc caggagagac ggccagcgtt      60
acctgtgggg gagacaacat tgggagtaag agtgtgcact ggtaccaaaa gaagccaggc     120
caggcccctg tgctggtcgt ctttgatgat agcgaccggc cctcagggat ccctgagcga     180
ttctctggct ccacctctgg gaacacggcc gccctgacca tcagcagggt cgaagccggg     240
gatgaggccg actattactg tcaggtgtgg gatagtagta tgatcatct ttatgtcttc     300 ggacccggga cccagctcac cgttta                                         327
```

<210> SEQ ID NO 101
<211> LENGTH: 321
<212> TYPE: DNA
<213> ORGANISM: Artificial sequence
<220> FEATURE:
<223> OTHER INFORMATION: Light chain variable region of SC04-010

<400> SEQUENCE: 101

```
gacatccaga tgacccagtc tccatcctcc ctgtctgcat ctgtaggaga cagagtcacc      60
atcacttgcc gggcaagtca gggcattaga aatgatttag ctggtatca gcagaaacca     120 gggaaagccc ctaagctcct gatctatgct gcatccagtt tacaaagtgg ggtcccatca     180
aggttcagcg gcagtggatc tgggacagat ttcactctca ccatcagcag cctgcagcct     240
gaagattttg caacttatta ctgtctacaa gattacaatt accctcggac gttcggccaa     300
gggaccaagg tggagatcaa a                                             321
```

<210> SEQ ID NO 102
<211> LENGTH: 330
<212> TYPE: DNA
<213> ORGANISM: Artificial sequence
<220> FEATURE:
<223> OTHER INFORMATION: Light chain variable region of SC04-018

<400> SEQUENCE: 102

```
cagcctgtgc tgactcagcc cctctcagcg tctgggaccc ccgggcagag ggtcaccatc      60
tcttgttctg gagacacctc caacatcgga agtaatactg tacactggta ccagcgcctc     120
ccaggaacgg cccccaaact cctcatccat aataataatc agcggccctc agggggtccct   180 gaccggttct ctggcgccaa gtctggcacc tcagcctccc tggccatcag tgggctccag     240
tctgaggatg aggctgatta tttctgtgca gcatgggatg acaacctgaa tggttatgtc     300
ttcggaactg ggaccaaggt caccgtccta                                      330
```

<210> SEQ ID NO 103
<211> LENGTH: 321
<212> TYPE: DNA
<213> ORGANISM: Artificial sequence
<220> FEATURE:
<223> OTHER INFORMATION: Light chain variablre region of SC04-021

<400> SEQUENCE: 103

```
gacatccaga tgacccagtc tccattctcc ctgtctgctt ctgtcggaga cagagttacc      60
atcacttgcc gggccagtca gggcattggc agttccttag cctggtatca gcaaaaacca     120
gggaaagccc ctaaactcct gatctacgct gcatccagtt tgcaaagtgg ggtcccatca     180
aggttcagcg gcagtggatc tgggacagat ttcactctca ccatcagcag cctgcagcct     240
gaagattttg caacttattt ctgtctgcag catcatgatt acccgctcac tttcggcgga     300
```

```
gggaccaagc tggagatcaa a                                              321
```

<210> SEQ ID NO 104
<211> LENGTH: 336
<212> TYPE: DNA
<213> ORGANISM: Artificial sequence
<220> FEATURE:
<223> OTHER INFORMATION: Light chain variable region of SC04-026

<400> SEQUENCE: 104

```
gatgttgtga tgactcagtc tccactctcc ctgcccgtca cccctggaga gccggcctcc     60
atctcctgca ggtctagtca gagcctcctg catagtaatg acatgattta cttggattgg    120
tacgtgcaga agccagggca gtctccacag cccctgatct atttgggttc tgatcgggcc    180
tccggggtcc ctgacaggtt cagtggcagt ggatcaggca cagattttac actgaatatc    240
agcagagtgg aggctgagga tgttggggtt tattactgca tgcaatctct acaaactcct    300
tggactttg gccaggggac caagctggag atcaaa                              336
```

<210> SEQ ID NO 105
<211> LENGTH: 321
<212> TYPE: DNA
<213> ORGANISM: Artificial sequence
<220> FEATURE:
<223> OTHER INFORMATION: Light chain variable region of SC04-031

<400> SEQUENCE: 105

```
gacatccaga tgacccagtc tccatctttc gtgtctgcat ctgtaggaga cagagtcacc     60
atcacttgtc gggcgagtca gggtattagc agttggttag cctggtatca gcagaaacca    120
gggaaagccc ctaagctcct gatctatgct gcatccagtt tgcaaagtgg ggtcccatca    180
aggttcagcg gcagtggatc tgggacagat ttcactctca ccatcagcag cctgcagcct    240
gaagattttg caacttacta ttgtcaacag gctaacagtt cccactcac tttcggcgga    300
gggaccaagg tggagatcaa a                                              321
```

<210> SEQ ID NO 106
<211> LENGTH: 321
<212> TYPE: DNA
<213> ORGANISM: Artificial sequence
<220> FEATURE:
<223> OTHER INFORMATION: Light chain variable region of SC04-038

<400> SEQUENCE: 106

```
gacatccagt tgactcagtc tccatcttcc gtgtctgcat ctgtaggaga cagagtcacc     60
atcacttgtc gggcgagtca gggtattagc ggctggttag cctggtatca gcagaaacca    120
gagaaagccc ctaagctcct gatctatgcg gcatccagtt tgcaacgtgg ggtcccatca    180
aggttcagcg gcagtggatc tgggacagat ttcactctca ccatcagcag cctgcagcct    240
gaagattttg caacttacta ttgtcaacag gctaacagtt cccccccac cttcggccaa    300
gggacacgac tggagattaa a                                              321
```

<210> SEQ ID NO 107
<211> LENGTH: 324
<212> TYPE: DNA
<213> ORGANISM: Artificial sequence
<220> FEATURE:
<223> OTHER INFORMATION: Light chain variable region of SC04-040

<400> SEQUENCE: 107

```
cagcctgtgc tgactcagcc cccctcggtg tcagtggccc caggacagac ggccaggatt     60
```

```
tcctgtgggg gagacaacat tggaactaat actgtgcagt ggtaccagca gaagccaggc      120
caggcccctg tcctggtcgt ctatgatgat agcgaccggc cctcaggat ccctgagcga       180 ttctctggct ccaactctgg ggacacggcc accctgacca tcagcagggt cgaggccggg      240
gatgaggccg attattactg tcaggtgtgg gatgacagta gtgatctggt ggtattcggc      300
ggagggacca aggtcaccgt ccta                                             324

<210> SEQ ID NO 108
<211> LENGTH: 321
<212> TYPE: DNA
<213> ORGANISM: Artificial sequence
<220> FEATURE:
<223> OTHER INFORMATION: Light chain variable region of SC04-060

<400> SEQUENCE: 108
gacatccaga tgacccagtc tccatcctcc ctgtctgcat ctgtaggaga cagagtcacc       60
atcacttgcc gggcaagtca gggcattagc acctatttaa attggtatca gcagaaacca      120
gggaaagccc ctaacctcct gatctacggt gcatctaatt tgcaaagtgg ggtcccatca      180
aggttcagtg gcagtgaatc tgggacagat ttcactctca ccatcagcag tctacaacct      240
gaagattttg caacttacta ctgtcagcag agtttcacta cccctcgcac gttcggccaa      300
gggaccaagc tggagatcaa a                                                321

<210> SEQ ID NO 109
<211> LENGTH: 321
<212> TYPE: DNA
<213> ORGANISM: Artificial sequence
<220> FEATURE:
<223> OTHER INFORMATION: Light chain variable region of SC04-073

<400> SEQUENCE: 109
gacatccagt tgacccagtc gccatccttc ctgtctgcat ctgtaggaga cagagtcacc       60
atcacttgcc gggccagtca cagtattagt agctggttgg cctggtatca gcagaaacca      120
gggaaagccc ctaagctcct gatctataag gcatctagtt tagaaagtgg ggtcccatca      180
aggttcagcg gcagtggatc tgggacagat ttcactctca ccatcagcag cctgcagcct      240
gaagattttg caacttatta ctgtctacaa gattacaatt accctcggac gttcggccaa      300
gggaccaagc tggagatcaa a                                                321

<210> SEQ ID NO 110
<211> LENGTH: 321
<212> TYPE: DNA
<213> ORGANISM: Artificial sequence
<220> FEATURE:
<223> OTHER INFORMATION: Light chain variable region of SC04-097

<400> SEQUENCE: 110
gacatccaga tgacccagtc tccatcctcc ctgtctgcat ctgtaggaga cagagtcacc       60
atcacttgcc gggcaagtca ggcattaga aatgatttag gctggtatca gcagaaacca       120
gggaaagccc ctaagctcct gatctatgct gcatccagtt tacaaagtgg ggtcccatca      180
aggttcagcg gcagtggatc tggcacagat ttcactctca ccatcagcag cctgcagcct      240
gaagattttg caacttatta ctgtctacaa gattacaatt accctcggac gttcggccaa      300
gggaccaagg tggagatcaa a                                                321

<210> SEQ ID NO 111
```

```
<211> LENGTH: 321
<212> TYPE: DNA
<213> ORGANISM: Artificial sequence
<220> FEATURE:
<223> OTHER INFORMATION: Light chain variable region of SC04-098

<400> SEQUENCE: 111
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagctcct gatctatgct gcatccagtt tgcaaagtgg ggtcccatca   180
aggttcagcg gcagtggatc tgggacagat ttcactctca ccatcagcag cctgcagcct   240
gaagattttg caacttatta ctgtcaacag cttaatagtt accctcccac tttcggcgga   300
gggaccaagg tggaaatcaa a                                             321

<210> SEQ ID NO 112
<211> LENGTH: 321
<212> TYPE: DNA
<213> ORGANISM: Artificial sequence
<220> FEATURE:
<223> OTHER INFORMATION: Light chain variable region of SC04-103

<400> SEQUENCE: 112
gacatccagt tgacccagtc tccatcttcc gtgtctgcat ctgtaggaga cagagtcacc    60
atcacttgtc gggcgagtca gggtattagc agctggttag cctggtatca gcagaagcca   120
gggaaagccc ctaggtccct gatctatgat gcatccagtt tgcaaagtgg ggtcccatca   180
aggttcagcg gcagtggatc tgggacagac tttactctca ccatcagcag cctgcagcct   240
gaagattttg caacttacta ttgtcaacag gctgacagtt cccgatcac cttcggccaa   300 gggacacgac tggagattaa a                                             321

<210> SEQ ID NO 113
<211> LENGTH: 327
<212> TYPE: DNA
<213> ORGANISM: Artificial sequence
<220> FEATURE:
<223> OTHER INFORMATION: Light chain variable region of SC04-104

<400> SEQUENCE: 113
gacatccagt tgacccagtc tccttccacc ctgtctgcat ctgtaggaga cagagtcacc    60
atcacttgcc gggccagtca gattcttggt cactggttgc ccttgtcctg gtatcagcag   120
aaaccaggta aagcccctaa actcctgatc tctaaggcgt ctagtttaga aagtggagtc   180
ccaccaaggt tcagcggcag tggatctggg tcagatttca ctctcaccat cagcagcctg   240
cagcccgatg attttgcaac ttattactgc ctccaatatc atgagtaccc gctcaccttc   300
ggcggaggga ccaagctgga gatcaaa                                       327

<210> SEQ ID NO 114
<211> LENGTH: 321
<212> TYPE: DNA
<213> ORGANISM: Artificial sequence
<220> FEATURE:
<223> OTHER INFORMATION: Light chain variable region of SC04-108

<400> SEQUENCE: 114
gacatccagt tgacccagtc tccatcctca ctgtctgcat ctgtaggaga cagagtcacc    60
atcacttgtc gggcgagtca ggcattagc agtcatttag tctggtatca gcagaaacca   120
gggaaagccc ctaagtccct gatctatgct gcatccagtt tgcaaagtgg ggtcccatca   180
```

```
aggttcagcg gcagtgaatc tgcgacagat ttcactctca ccatcagcag cctgcagcct      240
gaagattttg caacttatta ctgccaacag tattacagtt accctatcac cttcggccaa      300
gggacacgac tggagattaa a                                                321
```

<210> SEQ ID NO 115
<211> LENGTH: 321
<212> TYPE: DNA
<213> ORGANISM: Artificial sequence
<220> FEATURE:
<223> OTHER INFORMATION: Light chain variable region of SC04-120

<400> SEQUENCE: 115

```
gacatccagt tgacccagtc tccttccacc ctgtctgcat ctgtaggaga cagagtcacc      60
atcacttgcc gggccagtca gggcattaac agttatttag cctggtatca gcaagaacca     120
gggaaagccc ctaaactcct gatctatgct gcatccactt tgcaaagtgg ggtcccatca     180
aggttcagcg gcagtggatc tgggacagaa ttcactctca caatcagcag cctgcagcct     240
gaagattttg caacttatta ctgtcaacag cttaatagtt accccttcac tttcggccct     300
gggaccaaag tggatatcaa a                                               321
```

<210> SEQ ID NO 116
<211> LENGTH: 321
<212> TYPE: DNA
<213> ORGANISM: Artificial sequence
<220> FEATURE:
<223> OTHER INFORMATION: Light chain variable region of SC04-125

<400> SEQUENCE: 116

```
gacatccaga tgacccagtc tccatcttcc gtgtctgcat ctgtaggaga cagagtcacc      60
atcacttgtc gggcgagtca gggcattagc agttatttag cctggtatca gcaaaaacca     120
gggaaagccc ctaagctcct gatctatgat gcctccagtt tggaaagtgg ggtcccatca     180
aggttcagcg gcagtggatc tgggacagaa ttcactctca ccatcagcag cctgcagcct     240
gatgattttg caacttatta ctgtcaacaa cttaacagtt acccactcac tttcggcgga     300
gggaccaagg tggagatcaa a                                               321
```

<210> SEQ ID NO 117
<211> LENGTH: 327
<212> TYPE: DNA
<213> ORGANISM: Artificial sequence
<220> FEATURE:
<223> OTHER INFORMATION: Light chain variable region of SC04-126

<400> SEQUENCE: 117

```
cagtctgtgc tgactcagcc accctcagtg tcagtggccc caggaaagac ggccaggatt      60
acctgtgggg gaaacaacat tggaagtaaa agtgtgcact ggtaccagca gaagccaggc     120
caggcccctg tgctggtcat ctattatgat agcgaccggc cctcagggat ccctgagcga     180
ttctctggct ccaactctgg gaacacggcc accctgacca tcagcagggt cgaagccggg     240
gatgaggctg actattactg tcaggtgtgg gatagtagta gtgatcatcc ctatgtcttc     300
ggaactggga ccaagctgac cgtccta                                         327
```

<210> SEQ ID NO 118
<211> LENGTH: 321
<212> TYPE: DNA
<213> ORGANISM: Artificial sequence
<220> FEATURE:

<223> OTHER INFORMATION: Light chain variable region of SC04-140

<400> SEQUENCE: 118

| | |
|---|---|
| gacatccaga tgacccagtc tccatcctcc ctgtctgcat ctgtcggaga cagagtcacc | 60 |
| atcacttgcc gggcaagtca gggcattagc agtgctttag cctggtatca gcagaaacca | 120 |
| gggaaagctc ctaagctcct gatctatgat gcctccagtt tggaaagtgg ggtcccatca | 180 |
| aggttcagcg gcagtggatc tgggacagat ttcactctca ccatcagcag cctgcagcct | 240 |
| gaagattttg caacttatta ctgtcaacag tttaatagtt acccgctcac tttcggcgga | 300 |
| gggaccaagg tggaaatcaa a | 321 |

<210> SEQ ID NO 119
<211> LENGTH: 321
<212> TYPE: DNA
<213> ORGANISM: Artificial sequence
<220> FEATURE:
<223> OTHER INFORMATION: Light chain variable region of SC04-144

<400> SEQUENCE: 119

| | |
|---|---|
| gacatccagt tgacgcagtc tccatcctcc ctgtctgcat ctgtaggaga cagagtcacc | 60 |
| atcacttgcc gggccagtca gggcattagc agttatttag cctggtatca gcaaaaacca | 120 |
| gggaaaggcc ctaagctcct gatctatgct gcatccactt tacaaagtgg ggtcccatca | 180 |
| aggttcagcg gcagtggatc tgggacagac ttcagtctca ccatcagtag cctgcagcct | 240 |
| gaagatttag caacttatta ctgccaacag tatgatagtt accctctcac tttcggcgga | 300 |
| gggaccaagg tggaaatcaa a | 321 |

<210> SEQ ID NO 120
<211> LENGTH: 321
<212> TYPE: DNA
<213> ORGANISM: Artificial sequence
<220> FEATURE:
<223> OTHER INFORMATION: Light chain variable region of SC04-146

<400> SEQUENCE: 120

| | |
|---|---|
| gatgttgtga tgactcagtc tccagccacc ctgtctgtgt ctccagggga aagcgccaca | 60 |
| ctcttctgca gggccagtga gagtgtttat agcaacttgg cctggtatca gcacaaacct | 120 |
| ggccgggctc ccaggctcct catctatggt gcatccacca gggccactgg tatcccagcc | 180 |
| aggttcgatg gcactgggtc tgggacagac ttcacactca ccatcagcag cctgcagtct | 240 |
| gaagattttg cagtttatta ctgtcagcaa tataatgact ggccgatcac cttcggccaa | 300 |
| gggacacgac tggagattaa a | 321 |

<210> SEQ ID NO 121
<211> LENGTH: 321
<212> TYPE: DNA
<213> ORGANISM: Artificial sequence
<220> FEATURE:
<223> OTHER INFORMATION: Light chain variable region of SC04-164

<400> SEQUENCE: 121

| | |
|---|---|
| gacatccagt tgacccagtc tccatcttct gtgtctgcat ctgtaggaga cagagtcacc | 60 |
| atcacttgtc gggcgagtca gggtattagc agctggttag cctggtatca gcagaaacca | 120 |
| gggaaagccc ctaagctcct gatctatgct gcatccagtt tgcaaagtgg ggtcccatca | 180 |
| aggttcagcg gcagtggatc tgggacagat ttcactctca ctatcagcag cctgcagcct | 240 |
| gaagattttg caacttacta ttgtcaacag gctaacagtt cccgctcac tttcggcgga | 300 |

```
gggaccaaag tggatatcaa a                                              321
```

<210> SEQ ID NO 122
<211> LENGTH: 2107
<212> TYPE: DNA
<213> ORGANISM: Artificial sequence
<220> FEATURE:
<223> OTHER INFORMATION: Heavy chain CR57
<220> FEATURE:
<221> NAME/KEY: Intron
<222> LOCATION: (382)..(508)
<220> FEATURE:
<221> NAME/KEY: Intron
<222> LOCATION: (803)..(1193)
<220> FEATURE:
<221> NAME/KEY: Intron
<222> LOCATION: (1239)..(1356)
<220> FEATURE:
<221> NAME/KEY: Intron
<222> LOCATION: (1687)..(1783)

<400> SEQUENCE: 122

```
caggtgcagc tggtgcagag cggagccgag gtgaagaagc ccggcagcag cgtgaaggtg     60
agctgcaagg ccagcggcgg caccttcaac aggtacaccg tgaactgggt gagacaggcc    120
ccaggccagg gcctggagtg gatgggcggc atcatccctca tcttcggcac cgccaactac    180
gcccagagat ccagggcag gctcaccatc accgccgacg agagcaccag caccgcctac    240
atggagctga gcagcctgag aagcgatgac accgccgtgt acttctgcgc cagggagaac    300
ctggataaca gcggcaccta ctactacttc agcggctggt tcgaccctg ggccaggc    360 accctggtga ccgtgagctc aggtgagtgc ggccgcgagc ccagacactg gacgctgaac    420
ctcgcggaca gttaagaacc caggggcctc tgcgccctgg gccagctct gtcccacacc    480 gcggtcacat ggcaccacct ctcttgcagc ctccaccaag ggcccatcgg tcttccccct    540
ggcaccctcc tccaagagca cctctggggg cacagcggcc ctgggctgcc tggtcaagga    600
ctacttcccc gaaccggtga cggtgtcgtg gaactcaggc gccctgacca gcggcgtgca    660
caccttcccg gctgtcctac agtcctcagg actctactcc ctcagcagcg tggtgaccgt    720
gccctccagc agcttgggca cccagaccta catctgcaac gtgaatcaca agcccagcaa    780
caccaaggtg gacaagagag ttggtgagag gccagcacag ggagggaggg tgtctgctgg    840
aagccaggct cagcgctcct gcctggacgc atcccggcta tgcagtccca gtccagggca    900
gcaaggcagg ccccgtctgc ctcttcaccc ggaggcctct gcccgcccca ctcatgctca    960
gggagagggt cttctggctt ttccccagg ctctgggcag gcacaggcta ggtgcccta   1020 acccaggccc tgcacacaaa ggggcaggtg ctgggctcag acctgccaag agccatatcc   1080
gggaggaccc tgcccctgac ctaagcccac cccaaaggcc aaactctcca ctccctcagc   1140
tcggacacct tctctcctcc cagattccag taactcccaa tcttctctct gcagagccca   1200
aatcttgtga caaaactcac acatgcccac cgtgcccagg taagccagcc caggcctcgc   1260
cctccagctc aaggcgggac aggtgcccta gagtagcctg catccaggga caggccccag   1320
ccgggtgctg acacgtccac ctccatctct cctcagcac ctgaactcct gggggaccg    1380 tcagtcttcc tcttcccccc aaaacccaag gacaccctca tgatctcccg gacccctgag   1440
gtcacatgcg tggtggtgga cgtgagccac gaagaccctg aggtcaagtt caactggtac   1500
gtggacggcg tggaggtgca taatgccaag acaaagccgc gggaggagca gtacaacagc   1560
acgtaccgtg tggtcagcgt cctcaccgtc ctgcaccagg actggctgaa tggcaaggag   1620
```

-continued

```
tacaagtgca aggtctccaa caaagccctc ccagccccca tcgagaaaac catctccaaa    1680
gccaaaggtg ggacccgtgg ggtgcgaggg ccacatggac agaggccggc tcggcccacc    1740
ctctgccctg agagtgaccg ctgtaccaac tctgtccct acagggcagc ccgagaacc      1800 acaggtgtac accctgcccc catcccggga ggagatgacc aagaaccagg tcagcctgac    1860
ctgcctggtc aaaggcttct atcccagcga catcgccgtg gagtgggaga gcaatgggca    1920
gccggagaac aactacaaga ccacgcctcc cgtgctggac tccgacggct ccttcttcct    1980
ctatagcaag ctcaccgtgg acaagagcag gtggcagcag gggaacgtct tctcatgctc    2040
cgtgatgcat gaggctctgc acaaccacta cacgcagaag agcctctccc tgtctccggg    2100
taaatga                                                              2107
```

<210> SEQ ID NO 123
<211> LENGTH: 457
<212> TYPE: PRT
<213> ORGANISM: Artificial sequence
<220> FEATURE:
<223> OTHER INFORMATION: Heavy chain CR57

<400> SEQUENCE: 123

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Arg Tyr
            20                  25                  30

Thr Val Asn Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Arg Phe
    50                  55                  60

Gln Gly Arg Leu Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Phe Cys
                85                  90                  95

Ala Arg Glu Asn Leu Asp Asn Ser Gly Thr Tyr Tyr Tyr Phe Ser Gly
            100                 105                 110

Trp Phe Asp Pro Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270
```

```
Val Val Asp Val Ser His Glu Asp Pro Glu Val Lys Phe Asn Trp Tyr
            275                 280                 285

Val Asp Gly Val Glu Val His Asn Ala Lys Thr Lys Pro Arg Glu Glu
        290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 124
<211> LENGTH: 859
<212> TYPE: DNA
<213> ORGANISM: Artificial sequence
<220> FEATURE:
<223> OTHER INFORMATION: Light chain of CR57
<220> FEATURE:
<221> NAME/KEY: Intron
<222> LOCATION: (337)..(538)

<400> SEQUENCE: 124
cagagcgccc tcacccagcc cagaagcgtg agcggcagcc ctggccagag cgtgaccatc      60
agctgcaccg gcaccagcag cgacatcggc ggctacaact tcgtgagctg gtatcagcag     120
cacccgggca aggcccctaa gctcatgatc tacgacgcca ccaagagacc cagcggcgtg     180
cccgacagat tcagcggcag caagagcggc aacaccgcca gcctcaccat cagcggactg     240
caggccgagg acgaggccga ctactactgc tgcagctacg ccggcgacta cacccctggc     300
gtggtgttcg gcggaggcac caagcttacc gtcctaggta agtgcacttt gcggccgcta     360
ggaagaaact caaaacatca agattttaaa tacgcttctt ggtctccttg ctataattat     420
ctgggataag catgctgttt tctgtctgtc cctaacatgc cctgtgatta ccgcaaaca     480 acacacccaa gggcagaact tgttacttta aacaccatcc tgtttgcttc tttcctcagg     540
acagcccaag gctgcaccat ctgtgaccct gttccccccc tcctccgagg agctgcaggc     600
caacaaggcc accctggtgt gcctcatcag cgacttctac cctggcgccg tgaccgtggc     660
ctggaaggcc gacagcagcc ccgtgaaggc cggcgtggag accaccaccc ccagcaagca     720
gagcaacaac aagtacgccg ccagcagcta cctgagcctc acccccgagc agtggaagag     780
ccaccggagc tacagctgcc aggtgaccca cgagggcagc accgtggaga agaccgtggc     840
ccccaccgag tgcagctag                                                  859
```

<210> SEQ ID NO 125
<211> LENGTH: 218
<212> TYPE: PRT
<213> ORGANISM: Artificial sequence
<220> FEATURE:
<223> OTHER INFORMATION: Light chain of CR57

<400> SEQUENCE: 125

```
Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Ile Gly Gly Tyr
            20                  25                  30

Asn Phe Val Ser Trp Tyr Gln Gln His Pro Gly Lys Ala Pro Lys Leu
        35                  40                  45

Met Ile Tyr Asp Ala Thr Lys Arg Pro Ser Gly Val Pro Asp Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Cys Ser Tyr Ala Gly Asp
                85                  90                  95

Tyr Thr Pro Gly Val Val Phe Gly Gly Gly Thr Lys Leu Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215
```

<210> SEQ ID NO 126
<211> LENGTH: 2089
<212> TYPE: DNA
<213> ORGANISM: Artificial sequence
<220> FEATURE:
<223> OTHER INFORMATION: Heavy chain of CRJB

<400> SEQUENCE: 126

```
cagatcaccc tgaaggagac cggccccacc ctggtgaagc ccacccagac cctcaccctc      60
acctgcacct tcagcggctt cagcctgagc accagcggcg tgggcgtggg ctggatcaga     120 cagcccctg gcaaggccct ggagtgggtg accctcatct actgggacga cgacaagaga     180
tacagcccca gcctggagaa cagggtgacc atccggaagg acaccagcaa gaaccaggtg     240
gccctcacca tgaccaacat ggaccccctg gataccggca cctactactg cgcccacagg     300
cagcacatca gcagcttccc ctggttcgac agctggggcc agggcacact ggtgaccgtg     360
agctcaggtg agtgcggccg cgagcccaga cactggacgc tgaacctcgc ggacagttaa     420
gaacccaggg gcctctgcgc cctgggccca gctctgtccc acaccgcggt cacatggcac     480
cacctctctt gcagcctcca ccaagggccc atcggtcttc ccctggcac cctcctccaa     540
```

-continued

```
gagcacctct gggggcacag cggccctggg ctgcctggtc aaggactact tccccgaacc   600
ggtgacggtg tcgtggaact caggcgccct gaccagcggc gtgcacacct tcccggctgt   660
cctacagtcc tcaggactct actccctcag cagcgtggtg accgtgccct ccagcagctt   720
gggcacccag acctacatct gcaacgtgaa tcacaagccc agcaacacca aggtggacaa   780
gagagttggt gagaggccag cacagggagg agggtgtct gctggaagcc aggctcagcg   840
ctcctgcctg gacgcatccc ggctatgcag tcccagtcca gggcagcaag caggccccg    900 tctgcctctt cacccggagg cctctgcccg cccactcat gctcagggag agggtcttct    960 ggcttttcc ccaggctctg gcaggcaca ggctaggtgc ccctaaccca ggccctgcac    1020 acaaggggc aggtgctggg ctcagacctg ccaagagcca tatccgggag accctgccc    1080 ctgacctaag cccacccaa aggccaaact ctccactccc tcagctcgga cacttctct    1140 cctcccagat tccagtaact cccaatcttc tctctgcaga gcccaaatct tgtgacaaaa   1200
ctcacacatg cccaccgtgc ccaggtaagc cagcccaggc ctcgccctcc agctcaaggc   1260
gggacaggtg ccctagagta gcctgcatcc agggacaggc cccagccggg tgctgacacg   1320
tccacctcca tctcttcctc agcacctgaa ctcctggggg gaccgtcagt cttcctcttc   1380
cccccaaaac ccaaggacac cctcatgatc tcccggaccc ctgaggtcac atgcgtggtg   1440
gtggacgtga gccacgaaga ccctgaggtc aagttcaact ggtacgtgga cggcgtggag   1500
gtgcataatg ccaagacaaa gccgcgggag gagcagtaca acagcacgta ccgtgtggtc   1560
agcgtcctca ccgtcctgca ccaggactgg ctgaatggca aggagtacaa gtgcaaggtc   1620
tccaacaaag ccctcccagc ccccatcgag aaaaccatct ccaaagccaa aggtgggacc   1680
cgtggggtgc gagggccaca tggacagagg ccggctcggc ccaccctctg ccctgagagt   1740
gaccgctgta ccaacctctg tccctacagg gcagccccga gaaccacagg tgtacaccct   1800 gccccccatcc cgggaggaga tgaccaagaa ccaggtcagc ctgacctgcc tggtcaaagg   1860
cttctatccc agcgacatcg ccgtggagtg ggagagcaat gggcagccgg agaacaacta   1920
caagaccacg cctcccgtgc tggactccga cggctccttc ttcctctata gcaagctcac   1980
cgtggacaag agcaggtggc agcagggaa cgtcttctca tgctccgtga tgcatgaggc   2040
tctgcacaac cactacacgc agaagagcct ctccctgtct ccgggtaaa             2089
```

<210> SEQ ID NO 127
<211> LENGTH: 452
<212> TYPE: PRT
<213> ORGANISM: Artificial sequence
<220> FEATURE:
<223> OTHER INFORMATION: Heavy chain of CRJB

<400> SEQUENCE: 127

```
Gln Ile Thr Leu Lys Glu Thr Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Val Thr Leu Ile Tyr Trp Asp Asp Asp Lys Arg Tyr Ser Pro Ser
    50                  55                  60

Leu Glu Asn Arg Val Thr Ile Arg Lys Asp Thr Ser Lys Asn Gln Val
65                  70                  75                  80

Ala Leu Thr Met Thr Asn Met Asp Pro Leu Asp Thr Gly Thr Tyr Tyr
```

```
                85                  90                  95
Cys Ala His Arg Gln His Ile Ser Ser Phe Pro Trp Phe Asp Ser Trp
            100                 105                 110
Gly Gln Gly Thr Leu Val Thr Val Ser Ser Ala Ser Thr Lys Gly Pro
        115                 120                 125
Ser Val Phe Pro Leu Ala Pro Ser Ser Lys Ser Thr Ser Gly Gly Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
        195                 200                 205
His Lys Pro Ser Asn Thr Lys Val Asp Lys Arg Val Glu Pro Lys Ser
    210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Glu Glu Met Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly Lys
    450

<210> SEQ ID NO 128
<211> LENGTH: 841
<212> TYPE: DNA
<213> ORGANISM: Artificial sequence
<220> FEATURE:
<223> OTHER INFORMATION: Light chain of CRJB
```

<400> SEQUENCE: 128

```
agctacgtgc tcacccagcc ccccagcgtg agcgtggccc ctggcaagac cgccagaatc      60
aactgcggcg gcaacaacat cgagtaccgg agcgtgcact ggtatcagca gaagagcggc     120
caggcccccg tggccgtgat ctacgacaac agcgacagac ctagcggcat ccccgagaga     180
ttcagcggca gcaagagcgg caacaccgcc accctcacca tcagcagagt ggaggccggc     240
gacgaggccg actactactg ccaggtgtgg gacatcagca gcgatgtggt gttcggcgga     300
ggcaccaagc ttaccgtcct aggtaagtgc actttgcggc cgctaggaag aaactcaaaa     360
catcaagatt ttaaatacgc ttcttggtct ccttgctata attatctggg ataagcatgc     420
tgttttctgt ctgtccctaa catgccctgt gattatccgc aaacaacaca cccaagggca     480
gaactttgtt acttaaacac catcctgttt gcttctttcc tcaggacagc ccaaggctgc     540
accatctgtg accctgttcc cccctcctc cgaggagctg caggccaaca aggccaccct     600
ggtgtgcctc atcagcgact tctaccctgg cgccgtgacc gtggcctgga aggccgacag     660
cagccccgtg aaggccggcg tggagaccac caccccagc aagcagagca acaacaagta     720
cgccgccagc agctacctga gcctcacccc cgagcagtgg aagagccacc ggagctacag     780
ctgccaggtg acccacgagg cagcaccgt ggagaagacc gtggccccca ccgagtgcag     840
c                                                                    841
```

<210> SEQ ID NO 129
<211> LENGTH: 213
<212> TYPE: PRT
<213> ORGANISM: Artificial sequence
<220> FEATURE:
<223> OTHER INFORMATION: Light chain of CRJB

<400> SEQUENCE: 129

```
Ser Tyr Val Leu Thr Gln Pro Pro Ser Val Ser Val Ala Pro Gly Lys
  1               5                  10                  15

Thr Ala Arg Ile Asn Cys Gly Gly Asn Asn Ile Glu Tyr Arg Ser Val
             20                  25                  30

His Trp Tyr Gln Gln Lys Ser Gly Gln Ala Pro Val Ala Val Ile Tyr
         35                  40                  45

Asp Asn Ser Asp Arg Pro Ser Gly Ile Pro Glu Arg Phe Ser Gly Ser
     50                  55                  60

Lys Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ile Ser Ser Asp Val
                 85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
```

-continued

```
            195                 200                 205
Pro Thr Glu Cys Ser
    210

<210> SEQ ID NO 130
<211> LENGTH: 12
<212> TYPE: DNA
<213> ORGANISM: Lyssavirus Rabies
<220> FEATURE:
<221> NAME/KEY: misc_feature
<223> OTHER INFORMATION: Part of glycoprotein of CVS-11, E57A2, E57B1,
      E57B2, E57B3 and E57C3

<400> SEQUENCE: 130
atacaccatc tc                                                            12

<210> SEQ ID NO 131
<211> LENGTH: 12
<212> TYPE: DNA
<213> ORGANISM: Lyssavirus Rabies
<220> FEATURE:
<221> NAME/KEY: misc_feature
<223> OTHER INFORMATION: Part of glycoprotein of E57A3

<400> SEQUENCE: 131
atacaacatc tc                                                            12

<210> SEQ ID NO 132
<211> LENGTH: 18
<212> TYPE: DNA
<213> ORGANISM: Lyssavirus Rabies
<220> FEATURE:
<221> NAME/KEY: misc_feature
<223> OTHER INFORMATION: Part of glycoprotein of CVS-11

<400> SEQUENCE: 132
ctcaagttat gtggagtt                                                      18

<210> SEQ ID NO 133
<211> LENGTH: 18
<212> TYPE: DNA
<213> ORGANISM: Lyssavirus Rabies
<220> FEATURE:
<221> NAME/KEY: misc_feature
<223> OTHER INFORMATION: Part of glycoprotein of E57A2

<400> SEQUENCE: 133
ctcaagttat gtgaagtt                                                      18

<210> SEQ ID NO 134
<211> LENGTH: 18
<212> TYPE: DNA
<213> ORGANISM: Lyssavirus Rabies
<220> FEATURE:
<221> NAME/KEY: misc_feature
<223> OTHER INFORMATION: Part of glycoprotein of E57A3, E57B1 and E57B3

<400> SEQUENCE: 134
ctcgagttat gtggagtt                                                      18

<210> SEQ ID NO 135
<211> LENGTH: 18
<212> TYPE: DNA
<213> ORGANISM: Lyssavirus Rabies
<220> FEATURE:
<221> NAME/KEY: misc_feature
<223> OTHER INFORMATION: Part of glycoprotein of E57B2 and E57C3
```

<400> SEQUENCE: 135
ctcaatttat gtggagtt                                                    18

<210> SEQ ID NO 136
<211> LENGTH: 16
<212> TYPE: PRT
<213> ORGANISM: Lyssavirus Rabies
<220> FEATURE:
<221> NAME/KEY: MISC_FEATURE
<223> OTHER INFORMATION: Part of glycoprotein of CVS-11, E57A2, E57B1,
      E57B2, E57B3 and E57C3

<400> SEQUENCE: 136

Gly Pro Trp Ser Pro Ile Asp Ile His His Leu Ser Cys Pro Asn Asn
1               5                   10                  15

<210> SEQ ID NO 137
<211> LENGTH: 16
<212> TYPE: PRT
<213> ORGANISM: Lyssavirus Rabies
<220> FEATURE:
<221> NAME/KEY: MISC_FEATURE
<223> OTHER INFORMATION: Part of glycoprotein of E57A3

<400> SEQUENCE: 137

Gly Pro Trp Ser Pro Ile Asp Ile Gln His Leu Ser Cys Pro Asn Asn
1               5                   10                  15

<210> SEQ ID NO 138
<211> LENGTH: 23
<212> TYPE: PRT
<213> ORGANISM: Lyssavirus Rabies
<220> FEATURE:
<221> NAME/KEY: MISC_FEATURE
<223> OTHER INFORMATION: Part of glycoprotein of CVS-11

<400> SEQUENCE: 138

Ser Leu Lys Gly Ala Cys Arg Leu Lys Leu Cys Gly Val Leu Gly Leu
1               5                   10                  15

Arg Leu Met Asp Gly Thr Trp
            20

<210> SEQ ID NO 139
<211> LENGTH: 23
<212> TYPE: PRT
<213> ORGANISM: Lyssavirus Rabies
<220> FEATURE:
<221> NAME/KEY: MISC_FEATURE
<223> OTHER INFORMATION: Part of glycoprotein of E57A2

<400> SEQUENCE: 139

Ser Leu Lys Gly Ala Cys Arg Leu Lys Leu Cys Glu Val Leu Gly Leu
1               5                   10                  15

Arg Leu Met Asp Gly Thr Trp
            20

<210> SEQ ID NO 140
<211> LENGTH: 23
<212> TYPE: PRT
<213> ORGANISM: Lyssavirus Rabies
<220> FEATURE:
<221> NAME/KEY: MISC_FEATURE
<223> OTHER INFORMATION: Part of glycoprotein of E57A3, E57B1 and E57B3

<400> SEQUENCE: 140

```
Ser Leu Lys Gly Ala Cys Arg Leu Glu Leu Cys Gly Val Leu Gly Leu
1               5                   10                  15

Arg Leu Met Asp Gly Thr Trp
            20

<210> SEQ ID NO 141
<211> LENGTH: 23
<212> TYPE: PRT
<213> ORGANISM: Lyssavirus Rabies
<220> FEATURE:
<221> NAME/KEY: MISC_FEATURE
<223> OTHER INFORMATION: Part of glycoprotein of E57B2 and E57C3

<400> SEQUENCE: 141

Ser Leu Lys Gly Ala Cys Arg Leu Asn Leu Cys Gly Val Leu G

```
<212> TYPE: DNA
<213> ORGANISM: Lyssavirus Rabies
<220> FEATURE:
<221> NAME/KEY: misc_feature
<223> OTHER INFORMATION: Part of glycoprotein of EJB2D, EJB2E and EJB3F

<400> SEQUENCE: 146
tgtggagttc ctgga                                                      15

<210> SEQ ID NO 147
<211> LENGTH: 13
<212> TYPE: PRT
<213> ORGANISM: Lyssavirus Rabies
<220> FEATURE:
<221> NAME/KEY: MISC_FEATURE
<223> OTHER INFORMATION: Part of glycoprotein of CVS-11

<400> SEQUENCE: 147

Tyr Thr Ile Trp Met Pro Glu Asn Pro Arg Leu Gly Met
1               5                   10

<210> SEQ ID NO 148
<211> LENGTH: 13
<212> TYPE: PRT
<213> ORGANISM: Lyssavirus Rabies
<220> FEATURE:
<221> NAME/KEY: MISC_FEATURE
<223> OTHER INFORMATION: Part of glycoprotein of EJB2B, EJB2C, EJB2D,
      EJB2E, EJB2F and EJB3F

<400> SEQUENCE: 148

Tyr Thr Ile Trp Met Pro Glu Asp Pro Arg Leu Gly Met
1               5                   10

<210> SEQ ID NO 149
<211> LENGTH: 23
<212> TYPE: PRT
<213> ORGANISM: Lyssavirus Rabies
<220> FEATURE:
<221> NAME/KEY: MISC_FEATURE
<223> OTHER INFORMATION: Part of glycoprotein of CVS-11

<400> SEQUENCE: 149

Ser Leu Lys Gly Ala Cys Arg Leu Lys Leu Cys Gly Val Leu Gly Leu
1               5                   10                  15

Arg Leu Met Asp Gly Thr Trp
            20

<210> SEQ ID NO 150
<211> LENGTH: 23
<212> TYPE: PRT
<213> ORGANISM: Lyssavirus Rabies
<220> FEATURE:
<221> NAME/KEY: MISC_FEATURE
<223> OTHER INFORMATION: Part of glycoprotein of EJB2B, EJB2C and EJB2F

<400> SEQUENCE: 150

Ser Leu Lys Gly Ala Cys Arg Leu Lys Leu Cys Glu Val Pro Gly Leu
1               5                   10                  15

Arg Leu Met Asp Gly Thr Trp
            20

<210> SEQ ID NO 151
<211> LENGTH: 23
<212> TYPE: PRT
<213> ORGANISM: Lyssavirus Rabies
<220> FEATURE:
```

```
<221> NAME/KEY: MISC_FEATURE
<223> OTHER INFORMATION: Part of glycoprotein of EJB2D, EJB2E and EJB3F

<400> SEQUENCE: 151

Ser Leu Lys Gly Ala Cys Arg Leu Lys Leu Cys Gly Val Pro Gly Leu
1               5                   10                  15

Arg Leu Met Asp Gly Thr Trp
            20

<210> SEQ ID NO 152
<211> LENGTH: 24
<212> TYPE: DNA
<213> ORGANISM: Artificial sequence
<220> FEATURE:
<223> OTHER INFORMATION: Anti-sense primer HuCkappa

<400> SEQUENCE: 152
acactctccc ctgttgaagc tctt                                          24

<210> SEQ ID NO 153
<211> LENGTH: 23
<212> TYPE: DNA
<213> ORGANISM: Artificial sequence
<220> FEATURE:
<223> OTHER INFORMATION: Anti-sense primer HuClambda2

<400> SEQUENCE: 153
tgaacattct gtaggggcca ctg                                           23

<210> SEQ ID NO 154
<211> LENGTH: 23
<212> TYPE: DNA
<213> ORGANISM: Artificial sequence
<220> FEATURE:
<223> OTHER INFORMATION: Anti-sense primer HuClambda7

<400> SEQUENCE: 154
agagcattct gcaggggcca ctg                                           23

<210> SEQ ID NO 155
<211> LENGTH: 4941
<212> TYPE: DNA
<213> ORGANISM: Artificial sequence
<220> FEATURE:
<223> OTHER INFORMATION: Vector PDV-C06

<400> SEQUENCE: 155
aagcttgcat gcaaattcta tttcaaggag acagtcataa tgaaatacct attgcctacg    60
gcagccgctg gattgttatt actcgcggcc cagccggcca tggccgaggt gtttgactaa   120
tggggcgcgc tcagggaac cctggtcacc gtctcgagcg gtacgggcgg ttcaggcgga    180
accggcagcg gcactggcgg gtcgacggaa attgtgctca cacagtctcc agccaccctg   240
tctttgtctc caggggaaag agccaccctc tcctgcaggg ccagtcagag tgttagcagc   300
tacttagcct ggtaccaaca gaaacctggc caggctccca ggctcctcat ctatgatgca   360
tccaacaggg ccactggcat cccagccagg ttcagtggca gtgggtctgg gacagacttc   420
actctcacca tcagcagcct agagcctgaa gattttgcag tttattactg tcagcagcgt   480
agcaactggc ctccggcttt cggcggaggg accaaggtgg agatcaaacg tgcggccgca   540
catcatcatc accatcacgg ggccgcatat accgatattg aaatgaaccg cctgggcaaa   600
ggggccgcat agactgttga aagttgttta gcaaaacctc atacagaaaa ttcatttact   660
```

| | | | | | |
|---|---|---|---|---|---|
| aacgtctgga | aagacgacaa | aactttagat | cgttacgcta | actatgaggg | ctgtctgtgg | 720 |
| aatgctacag | gcgttgtggt | ttgtactggt | gacgaaactc | agtgttacgg | tacatgggtt | 780 |
| cctattgggc | ttgctatccc | tgaaaatgag | ggtggtggct | ctgagggtgg | cggttctgag | 840 |
| ggtggcggtt | ctgagggtgg | cggtactaaa | cctcctgagt | acggtgatac | acctattccg | 900 |
| ggctatactt | atatcaaccc | tctcgacggc | acttatccgc | ctggtactga | gcaaaacccc | 960 |
| gctaatccta | atccttctct | tgaggagtct | cagcctctta | atactttcat | gtttcagaat | 1020 |
| aataggttcc | gaaataggca | gggtgcatta | actgtttata | cgggcactgt | tactcaaggc | 1080 |
| actgaccccg | ttaaaactta | ttaccagtac | actcctgtat | catcaaaagc | catgtatgac | 1140 |
| gcttactgga | acggtaaatt | cagagactgc | gctttccatt | ctggctttaa | tgaggatcca | 1200 |
| ttcgtttgtg | aatatcaagg | ccaatcgtct | gacctgcctc | aacctcctgt | caatgctggc | 1260 |
| ggcggctctg | gtggtggttc | tggtggcggc | tctgagggtg | gcggctctga | gggtggcggt | 1320 |
| tctgagggtg | gcggctctga | gggtggcggt | tccggtggcg | gctccggttc | cggtgatttt | 1380 |
| gattatgaaa | aaatggcaaa | cgctaataag | ggggctatga | ccgaaaatgc | cgatgaaaac | 1440 |
| gcgctacagt | ctgacgctaa | aggcaaactt | gattctgtcg | ctactgatta | cggtgctgct | 1500 |
| atcgatggtt | tcattggtga | cgtttccggc | cttgctaatg | gtaatggtgc | tactggtgat | 1560 |
| tttgctggct | ctaattccca | aatggctcaa | gtcggtgacg | gtgataattc | acctttaatg | 1620 |
| aataatttcc | gtcaatattt | accttctttg | cctcagtcgg | ttgaatgtcg | cccttatgtc | 1680 |
| tttggcgctg | gtaaaccata | tgaattttct | attgattgtg | acaaaataaa | cttattccgt | 1740 |
| ggtgtctttg | cgtttctttt | atatgttgcc | acctttatgt | atgtattttc | gacgtttgct | 1800 |
| aacatactgc | gtaataagga | gtcttaataa | gaattcactg | gccgtcgttt | tacaacgtcg | 1860 |
| tgactgggaa | aaccctggcg | ttacccaact | taatcgcctt | gcagcacatc | cccctttcgc | 1920 |
| cagctggcgt | aatagcgaag | aggcccgcac | cgatcgccct | tcccaacagt | tgcgcagcct | 1980 |
| gaatggcgaa | tggcgcctga | tgcggtattt | tctccttacg | catctgtgcg | gtatttcaca | 2040 |
| ccgcatacgt | caaagcaacc | atagtacgcg | ccctgtagcg | gcgcattaag | cgcggcgggt | 2100 |
| gtggtggtta | cgcgcagcgt | gaccgctaca | cttgccagcg | ccctagcgcc | cgctcctttc | 2160 |
| gctttcttcc | cttcctttct | cgccacgttc | gccggctttc | cccgtcaagc | tctaaatcgg | 2220 |
| gggctccctt | tagggttccg | atttagtgct | ttacggcacc | tcgaccccaa | aaaacttgat | 2280 |
| ttgggtgatg | gttcacgtag | tgggccatcg | ccctgataga | cggtttttcg | ccctttgacg | 2340 |
| ttggagtcca | cgttctttaa | tagtggactc | ttgttccaaa | ctggaacaac | actcaaccct | 2400 |
| atctcgggct | attcttttga | tttataaggg | attttgccga | tttcggccta | ttggttaaaa | 2460 |
| aatgagctga | tttaacaaaa | atttaacgcg | aattttaaca | aaatattaac | gtttacaatt | 2520 |
| ttatggtgca | ctctcagtac | aatctgctct | gatgccgcat | agttaagcca | gccccgacac | 2580 |
| ccgccaacac | ccgctgacgc | gccctgacgg | gcttgtctgc | tcccggcatc | cgcttacaga | 2640 |
| caagctgtga | ccgtctccgg | gagctgcatg | tgtcagaggt | tttcaccgtc | atcaccgaaa | 2700 |
| cgcgcgagac | gaaagggcct | cgtgatacgc | ctatttttat | aggttaatgt | catgataata | 2760 |
| atggtttctt | agacgtcagg | tggcactttt | cggggaaatg | tgcgcggaac | ccctatttgt | 2820 |
| ttatttttct | aaatacattc | aaatatgtat | ccgctcatga | gacaataacc | ctgataaatg | 2880 |
| cttcaataat | attgaaaaag | gaagagtatg | agtattcaac | atttccgtgt | cgcccttatt | 2940 |
| ccctttttg | cggcattttg | ccttcctgtt | tttgctcacc | cagaaacgct | ggtgaaagta | 3000 |
| aaagatgctg | aagatcagtt | gggtgcacga | gtgggttaca | tcgaactgga | tctcaacagc | 3060 |

| | |
|---|---|
| ggtaagatcc ttgagagttt tcgccccgaa gaacgttttc caatgatgag cacttttaaa | 3120 |
| gttctgctat gtggcgcggt attatcccgt attgacgccg ggcaagagca actcggtcgc | 3180 |
| cgcatacact attctcagaa tgacttggtt gagtactcac cagtcacaga aaagcatctt | 3240 |
| acggatggca tgacagtaag agaattatgc agtgctgcca taaccatgag tgataacact | 3300 |
| gcggccaact tacttctgac aacgatcgga ggaccgaagg agctaaccgc ttttttgcac | 3360 |
| aacatggggg atcatgtaac tcgccttgat cgttgggaac cggagctgaa tgaagccata | 3420 |
| ccaaacgacg agcgtgacac cacgatgcct gtagcaatgg caacaacgtt gcgcaaacta | 3480 |
| ttaactggcg aactacttac tctagcttcc cggcaacaat taatagactg gatggaggcg | 3540 |
| gataaagttg caggaccact tctgcgctcg gcccttccgg ctggctggtt tattgctgat | 3600 |
| aaatctggag ccggtgagcg tgggtctcgc ggtatcattg cagcactggg gccagatggt | 3660 |
| aagccctccc gtatcgtagt tatctacacg acggggagtc aggcaactat ggatgaacga | 3720 |
| aatagacaga tcgctgagat aggtgcctca ctgattaagc attggtaact gtcagaccaa | 3780 |
| gtttactcat atatacttta gattgattta aaacttcatt tttaatttaa aaggatctag | 3840 |
| gtgaagatcc ttttgataa tctcatgacc aaaatccctt aacgtgagtt tcgttccac | 3900 |
| tgagcgtcag accccgtaga aaagatcaaa ggatcttctt gagatccttt ttttctgcgc | 3960 |
| gtaatctgct gcttgcaaac aaaaaaacca ccgctaccag cggtggtttg tttgccggat | 4020 |
| caagagctac caactctttt tccgaaggta actggcttca gcagagcgca gataccaaat | 4080 |
| actgtccttc tagtgtagcc gtagttaggc caccacttca agaactctgt agcaccgcct | 4140 |
| acatacctcg ctctgctaat cctgttacca gtggctgctg ccagtggcga taagtcgtgt | 4200 |
| cttaccgggt tggactcaag acgatagtta ccggataagg cgcagcggtc gggctgaacg | 4260 |
| gggggttcgt gcacacagcc cagcttggag cgaacgacct acaccgaact gagatacctca | 4320 |
| cagcgtgagc tatgagaaag cgccacgctt cccgaaggga gaaaggcgga caggtatccg | 4380 |
| gtaagcggca gggtcggaac aggagagcgc acgagggagc ttccagggg aaacgcctgg | 4440 |
| tatctttata gtcctgtcgg gtttcgccac ctctgacttg agcgtcgatt tttgtgatgc | 4500 |
| tcgtcagggg ggcggagcct atggaaaaac gccagcaacg cggccttttt acggttcctg | 4560 |
| gccttttgct ggccttttgc tcacatgttc tttcctgcgt tatcccctga ttctgtggat | 4620 |
| aaccgtatta ccgcctttga gtgagctgat accgctcgcc gcagccgaac gaccgagcgc | 4680 |
| agcgagtcag tgagcgagga agcggaagag cgcccaatac gcaaaccgcc tctccccgcg | 4740 |
| cgttggccga ttcattaatg cagctggcac gacaggtttc ccgactggaa agcgggcagt | 4800 |
| gagcgcaacg caattaatgt gagttagctc actcattagg caccccaggc tttacacttt | 4860 |
| atgcttccgg ctcgtatgtt gtgtggaatt gtgagcggat aacaatttca cacaggaaac | 4920 |
| agctatgacc atgattacgc c | 4941 |

<210> SEQ ID NO 156
<211> LENGTH: 24
<212> TYPE: DNA
<213> ORGANISM: Artificial sequence
<220> FEATURE:
<223> OTHER INFORMATION: Anti-sense primer HuCIgG

<400> SEQUENCE: 156

| | |
|---|---|
| gtccaccttg gtgttgctgg gctt | 24 |

<210> SEQ ID NO 157

<211> LENGTH: 741
<212> TYPE: DNA
<213> ORGANISM: Artificial sequence
<220> FEATURE:
<223> OTHER INFORMATION: SC04-001
<220> FEATURE:
<221> NAME/KEY: CDS
<222> LOCATION: (1)..(741)

<400> SEQUENCE: 157

```
gcc atg gcc gag gtg cag ctg gtg gag tct ggg gga ggt gtg gta cgg      48
Ala Met Ala Glu Val Gln Leu Val Glu Ser Gly Gly Gly Val Val Arg
1               5                   10                  15 cct ggg ggg tcc ctg aga ctc tcc tgt gca gcc tct gga ttc acc ttt      96
Pro Gly Gly Ser Leu Arg Leu Ser Cys Ala Ala Ser Gly Phe Thr Phe
            20                  25                  30 gat gat tat ggc atg agc tgg gtc cgc caa gct cca ggg aag ggg ctg     144
Asp Asp Tyr Gly Met Ser Trp Val Arg Gln Ala Pro Gly Lys Gly Leu
        35                  40                  45 gag tgg gtc tct ggt att aat tgg aat ggt ggt agc aca ggt tat gca     192
Glu Trp Val Ser Gly Ile Asn Trp Asn Gly Gly Ser Thr Gly Tyr Ala
    50                  55                  60 gac tct gtg aag ggc cga ttc acc atc tcc aga gac aac gcc aag aac     240
Asp Ser Val Lys Gly Arg Phe Thr Ile Ser Arg Asp Asn Ala Lys Asn
65                  70                  75                  80 tcc ctg tat ctg caa atg aac agt ctg aga gcc gag gac acg gcc gtg     288
Ser Leu Tyr Leu Gln Met Asn Ser Leu Arg Ala Glu Asp Thr Ala Val
                85                  90                  95 tat tac tgt gca aag ggc ctt tat ggg gag ctt ttt gac tac tgg ggc     336
Tyr Tyr Cys Ala Lys Gly Leu Tyr Gly Glu Leu Phe Asp Tyr Trp Gly
            100                 105                 110 caa ggt acc ctg gtc acc gtc tcg aga ggt gga ggc ggt tca ggc gga     384
Gln Gly Thr Leu Val Thr Val Ser Arg Gly Gly Gly Gly Ser Gly Gly
        115                 120                 125 ggt ggc tct ggc ggt ggc gga tcg tct gag ctg act cag gac cct gct     432
Gly Gly Ser Gly Gly Gly Gly Ser Ser Glu Leu Thr Gln Asp Pro Ala
    130                 135                 140 gtg tct gtg gcc ttg gga cag aca gtc agg atc aca tgc caa gga gac     480
Val Ser Val Ala Leu Gly Gln Thr Val Arg Ile Thr Cys Gln Gly Asp
145                 150                 155                 160 agc ctc aga agc tat tat gca agc tgg tac cag cag aag cca gga cag     528
Ser Leu Arg Ser Tyr Tyr Ala Ser Trp Tyr Gln Gln Lys Pro Gly Gln
                165                 170                 175 gcc cct gta ctt gtc atc tat ggt aaa aac aac cgg ccc tca ggg atc     576
Ala Pro Val Leu Val Ile Tyr Gly Lys Asn Asn Arg Pro Ser Gly Ile
            180                 185                 190 cca gac cga ttc tct ggc tcc agc tca gga aac aca gct tcc ttg acc     624
Pro Asp Arg Phe Ser Gly Ser Ser Ser Gly Asn Thr Ala Ser Leu Thr
        195                 200                 205 atc act ggg gct cag gcg gaa gat gag gct gac tat tac tgt aac tcc     672
Ile Thr Gly Ala Gln Ala Glu Asp Glu Ala Asp Tyr Tyr Cys Asn Ser
    210                 215                 220 cgg gac agc agt ggt aac cat gtg gta ttc ggc gga ggg acc aag ctg     720
Arg Asp Ser Ser Gly Asn His Val Val Phe Gly Gly Gly Thr Lys Leu
225                 230                 235                 240 acc gtc cta ggt gcg gcc gca                                         741
Thr Val Leu Gly Ala Ala Ala
                245
```

<210> SEQ ID NO 158
<211> LENGTH: 247
<212> TYPE: PRT

<213> ORGANISM: Artificial sequence
<220> FEATURE:
<223> OTHER INFORMATION: Synthetic Construct

<400> SEQUENCE: 158

```
Ala Met Ala Glu Val Gln Leu Val Glu Ser Gly Gly Val Val Arg
1               5                   10                  15

Pro Gly Gly Ser Leu Arg Leu Ser Cys Ala Ala Ser Gly Phe Thr Phe
            20                  25                  30

Asp Asp Tyr Gly Met Ser Trp Val Arg Gln Ala Pro Gly Lys Gly Leu
        35                  40                  45

Glu Trp Val Ser Gly Ile Asn Trp Asn Gly Ser Thr Gly Tyr Ala
    50                  55                  60

Asp Ser Val Lys Gly Arg Phe Thr Ile Ser Arg Asp Asn Ala Lys Asn
65                  70                  75                  80

Ser Leu Tyr Leu Gln Met Asn Ser Leu Arg Ala Glu Asp Thr Ala Val
                85                  90                  95

Tyr Tyr Cys Ala Lys Gly Leu Tyr Gly Glu Leu Phe Asp Tyr Trp Gly
            100                 105                 110

Gln Gly Thr Leu Val Thr Val Ser Arg Gly Gly Gly Ser Gly Gly
            115                 120                 125

Gly Gly Ser Gly Gly Gly Ser Ser Glu Leu Thr Gln Asp Pro Ala
        130                 135                 140

Val Ser Val Ala Leu Gly Gln Thr Val Arg Ile Thr Cys Gln Gly Asp
145                 150                 155                 160

Ser Leu Arg Ser Tyr Tyr Ala Ser Trp Tyr Gln Gln Lys Pro Gly Gln
                165                 170                 175

Ala Pro Val Leu Val Ile Tyr Gly Lys Asn Asn Arg Pro Ser Gly Ile
            180                 185                 190

Pro Asp Arg Phe Ser Gly Ser Ser Gly Asn Thr Ala Ser Leu Thr
        195                 200                 205

Ile Thr Gly Ala Gln Ala Glu Asp Glu Ala Asp Tyr Tyr Cys Asn Ser
    210                 215                 220

Arg Asp Ser Ser Gly Asn His Val Val Phe Gly Gly Gly Thr Lys Leu
225                 230                 235                 240

Thr Val Leu Gly Ala Ala Ala
                245
```

<210> SEQ ID NO 159
<211> LENGTH: 741
<212> TYPE: DNA
<213> ORGANISM: Artificial sequence
<220> FEATURE:
<223> OTHER INFORMATION: SC04-004
<220> FEATURE:
<221> NAME/KEY: CDS
<222> LOCATION: (1)..(741)

<400> SEQUENCE: 159

```
tcc atg gct gag gtg cag ctg gtg gag tct ggg gga ggc ttg gtc cag        48
Ser Met Ala Glu Val Gln Leu Val Glu Ser Gly Gly Gly Leu Val Gln
1               5                   10                  15 cct ggg ggg tcc ctg aga ctc tcc tgt gca gcc tct gga ttc acc ttc        96
Pro Gly Gly Ser Leu Arg Leu Ser Cys Ala Ala Ser Gly Phe Thr Phe
            20                  25                  30 agc aac tac tgg atg aac tgg gtc cgc cag gcg ccc ggg aag ggg ctg      144
Ser Asn Tyr Trp Met Asn Trp Val Arg Gln Ala Pro Gly Lys Gly Leu
        35                  40                  45
```

```
gag tgg gtc tca gct att agt ggt agt ggt ggt agc aca tac tac gca      192
Glu Trp Val Ser Ala Ile Ser Gly Ser Gly Gly Ser Thr Tyr Tyr Ala
 50                  55                  60 gac tcc gtg aag ggc cgg ttc acc atc tcc aga gac aat tcc aag aac      240
Asp Ser Val Lys Gly Arg Phe Thr Ile Ser Arg Asp Asn Ser Lys Asn
 65                  70                  75                  80 acg ctg tat ctg caa atg aac agc ctg aga gcc gag gac acg gct gtg      288
Thr Leu Tyr Leu Gln Met Asn Ser Leu Arg Ala Glu Asp Thr Ala Val
                 85                  90                  95 tat tac tgt gcc aaa gac tac ctc tac ccc acc acc gac ttc gat tac      336
Tyr Tyr Cys Ala Lys Asp Tyr Leu Tyr Pro Thr Thr Asp Phe Asp Tyr
            100                 105                 110 tgg ggc cag ggc acc ctg gtg acc gtc tcg agt gga acc gga ggt tcc      384
Trp Gly Gln Gly Thr Leu Val Thr Val Leu Glu Gly Thr Gly Gly Ser
        115                 120                 125 ggc gga acc ggg tct ggg act ggt acg agc gag ctc acc cag tct cca      432
Gly Gly Thr Gly Ser Gly Thr Gly Thr Ser Glu Leu Thr Gln Ser Pro
    130                 135                 140 tcc tcc ctg tct gca tct gta gga gac aga gtc acc atc act tgc cgg      480
Ser Ser Leu Ser Ala Ser Val Gly Asp Arg Val Thr Ile Thr Cys Arg
145                 150                 155                 160 gca agt cag agc att agc agc tac tta aat tgg tat cag cag aaa cca      528
Ala Ser Gln Ser Ile Ser Ser Tyr Leu Asn Trp Tyr Gln Gln Lys Pro
                165                 170                 175 ggg aaa gcc cct aag ctc ctg atc tat gct gca tcc agt ttg caa agt      576
Gly Lys Ala Pro Lys Leu Leu Ile Tyr Ala Ala Ser Ser Leu Gln Ser
            180                 185                 190 ggg gtc cca tca agg ttc agt ggc agt gga tct ggg aca gat ttc act      624
Gly Val Pro Ser Arg Phe Ser Gly Ser Gly Ser Gly Thr Asp Phe Thr
        195                 200                 205 ctc acc atc agc agt ctg caa cct gaa gat ttt gca act tac tac tgt      672
Leu Thr Ile Ser Ser Leu Gln Pro Glu Asp Phe Ala Thr Tyr Tyr Cys
    210                 215                 220 caa cag agt tac agt acc cct cca acg ttc ggc caa ggg acc aag gtg      720
Gln Gln Ser Tyr Ser Thr Pro Pro Thr Phe Gly Gln Gly Thr Lys Val
225                 230                 235                 240 gag atc aaa cgt gcg gcc gca                                          741
Glu Ile Lys Arg Ala Ala Ala
                245
```

<210> SEQ ID NO 160
<211> LENGTH: 247
<212> TYPE: PRT
<213> ORGANISM: Artificial sequence
<220> FEATURE:
<223> OTHER INFORMATION: Synthetic Construct

<400> SEQUENCE: 160

```
Ser Met Ala Glu Val Gln Leu Val Glu Ser Gly Gly Gly Leu Val Gln
  1               5                  10                  15

Pro Gly Gly Ser Leu Arg Leu Ser Cys Ala Ala Ser Gly Phe Thr Phe
             20                  25                  30

Ser Asn Tyr Trp Met Asn Trp Val Arg Gln Ala Pro Gly Lys Gly Leu
         35                  40                  45

Glu Trp Val Ser Ala Ile Ser Gly Ser Gly Gly Ser Thr Tyr Tyr Ala
 50                  55                  60

Asp Ser Val Lys Gly Arg Phe Thr Ile Ser Arg Asp Asn Ser Lys Asn
 65                  70                  75                  80

Thr Leu Tyr Leu Gln Met Asn Ser Leu Arg Ala Glu Asp Thr Ala Val
                 85                  90                  95
```

Tyr Tyr Cys Ala Lys Asp Tyr Leu Tyr Pro Thr Thr Asp Phe Asp Tyr
            100                 105                 110

Trp Gly Gln Gly Thr Leu Val Thr Val Leu Glu Gly Thr Gly Gly Ser
        115                 120                 125

Gly Gly Thr Gly Ser Gly Thr Gly Thr Ser Glu Leu Thr Gln Ser Pro
    130                 135                 140

Ser Ser Leu Ser Ala Ser Val Gly Asp Arg Val Thr Ile Thr Cys Arg
145                 150                 155                 160

Ala Ser Gln Ser Ile Ser Ser Tyr Leu Asn Trp Tyr Gln Gln Lys Pro
                165                 170                 175

Gly Lys Ala Pro Lys Leu Leu Ile Tyr Ala Ala Ser Ser Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Thr Pro Pro Thr Phe Gly Gln Gly Thr Lys Val
225                 230                 235                 240

Glu Ile Lys Arg Ala Ala Ala
                245

<210> SEQ ID NO 161
<211> LENGTH: 756
<212> TYPE: DNA
<213> ORGANISM: Artificial sequence
<220> FEATURE:
<223> OTHER INFORMATION: SC04-008
<220> FEATURE:
<221> NAME/KEY: CDS
<222> LOCATION: (1)..(756)

<400> SEQUENCE: 161

```
gcc atg gcc cag gtc acc ttg aag gag tct ggt cct acg ctg gtg aaa        48
Ala Met Ala Gln Val Thr Leu Lys Glu Ser Gly Pro Thr Leu Val Lys
1               5                   10                  15 ccc aca cag acc ctc acg ctg acc tgc acc ttc tct ggg ttc tca ctc        96
Pro Thr Gln Thr Leu Thr Leu Thr Cys Thr Phe Ser Gly Phe Ser Leu
            20                  25                  30 agc act agt gga gtg ggt gtg ggc tgg atc cgt cag ccc cca gga aag       144
Ser Thr Ser Gly Val Gly Val Gly Trp Ile Arg Gln Pro Pro Gly Lys
        35                  40                  45 gcc ctg gag tgg ctt gca cgc att gat tgg gat gat gat aaa tac tac       192
Ala Leu Glu Trp Leu Ala Arg Ile Asp Trp Asp Asp Asp Lys Tyr Tyr
    50                  55                  60 agc aca tct ctg aag acc agg ctc acc atc tcc aag gac acc tcc aaa       240
Ser Thr Ser Leu Lys Thr Arg Leu Thr Ile Ser Lys Asp Thr Ser Lys
65                  70                  75                  80 aac cag gtg gtc ctt aca atg acc aac atg gac cct gtg gac aca gcc       288
Asn Gln Val Val Leu Thr Met Thr Asn Met Asp Pro Val Asp Thr Ala
                85                  90                  95 acg tat tac tgt gca cgg atg ggt ttc act gga acc tac ttt gac tac       336
Thr Tyr Tyr Cys Ala Arg Met Gly Phe Thr Gly Thr Tyr Phe Asp Tyr
            100                 105                 110 tgg ggc cag ggc acc ctg gtc acc gtc tcg agc ggt acg ggc ggt tca       384
Trp Gly Gln Gly Thr Leu Val Thr Val Ser Ser Gly Thr Gly Gly Ser
        115                 120                 125 ggc gga acc ggc agc ggc act ggc ggg tcg acg cag gct gtg ctg act       432
Gly Gly Thr Gly Ser Gly Thr Gly Gly Ser Thr Gln Ala Val Leu Thr
    130                 135                 140
```

```
cag ccg tcc tcg gtg tca gtg gcc cca gga gag acg gcc agc gtt acc    480
Gln Pro Ser Ser Val Ser Val Ala Pro Gly Glu Thr Ala Ser Val Thr
145                 150                 155                 160 tgt ggg gga gac aac att ggg agt aag agt gtg cac tgg tac caa aag    528
Cys Gly Gly Asp Asn Ile Gly Ser Lys Ser Val His Trp Tyr Gln Lys
                165                 170                 175 aag cca ggc cag gcc cct gtg ctg gtc gtc ttt gat gat agc gac cgg    576
Lys Pro Gly Gln Ala Pro Val Leu Val Val Phe Asp Asp Ser Asp Arg
            180                 185                 190 ccc tca ggg atc cct gag cga ttc tct ggc tcc acc tct ggg aac acg    624
Pro Ser Gly Ile Pro Glu Arg Phe Ser Gly Ser Thr Ser Gly Asn Thr
        195                 200                 205 gcc gcc ctg acc atc agc agg gtc gaa gcc ggg gat gag gcc gac tat    672
Ala Ala Leu Thr Ile Ser Arg Val Glu Ala Gly Asp Glu Ala Asp Tyr
    210                 215                 220 tac tgt cag gtg tgg gat agt agt aat gat cat ctt tat gtc ttc gga    720
Tyr Cys Gln Val Trp Asp Ser Ser Asn Asp His Leu Tyr Val Phe Gly
225                 230                 235                 240 ccc ggg acc cag ctc acc gtt tta agt gcg gcc gca                    756
Pro Gly Thr Gln Leu Thr Val Leu Ser Ala Ala Ala
                245                 250

<210> SEQ ID NO 162
<211> LENGTH: 252
<212> TYPE: PRT
<213> ORGANISM: Artificial sequence
<220> FEATURE:
<223> OTHER INFORMATION: Synthetic Construct

<400> SEQUENCE: 162

Ala Met Ala Gln Val Thr Leu Lys Glu Ser Gly Pro Thr Leu Val Lys
1               5                   10                  15

Pro Thr Gln Thr Leu Thr Leu Thr Cys Thr Phe Ser Gly Phe Ser Leu
            20                  25                  30

Ser Thr Ser Gly Val Gly Val Gly Trp Ile Arg Gln Pro Pro Gly Lys
        35                  40                  45

Ala Leu Glu Trp Leu Ala Arg Ile Asp Trp Asp Asp Lys Tyr Tyr
    50                  55                  60

Ser Thr Ser Leu Lys Thr Arg Leu Thr Ile Ser Lys Asp Thr Ser Lys
65                  70                  75                  80

Asn Gln Val Val Leu Thr Met Thr Asn Met Asp Pro Val Asp Thr Ala
                85                  90                  95

Thr Tyr Tyr Cys Ala Arg Met Gly Phe Thr Gly Thr Tyr Phe Asp Tyr
            100                 105                 110

Trp Gly Gln Gly Thr Leu Val Thr Val Ser Ser Gly Thr Gly Gly Ser
        115                 120                 125

Gly Gly Thr Gly Ser Gly Thr Gly Gly Ser Thr Gln Ala Val Leu Thr
    130                 135                 140

Gln Pro Ser Ser Val Ser Val Ala Pro Gly Glu Thr Ala Ser Val Thr
145                 150                 155                 160

Cys Gly Gly Asp Asn Ile Gly Ser Lys Ser Val His Trp Tyr Gln Lys
                165                 170                 175

Lys Pro Gly Gln Ala Pro Val Leu Val Val Phe Asp Asp Ser Asp Arg
            180                 185                 190

Pro Ser Gly Ile Pro Glu Arg Phe Ser Gly Ser Thr Ser Gly Asn Thr
        195                 200                 205

Ala Ala Leu Thr Ile Ser Arg Val Glu Ala Gly Asp Glu Ala Asp Tyr
```

Tyr Cys Gln Val Trp Asp Ser Ser Asn Asp His Leu Tyr Val Phe Gly
225                 230                 235                 240

Pro Gly Thr Gln Leu Thr Val Leu Ser Ala Ala Ala
                245                 250

<210> SEQ ID NO 163
<211> LENGTH: 759
<212> TYPE: DNA
<213> ORGANISM: Artificial sequence
<220> FEATURE:
<223> OTHER INFORMATION: SC04-010
<220> FEATURE:
<221> NAME/KEY: CDS
<222> LOCATION: (1)..(759)

<400> SEQUENCE: 163

| gcc atg gcc cag gtg cag ctg gtg cag tct ggg gga gac ttg gtc cag | 48 |
|---|---|
| Ala Met Ala Gln Val Gln Leu Val Gln Ser Gly Gly Asp Leu Val Gln | |
| 1           5                  10                  15           | |

| cct ggg agg tcc ctg aga ctc tcc tgt gca gcc tct gga ttc acc ttc | 96 |
|---|---|
| Pro Gly Arg Ser Leu Arg Leu Ser Cys Ala Ala Ser Gly Phe Thr Phe | |
|             20                  25                  30          | |

| agt agc tat ggc atg cac tgg gtc cgc cag gct cca ggc aag ggg ctg | 144 |
|---|---|
| Ser Ser Tyr Gly Met His Trp Val Arg Gln Ala Pro Gly Lys Gly Leu | |
|         35                  40                  45              | |

| gag tgg gtg gca gat ata tca tat gat gga agt aat aaa tac tat gca | 192 |
|---|---|
| Glu Trp Val Ala Asp Ile Ser Tyr Asp Gly Ser Asn Lys Tyr Tyr Ala | |
|     50                  55                  60                  | |

| gac tcc gtg aag ggc cga ttc acc att tcc aga gac aat tcc aag aac | 240 |
|---|---|
| Asp Ser Val Lys Gly Arg Phe Thr Ile Ser Arg Asp Asn Ser Lys Asn | |
| 65                  70                  75                  80  | |

| acg ctg tat ctg caa atg aac agc ctg aga gct gag gac acg gct gtg | 288 |
|---|---|
| Thr Leu Tyr Leu Gln Met Asn Ser Leu Arg Ala Glu Asp Thr Ala Val | |
|                 85                  90                  95      | |

| tat tac tgt gcg aaa gat ggg ctg gat tta act gga acg att cag cca | 336 |
|---|---|
| Tyr Tyr Cys Ala Lys Asp Gly Leu Asp Leu Thr Gly Thr Ile Gln Pro | |
|             100                 105                 110         | |

| ttt ggc tac tgg ggc cag gga acc ctg gtc acc gtc tcg agc ggt acg | 384 |
|---|---|
| Phe Gly Tyr Trp Gly Gln Gly Thr Leu Val Thr Val Ser Ser Gly Thr | |
|         115                 120                 125             | |

| ggc ggt tca ggc gga acc ggc agc ggc act ggg tcg acg gac atc | 432 |
|---|---|
| Gly Gly Ser Gly Gly Thr Gly Ser Gly Thr Gly Gly Ser Thr Asp Ile | |
|     130                 135                 140                 | |

| cag atg acc cag tct cca tcc tcc ctg tct gca tct gta gga gac aga | 480 |
|---|---|
| Gln Met Thr Gln Ser Pro Ser Ser Leu Ser Ala Ser Val Gly Asp Arg | |
| 145                 150                 155                 160 | |

| gtc acc atc act tgc cgg gca agt cag ggc att aga aat gat tta ggc | 528 |
|---|---|
| Val Thr Ile Thr Cys Arg Ala Ser Gln Gly Ile Arg Asn Asp Leu Gly | |
|                 165                 170                 175     | |

| tgg tat cag cag aaa cca ggg aaa gcc cct aag ctc ctg atc tat gct | 576 |
|---|---|
| Trp Tyr Gln Gln Lys Pro Gly Lys Ala Pro Lys Leu Leu Ile Tyr Ala | |
|             180                 185                 190         | |

| gca tcc agt tta caa agt ggg gtc cca tca agg ttc agc ggc agt gga | 624 |
|---|---|
| Ala Ser Ser Leu Gln Ser Gly Val Pro Ser Arg Phe Ser Gly Ser Gly | |
|         195                 200                 205             | |

| tct ggc aca gat ttc act ctc acc atc agc agc ctg cag cct gaa gat | 672 |
|---|---|
| Ser Gly Thr Asp Phe Thr Leu Thr Ile Ser Ser Leu Gln Pro Glu Asp | |
|     210                 215                 220                 | |

| ttt gca act tat tac tgt cta caa gat tac aat tac cct cgg acg ttc | 720 |
|---|---|
| Phe Ala Thr Tyr Tyr Cys Leu Gln Asp Tyr Asn Tyr Pro Arg Thr Phe | |

```
                225                 230                 235                 240
ggc caa ggg acc aag gtg gag atc aaa cgt gcg gcc gca                              759
Gly Gln Gly Thr Lys Val Glu Ile Lys Arg Ala Ala Ala
                245                 250
```

<210> SEQ ID NO 164
<211> LENGTH: 253
<212> TYPE: PRT
<213> ORGANISM: Artificial sequence
<220> FEATURE:
<223> OTHER INFORMATION: Synthetic Construct

<400> SEQUENCE: 164

Ala Met Ala Gln Val Gln Leu Val Gln Ser Gly Gly Asp Leu Val Gln
1               5                   10                  15

Pro Gly Arg Ser Leu Arg Leu Ser Cys Ala Ala Ser Gly Phe Thr Phe
            20                  25                  30

Ser Ser Tyr Gly Met His Trp Val Arg Gln Ala Pro Gly Lys Gly Leu
        35                  40                  45

Glu Trp Val Ala Asp Ile Ser Tyr Asp Gly Ser Asn Lys Tyr Tyr Ala
    50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Lys Asp Gly Leu Asp Leu Thr Gly Thr Ile Gln Pro
            100                 105                 110

Phe Gly Tyr Trp Gly Gln Gly Thr Leu Val Thr Val Ser Ser Gly Thr
        115                 120                 125

Gly Gly Ser Gly Gly Thr Gly Ser Gly Thr Gly Gly Ser Thr Asp Ile
    130                 135                 140

Gln Met Thr Gln Ser Pro Ser Ser Leu Ser Ala Ser Val Gly Asp Arg
145                 150                 155                 160

Val Thr Ile Thr Cys Arg Ala Ser Gln Gly Ile Arg Asn Asp Leu Gly
                165                 170                 175

Trp Tyr Gln Gln Lys Pro Gly Lys Ala Pro Lys Leu Leu Ile Tyr Ala
            180                 185                 190

Ala Ser Ser Leu Gln Ser Gly Val Pro Ser Arg Phe Ser Gly Ser Gly
        195                 200                 205

Ser Gly Thr Asp Phe Thr Leu Thr Ile Ser Ser Leu Gln Pro Glu Asp
    210                 215                 220

Phe Ala Thr Tyr Tyr Cys Leu Gln Asp Tyr Asn Tyr Pro Arg Thr Phe
225                 230                 235                 240

Gly Gln Gly Thr Lys Val Glu Ile Lys Arg Ala Ala Ala
                245                 250

<210> SEQ ID NO 165
<211> LENGTH: 756
<212> TYPE: DNA
<213> ORGANISM: Artificial sequence
<220> FEATURE:
<223> OTHER INFORMATION: SC04-018
<220> FEATURE:
<221> NAME/KEY: CDS
<222> LOCATION: (1)..(756)

<400> SEQUENCE: 165

```
gcc atg gcc gag gtg cag ctg gtg gag tct ggc cca gga ctg gtg agg          48
Ala Met Ala Glu Val Gln Leu Val Glu Ser Gly Pro Gly Leu Val Arg
```

```
                1               5                   10                  15
    cct tcg ggg acc ctg tcc ctc acc tgc gct gtc tct ggt ggc tcc atc       96
    Pro Ser Gly Thr Leu Ser Leu Thr Cys Ala Val Ser Gly Gly Ser Ile
                    20                  25                  30 agc agt agt aac tgg tgg agt tgg gtc cgc cag ccc cca ggg aag ggg      144
    Ser Ser Ser Asn Trp Trp Ser Trp Val Arg Gln Pro Pro Gly Lys Gly
                    35                  40                  45 ctg gag tgg att ggg gaa atc tat cat agt ggg agc acc aac tac aac      192
    Leu Glu Trp Ile Gly Glu Ile Tyr His Ser Gly Ser Thr Asn Tyr Asn
    50                  55                  60 ccg tcc ctc aag agt cga gtc acc ata tca gta gac aag tcc aag aac      240
    Pro Ser Leu Lys Ser Arg Val Thr Ile Ser Val Asp Lys Ser Lys Asn
    65                  70                  75                  80 cag ttc tcc ctg aag ctg agc tct gtg acc gcc gcg gac acg gcc gtg      288
    Gln Phe Ser Leu Lys Leu Ser Ser Val Thr Ala Ala Asp Thr Ala Val
                    85                  90                  95 tat tac tgt gcg aga gtt tct gtg act acg ggt gct ttt aat atc tgg      336
    Tyr Tyr Cys Ala Arg Val Ser Val Thr Thr Gly Ala Phe Asn Ile Trp
                    100                 105                 110 ggc caa ggg aca atg gtc acc gtc tcg agc ggt acg ggc ggt tca ggc      384
    Gly Gln Gly Thr Met Val Thr Val Ser Ser Gly Thr Gly Gly Ser Gly
                    115                 120                 125 gga acc ggc agc ggc act ggg tcg acg cag cct gtg ctg act cag          432
    Gly Thr Gly Ser Gly Thr Gly Gly Ser Thr Gln Pro Val Leu Thr Gln
    130                 135                 140 ccc ctc tca gcg tct ggg acc ccc ggg cag agg gtc acc atc tct tgt      480
    Pro Leu Ser Ala Ser Gly Thr Pro Gly Gln Arg Val Thr Ile Ser Cys
    145                 150                 155                 160 tct gga gac acc tcc aac atc gga agt aat act gta cac tgg tac cag      528
    Ser Gly Asp Thr Ser Asn Ile Gly Ser Asn Thr Val His Trp Tyr Gln
                    165                 170                 175 cgc ctc cca gga acg gcc ccc aaa ctc ctc atc cat aat aat aat cag      576
    Arg Leu Pro Gly Thr Ala Pro Lys Leu Leu Ile His Asn Asn Asn Gln
                    180                 185                 190 cgg ccc tca ggg gtc cct gac cgg ttc tct ggc gcc aag tct ggc acc      624
    Arg Pro Ser Gly Val Pro Asp Arg Phe Ser Gly Ala Lys Ser Gly Thr
                    195                 200                 205 tca gcc tcc ctg gcc atc agt ggg ctc cag tct gag gat gag gct gat      672
    Ser Ala Ser Leu Ala Ile Ser Gly Leu Gln Ser Glu Asp Glu Ala Asp
    210                 215                 220 tat ttc tgt gca gca tgg gat gac aac ctg aat ggt tat gtc ttc gga      720
    Tyr Phe Cys Ala Ala Trp Asp Asp Asn Leu Asn Gly Tyr Val Phe Gly
    225                 230                 235                 240 act ggg acc aag gtc acc gtc cta ggt gcg gcc gca                      756
    Thr Gly Thr Lys Val Thr Val Leu Gly Ala Ala Ala
                    245                 250

<210> SEQ ID NO 166
<211> LENGTH: 252
<212> TYPE: PRT
<213> ORGANISM: Artificial sequence
<220> FEATURE:
<223> OTHER INFORMATION: Synthetic Construct

<400> SEQUENCE: 166

Ala Met Ala Glu Val Gln Leu Val Glu Ser Gly Pro Gly Leu Val Arg
1               5                   10                  15

Pro Ser Gly Thr Leu Ser Leu Thr Cys Ala Val Ser Gly Gly Ser Ile
                20                  25                  30

Ser Ser Ser Asn Trp Trp Ser Trp Val Arg Gln Pro Pro Gly Lys Gly
```

```
            35                  40                  45
Leu Glu Trp Ile Gly Glu Ile Tyr His Ser Gly Ser Thr Asn Tyr Asn
 50                  55                  60

Pro Ser Leu Lys Ser Arg Val Thr Ile Ser Val Asp Lys Ser Lys Asn
65                  70                  75                  80

Gln Phe Ser Leu Lys Leu Ser Ser Val Thr Ala Ala Asp Thr Ala Val
                85                  90                  95

Tyr Tyr Cys Ala Arg Val Ser Val Thr Thr Gly Ala Phe Asn Ile Trp
            100                 105                 110

Gly Gln Gly Thr Met Val Thr Val Ser Ser Gly Thr Gly Gly Ser Gly
        115                 120                 125

Gly Thr Gly Ser Gly Thr Gly Gly Ser Thr Gln Pro Val Leu Thr Gln
    130                 135                 140

Pro Leu Ser Ala Ser Gly Thr Pro Gly Gln Arg Val Thr Ile Ser Cys
145                 150                 155                 160

Ser Gly Asp Thr Ser Asn Ile Gly Ser Asn Thr Val His Trp Tyr Gln
                165                 170                 175

Arg Leu Pro Gly Thr Ala Pro Lys Leu Leu Ile His Asn Asn Asn Gln
            180                 185                 190

Arg Pro Ser Gly Val Pro Asp Arg Phe Ser Gly Ala Lys Ser Gly Thr
        195                 200                 205

Ser Ala Ser Leu Ala Ile Ser Gly Leu Gln Ser Glu Asp Glu Ala Asp
    210                 215                 220

Tyr Phe Cys Ala Ala Trp Asp Asp Asn Leu Asn Gly Tyr Val Phe Gly
225                 230                 235                 240

Thr Gly Thr Lys Val Thr Val Leu Gly Ala Ala Ala
                245                 250

<210> SEQ ID NO 167
<211> LENGTH: 747
<212> TYPE: DNA
<213> ORGANISM: Artificial sequence
<220> FEATURE:
<223> OTHER INFORMATION: SC04-021
<220> FEATURE:
<221> NAME/KEY: CDS
<222> LOCATION: (1)..(747)

<400> SEQUENCE: 167 gcc atg gcc gag gtg cag ctg gtg gag tct ggg gga ggc gtg gtc cag      48
Ala Met Ala Glu Val Gln Leu Val Glu Ser Gly Gly Gly Val Val Gln
1               5                   10                  15 cct ggg agg tcc ctg aga ctc tcc tgt gca gcc tct gga ttc acc ttc      96
Pro Gly Arg Ser Leu Arg Leu Ser Cys Ala Ala Ser Gly Phe Thr Phe
            20                  25                  30 agt agc tat ggc atg cac tgg gtc cgc cag gct cca ggc aag ggg ctg     144
Ser Ser Tyr Gly Met His Trp Val Arg Gln Ala Pro Gly Lys Gly Leu
        35                  40                  45 gag tgg gtg gca gtt ata tca tat gat gga agt agt aaa tat tat gca     192
Glu Trp Val Ala Val Ile Ser Tyr Asp Gly Ser Ser Lys Tyr Tyr Ala
    50                  55                  60 gac tcc gtg aag ggc cga ttc acc atc tcc aga gac aat tcc aag aac     240
Asp Ser Val Lys Gly Arg Phe Thr Ile Ser Arg Asp Asn Ser Lys Asn
65                  70                  75                  80 acg ctg tat ctg caa atg aac agc ctg aga gct gag gac acg gct gtg     288
Thr Leu Tyr Leu Gln Met Asn Ser Leu Arg Ala Glu Asp Thr Ala Val
                85                  90                  95 tat tac tgt gcg aaa ggg tcc gtc ctc ggt gat gct ttt gat atc tgg     336
Tyr Tyr Cys Ala Lys Gly Ser Val Leu Gly Asp Ala Phe Asp Ile Trp
```

|  |  |  |  |  |  |  |  |  |  |  |  |  |
|---|---|---|---|---|---|---|---|---|---|---|---|---|
| Tyr | Tyr | Cys | Ala | Lys | Gly | Ser | Val | Leu | Gly | Asp | Ala | Phe | Asp | Ile | Trp |
|  |  |  | 100 |  |  |  | 105 |  |  |  | 110 |  |

```
ggc caa ggg aca atg gtc acc gtc tcg agc ggt acg ggc ggt tca ggc      384
Gly Gln Gly Thr Met Val Thr Val Ser Ser Gly Thr Gly Gly Ser Gly
        115                 120                 125 gga acc ggc agc ggc act ggc ggg tcg acg gac atc cag atg acc cag      432
Gly Thr Gly Ser Gly Thr Gly Gly Ser Thr Asp Ile Gln Met Thr Gln
130                 135                 140 tct cca ttc tcc ctg tct gct tct gtc gga gac aga gtt acc atc act      480
Ser Pro Phe Ser Leu Ser Ala Ser Val Gly Asp Arg Val Thr Ile Thr
145                 150                 155                 160 tgc cgg gcc agt cag ggc att ggc agt tcc tta gcc tgg tat cag caa      528
Cys Arg Ala Ser Gln Gly Ile Gly Ser Ser Leu Ala Trp Tyr Gln Gln
                165                 170                 175 aaa cca ggg aaa gcc cct aaa ctc ctg atc tac gct gca tcc agt ttg      576
Lys Pro Gly Lys Ala Pro Lys Leu Leu Ile Tyr Ala Ala Ser Ser Leu
            180                 185                 190 caa agt ggg gtc cca tca agg ttc agc ggc agt gga tct ggg aca gat      624
Gln Ser Gly Val Pro Ser Arg Phe Ser Gly Ser Gly Ser Gly Thr Asp
        195                 200                 205 ttc act ctc acc atc agc agc ctg cag cct gaa gat ttt gca act tat      672
Phe Thr Leu Thr Ile Ser Ser Leu Gln Pro Glu Asp Phe Ala Thr Tyr
210                 215                 220 ttc tgt ctg cag cat cat gat tac ccg ctc act ttc ggc gga ggg acc      720
Phe Cys Leu Gln His His Asp Tyr Pro Leu Thr Phe Gly Gly Gly Thr
225                 230                 235                 240 aag ctg gag atc aaa cgt gcg gcc gca                                  747
Lys Leu Glu Ile Lys Arg Ala Ala Ala
                245
```

<210> SEQ ID NO 168
<211> LENGTH: 249
<212> TYPE: PRT
<213> ORGANISM: Artificial sequence
<220> FEATURE:
<223> OTHER INFORMATION: Synthetic Construct

<400> SEQUENCE: 168

```
Ala Met Ala Glu Val Gln Leu Val Glu Ser Gly Gly Gly Val Val Gln
1               5                   10                  15

Pro Gly Arg Ser Leu Arg Leu Ser Cys Ala Ala Ser Gly Phe Thr Phe
            20                  25                  30

Ser Ser Tyr Gly Met His Trp Val Arg Gln Ala Pro Gly Lys Gly Leu
        35                  40                  45

Glu Trp Val Ala Val Ile Ser Tyr Asp Gly Ser Ser Lys Tyr Tyr Ala
    50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Lys Gly Ser Val Leu Gly Asp Ala Phe Asp Ile Trp
            100                 105                 110

Gly Gln Gly Thr Met Val Thr Val Ser Ser Gly Thr Gly Gly Ser Gly
        115                 120                 125

Gly Thr Gly Ser Gly Thr Gly Gly Ser Thr Asp Ile Gln Met Thr Gln
    130                 135                 140

Ser Pro Phe Ser Leu Ser Ala Ser Val Gly Asp Arg Val Thr Ile Thr
145                 150                 155                 160
```

```
Cys Arg Ala Ser Gln Gly Ile Gly Ser Ser Leu Ala Trp Tyr Gln Gln
                165                 170                 175

Lys Pro Gly Lys Ala Pro Lys Leu Leu Ile Tyr Ala Ala Ser Ser Leu
            180                 185                 190

Gln Ser Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Thr Tyr
    210                 215                 220

Phe Cys Leu Gln His His Asp Tyr Pro Leu Thr Phe Gly Gly Gly Thr
225                 230                 235                 240

Lys Leu Glu Ile Lys Arg Ala Ala Ala
                245

<210> SEQ ID NO 169
<211> LENGTH: 768
<212> TYPE: DNA
<213> ORGANISM: Artificial sequence
<220> FEATURE:
<223> OTHER INFORMATION: SC04-026
<220> FEATURE:
<221> NAME/KEY: CDS
<222> LOCATION: (1)..(768)

<400> SEQUENCE: 169 gcc atg gcc gag gtg cag ctg gtg gag tct gga gca gag gtg aag aag      48
Ala Met Ala Glu Val Gln Leu Val Glu Ser Gly Ala Glu Val Lys Lys
1               5                   10                  15 ccg ggg gaa tct ctg aag atc tcc tgt aag ggt tct gga tac aac ttt      96
Pro Gly Glu Ser Leu Lys Ile Ser Cys Lys Gly Ser Gly Tyr Asn Phe
            20                  25                  30 ccc tac tcc tgg atc gcc tgg gtg cgc cag atg ccc ggg aaa ggc ctg     144
Pro Tyr Ser Trp Ile Ala Trp Val Arg Gln Met Pro Gly Lys Gly Leu
        35                  40                  45 gag tgg atg ggg atc atc ttt cct ggt gac tct gac acc aga tat agt     192
Glu Trp Met Gly Ile Ile Phe Pro Gly Asp Ser Asp Thr Arg Tyr Ser
    50                  55                  60 ccg ccc ttc caa ggc cag gtc acc atc tca gcc gac aac tcc aaa agc     240
Pro Pro Phe Gln Gly Gln Val Thr Ile Ser Ala Asp Asn Ser Lys Ser
65                  70                  75                  80 acc gcc tac ctg cag tgg agt agc ctg aag gcc tcg gac acc gcc atg     288
Thr Ala Tyr Leu Gln Trp Ser Ser Leu Lys Ala Ser Asp Thr Ala Met
                85                  90                  95 tat tac tgt gcg cgg acc tcg aac tgg aac tat ttg gac cgg ttc gac     336
Tyr Tyr Cys Ala Arg Thr Ser Asn Trp Asn Tyr Leu Asp Arg Phe Asp
            100                 105                 110 ccc tgg ggc cag ggc acc ctg gtc acc gtc tcg agc ggt acg ggc ggt     384
Pro Trp Gly Gln Gly Thr Leu Val Thr Val Ser Ser Gly Thr Gly Gly
        115                 120                 125 tca ggc gga acc ggc agc ggc act ggc ggg tcg acg gat gtt gtg atg     432
Ser Gly Gly Thr Gly Ser Gly Thr Gly Gly Ser Thr Asp Val Val Met
    130                 135                 140 act cag tct cca ctc tcc ctg ccc gtc acc cct gga gag ccg gcc tcc     480
Thr Gln Ser Pro Leu Ser Leu Pro Val Thr Pro Gly Glu Pro Ala Ser
145                 150                 155                 160 atc tcc tgc agg tct agt cag agc ctc ctg cat agt aat gga cat gat     528
Ile Ser Cys Arg Ser Ser Gln Ser Leu Leu His Ser Asn Gly His Asp
                165                 170                 175 tac ttg gat tgg tac gtg cag aag cca ggg cag tct cca cag ccc ctg     576
Tyr Leu Asp Trp Tyr Val Gln Lys Pro Gly Gln Ser Pro Gln Pro Leu
            180                 185                 190
```

```
atc tat ttg ggt tct gat cgg gcc tcc ggg gtc cct gac agg ttc agt    624
Ile Tyr Leu Gly Ser Asp Arg Ala Ser Gly Val Pro Asp Arg Phe Ser
        195                 200                 205 ggc agt gga tca ggc aca cat ttt aca ctg aat atc agc aga gtg gag    672
Gly Ser Gly Ser Gly Thr His Phe Thr Leu Asn Ile Ser Arg Val Glu
    210                 215                 220 gct gag gat gtt ggg gtt tat tac tgc atg caa tct cta caa act cct    720
Ala Glu Asp Val Gly Val Tyr Tyr Cys Met Gln Ser Leu Gln Thr Pro
225                 230                 235                 240 tgg act ttt ggc cag ggg acc aag ctg gag atc aaa cgt gcg gcc gca    768
Trp Thr Phe Gly Gln Gly Thr Lys Leu Glu Ile Lys Arg Ala Ala Ala
                245                 250                 255
```

<210> SEQ ID NO 170
<211> LENGTH: 256
<212> TYPE: PRT
<213> ORGANISM: Artificial sequence
<220> FEATURE:
<223> OTHER INFORMATION: Synthetic Construct

<400> SEQUENCE: 170

```
Ala Met Ala Glu Val Gln Leu Val Glu Ser Gly Ala Glu Val Lys Lys
1               5                   10                  15

Pro Gly Glu Ser Leu Lys Ile Ser Cys Lys Gly Ser Gly Tyr Asn Phe
            20                  25                  30

Pro Tyr Ser Trp Ile Ala Trp Val Arg Gln Met Pro Gly Lys Gly Leu
        35                  40                  45

Glu Trp Met Gly Ile Ile Phe Pro Gly Asp Ser Asp Thr Arg Tyr Ser
    50                  55                  60

Pro Pro Phe Gln Gly Gln Val Thr Ile Ser Ala Asp Asn Ser Lys Ser
65                  70                  75                  80

Thr Ala Tyr Leu Gln Trp Ser Ser Leu Lys Ala Ser Asp Thr Ala Met
                85                  90                  95

Tyr Tyr Cys Ala Arg Thr Ser Asn Trp Asn Tyr Leu Asp Arg Phe Asp
            100                 105                 110

Pro Trp Gly Gln Gly Thr Leu Val Thr Val Ser Ser Gly Thr Gly Gly
        115                 120                 125

Ser Gly Gly Thr Gly Ser Gly Thr Gly Ser Thr Asp Val Val Met
    130                 135                 140

Thr Gln Ser Pro Leu Ser Leu Pro Val Thr Pro Gly Glu Pro Ala Ser
145                 150                 155                 160

Ile Ser Cys Arg Ser Ser Gln Ser Leu Leu His Ser Asn Gly His Asp
                165                 170                 175

Tyr Leu Asp Trp Tyr Val Gln Lys Pro Gly Gln Ser Pro Gln Pro Leu
            180                 185                 190

Ile Tyr Leu Gly Ser Asp Arg Ala Ser Gly Val Pro Asp Arg Phe Ser
        195                 200                 205

Gly Ser Gly Ser Gly Thr His Phe Thr Leu Asn Ile Ser Arg Val Glu
    210                 215                 220

Ala Glu Asp Val Gly Val Tyr Tyr Cys Met Gln Ser Leu Gln Thr Pro
225                 230                 235                 240

Trp Thr Phe Gly Gln Gly Thr Lys Leu Glu Ile Lys Arg Ala Ala Ala
                245                 250                 255
```

<210> SEQ ID NO 171
<211> LENGTH: 747
<212> TYPE: DNA
<213> ORGANISM: Artificial sequence
<220> FEATURE:
<223> OTHER INFORMATION: SC04-031
<220> FEATURE:
<221> NAME/KEY: CDS
<222> LOCATION: (1)..(747)

<400> SEQUENCE: 171

```
gcc atg gcc gag gtg cag ctg gtg gag tct ggg gga ggc gtg gtc cag      48
Ala Met Ala Glu Val Gln Leu Val Glu Ser Gly Gly Gly Val Val Gln
1               5                   10                  15 cct ggg agg tcc ctg aga ctc tcc tgt gca gcc tct gga ttc acc ttc      96
Pro Gly Arg Ser Leu Arg Leu Ser Cys Ala Ala Ser Gly Phe Thr Phe
            20                  25                  30 agt agc tat ggc atg cac tgg gtc cgc cag gct cca ggc aag ggg ctg     144
Ser Ser Tyr Gly Met His Trp Val Arg Gln Ala Pro Gly Lys Gly Leu
        35                  40                  45 gag tgg gtg gca gtt ata tca tat gat gga agt aat aaa tac tat gca     192
Glu Trp Val Ala Val Ile Ser Tyr Asp Gly Ser Asn Lys Tyr Tyr Ala
50                  55                  60 gac tcc gtg aag ggc cga ttc acc atc tcc aga gac aat tcc aag aac     240
Asp Ser Val Lys Gly Arg Phe Thr Ile Ser Arg Asp Asn Ser Lys Asn
65                  70                  75                  80 acg ctg tat ctg caa atg aac agc ctg aga gct gag gac acg gct gtg     288
Thr Leu Tyr Leu Gln Met Asn Ser Leu Arg Ala Glu Asp Thr Ala Val
                85                  90                  95 tat tac tgt gcg aaa ggg tcc gtc ctc ggt gat gct ttt gat atc tgg     336
Tyr Tyr Cys Ala Lys Gly Ser Val Leu Gly Asp Ala Phe Asp Ile Trp
            100                 105                 110 ggc caa ggg aca atg gtc acc gtc tcg agc ggt acg ggc ggt tca ggc     384
Gly Gln Gly Thr Met Val Thr Val Ser Ser Gly Thr Gly Gly Ser Gly
        115                 120                 125 gga acc ggc agc ggc act ggc ggg tcg acg gac atc cag atg acc cag     432
Gly Thr Gly Ser Gly Thr Gly Gly Ser Thr Asp Ile Gln Met Thr Gln
    130                 135                 140 tct cca tct ttc gtg tct gca tct gta gga gac aga gtc acc atc act     480
Ser Pro Ser Phe Val Ser Ala Ser Val Gly Asp Arg Val Thr Ile Thr
145                 150                 155                 160 tgt cgg gcg agt cag ggt att agc agt tgg tta gcc tgg tat cag cag     528
Cys Arg Ala Ser Gln Gly Ile Ser Ser Trp Leu Ala Trp Tyr Gln Gln
                165                 170                 175 aaa cca ggg aaa gcc cct aag ctc ctg atc tat gct gca tcc agt ttg     576
Lys Pro Gly Lys Ala Pro Lys Leu Leu Ile Tyr Ala Ala Ser Ser Leu
            180                 185                 190 caa agt ggg gtc cca tca agg ttc agc ggc agt gga tct ggg aca gat     624
Gln Ser Gly Val Pro Ser Arg Phe Ser Gly Ser Gly Ser Gly Thr Asp
        195                 200                 205 ttc act ctc acc atc agc agc ctg cag cct gaa gat ttt gca act tac     672
Phe Thr Leu Thr Ile Ser Ser Leu Gln Pro Glu Asp Phe Ala Thr Tyr
    210                 215                 220 tat tgt caa cag gct aac agt ttc cca ctc act ttc ggc gga ggg acc     720
Tyr Cys Gln Gln Ala Asn Ser Phe Pro Leu Thr Phe Gly Gly Gly Thr
225                 230                 235                 240 aag gtg gag atc aaa cga gcg gcc gca                                 747
Lys Val Glu Ile Lys Arg Ala Ala Ala
                245
```

<210> SEQ ID NO 172
<211> LENGTH: 249
<212> TYPE: PRT
<213> ORGANISM: Artificial sequence
<220> FEATURE:
<223> OTHER INFORMATION: Synthetic Construct

<400> SEQUENCE: 172

Ala Met Ala Glu Val Gln Leu Val Glu Ser Gly Gly Gly Val Val Gln
1               5                   10                  15

Pro Gly Arg Ser Leu Arg Leu Ser Cys Ala Ala Ser Gly Phe Thr Phe
            20                  25                  30

Ser Ser Tyr Gly Met His Trp Val Arg Gln Ala Pro Gly Lys Gly Leu
        35                  40                  45

Glu Trp Val Ala Val Ile Ser Tyr Asp Gly Ser Asn Lys Tyr Tyr Ala
50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Lys Gly Ser Val Leu Gly Asp Ala Phe Asp Ile Trp
            100                 105                 110

Gly Gln Gly Thr Met Val Thr Val Ser Ser Gly Thr Gly Gly Ser Gly
        115                 120                 125

Gly Thr Gly Ser Gly Thr Gly Gly Ser Thr Asp Ile Gln Met Thr Gln
130                 135                 140

Ser Pro Ser Phe Val Ser Ala Ser Val Gly Asp Arg Val Thr Ile Thr
145                 150                 155                 160

Cys Arg Ala Ser Gln Gly Ile Ser Ser Trp Leu Ala Trp Tyr Gln Gln
                165                 170                 175

Lys Pro Gly Lys Ala Pro Lys Leu Leu Ile Tyr Ala Ala Ser Ser Leu
            180                 185                 190

Gln Ser Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Thr Tyr
210                 215                 220

Tyr Cys Gln Gln Ala Asn Ser Phe Pro Leu Thr Phe Gly Gly Gly Thr
225                 230                 235                 240

Lys Val Glu Ile Lys Arg Ala Ala Ala
                245

<210> SEQ ID NO 173
<211> LENGTH: 747
<212> TYPE: DNA
<213> ORGANISM: Artificial sequence
<220> FEATURE:
<223> OTHER INFORMATION: SC04-038
<220> FEATURE:
<221> NAME/KEY: CDS
<222> LOCATION: (1)..(747)

<400> SEQUENCE: 173 gcc atg gcc cag gtg cag ctg gtg caa tct ggg gga ggc gtg gtc cag     48
Ala Met Ala Gln Val Gln Leu Val Gln Ser Gly Gly Gly Val Val Gln
1               5                   10                  15 cct ggg agg tcc ctg aga ctc tcc tgt gca gcc tct gga ttc acc ttc     96
Pro Gly Arg Ser Leu Arg Leu Ser Cys Ala Ala Ser Gly Phe Thr Phe
            20                  25                  30 agt agc tat ggc atg cac tgg gtc cgc cag gct cca ggc aag ggg ctg    144
Ser Ser Tyr Gly Met His Trp Val Arg Gln Ala Pro Gly Lys Gly Leu
        35                  40                  45 gag tgg gtg gca gtt ata tca tat gat gga agt agt aaa tat tat gca    192
Glu Trp Val Ala Val Ile Ser Tyr Asp Gly Ser Ser Lys Tyr Tyr Ala
50                  55                  60

```
gac tcc gtg aag ggc cga ttc acc atc tcc aga gac aat tcc aag aac      240
Asp Ser Val Lys Gly Arg Phe Thr Ile Ser Arg Asp Asn Ser Lys Asn
 65                  70                  75                  80 acg ctg tat ctg caa atg aac agc ctg aga gct gag gac acg gct gtg      288
Thr Leu Tyr Leu Gln Met Asn Ser Leu Arg Ala Glu Asp Thr Ala Val
             85                  90                  95 tat tac tgt gcg aaa ggg tcc gtc ctc ggt gat gct ttt gat atc tgg      336
Tyr Tyr Cys Ala Lys Gly Ser Val Leu Gly Asp Ala Phe Asp Ile Trp
            100                 105                 110 ggc caa ggg aca atg gtc acc gtc tcg agc ggt acg ggc ggt tca ggc      384
Gly Gln Gly Thr Met Val Thr Val Ser Ser Gly Thr Gly Gly Ser Gly
                115                 120                 125 gga acc ggc agc ggc act ggc ggg tcg acg gac atc cag ttg act cag      432
Gly Thr Gly Ser Gly Thr Gly Gly Ser Thr Asp Ile Gln Leu Thr Gln
130                 135                 140 tct cca tct tcc gtg tct gca tct gta gga gac aga gtc acc atc act      480
Ser Pro Ser Ser Val Ser Ala Ser Val Gly Asp Arg Val Thr Ile Thr
145                 150                 155                 160 tgt cgg gcg agt cag ggt att agc ggc tgg tta gcc tgg tat cag cag      528
Cys Arg Ala Ser Gln Gly Ile Ser Gly Trp Leu Ala Trp Tyr Gln Gln
                165                 170                 175 aaa cca gag aaa gcc cct aag ctc ctg atc tat gcg gca tcc agt ttg      576
Lys Pro Glu Lys Ala Pro Lys Leu Leu Ile Tyr Ala Ala Ser Ser Leu
            180                 185                 190 caa cgt ggg gtc cca tca agg ttc agc ggc agt gga tct ggg aca gat      624
Gln Arg Gly Val Pro Ser Arg Phe Ser Gly Ser Gly Ser Gly Thr Asp
        195                 200                 205 ttc act ctc acc atc agc agc ctg cag cct gaa gat ttt gca act tac      672
Phe Thr Leu Thr Ile Ser Ser Leu Gln Pro Glu Asp Phe Ala Thr Tyr
210                 215                 220 tat tgt caa cag gct aac agt ttc ccc ccc acc ttc ggc caa ggg aca      720
Tyr Cys Gln Gln Ala Asn Ser Phe Pro Pro Thr Phe Gly Gln Gly Thr
225                 230                 235                 240 cga ctg gag att aaa cgt gcg gcc gca                                  747
Arg Leu Glu Ile Lys Arg Ala Ala Ala
                245

<210> SEQ ID NO 174
<211> LENGTH: 249
<212> TYPE: PRT
<213> ORGANISM: Artificial sequence
<220> FEATURE:
<223> OTHER INFORMATION: Synthetic Construct

<400> SEQUENCE: 174

Ala Met Ala Gln Val Gln Leu Val Gln Ser Gly Gly Gly Val Val Gln
 1               5                  10                  15

Pro Gly Arg Ser Leu Arg Leu Ser Cys Ala Ala Ser Gly Phe Thr Phe
             20                  25                  30

Ser Ser Tyr Gly Met His Trp Val Arg Gln Ala Pro Gly Lys Gly Leu
         35                  40                  45

Glu Trp Val Ala Val Ile Ser Tyr Asp Gly Ser Ser Lys Tyr Tyr Ala
     50                  55                  60

Asp Ser Val Lys Gly Arg Phe Thr Ile Ser Arg Asp Asn Ser Lys Asn
 65                  70                  75                  80

Thr Leu Tyr Leu Gln Met Asn Ser Leu Arg Ala Glu Asp Thr Ala Val
             85                  90                  95

Tyr Tyr Cys Ala Lys Gly Ser Val Leu Gly Asp Ala Phe Asp Ile Trp
            100                 105                 110
```

```
Gly Gln Gly Thr Met Val Thr Val Ser Ser Gly Thr Gly Ser Gly
        115                 120                 125

Gly Thr Gly Ser Gly Thr Gly Ser Thr Asp Ile Gln Leu Thr Gln
    130                 135                 140

Ser Pro Ser Ser Val Ser Ala Ser Val Gly Asp Arg Val Thr Ile Thr
145                 150                 155                 160

Cys Arg Ala Ser Gln Gly Ile Ser Gly Trp Leu Ala Trp Tyr Gln Gln
                165                 170                 175

Lys Pro Glu Lys Ala Pro Lys Leu Leu Ile Tyr Ala Ala Ser Ser Leu
            180                 185                 190

Gln Arg Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Thr Tyr
    210                 215                 220

Tyr Cys Gln Gln Ala Asn Ser Phe Pro Pro Thr Phe Gly Gln Gly Thr
225                 230                 235                 240

Arg Leu Glu Ile Lys Arg Ala Ala Ala
                245

<210> SEQ ID NO 175
<211> LENGTH: 747
<212> TYPE: DNA
<213> ORGANISM: Artificial sequence
<220> FEATURE:
<223> OTHER INFORMATION: SC04-040
<220> FEATURE:
<221> NAME/KEY: CDS
<222> LOCATION: (1)..(747)

<400> SEQUENCE: 175 gcc atg gcc cag gtg cag ctg gtg cag tct ggg gga ggc gtg gtc cag      48
Ala Met Ala Gln Val Gln Leu Val Gln Ser Gly Gly Gly Val Val Gln
1               5                   10                  15 cct ggg agg tcc ctg aga ctc tcc tgt gca gcc tct gga ttc acc ttc      96
Pro Gly Arg Ser Leu Arg Leu Ser Cys Ala Ala Ser Gly Phe Thr Phe
            20                  25                  30 ggt agc tat ggc atg cac tgg gtc cgc cag gct cca ggc aag ggg ctg     144
Gly Ser Tyr Gly Met His Trp Val Arg Gln Ala Pro Gly Lys Gly Leu
        35                  40                  45 gag tgg gtg gca act ata ttc tat gat gga agt tat aaa gac tat gca     192
Glu Trp Val Ala Thr Ile Phe Tyr Asp Gly Ser Tyr Lys Asp Tyr Ala
    50                  55                  60 gac tcc gtg aag ggc cga ttc acc atc tcc aga gac aat tcc aag aac     240
Asp Ser Val Lys Gly Arg Phe Thr Ile Ser Arg Asp Asn Ser Lys Asn
65                  70                  75                  80 acg ctg tat ctg caa atg aac agc ctg aga gct gag gac acg gct gtg     288
Thr Leu Tyr Leu Gln Met Asn Ser Leu Arg Ala Glu Asp Thr Ala Val
                85                  90                  95 tat tac tgt gcg aaa ggc agt aag gta ggc gac ttt gac tac tgg ggc     336
Tyr Tyr Cys Ala Lys Gly Ser Lys Val Gly Asp Phe Asp Tyr Trp Gly
            100                 105                 110 cag gga acc ctg gtc acc gtc tcg agc ggt acg ggc ggt tca ggc gga     384
Gln Gly Thr Leu Val Thr Val Ser Ser Gly Thr Gly Gly Ser Gly Gly
        115                 120                 125 acc ggc agc ggc act ggc ggg tcg acg cag cct gtg ctg act cag ccc     432
Thr Gly Ser Gly Thr Gly Gly Ser Thr Gln Pro Val Leu Thr Gln Pro
    130                 135                 140 ccc tcg gtg tca gtg gcc cca gga cag acg gcc agg att tcc tgt ggg     480
Pro Ser Val Ser Val Ala Pro Gly Gln Thr Ala Arg Ile Ser Cys Gly
145                 150                 155                 160
```

```
                145                 150                 155                 160
gga gac aac att gga act aat act gtg cag tgg tac cag cag aag cca         528
Gly Asp Asn Ile Gly Thr Asn Thr Val Gln Trp Tyr Gln Gln Lys Pro
                165                 170                 175 ggc cag gcc cct gtc ctg gtc gtc tat gat gat agc gac cgg ccc tca         576
Gly Gln Ala Pro Val Leu Val Val Tyr Asp Asp Ser Asp Arg Pro Ser
            180                 185                 190 ggg atc cct gag cga ttc tct ggc tcc aac tct ggg gac acg gcc acc         624
Gly Ile Pro Glu Arg Phe Ser Gly Ser Asn Ser Gly Asp Thr Ala Thr
        195                 200                 205 ctg acc atc agc agg gtc gag gcc ggg gat gag gcc gat tat tac tgt         672
Leu Thr Ile Ser Arg Val Glu Ala Gly Asp Glu Ala Asp Tyr Tyr Cys
    210                 215                 220 cag gtg tgg gat gac agt agt gat ctg gtg gta ttc ggc gga ggg acc         720
Gln Val Trp Asp Asp Ser Ser Asp Leu Val Val Phe Gly Gly Gly Thr
225                 230                 235                 240 aag gtc acc gtc cta ggt gcg gcc gca                                     747
Lys Val Thr Val Leu Gly Ala Ala Ala
                245

<210> SEQ ID NO 176
<211> LENGTH: 249
<212> TYPE: PRT
<213> ORGANISM: Artificial sequence
<220> FEATURE:
<223> OTHER INFORMATION: Synthetic Construct

<400> SEQUENCE: 176

Ala Met Ala Gln Val Gln Leu Val Gln Ser Gly Gly Val Val Gln
1               5                   10                  15

Pro Gly Arg Ser Leu Arg Leu Ser Cys Ala Ala Ser Gly Phe Thr Phe
            20                  25                  30

Gly Ser Tyr Gly Met His Trp Val Arg Gln Ala Pro Gly Lys Gly Leu
        35                  40                  45

Glu Trp Val Ala Thr Ile Phe Tyr Asp Gly Ser Tyr Lys Asp Tyr Ala
    50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Lys Gly Ser Lys Val Gly Asp Phe Asp Tyr Trp Gly
            100                 105                 110

Gln Gly Thr Leu Val Thr Val Ser Ser Gly Thr Gly Gly Ser Gly Gly
        115                 120                 125

Thr Gly Ser Gly Thr Gly Gly Ser Thr Gln Pro Val Leu Thr Gln Pro
    130                 135                 140

Pro Ser Val Ser Val Ala Pro Gly Gln Thr Ala Arg Ile Ser Cys Gly
145                 150                 155                 160

Gly Asp Asn Ile Gly Thr Asn Thr Val Gln Trp Tyr Gln Gln Lys Pro
                165                 170                 175

Gly Gln Ala Pro Val Leu Val Val Tyr Asp Asp Ser Asp Arg Pro Ser
            180                 185                 190

Gly Ile Pro Glu Arg Phe Ser Gly Ser Asn Ser Gly Asp Thr Ala Thr
        195                 200                 205

Leu Thr Ile Ser Arg Val Glu Ala Gly Asp Glu Ala Asp Tyr Tyr Cys
    210                 215                 220

Gln Val Trp Asp Asp Ser Ser Asp Leu Val Val Phe Gly Gly Gly Thr
```

<210> SEQ ID NO 177
<211> LENGTH: 774
<212> TYPE: DNA
<213> ORGANISM: Artificial sequence
<220> FEATURE:
<223> OTHER INFORMATION: SC04-060
<220> FEATURE:
<221> NAME/KEY: CDS
<222> LOCATION: (1)..(774)

<400> SEQUENCE: 177

```
gcc atg gcc cag gtg cag ctg gtg gag tct ggc cca gga ctg gtg aag      48
Ala Met Ala Gln Val Gln Leu Val Glu Ser Gly Pro Gly Leu Val Lys
1               5                   10                  15 gct tcg gag acc ctg tcc ctc act tgc acg gtc tct gat ggc tcc atc      96
Ala Ser Glu Thr Leu Ser Leu Thr Cys Thr Val Ser Asp Gly Ser Ile
            20                  25                  30 agt agt ttc tac tgg agc tgg atc cgg cag ccc ccc ggg aag gga ctg     144
Ser Ser Phe Tyr Trp Ser Trp Ile Arg Gln Pro Pro Gly Lys Gly Leu
        35                  40                  45 gag tgg gtt ggg gaa atc cag gac act ggg agg acc aat tac aac ccc     192
Glu Trp Val Gly Glu Ile Gln Asp Thr Gly Arg Thr Asn Tyr Asn Pro
    50                  55                  60 tcc ctc aag agt cga gtc act ata tca cta gac acg tcc aag aac cag     240
Ser Leu Lys Ser Arg Val Thr Ile Ser Leu Asp Thr Ser Lys Asn Gln
65                  70                  75                  80 ttc tcc ctg acg ttg agc tct gtg acc gct gcg gac acg gcc gtg tat     288
Phe Ser Leu Thr Leu Ser Ser Val Thr Ala Ala Asp Thr Ala Val Tyr
                85                  90                  95 tac tgc gcg aga gag aag gag aaa tac tct gat aga agc ggt tat tcg     336
Tyr Cys Ala Arg Glu Lys Glu Lys Tyr Ser Asp Arg Ser Gly Tyr Ser
            100                 105                 110 tac tac tac tat tac atg gac gtc tgg ggc aaa ggg acc acg gtc acc     384
Tyr Tyr Tyr Tyr Tyr Met Asp Val Trp Gly Lys Gly Thr Thr Val Thr
        115                 120                 125 gtc tcg agc ggt acg ggc ggt tca ggc gga acc ggc agc ggc act ggc     432
Val Ser Ser Gly Thr Gly Gly Ser Gly Gly Thr Gly Ser Gly Thr Gly
    130                 135                 140 ggg tcg acg gac atc cag atg acc cag tct cca tcc tcc ctg tct gca     480
Gly Ser Thr Asp Ile Gln Met Thr Gln Ser Pro Ser Ser Leu Ser Ala
145                 150                 155                 160 tct gta gga gac aga gtc acc atc act tgc cgg gca agt cag ggc att     528
Ser Val Gly Asp Arg Val Thr Ile Thr Cys Arg Ala Ser Gln Gly Ile
                165                 170                 175 agc acc tat tta aat tgg tat cag cag aaa cca ggg aaa gcc cct aac     576
Ser Thr Tyr Leu Asn Trp Tyr Gln Gln Lys Pro Gly Lys Ala Pro Asn
            180                 185                 190 ctc ctg atc tac ggt gca tct aat ttg caa agt ggg gtc cca tca agg     624
Leu Leu Ile Tyr Gly Ala Ser Asn Leu Gln Ser Gly Val Pro Ser Arg
        195                 200                 205 ttc agt ggc agt gaa tct ggg aca gat ttc act ctc acc atc agc agt     672
Phe Ser Gly Ser Glu Ser Gly Thr Asp Phe Thr Leu Thr Ile Ser Ser
    210                 215                 220 cta caa cct gaa gat ttt gca act tac tac tgt cag cag agt ttc act     720
Leu Gln Pro Glu Asp Phe Ala Thr Tyr Tyr Cys Gln Gln Ser Phe Thr
225                 230                 235                 240 acc cct cgc acg ttc ggc caa ggg acc aag ctg gag atc aaa cgt gcg     768
```

Thr Pro Arg Thr Phe Gly Gln Gly Thr Lys Leu Glu Ile Lys Arg Ala
                245                 250                 255 gcc gca                                                              774
Ala Ala <210> SEQ ID NO 178
<211> LENGTH: 258
<212> TYPE: PRT
<213> ORGANISM: Artificial sequence
<220> FEATURE:
<223> OTHER INFORMATION: Synthetic Construct

<400> SEQUENCE: 178

Ala Met Ala Gln Val Gln Leu Val Glu Ser Gly Pro Gly Leu Val Lys
1               5                   10                  15

Ala Ser Glu Thr Leu Ser Leu Thr Cys Thr Val Ser Asp Gly Ser Ile
            20                  25                  30

Ser Ser Phe Tyr Trp Ser Trp Ile Arg Gln Pro Pro Gly Lys Gly Leu
        35                  40                  45

Glu Trp Val Gly Glu Ile Gln Asp Thr Gly Arg Thr Asn Tyr Asn Pro
    50                  55                  60

Ser Leu Lys Ser Arg Val Thr Ile Ser Leu Asp Thr Ser Lys Asn Gln
65                  70                  75                  80

Phe Ser Leu Thr Leu Ser Ser Val Thr Ala Ala Asp Thr Ala Val Tyr
                85                  90                  95

Tyr Cys Ala Arg Glu Lys Glu Lys Tyr Ser Asp Arg Ser Gly Tyr Ser
            100                 105                 110

Tyr Tyr Tyr Tyr Tyr Met Asp Val Trp Gly Lys Gly Thr Thr Val Thr
        115                 120                 125

Val Ser Ser Gly Thr Gly Gly Ser Gly Gly Thr Gly Ser Gly Thr Gly
    130                 135                 140

Gly Ser Thr Asp Ile Gln Met Thr Gln Ser Pro Ser Ser Leu Ser Ala
145                 150                 155                 160

Ser Val Gly Asp Arg Val Thr Ile Thr Cys Arg Ala Ser Gln Gly Ile
                165                 170                 175

Ser Thr Tyr Leu Asn Trp Tyr Gln Gln Lys Pro Gly Lys Ala Pro Asn
            180                 185                 190

Leu Leu Ile Tyr Gly Ala Ser Asn Leu Gln Ser Gly Val Pro Ser Arg
        195                 200                 205

Phe Ser Gly Ser Glu Ser Gly Thr Asp Phe Thr Leu Thr Ile Ser Ser
    210                 215                 220

Leu Gln Pro Glu Asp Phe Ala Thr Tyr Tyr Cys Gln Gln Ser Phe Thr
225                 230                 235                 240

Thr Pro Arg Thr Phe Gly Gln Gly Thr Lys Leu Glu Ile Lys Arg Ala
                245                 250                 255

Ala Ala

<210> SEQ ID NO 179
<211> LENGTH: 759
<212> TYPE: DNA
<213> ORGANISM: Artificial sequence
<220> FEATURE:
<223> OTHER INFORMATION: SC04-073
<220> FEATURE:
<221> NAME/KEY: CDS
<222> LOCATION: (1)..(759)

<400> SEQUENCE: 179

| | | |
|---|---|---|
| gcc atg gcc cag gtg cag ctg gtg cag tct ggg gga ggc gtg gcc cag<br>Ala Met Ala Gln Val Gln Leu Val Gln Ser Gly Gly Gly Val Ala Gln<br>1               5                   10                  15 | | 48 |
| cct ggg agg tcc ctg aga ctc tcc tgt gca gcg tct gga ttc acc ttc<br>Pro Gly Arg Ser Leu Arg Leu Ser Cys Ala Ala Ser Gly Phe Thr Phe<br>            20                  25                  30 | | 96 |
| agt agt tat ggc atg cac tgg gtc cgc cag gct cca ggc aag ggg ctg<br>Ser Ser Tyr Gly Met His Trp Val Arg Gln Ala Pro Gly Lys Gly Leu<br>        35                  40                  45 | | 144 |
| gag tgg gtg gca gat ata tca tat gat gga agt aat aaa tac tat gca<br>Glu Trp Val Ala Asp Ile Ser Tyr Asp Gly Ser Asn Lys Tyr Tyr Ala<br>    50                  55                  60 | | 192 |
| gac tcc gtg aag ggc cga ttc acc att tcc aga gac aat tcc aag aac<br>Asp Ser Val Lys Gly Arg Phe Thr Ile Ser Arg Asp Asn Ser Lys Asn<br>65                  70                  75                  80 | | 240 |
| acg ctg tat ctg caa atg aac agc ctg aga gct gag gac acg gct gtg<br>Thr Leu Tyr Leu Gln Met Asn Ser Leu Arg Ala Glu Asp Thr Ala Val<br>                85                  90                  95 | | 288 |
| tat tac tgt gcg aaa gat ggg ctg gat tta act gga acg att cag cca<br>Tyr Tyr Cys Ala Lys Asp Gly Leu Asp Leu Thr Gly Thr Ile Gln Pro<br>            100                 105                 110 | | 336 |
| ttt ggc tac tgg ggc cag ggc acc ctg gtc acc gtc tcg agc ggt acg<br>Phe Gly Tyr Trp Gly Gln Gly Thr Leu Val Thr Val Ser Ser Gly Thr<br>        115                 120                 125 | | 384 |
| ggc ggt tca ggc gga acc ggc agc ggc act ggg tcg acg gac atc<br>Gly Gly Ser Gly Gly Thr Gly Ser Gly Thr Gly Gly Ser Thr Asp Ile<br>    130                 135                 140 | | 432 |
| cag ttg acc cag tcg cca tcc ttc ctg tct gca tct gta gga gac aga<br>Gln Leu Thr Gln Ser Pro Ser Phe Leu Ser Ala Ser Val Gly Asp Arg<br>145                 150                 155                 160 | | 480 |
| gtc acc atc act tgc cgg gcc agt cac agt att agt agc tgg ttg gcc<br>Val Thr Ile Thr Cys Arg Ala Ser His Ser Ile Ser Ser Trp Leu Ala<br>                165                 170                 175 | | 528 |
| tgg tat cag cag aaa cca ggg aaa gcc cct aag ctc ctg atc tat aag<br>Trp Tyr Gln Gln Lys Pro Gly Lys Ala Pro Lys Leu Leu Ile Tyr Lys<br>            180                 185                 190 | | 576 |
| gca tct agt tta gaa agt ggg gtc cca tca agg ttc agc ggc agt gga<br>Ala Ser Ser Leu Glu Ser Gly Val Pro Ser Arg Phe Ser Gly Ser Gly<br>        195                 200                 205 | | 624 |
| tct ggg aca gat ttc act ctc acc atc agc agc ctg cag cct gaa gat<br>Ser Gly Thr Asp Phe Thr Leu Thr Ile Ser Ser Leu Gln Pro Glu Asp<br>    210                 215                 220 | | 672 |
| ttt gca act tat tac tgt cta caa gat tac aat tac cct cgg acg ttc<br>Phe Ala Thr Tyr Tyr Cys Leu Gln Asp Tyr Asn Tyr Pro Arg Thr Phe<br>225                 230                 235                 240 | | 720 |
| ggc caa ggg acc aag ctg gag atc aaa cgt gcg gcc gca<br>Gly Gln Gly Thr Lys Leu Glu Ile Lys Arg Ala Ala Ala<br>                245                 250 | | 759 |

<210> SEQ ID NO 180
<211> LENGTH: 253
<212> TYPE: PRT
<213> ORGANISM: Artificial sequence
<220> FEATURE:
<223> OTHER INFORMATION: Synthetic Construct

<400> SEQUENCE: 180

Ala Met Ala Gln Val Gln Leu Val Gln Ser Gly Gly Gly Val Ala Gln
1               5                   10                  15

Pro Gly Arg Ser Leu Arg Leu Ser Cys Ala Ala Ser Gly Phe Thr Phe
            20                  25                  30

```
Ser Ser Tyr Gly Met His Trp Val Arg Gln Ala Pro Gly Lys Gly Leu
        35                  40                  45

Glu Trp Val Ala Asp Ile Ser Tyr Asp Gly Ser Asn Lys Tyr Tyr Ala
    50                  55                  60

Asp Ser Val Lys Gly Arg Phe Thr Ile Ser Arg Asp Asn Ser Lys Asn
 65                  70                  75                  80

Thr Leu Tyr Leu Gln Met Asn Ser Leu Arg Ala Glu Asp Thr Ala Val
                85                  90                  95

Tyr Tyr Cys Ala Lys Asp Gly Leu Asp Leu Thr Gly Thr Ile Gln Pro
            100                 105                 110

Phe Gly Tyr Trp Gly Gln Gly Thr Leu Val Thr Val Ser Ser Gly Thr
            115                 120                 125

Gly Gly Ser Gly Gly Thr Gly Ser Gly Thr Gly Ser Thr Asp Ile
        130                 135                 140

Gln Leu Thr Gln Ser Pro Ser Phe Leu Ser Ala Ser Val Gly Asp Arg
145                 150                 155                 160

Val Thr Ile Thr Cys Arg Ala Ser His Ser Ile Ser Ser Trp Leu Ala
                165                 170                 175

Trp Tyr Gln Gln Lys Pro Gly Lys Ala Pro Lys Leu Leu Ile Tyr Lys
            180                 185                 190

Ala Ser Ser Leu Glu Ser Gly Val Pro Ser Arg Phe Ser Gly Ser Gly
            195                 200                 205

Ser Gly Thr Asp Phe Thr Leu Thr Ile Ser Ser Leu Gln Pro Glu Asp
        210                 215                 220

Phe Ala Thr Tyr Tyr Cys Leu Gln Asp Tyr Asn Tyr Pro Arg Thr Phe
225                 230                 235                 240

Gly Gln Gly Thr Lys Leu Glu Ile Lys Arg Ala Ala Ala
                245                 250

<210> SEQ ID NO 181
<211> LENGTH: 753
<212> TYPE: DNA
<213> ORGANISM: Artificial sequence
<220> FEATURE:
<223> OTHER INFORMATION: SC04-097
<220> FEATURE:
<221> NAME/KEY: CDS
<222> LOCATION: (1)..(753)

<400> SEQUENCE: 181 gcc atg gcc gaa gtg cag ctg gtg cag tct ggg gga cac ttg gta cag      48
Ala Met Ala Glu Val Gln Leu Val Gln Ser Gly Gly His Leu Val Gln
  1               5                  10                  15 cct ggg ggg tcc ctg aga ctc tcc tgt gca gcc tct gga ttc acc ttt      96
Pro Gly Gly Ser Leu Arg Leu Ser Cys Ala Ala Ser Gly Phe Thr Phe
             20                  25                  30 agc agc tat gcc atg agc tgg gtc cgc cag gct cca ggg aag ggg ctg     144
Ser Ser Tyr Ala Met Ser Trp Val Arg Gln Ala Pro Gly Lys Gly Leu
         35                  40                  45 gag tgg gtc tca ctt att att ggt agc ggt cgt agc aca tac tac gca     192
Glu Trp Val Ser Leu Ile Ile Gly Ser Gly Arg Ser Thr Tyr Tyr Ala
     50                  55                  60 gac tcc gtg aag ggc cgg ttc acc atc tcc aga gac aat tcc aag aac     240
Asp Ser Val Lys Gly Arg Phe Thr Ile Ser Arg Asp Asn Ser Lys Asn
 65                  70                  75                  80 acg ctg tat ctg caa atg aac agc ctg aga gcc gag gac acg gcc gta     288
Thr Leu Tyr Leu Gln Met Asn Ser Leu Arg Ala Glu Asp Thr Ala Val
                 85                  90                  95
```

```
tat tac tgt gcg aaa acc gcg agt aat ctt gga agg ggg ggt atg gac    336
Tyr Tyr Cys Ala Lys Thr Ala Ser Asn Leu Gly Arg Gly Gly Met Asp
            100                 105                 110 gtc tgg ggc caa ggg acc acg gtc acc gtc tcg agc ggt acg ggc ggt    384
Val Trp Gly Gln Gly Thr Thr Val Thr Val Ser Ser Gly Thr Gly Gly
            115                 120                 125 tca ggc gga acc ggc agc ggc act ggc ggg tcg acg gac att cag ttg    432
Ser Gly Gly Thr Gly Ser Gly Thr Gly Gly Ser Thr Asp Ile Gln Leu
130                 135                 140 acc cag tct cca tcc tcc ctg tct gca tct gtg gga gac aga gtc act    480
Thr Gln Ser Pro Ser Ser Leu Ser Ala Ser Val Gly Asp Arg Val Thr
145                 150                 155                 160 atc act tgc cgg gcc agt cag ggc att agc agt cat tta gcc tgg tat    528
Ile Thr Cys Arg Ala Ser Gln Gly Ile Ser Ser His Leu Ala Trp Tyr
            165                 170                 175 cag caa aaa cca ggg aaa gcc cct aag ctc ctg atc tat gct gca tcc    576
Gln Gln Lys Pro Gly Lys Ala Pro Lys Leu Leu Ile Tyr Ala Ala Ser
            180                 185                 190 agt ttg caa agt ggg gtc cca tca agg ttc agc ggc agt gga tct ggg    624
Ser Leu Gln Ser Gly Val Pro Ser Arg Phe Ser Gly Ser Gly Ser Gly
            195                 200                 205 aca gaa ttc act ctc acc atc agc agc ctg cag cct gaa gat ttt gca    672
Thr Glu Phe Thr Leu Thr Ile Ser Ser Leu Gln Pro Glu Asp Phe Ala
210                 215                 220 act tat tac tgt caa cag ttt aat agt tac ccg atc acc ttc ggc caa    720
Thr Tyr Tyr Cys Gln Gln Phe Asn Ser Tyr Pro Ile Thr Phe Gly Gln
225                 230                 235                 240 ggg aca cga ctg gag att aaa cgt gcg gcc gca                        753
Gly Thr Arg Leu Glu Ile Lys Arg Ala Ala Ala
            245                 250

<210> SEQ ID NO 182
<211> LENGTH: 251
<212> TYPE: PRT
<213> ORGANISM: Artificial sequence
<220> FEATURE:
<223> OTHER INFORMATION: Synthetic Construct

<400> SEQUENCE: 182

Ala Met Ala Glu Val Gln Leu Val Gln Ser Gly Gly His Leu Val Gln
1               5                   10                  15

Pro Gly Gly Ser Leu Arg Leu Ser Cys Ala Ala Ser Gly Phe Thr Phe
            20                  25                  30

Ser Ser Tyr Ala Met Ser Trp Val Arg Gln Ala Pro Gly Lys Gly Leu
        35                  40                  45

Glu Trp Val Ser Leu Ile Ile Gly Ser Gly Arg Ser Thr Tyr Tyr Ala
    50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Lys Thr Ala Ser Asn Leu Gly Arg Gly Gly Met Asp
            100                 105                 110

Val Trp Gly Gln Gly Thr Thr Val Thr Val Ser Ser Gly Thr Gly Gly
        115                 120                 125

Ser Gly Gly Thr Gly Ser Gly Thr Gly Gly Ser Thr Asp Ile Gln Leu
    130                 135                 140

Thr Gln Ser Pro Ser Ser Leu Ser Ala Ser Val Gly Asp Arg Val Thr
```

```
                145                 150                 155                 160
Ile Thr Cys Arg Ala Ser Gln Gly Ile Ser Ser His Leu Ala Trp Tyr
                    165                 170                 175

Gln Gln Lys Pro Gly Lys Ala Pro Lys Leu Leu Ile Tyr Ala Ala Ser
                180                 185                 190

Ser Leu Gln Ser Gly Val Pro Ser Arg Phe Ser Gly Ser Gly Ser Gly
                195                 200                 205

Thr Glu Phe Thr Leu Thr Ile Ser Ser Leu Gln Pro Glu Asp Phe Ala
        210                 215                 220

Thr Tyr Tyr Cys Gln Gln Phe Asn Ser Tyr Pro Ile Thr Phe Gly Gln
225                 230                 235                 240

Gly Thr Arg Leu Glu Ile Lys Arg Ala Ala Ala
                245                 250

<210> SEQ ID NO 183
<211> LENGTH: 747
<212> TYPE: DNA
<213> ORGANISM: Artificial sequence
<220> FEATURE:
<223> OTHER INFORMATION: SC04-098
<220> FEATURE:
<221> NAME/KEY: CDS
<222> LOCATION: (1)..(747)

<400> SEQUENCE: 183
```

| | | | | | | | | | | | | | | | | |
|---|---|---|---|---|---|---|---|---|---|---|---|---|---|---|---|---|
| gcc | atg | gcc | gaa | gtg | cag | ctg | gtg | cag | tct | ggg | gga | ggc | gcg | gtc | cag | 48 |
| Ala | Met | Ala | Glu | Val | Gln | Leu | Val | Gln | Ser | Gly | Gly | Gly | Ala | Val | Gln | |
| 1 | | | | 5 | | | | | 10 | | | | | 15 | | |
| cct | ggg | agg | tcc | ctg | aga | ctc | tcc | tgt | gca | gcc | tct | gga | ttc | acc | ttc | 96 |
| Pro | Gly | Arg | Ser | Leu | Arg | Leu | Ser | Cys | Ala | Ala | Ser | Gly | Phe | Thr | Phe | |
| | | 20 | | | | | 25 | | | | | 30 | | | | |
| agt | agc | tat | ggc | atg | cac | tgg | gtc | cgc | cag | gct | cca | ggc | aag | ggg | ctg | 144 |
| Ser | Ser | Tyr | Gly | Met | His | Trp | Val | Arg | Gln | Ala | Pro | Gly | Lys | Gly | Leu | |
| | 35 | | | | | 40 | | | | | 45 | | | | | |
| gag | tgg | gtg | gct | gtt | ata | tta | tat | gat | gga | agt | gat | aaa | ttc | tat | gca | 192 |
| Glu | Trp | Val | Ala | Val | Ile | Leu | Tyr | Asp | Gly | Ser | Asp | Lys | Phe | Tyr | Ala | |
| 50 | | | | | 55 | | | | | 60 | | | | | | |
| gac | tcc | gtg | aag | ggc | cga | ttc | acc | atc | tcc | aga | gac | aat | tcc | aag | aac | 240 |
| Asp | Ser | Val | Lys | Gly | Arg | Phe | Thr | Ile | Ser | Arg | Asp | Asn | Ser | Lys | Asn | |
| 65 | | | | 70 | | | | | 75 | | | | | 80 | | |
| acg | ctg | tat | ctg | cag | atg | aac | agc | ctg | aga | gct | gag | gac | acg | gct | gtg | 288 |
| Thr | Leu | Tyr | Leu | Gln | Met | Asn | Ser | Leu | Arg | Ala | Glu | Asp | Thr | Ala | Val | |
| | | | | 85 | | | | | 90 | | | | | 95 | | |
| tat | tac | tgt | gcg | aaa | gta | gca | gtg | gct | ggt | acg | cac | ttt | gac | tac | tgg | 336 |
| Tyr | Tyr | Cys | Ala | Lys | Val | Ala | Val | Ala | Gly | Thr | His | Phe | Asp | Tyr | Trp | |
| | | | 100 | | | | | 105 | | | | | 110 | | | |
| ggc | cag | gga | acc | ctg | gtc | acc | gtc | tcg | agc | ggt | acg | ggc | ggt | tca | ggc | 384 |
| Gly | Gln | Gly | Thr | Leu | Val | Thr | Val | Ser | Ser | Gly | Thr | Gly | Gly | Ser | Gly | |
| | | 115 | | | | | 120 | | | | | 125 | | | | |
| gga | acc | ggc | agc | ggc | act | ggc | ggg | tcg | acg | gac | atc | cag | atg | acc | cag | 432 |
| Gly | Thr | Gly | Ser | Gly | Thr | Gly | Gly | Ser | Thr | Asp | Ile | Gln | Met | Thr | Gln | |
| | 130 | | | | | 135 | | | | | 140 | | | | | |
| tct | cca | tcc | tcc | ctg | tct | gca | tct | gta | gga | gac | aga | gtc | acc | atc | act | 480 |
| Ser | Pro | Ser | Ser | Leu | Ser | Ala | Ser | Val | Gly | Asp | Arg | Val | Thr | Ile | Thr | |
| 145 | | | | | 150 | | | | | 155 | | | | | 160 | |
| tgc | cgg | gca | agt | cag | ggc | att | aga | aat | gat | tta | ggc | tgg | tat | cag | cag | 528 |
| Cys | Arg | Ala | Ser | Gln | Gly | Ile | Arg | Asn | Asp | Leu | Gly | Trp | Tyr | Gln | Gln | |
| | | | | 165 | | | | | 170 | | | | | 175 | | |
| aaa | cca | ggg | aaa | gcc | cct | aag | ctc | ctg | atc | tat | gct | gca | tcc | agt | ttg | 576 |
| Lys | Pro | Gly | Lys | Ala | Pro | Lys | Leu | Leu | Ile | Tyr | Ala | Ala | Ser | Ser | Leu | |

```
                         180                     185                     190
caa agt ggg gtc cca tca agg ttc agc ggc agt gga tct ggg aca gat         624
Gln Ser Gly Val Pro Ser Arg Phe Ser Gly Ser Gly Ser Gly Thr Asp
        195                     200                     205 ttc act ctc acc atc agc agc ctg cag cct gaa gat ttt gca act tat         672
Phe Thr Leu Thr Ile Ser Ser Leu Gln Pro Glu Asp Phe Ala Thr Tyr
210                     215                     220 tac tgt caa cag ctt aat agt tac cct ccc act ttc ggc gga ggg acc         720
Tyr Cys Gln Gln Leu Asn Ser Tyr Pro Pro Thr Phe Gly Gly Gly Thr
225                     230                     235                     240 aag gtg gaa atc aaa cgt gcg gcc gca                                     747
Lys Val Glu Ile Lys Arg Ala Ala Ala
                245

<210> SEQ ID NO 184
<211> LENGTH: 249
<212> TYPE: PRT
<213> ORGANISM: Artificial sequence
<220> FEATURE:
<223> OTHER INFORMATION: Synthetic Construct

<400> SEQUENCE: 184

Ala Met Ala Glu Val Gln Leu Val Gln Ser Gly Gly Gly Val Gln
1               5                   10                  15

Pro Gly Arg Ser Leu Arg Leu Ser Cys Ala Ala Ser Gly Phe Thr Phe
                20                  25                  30

Ser Ser Tyr Gly Met His Trp Val Arg Gln Ala Pro Gly Lys Gly Leu
            35                  40                  45

Glu Trp Val Ala Val Ile Leu Tyr Asp Gly Ser Asp Lys Phe Tyr Ala
50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Lys Val Ala Val Ala Gly Thr His Phe Asp Tyr Trp
                100                 105                 110

Gly Gln Gly Thr Leu Val Thr Val Ser Ser Gly Thr Gly Gly Ser Gly
            115                 120                 125

Gly Thr Gly Ser Gly Thr Gly Gly Ser Thr Asp Ile Gln Met Thr Gln
130                 135                 140

Ser Pro Ser Ser Leu Ser Ala Ser Val Gly Asp Arg Val Thr Ile Thr
145                 150                 155                 160

Cys Arg Ala Ser Gln Gly Ile Arg Asn Asp Leu Gly Trp Tyr Gln Gln
                165                 170                 175

Lys Pro Gly Lys Ala Pro Lys Leu Leu Ile Tyr Ala Ala Ser Ser Leu
            180                 185                 190

Gln Ser Gly Val Pro Ser Arg Phe Ser Gly Ser Gly Ser Gly Thr Asp
            195                 200                 205

Phe Thr Leu Thr Ile Ser Ser Leu Gln Pro Glu Asp Phe Ala Thr Tyr
210                 215                 220

Tyr Cys Gln Gln Leu Asn Ser Tyr Pro Pro Thr Phe Gly Gly Gly Thr
225                 230                 235                 240

Lys Val Glu Ile Lys Arg Ala Ala Ala
                245

<210> SEQ ID NO 185
<211> LENGTH: 747
```

```
<212> TYPE: DNA
<213> ORGANISM: Artificial sequence
<220> FEATURE:
<223> OTHER INFORMATION: SC04-103
<220> FEATURE:
<221> NAME/KEY: CDS
<222> LOCATION: (1)..(747)

<400> SEQUENCE: 185
```

| | | | | | | | | | | | | | | | | |
|---|---|---|---|---|---|---|---|---|---|---|---|---|---|---|---|---|
| gcc | atg | gcc | cag | gtg | cag | ctg | cag | gag | tcg | ggg | gga | ggc | gtg | gtc | cag | 48 |
| Ala | Met | Ala | Gln | Val | Gln | Leu | Gln | Glu | Ser | Gly | Gly | Gly | Val | Val | Gln | |
| 1 | | | 5 | | | | | 10 | | | | | 15 | | | |
| cct | ggg | agg | tcc | ctg | aga | ctc | tcc | tgt | gca | gcc | tct | gga | ttc | acc | ttc | 96 |
| Pro | Gly | Arg | Ser | Leu | Arg | Leu | Ser | Cys | Ala | Ala | Ser | Gly | Phe | Thr | Phe | |
| | | | 20 | | | | | 25 | | | | | 30 | | | |
| agt | agc | tat | ggc | atg | cac | tgg | gtc | cgc | cag | gct | cca | ggc | aag | ggg | ctg | 144 |
| Ser | Ser | Tyr | Gly | Met | His | Trp | Val | Arg | Gln | Ala | Pro | Gly | Lys | Gly | Leu | |
| | | 35 | | | | | 40 | | | | | 45 | | | | |
| gag | tgg | gtg | gca | gtt | ata | tta | tat | gat | gga | agt | gat | aaa | tac | tat | gca | 192 |
| Glu | Trp | Val | Ala | Val | Ile | Leu | Tyr | Asp | Gly | Ser | Asp | Lys | Tyr | Tyr | Ala | |
| 50 | | | | | 55 | | | | | 60 | | | | | | |
| gac | tcc | gtg | aag | ggc | cga | ttc | acc | atc | tcc | aga | gac | aat | tcc | aag | aac | 240 |
| Asp | Ser | Val | Lys | Gly | Arg | Phe | Thr | Ile | Ser | Arg | Asp | Asn | Ser | Lys | Asn | |
| 65 | | | | | 70 | | | | | 75 | | | | | 80 | |
| acg | ctg | tat | ctg | caa | atg | aac | agc | ctg | aga | gct | gag | gac | acg | gct | gtg | 288 |
| Thr | Leu | Tyr | Leu | Gln | Met | Asn | Ser | Leu | Arg | Ala | Glu | Asp | Thr | Ala | Val | |
| | | | | 85 | | | | | 90 | | | | | 95 | | |
| tat | tac | tgt | gcg | aaa | gtc | gct | gtg | gct | ggg | gaa | agc | ttt | gac | tcc | tgg | 336 |
| Tyr | Tyr | Cys | Ala | Lys | Val | Ala | Val | Ala | Gly | Glu | Ser | Phe | Asp | Ser | Trp | |
| | | | 100 | | | | | 105 | | | | | 110 | | | |
| ggc | cgg | ggc | acc | ctg | gtc | acc | gtc | tcg | agc | ggt | acg | ggc | ggt | tca | ggc | 384 |
| Gly | Arg | Gly | Thr | Leu | Val | Thr | Val | Ser | Ser | Gly | Thr | Gly | Gly | Ser | Gly | |
| | | 115 | | | | | 120 | | | | | 125 | | | | |
| gga | acc | ggc | agc | ggc | act | ggc | ggg | tcg | acg | gac | atc | cag | ttg | acc | cag | 432 |
| Gly | Thr | Gly | Ser | Gly | Thr | Gly | Gly | Ser | Thr | Asp | Ile | Gln | Leu | Thr | Gln | |
| 130 | | | | | 135 | | | | | 140 | | | | | | |
| tct | cca | tct | tcc | gtg | tct | gca | tct | gta | gga | gac | aga | gtc | acc | atc | act | 480 |
| Ser | Pro | Ser | Ser | Val | Ser | Ala | Ser | Val | Gly | Asp | Arg | Val | Thr | Ile | Thr | |
| 145 | | | | | 150 | | | | | 155 | | | | | 160 | |
| tgt | cgg | gcg | agt | cag | ggt | att | agc | agc | tgg | tta | gcc | tgg | tat | cag | cag | 528 |
| Cys | Arg | Ala | Ser | Gln | Gly | Ile | Ser | Ser | Trp | Leu | Ala | Trp | Tyr | Gln | Gln | |
| | | | | 165 | | | | | 170 | | | | | 175 | | |
| aag | cca | ggg | aaa | gcc | cct | agg | tcc | ctg | atc | tat | gat | gca | tcc | agt | ttg | 576 |
| Lys | Pro | Gly | Lys | Ala | Pro | Arg | Ser | Leu | Ile | Tyr | Asp | Ala | Ser | Ser | Leu | |
| | | | 180 | | | | | 185 | | | | | 190 | | | |
| caa | agt | ggg | gtc | cca | tca | agg | ttc | agc | ggc | agt | gga | tct | ggg | aca | gac | 624 |
| Gln | Ser | Gly | Val | Pro | Ser | Arg | Phe | Ser | Gly | Ser | Gly | Ser | Gly | Thr | Asp | |
| | | 195 | | | | | 200 | | | | | 205 | | | | |
| ttt | act | ctc | acc | atc | agc | agc | ctg | cag | cct | gaa | gat | ttt | gca | act | tac | 672 |
| Phe | Thr | Leu | Thr | Ile | Ser | Ser | Leu | Gln | Pro | Glu | Asp | Phe | Ala | Thr | Tyr | |
| 210 | | | | | 215 | | | | | 220 | | | | | | |
| tat | tgt | caa | cag | gct | gac | agt | ttc | ccg | atc | acc | ttc | ggc | caa | ggg | aca | 720 |
| Tyr | Cys | Gln | Gln | Ala | Asp | Ser | Phe | Pro | Ile | Thr | Phe | Gly | Gln | Gly | Thr | |
| 225 | | | | | 230 | | | | | 235 | | | | | 240 | |
| cga | ctg | gag | att | aaa | cgt | gcg | gcc | gca | | | | | | | | 747 |
| Arg | Leu | Glu | Ile | Lys | Arg | Ala | Ala | Ala | | | | | | | | |
| | | | | 245 | | | | | | | | | | | | |

```
<210> SEQ ID NO 186
<211> LENGTH: 249
<212> TYPE: PRT
<213> ORGANISM: Artificial sequence
```

```
<220> FEATURE:
<223> OTHER INFORMATION: Synthetic Construct

<400> SEQUENCE: 186

Ala Met Ala Gln Val Gln Leu Gln Glu Ser Gly Gly Gly Val Val Gln
1               5                   10                  15

Pro Gly Arg Ser Leu Arg Leu Ser Cys Ala Ala Ser Gly Phe Thr Phe
            20                  25                  30

Ser Ser Tyr Gly Met His Trp Val Arg Gln Ala Pro Gly Lys Gly Leu
        35                  40                  45

Glu Trp Val Ala Val Ile Leu Tyr Asp Gly Ser Asp Lys Tyr Tyr Ala
    50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Lys Val Ala Val Ala Gly Glu Ser Phe Asp Ser Trp
            100                 105                 110

Gly Arg Gly Thr Leu Val Thr Val Ser Ser Gly Thr Gly Gly Ser Gly
        115                 120                 125

Gly Thr Gly Ser Gly Thr Gly Gly Ser Thr Asp Ile Gln Leu Thr Gln
    130                 135                 140

Ser Pro Ser Ser Val Ser Ala Ser Val Gly Asp Arg Val Thr Ile Thr
145                 150                 155                 160

Cys Arg Ala Ser Gln Gly Ile Ser Ser Trp Leu Ala Trp Tyr Gln Gln
                165                 170                 175

Lys Pro Gly Lys Ala Pro Arg Ser Leu Ile Tyr Asp Ala Ser Ser Leu
            180                 185                 190

Gln Ser Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Thr Tyr
    210                 215                 220

Tyr Cys Gln Gln Ala Asp Ser Phe Pro Ile Thr Phe Gly Gln Gly Thr
225                 230                 235                 240

Arg Leu Glu Ile Lys Arg Ala Ala Ala
                245

<210> SEQ ID NO 187
<211> LENGTH: 759
<212> TYPE: DNA
<213> ORGANISM: Artificial sequence
<220> FEATURE:
<223> OTHER INFORMATION: SC04-104
<220> FEATURE:
<221> NAME/KEY: CDS
<222> LOCATION: (1)..(759)

<400> SEQUENCE: 187 gcc atg gcc cag gtg cag ctg cag gag tcg ggg gga ggc gtg gtc cag      48
Ala Met Ala Gln Val Gln Leu Gln Glu Ser Gly Gly Gly Val Val Gln
1               5                   10                  15 cct ggg agg tcc ctg aga ctc tcc tgt gca gcc tct gga ttc acc ttc      96
Pro Gly Arg Ser Leu Arg Leu Ser Cys Ala Ala Ser Gly Phe Thr Phe
            20                  25                  30 agt agc tat ggc atg cac tgg gtc cgc cag gct cca ggc aag ggg ctg     144
Ser Ser Tyr Gly Met His Trp Val Arg Gln Ala Pro Gly Lys Gly Leu
        35                  40                  45 gag tgg gtg gca act ata tca tat gat gga aat gtt aaa gac tat gca     192
```

```
            Glu Trp Val Ala Thr Ile Ser Tyr Asp Gly Asn Val Lys Asp Tyr Ala
                 50                  55                  60 gac tcc gtg aag ggc cga ttc acc atc tcc aga gac aat tcc aag aac        240
Asp Ser Val Lys Gly Arg Phe Thr Ile Ser Arg Asp Asn Ser Lys Asn
 65                  70                  75                  80 acg ctg tat ctg caa atg aac agc ctg aga act gag gac acg gct gtg        288
Thr Leu Tyr Leu Gln Met Asn Ser Leu Arg Thr Glu Asp Thr Ala Val
                 85                  90                  95 tat tac tgt gcg aaa ata gtg gtg gtg acc gcc ctc gat gct ttt gat        336
Tyr Tyr Cys Ala Lys Ile Val Val Val Thr Ala Leu Asp Ala Phe Asp
                100                 105                 110 atc tgg ggc caa ggg aca atg gtc acc gtc tcg agc ggt acg ggc ggt        384
Ile Trp Gly Gln Gly Thr Met Val Thr Val Ser Ser Gly Thr Gly Gly
                115                 120                 125 tca gga gga acc ggc agc ggc act ggc ggg tcg acg gac atc cag ttg        432
Ser Gly Gly Thr Gly Ser Gly Thr Gly Gly Ser Thr Asp Ile Gln Leu
            130                 135                 140 acc cag tct cct tcc acc ctg tct gca tct gta gga gac aga gtc acc        480
Thr Gln Ser Pro Ser Thr Leu Ser Ala Ser Val Gly Asp Arg Val Thr
145                 150                 155                 160 atc act tgc cgg gcc agt cag att ctt ggt cac tgg ttg ccc ttg tcc        528
Ile Thr Cys Arg Ala Ser Gln Ile Leu Gly His Trp Leu Pro Leu Ser
                165                 170                 175 tgg tat cag cag aaa cca ggt aaa gcc cct aaa ctc ctg atc tct aag        576
Trp Tyr Gln Gln Lys Pro Gly Lys Ala Pro Lys Leu Leu Ile Ser Lys
                180                 185                 190 gcg tct agt tta gaa agt gga gtc cca cca agg ttc agc ggc agt gga        624
Ala Ser Ser Leu Glu Ser Gly Val Pro Pro Arg Phe Ser Gly Ser Gly
            195                 200                 205 tct ggg tca gat ttc act ctc acc atc agc agc ctg cag ccc gat gat        672
Ser Gly Ser Asp Phe Thr Leu Thr Ile Ser Ser Leu Gln Pro Asp Asp
210                 215                 220 ttt gca act tat tac tgc ctc caa tat cat gag tac ccg ctc acc ttc        720
Phe Ala Thr Tyr Tyr Cys Leu Gln Tyr His Glu Tyr Pro Leu Thr Phe
225                 230                 235                 240 ggc gga ggg acc aag ctg gag atc aaa cgt gcg gcc gca                    759
Gly Gly Gly Thr Lys Leu Glu Ile Lys Arg Ala Ala Ala
                245                 250

<210> SEQ ID NO 188
<211> LENGTH: 253
<212> TYPE: PRT
<213> ORGANISM: Artificial sequence
<220> FEATURE:
<223> OTHER INFORMATION: Synthetic Construct

<400> SEQUENCE: 188

Ala Met Ala Gln Val Gln Leu Gln Glu Ser Gly Gly Gly Val Val Gln
 1               5                  10                  15

Pro Gly Arg Ser Leu Arg Leu Ser Cys Ala Ala Ser Gly Phe Thr Phe
                 20                  25                  30

Ser Ser Tyr Gly Met His Trp Val Arg Gln Ala Pro Gly Lys Gly Leu
             35                  40                  45

Glu Trp Val Ala Thr Ile Ser Tyr Asp Gly Asn Val Lys Asp Tyr Ala
     50                  55                  60

Asp Ser Val Lys Gly Arg Phe Thr Ile Ser Arg Asp Asn Ser Lys Asn
 65                  70                  75                  80

Thr Leu Tyr Leu Gln Met Asn Ser Leu Arg Thr Glu Asp Thr Ala Val
                 85                  90                  95
```

```
Tyr Tyr Cys Ala Lys Ile Val Val Thr Ala Leu Asp Ala Phe Asp
             100                 105                 110

Ile Trp Gly Gln Gly Thr Met Val Thr Val Ser Ser Gly Thr Gly Gly
    115                 120                 125

Ser Gly Gly Thr Gly Ser Gly Thr Gly Gly Ser Thr Asp Ile Gln Leu
    130                 135                 140

Thr Gln Ser Pro Ser Thr Leu Ser Ala Ser Val Gly Asp Arg Val Thr
145                 150                 155                 160

Ile Thr Cys Arg Ala Ser Gln Ile Leu Gly His Trp Leu Pro Leu Ser
                165                 170                 175

Trp Tyr Gln Gln Lys Pro Gly Lys Ala Pro Lys Leu Leu Ile Ser Lys
            180                 185                 190

Ala Ser Ser Leu Glu Ser Gly Val Pro Pro Arg Phe Ser Gly Ser Gly
        195                 200                 205

Ser Gly Ser Asp Phe Thr Leu Thr Ile Ser Ser Leu Gln Pro Asp Asp
    210                 215                 220

Phe Ala Thr Tyr Tyr Cys Leu Gln Tyr His Glu Tyr Pro Leu Thr Phe
225                 230                 235                 240

Gly Gly Gly Thr Lys Leu Glu Ile Lys Arg Ala Ala Ala
                245                 250
```

<210> SEQ ID NO 189
<211> LENGTH: 750
<212> TYPE: DNA
<213> ORGANISM: Artificial sequence
<220> FEATURE:
<223> OTHER INFORMATION: SC04-108
<220> FEATURE:
<221> NAME/KEY: CDS
<222> LOCATION: (1)..(750)

<400> SEQUENCE: 189

```
gcc atg gcc gaa gtg cag ctg gtg cag tct ggg gga ggc ttg gta cag      48
Ala Met Ala Glu Val Gln Leu Val Gln Ser Gly Gly Gly Leu Val Gln
 1               5                  10                  15 cct ggg ggg tcc ctg aga ctc tcc tgt gca gcg tct gga ttc acc ttc      96
Pro Gly Gly Ser Leu Arg Leu Ser Cys Ala Ala Ser Gly Phe Thr Phe
             20                  25                  30 agt agc tat ggc atg cac tgg gtc cgc cag gct cca ggc aag ggg ctg     144
Ser Ser Tyr Gly Met His Trp Val Arg Gln Ala Pro Gly Lys Gly Leu
         35                  40                  45 gag tgg gtg gca gtt ata tta tat gat gga agt gat aag ttc tat gca     192
Glu Trp Val Ala Val Ile Leu Tyr Asp Gly Ser Asp Lys Phe Tyr Ala
     50                  55                  60 gac tcc gtg aag ggc cga ttc acc atc tcc aga gac aat tcc aag gac     240
Asp Ser Val Lys Gly Arg Phe Thr Ile Ser Arg Asp Asn Ser Lys Asp
 65                  70                  75                  80 acg ctg tat ctg caa atg aac agc ctg aga gct gag gac acg gct gtg     288
Thr Leu Tyr Leu Gln Met Asn Ser Leu Arg Ala Glu Asp Thr Ala Val
                 85                  90                  95 tat tac tgt gcg aaa ttt atg ata gta gca gat gat gct ttt gat atc     336
Tyr Tyr Cys Ala Lys Phe Met Ile Val Ala Asp Asp Ala Phe Asp Ile
            100                 105                 110 tgg ggc caa ggg aca atg gtc acc gtc tcg agc ggt acg ggc ggt tca     384
Trp Gly Gln Gly Thr Met Val Thr Val Ser Ser Gly Thr Gly Gly Ser
        115                 120                 125 ggc gga acc ggc agc ggc act ggc ggg tcg acg gac atc cag ttg acc     432
Gly Gly Thr Gly Ser Gly Thr Gly Gly Ser Thr Asp Ile Gln Leu Thr
    130                 135                 140
```

| | | |
|---|---|---|
| cag tct cca tcc tca ctg tct gca tct gta gga gac aga gtc acc atc<br>Gln Ser Pro Ser Ser Leu Ser Ala Ser Val Gly Asp Arg Val Thr Ile<br>145                              150                     155                  160 | 480 |
| act tgt cgg gcg agt cag ggc att agc agt cat tta gtc tgg tat cag<br>Thr Cys Arg Ala Ser Gln Gly Ile Ser Ser His Leu Val Trp Tyr Gln<br>                        165                     170                  175 | 528 |
| cag aaa cca ggg aaa gcc cct aag tcc ctg atc tat gct gca tcc agt<br>Gln Lys Pro Gly Lys Ala Pro Lys Ser Leu Ile Tyr Ala Ala Ser Ser<br>                180                     185                  190 | 576 |
| ttg caa agt ggg gtc cca tca agg ttc agc ggc agt gaa tct gcg aca<br>Leu Gln Ser Gly Val Pro Ser Arg Phe Ser Gly Ser Glu Ser Ala Thr<br>195                            200                     205 | 624 |
| gat ttc act ctc acc atc agc agc ctg cag cct gaa gat ttt gca act<br>Asp Phe Thr Leu Thr Ile Ser Ser Leu Gln Pro Glu Asp Phe Ala Thr<br>210                            215                    220 | 672 |
| tat tac tgc caa cag tat tac agt tac cct atc acc ttc ggc caa ggg<br>Tyr Tyr Cys Gln Gln Tyr Tyr Ser Tyr Pro Ile Thr Phe Gly Gln Gly<br>225                            230                    235                  240 | 720 |
| aca cga ctg gag att aaa cgt gcg gcc gca<br>Thr Arg Leu Glu Ile Lys Arg Ala Ala Ala<br>                        245                     250 | 750 |

```
<210> SEQ ID NO 190
<211> LENGTH: 250
<212> TYPE: PRT
<213> ORGANISM: Artificial sequence
<220> FEATURE:
<223> OTHER INFORMATION: Synthetic Construct

<400> SEQUENCE: 190

Ala Met Ala Glu Val Gln Leu Val Gln Ser Gly Gly Gly Leu Val Gln
1               5                   10                  15

Pro Gly Gly Ser Leu Arg Leu Ser Cys Ala Ala Ser Gly Phe Thr Phe
            20                  25                  30

Ser Ser Tyr Gly Met His Trp Val Arg Gln Ala Pro Gly Lys Gly Leu
        35                  40                  45

Glu Trp Val Ala Val Ile Leu Tyr Asp Gly Ser Asp Lys Phe Tyr Ala
    50                  55                  60

Asp Ser Val Lys Gly Arg Phe Thr Ile Ser Arg Asp Asn Ser Lys Asp
65                  70                  75                  80

Thr Leu Tyr Leu Gln Met Asn Ser Leu Arg Ala Glu Asp Thr Ala Val
                85                  90                  95

Tyr Tyr Cys Ala Lys Phe Met Ile Val Ala Asp Ala Phe Asp Ile
            100                 105                 110

Trp Gly Gln Gly Thr Met Val Thr Val Ser Ser Gly Thr Gly Gly Ser
        115                 120                 125

Gly Gly Thr Gly Ser Gly Thr Gly Gly Ser Thr Asp Ile Gln Leu Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Gly Ile Ser Ser His Leu Val Trp Tyr Gln
                165                 170                 175

Gln Lys Pro Gly Lys Ala Pro Lys Ser Leu Ile Tyr Ala Ala Ser Ser
            180                 185                 190

Leu Gln Ser Gly Val Pro Ser Arg Phe Ser Gly Ser Glu Ser Ala Thr
        195                 200                 205

Asp Phe Thr Leu Thr Ile Ser Ser Leu Gln Pro Glu Asp Phe Ala Thr
    210                 215                 220
```

```
Tyr Tyr Cys Gln Gln Tyr Tyr Ser Tyr Pro Ile Thr Phe Gly Gln Gly
225                 230                 235                 240

Thr Arg Leu Glu Ile Lys Arg Ala Ala Ala
                245                 250

<210> SEQ ID NO 191
<211> LENGTH: 744
<212> TYPE: DNA
<213> ORGANISM: Artificial sequence
<220> FEATURE:
<223> OTHER INFORMATION: SC04-120
<220> FEATURE:
<221> NAME/KEY: CDS
<222> LOCATION: (1)..(744)

<400> SEQUENCE: 191 gcc atg gcc gag gtg cag ctg gtg cag tct ggg gga ggc ttg gta cag        48
Ala Met Ala Glu Val Gln Leu Val Gln Ser Gly Gly Gly Leu Val Gln
1               5                   10                  15 cct ggc agg tcc ctg aga ctc tcc tgt gca gcc tct gga ttc acc ttc        96
Pro Gly Arg Ser Leu Arg Leu Ser Cys Ala Ala Ser Gly Phe Thr Phe
            20                  25                  30 agt acc tat ggc atg cac tgg gtc cgc cag gct cca ggc aag ggg ctg       144
Ser Thr Tyr Gly Met His Trp Val Arg Gln Ala Pro Gly Lys Gly Leu
        35                  40                  45 gag tgg gtg gca act ata tca tat gat gga agt att aaa gac tat gca       192
Glu Trp Val Ala Thr Ile Ser Tyr Asp Gly Ser Ile Lys Asp Tyr Ala
    50                  55                  60 gac tcc gag aag ggc cga ttc acc atc tcc aga gac aat tcc aag aac       240
Asp Ser Glu Lys Gly Arg Phe Thr Ile Ser Arg Asp Asn Ser Lys Asn
65                  70                  75                  80 acg ctg tat ctg caa atg aac agc ctg aga gct gag gac acg gct gtg       288
Thr Leu Tyr Leu Gln Met Asn Ser Leu Arg Ala Glu Asp Thr Ala Val
                85                  90                  95 tat tac tgt gcg aaa ggg ggg aag act gga gag ttt gac tac tgg ggc       336
Tyr Tyr Cys Ala Lys Gly Gly Lys Thr Gly Glu Phe Asp Tyr Trp Gly
            100                 105                 110 cag gga acc ctg gtc acc gtc tcg agc ggt acg ggc ggt tca ggc gga       384
Gln Gly Thr Leu Val Thr Val Ser Ser Gly Thr Gly Gly Ser Gly Gly
        115                 120                 125 acc ggc agc ggc act ggc ggg tcg acg gac atc cag ttg acc cag tct       432
Thr Gly Ser Gly Thr Gly Gly Ser Thr Asp Ile Gln Leu Thr Gln Ser
    130                 135                 140 cct tcc acc ctg tct gca tct gta gga gac aga gtc acc atc act tgc       480
Pro Ser Thr Leu Ser Ala Ser Val Gly Asp Arg Val Thr Ile Thr Cys
145                 150                 155                 160 cgg gcc agt cag ggc att aac agt tat tta gcc tgg tat cag caa gaa       528
Arg Ala Ser Gln Gly Ile Asn Ser Tyr Leu Ala Trp Tyr Gln Gln Glu
                165                 170                 175 cca ggg aaa gcc cct aaa ctc ctg atc tat gct gca tcc act ttg caa       576
Pro Gly Lys Ala Pro Lys Leu Leu Ile Tyr Ala Ala Ser Thr Leu Gln
            180                 185                 190 agt ggg gtc cca tca agg ttc agc ggc agt gga tct ggg aca gaa ttc       624
Ser Gly Val Pro Ser Arg Phe Ser Gly Ser Gly Ser Gly Thr Glu Phe
        195                 200                 205 act ctc aca atc agc agc ctg cag cct gaa gat ttt gca act tat tac       672
Thr Leu Thr Ile Ser Ser Leu Gln Pro Glu Asp Phe Ala Thr Tyr Tyr
    210                 215                 220 tgt caa cag ctt aat agt tac ccc ttc act ttc ggc cct ggg acc aaa       720
Cys Gln Gln Leu Asn Ser Tyr Pro Phe Thr Phe Gly Pro Gly Thr Lys
225                 230                 235                 240
```

```
gtg gat atc aaa cgt gcg gcc gca                                    744
Val Asp Ile Lys Arg Ala Ala Ala
            245
```

<210> SEQ ID NO 192
<211> LENGTH: 248
<212> TYPE: PRT
<213> ORGANISM: Artificial sequence
<220> FEATURE:
<223> OTHER INFORMATION: Synthetic Construct

<400> SEQUENCE: 192

```
Ala Met Ala Glu Val Gln Leu Val Gln Ser Gly Gly Gly Leu Val Gln
1               5                   10                  15

Pro Gly Arg Ser Leu Arg Leu Ser Cys Ala Ala Ser Gly Phe Thr Phe
            20                  25                  30

Ser Thr Tyr Gly Met His Trp Val Arg Gln Ala Pro Gly Lys Gly Leu
        35                  40                  45

Glu Trp Val Ala Thr Ile Ser Tyr Asp Gly Ser Ile Lys Asp Tyr Ala
    50                  55                  60

Asp Ser Glu Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Lys Gly Gly Lys Thr Gly Glu Phe Asp Tyr Trp Gly
            100                 105                 110

Gln Gly Thr Leu Val Thr Val Ser Ser Gly Thr Gly Gly Ser Gly Gly
        115                 120                 125

Thr Gly Ser Gly Thr Gly Gly Ser Thr Asp Ile Gln Leu Thr Gln Ser
    130                 135                 140

Pro Ser Thr Leu Ser Ala Ser Val Gly Asp Arg Val Thr Ile Thr Cys
145                 150                 155                 160

Arg Ala Ser Gln Gly Ile Asn Ser Tyr Leu Ala Trp Tyr Gln Gln Glu
                165                 170                 175

Pro Gly Lys Ala Pro Lys Leu Leu Ile Tyr Ala Ala Ser Thr Leu Gln
            180                 185                 190

Ser Gly Val Pro Ser Arg Phe Ser Gly Ser Gly Ser Gly Thr Glu Phe
        195                 200                 205

Thr Leu Thr Ile Ser Ser Leu Gln Pro Glu Asp Phe Ala Thr Tyr Tyr
    210                 215                 220

Cys Gln Gln Leu Asn Ser Tyr Pro Phe Thr Phe Gly Pro Gly Thr Lys
225                 230                 235                 240

Val Asp Ile Lys Arg Ala Ala Ala
            245
```

<210> SEQ ID NO 193
<211> LENGTH: 747
<212> TYPE: DNA
<213> ORGANISM: Artificial sequence
<220> FEATURE:
<223> OTHER INFORMATION: SC04-125
<220> FEATURE:
<221> NAME/KEY: CDS
<222> LOCATION: (1)..(747)

<400> SEQUENCE: 193

```
gcc atg gcc cag gtg cag ctg gtg gag tct ggg gga ggc gtg gtc cag    48
Ala Met Ala Gln Val Gln Leu Val Glu Ser Gly Gly Gly Val Val Gln
1               5                   10                  15
```

```
cct ggg agg tcc ctg aga ctc tcc tgt gca gcc tct gga ttc acc ttc      96
Pro Gly Arg Ser Leu Arg Leu Ser Cys Ala Ala Ser Gly Phe Thr Phe
         20                  25                  30 agt agc tat ggc atg cac tgg gtc cgc cag gct cca ggc aag ggg ctg     144
Ser Ser Tyr Gly Met His Trp Val Arg Gln Ala Pro Gly Lys Gly Leu
         35                  40                  45 gag tgg gtg gca gtt ata tca tat gat gga agt gat aaa tac tat gca     192
Glu Trp Val Ala Val Ile Ser Tyr Asp Gly Ser Asp Lys Tyr Tyr Ala
 50                  55                  60 gac tcc gtg aag ggc cga ttc acc atc tcc aga gac aat tcc aag aac     240
Asp Ser Val Lys Gly Arg Phe Thr Ile Ser Arg Asp Asn Ser Lys Asn
 65                  70                  75                  80 acg ctc tat ctg caa atg aac agc ttg aga gct gag gac acg gct gtg     288
Thr Leu Tyr Leu Gln Met Asn Ser Leu Arg Ala Glu Asp Thr Ala Val
                 85                  90                  95 tat tac tgt gcg aag ata gca aca gct ggt acc ggg ttt gac tac tgg     336
Tyr Tyr Cys Ala Lys Ile Ala Thr Ala Gly Thr Gly Phe Asp Tyr Trp
                100                 105                 110 ggc cag gga acc ctg gtc acc gtc tcg agc ggt acg ggc ggt tca ggc     384
Gly Gln Gly Thr Leu Val Thr Val Ser Ser Gly Thr Gly Gly Ser Gly
            115                 120                 125 gga acc ggc agc ggc act ggc ggg tcg acg gac atc cag atg acc cag     432
Gly Thr Gly Ser Gly Thr Gly Gly Ser Thr Asp Ile Gln Met Thr Gln
130                 135                 140 tct cca tct tcc gtg tct gca tct gta gga gac aga gtc acc atc act     480
Ser Pro Ser Ser Val Ser Ala Ser Val Gly Asp Arg Val Thr Ile Thr
145                 150                 155                 160 tgt cgg gcg agt cag ggc att agc agt tat tta gcc tgg tat cag caa     528
Cys Arg Ala Ser Gln Gly Ile Ser Ser Tyr Leu Ala Trp Tyr Gln Gln
                165                 170                 175 aaa cca ggg aaa gcc cct aag ctc ctg atc tat gat gcc tcc agt ttg     576
Lys Pro Gly Lys Ala Pro Lys Leu Leu Ile Tyr Asp Ala Ser Ser Leu
            180                 185                 190 gaa agt ggg gtc cca tca agg ttc agc ggc agt gga tct ggg aca gaa     624
Glu Ser Gly Val Pro Ser Arg Phe Ser Gly Ser Gly Ser Gly Thr Glu
        195                 200                 205 ttc act ctc acc atc agc agc ctg cag cct gat gat ttt gca act tat     672
Phe Thr Leu Thr Ile Ser Ser Leu Gln Pro Asp Asp Phe Ala Thr Tyr
    210                 215                 220 tac tgt caa caa ctt aac agt tac cca ctc act ttc ggc gga ggg acc     720
Tyr Cys Gln Gln Leu Asn Ser Tyr Pro Leu Thr Phe Gly Gly Gly Thr
225                 230                 235                 240 aag gtg gag atc aaa cgt gcg gcc gca                                 747
Lys Val Glu Ile Lys Arg Ala Ala Ala
                245
```

<210> SEQ ID NO 194
<211> LENGTH: 249
<212> TYPE: PRT
<213> ORGANISM: Artificial sequence
<220> FEATURE:
<223> OTHER INFORMATION: Synthetic Construct

<400> SEQUENCE: 194

```
Ala Met Ala Gln Val Gln Leu Val Glu Ser Gly Gly Gly Val Val Gln
 1               5                  10                  15

Pro Gly Arg Ser Leu Arg Leu Ser Cys Ala Ala Ser Gly Phe Thr Phe
             20                  25                  30

Ser Ser Tyr Gly Met His Trp Val Arg Gln Ala Pro Gly Lys Gly Leu
         35                  40                  45
```

```
Glu Trp Val Ala Val Ile Ser Tyr Asp Gly Ser Asp Lys Tyr Tyr Ala
 50                  55                  60

Asp Ser Val Lys Gly Arg Phe Thr Ile Ser Arg Asp Asn Ser Lys Asn
 65                  70                  75                  80

Thr Leu Tyr Leu Gln Met Asn Ser Leu Arg Ala Glu Asp Thr Ala Val
                 85                  90                  95

Tyr Tyr Cys Ala Lys Ile Ala Thr Ala Gly Thr Gly Phe Asp Tyr Trp
            100                 105                 110

Gly Gln Gly Thr Leu Val Thr Val Ser Ser Gly Thr Gly Ser Gly
        115                 120                 125

Gly Thr Gly Ser Gly Thr Gly Gly Ser Thr Asp Ile Gln Met Thr Gln
    130                 135                 140

Ser Pro Ser Ser Val Ser Ala Ser Val Gly Asp Arg Val Thr Ile Thr
145                 150                 155                 160

Cys Arg Ala Ser Gln Gly Ile Ser Ser Tyr Leu Ala Trp Tyr Gln Gln
                165                 170                 175

Lys Pro Gly Lys Ala Pro Lys Leu Leu Ile Tyr Asp Ala Ser Ser Leu
            180                 185                 190

Glu Ser Gly Val Pro Ser Arg Phe Ser Gly Ser Gly Ser Gly Thr Glu
        195                 200                 205

Phe Thr Leu Thr Ile Ser Ser Leu Gln Pro Asp Asp Phe Ala Thr Tyr
    210                 215                 220

Tyr Cys Gln Gln Leu Asn Ser Tyr Pro Leu Thr Phe Gly Gly Gly Thr
225                 230                 235                 240

Lys Val Glu Ile Lys Arg Ala Ala Ala
                245
```

<210> SEQ ID NO 195
<211> LENGTH: 756
<212> TYPE: DNA
<213> ORGANISM: Artificial sequence
<220> FEATURE:
<223> OTHER INFORMATION: SC04-126
<220> FEATURE:
<221> NAME/KEY: CDS
<222> LOCATION: (1)..(756)

<400> SEQUENCE: 195

```
gcc atg gcc cag gtc acc ttg aag gag tct ggt ccc acg ctg gtg aac      48
Ala Met Ala Gln Val Thr Leu Lys Glu Ser Gly Pro Thr Leu Val Asn
1               5                   10                  15 ccc aca cag acc ctc acg ttg acc tgc acc ttc tct ggg ttc tcg ctc      96
Pro Thr Gln Thr Leu Thr Leu Thr Cys Thr Phe Ser Gly Phe Ser Leu
                20                  25                  30 agc act ggt gga gtg ggt gtg ggc tgg ttc cgt cag ccc cca ggg aag     144
Ser Thr Gly Gly Val Gly Val Gly Trp Phe Arg Gln Pro Pro Gly Lys
            35                  40                  45 gcc ctg gag tgg ctt gca cgc att gat tgg gat gat gat aaa tac tac     192
Ala Leu Glu Trp Leu Ala Arg Ile Asp Trp Asp Asp Asp Lys Tyr Tyr
        50                  55                  60 agc aca tct ctg aag acc agg ctc acc atc tcc aag gac acc tcc aaa     240
Ser Thr Ser Leu Lys Thr Arg Leu Thr Ile Ser Lys Asp Thr Ser Lys
65                  70                  75                  80 atc cag gtg gtc ctt aca atg acc aac atg gac cct gtg gac aca gcc     288
Ile Gln Val Val Leu Thr Met Thr Asn Met Asp Pro Val Asp Thr Ala
                85                  90                  95 acg tat tac tgt gca cgg atg ggt ttc act gga acc tac ttt gac tac     336
Thr Tyr Tyr Cys Ala Arg Met Gly Phe Thr Gly Thr Tyr Phe Asp Tyr
```

```
                    100                 105                 110
tgg ggc cag ggc acc ctg gtc acc gtc tcg agc ggt acg ggc ggt tca    384
Trp Gly Gln Gly Thr Leu Val Thr Val Ser Ser Gly Thr Gly Gly Ser
                115                 120                 125 ggc gga acc ggc agc ggc act ggc ggg tcg acg cag tct gtg ctg act    432
Gly Gly Thr Gly Ser Gly Thr Gly Gly Ser Thr Gln Ser Val Leu Thr
            130                 135                 140 cag cca ccc tca gtg tca gtg gcc cca gga aag acg gcc agg att acc    480
Gln Pro Pro Ser Val Ser Val Ala Pro Gly Lys Thr Ala Arg Ile Thr
145                 150                 155                 160 tgt ggg gga aac aac att gga agt aaa agt gtg cac tgg tac cag cag    528
Cys Gly Gly Asn Asn Ile Gly Ser Lys Ser Val His Trp Tyr Gln Gln
                165                 170                 175 aag cca ggc cag gcc cct gtg ctg gtc atc tat tat gat agc gac cgg    576
Lys Pro Gly Gln Ala Pro Val Leu Val Ile Tyr Tyr Asp Ser Asp Arg
            180                 185                 190 ccc tca ggg atc cct gag cga ttc tct ggc tcc aac tct ggg aac acg    624
Pro Ser Gly Ile Pro Glu Arg Phe Ser Gly Ser Asn Ser Gly Asn Thr
        195                 200                 205 gcc acc ctg acc atc agc agg gtc gaa gcc ggg gat gag gct gac tat    672
Ala Thr Leu Thr Ile Ser Arg Val Glu Ala Gly Asp Glu Ala Asp Tyr
    210                 215                 220 tac tgt cag gtg tgg gat agt agt agt gat cat ccc tat gtc ttc gga    720
Tyr Cys Gln Val Trp Asp Ser Ser Ser Asp His Pro Tyr Val Phe Gly
225                 230                 235                 240 act ggg acc aag ctg acc gtc cta ggt gcg gcc gca                    756
Thr Gly Thr Lys Leu Thr Val Leu Gly Ala Ala Ala
                245                 250

<210> SEQ ID NO 196
<211> LENGTH: 252
<212> TYPE: PRT
<213> ORGANISM: Artificial sequence
<220> FEATURE:
<223> OTHER INFORMATION: Synthetic Construct

<400> SEQUENCE: 196

Ala Met Ala Gln Val Thr Leu Lys Glu Ser Gly Pro Thr Leu Val Asn
1               5                   10                  15

Pro Thr Gln Thr Leu Thr Leu Thr Cys Thr Phe Ser Gly Phe Ser Leu
            20                  25                  30

Ser Thr Gly Gly Val Gly Val Gly Trp Phe Arg Gln Pro Pro Gly Lys
        35                  40                  45

Ala Leu Glu Trp Leu Ala Arg Ile Asp Trp Asp Asp Lys Tyr Tyr
    50                  55                  60

Ser Thr Ser Leu Lys Thr Arg Leu Thr Ile Ser Lys Asp Thr Ser Lys
65                  70                  75                  80

Ile Gln Val Val Leu Thr Met Thr Asn Met Asp Pro Val Asp Thr Ala
                85                  90                  95

Thr Tyr Tyr Cys Ala Arg Met Gly Phe Thr Gly Thr Tyr Phe Asp Tyr
            100                 105                 110

Trp Gly Gln Gly Thr Leu Val Thr Val Ser Ser Gly Thr Gly Gly Ser
        115                 120                 125

Gly Gly Thr Gly Ser Gly Thr Gly Gly Ser Thr Gln Ser Val Leu Thr
    130                 135                 140

Gln Pro Pro Ser Val Ser Val Ala Pro Gly Lys Thr Ala Arg Ile Thr
145                 150                 155                 160

Cys Gly Gly Asn Asn Ile Gly Ser Lys Ser Val His Trp Tyr Gln Gln
```

```
                165                 170                 175
Lys Pro Gly Gln Ala Pro Val Leu Val Ile Tyr Tyr Asp Ser Asp Arg
            180                 185                 190

Pro Ser Gly Ile Pro Glu Arg Phe Ser Gly Ser Asn Ser Gly Asn Thr
            195                 200                 205

Ala Thr Leu Thr Ile Ser Arg Val Glu Ala Gly Asp Glu Ala Asp Tyr
    210                 215                 220

Tyr Cys Gln Val Trp Asp Ser Ser Asp His Pro Tyr Val Phe Gly
225                 230                 235                 240

Thr Gly Thr Lys Leu Thr Val Leu Gly Ala Ala Ala
            245                 250

<210> SEQ ID NO 197
<211> LENGTH: 747
<212> TYPE: DNA
<213> ORGANISM: Artificial sequence
<220> FEATURE:
<223> OTHER INFORMATION: SC04-140
<220> FEATURE:
<221> NAME/KEY: CDS
<222> LOCATION: (1)..(747)

<400> SEQUENCE: 197 gcc atg gcc cag atg cag ctg gtg cag tct ggg gga ggc gtg gtc cag    48
Ala Met Ala Gln Met Gln Leu Val Gln Ser Gly Gly Gly Val Val Gln
1               5                   10                  15 cct ggg agg tcc ctg aga ctc tcc tgt gca gcc tct gga ttc acc ttc    96
Pro Gly Arg Ser Leu Arg Leu Ser Cys Ala Ala Ser Gly Phe Thr Phe
            20                  25                  30 agt agc tat ggc atg cac tgg gtc cgc cag gct cca ggc aag ggg ctg   144
Ser Ser Tyr Gly Met His Trp Val Arg Gln Ala Pro Gly Lys Gly Leu
        35                  40                  45 gag tgg gtg gca gtt ata tta tat gat gga agt aat aaa tac tat gca   192
Glu Trp Val Ala Val Ile Leu Tyr Asp Gly Ser Asn Lys Tyr Tyr Ala
    50                  55                  60 gac tcc gtg aag ggc cga ttc acc atc tcc aga gac aat tcc aag aac   240
Asp Ser Val Lys Gly Arg Phe Thr Ile Ser Arg Asp Asn Ser Lys Asn
65                  70                  75                  80 gcg ttg tat ctg caa atg aac agc ctg aga gct gag gac acg gct gtg   288
Ala Leu Tyr Leu Gln Met Asn Ser Leu Arg Ala Glu Asp Thr Ala Val
                85                  90                  95 tat tac tgt gcg aag gtg acc aac ccc gga gat gct ttt gat atc tgg   336
Tyr Tyr Cys Ala Lys Val Thr Asn Pro Gly Asp Ala Phe Asp Ile Trp
            100                 105                 110 ggc caa ggg acc atg gtc acc gtc tcg agc ggt acg ggc ggt tca ggc   384
Gly Gln Gly Thr Met Val Thr Val Ser Ser Gly Thr Gly Gly Ser Gly
        115                 120                 125 gga acc ggc agc ggc act ggc ggg tcg acg gac atc cag atg acc cag   432
Gly Thr Gly Ser Gly Thr Gly Gly Ser Thr Asp Ile Gln Met Thr Gln
130                 135                 140 tct cca tcc tcc ctg tct gca tct gtc gga gac aga gtc acc atc act   480
Ser Pro Ser Ser Leu Ser Ala Ser Val Gly Asp Arg Val Thr Ile Thr
145                 150                 155                 160 tgc cgg gca agt cag ggc att agc agt gct tta gcc tgg tat cag cag   528
Cys Arg Ala Ser Gln Gly Ile Ser Ser Ala Leu Ala Trp Tyr Gln Gln
                165                 170                 175 aaa cca ggg aaa gct cct aag ctc ctg atc tat gat gcc tcc agt ttg   576
Lys Pro Gly Lys Ala Pro Lys Leu Leu Ile Tyr Asp Ala Ser Ser Leu
            180                 185                 190 gaa agt ggg gtc cca tca agg ttc agc ggc agt gga tct ggg aca gat   624
Glu Ser Gly Val Pro Ser Arg Phe Ser Gly Ser Gly Ser Gly Thr Asp
```

```
Glu Ser Gly Val Pro Ser Arg Phe Ser Gly Ser Gly Ser Gly Thr Asp
            195                 200                 205 ttc act ctc acc atc agc agc ctg cag cct gaa gat ttt gca act tat      672
Phe Thr Leu Thr Ile Ser Ser Leu Gln Pro Glu Asp Phe Ala Thr Tyr
    210                 215                 220 tac tgt caa cag ttt aat agt tac ccg ctc act ttc ggc gga ggg acc      720
Tyr Cys Gln Gln Phe Asn Ser Tyr Pro Leu Thr Phe Gly Gly Gly Thr
225                 230                 235                 240 aag gtg gaa atc aaa cgt gcg gcc gca                                  747
Lys Val Glu Ile Lys Arg Ala Ala Ala
                245

<210> SEQ ID NO 198
<211> LENGTH: 249
<212> TYPE: PRT
<213> ORGANISM: Artificial sequence
<220> FEATURE:
<223> OTHER INFORMATION: Synthetic Construct

<400> SEQUENCE: 198

Ala Met Ala Gln Met Gln Leu Val Gln Ser Gly Gly Gly Val Val Gln
1               5                   10                  15

Pro Gly Arg Ser Leu Arg Leu Ser Cys Ala Ala Ser Gly Phe Thr Phe
            20                  25                  30

Ser Ser Tyr Gly Met His Trp Val Arg Gln Ala Pro Gly Lys Gly Leu
        35                  40                  45

Glu Trp Val Ala Val Ile Leu Tyr Asp Gly Ser Asn Lys Tyr Tyr Ala
    50                  55                  60

Asp Ser Val Lys Gly Arg Phe Thr Ile Ser Arg Asp Asn Ser Lys Asn
65                  70                  75                  80

Ala Leu Tyr Leu Gln Met Asn Ser Leu Arg Ala Glu Asp Thr Ala Val
                85                  90                  95

Tyr Tyr Cys Ala Lys Val Thr Asn Pro Gly Asp Ala Phe Asp Ile Trp
            100                 105                 110

Gly Gln Gly Thr Met Val Thr Val Ser Ser Gly Thr Gly Gly Ser Gly
        115                 120                 125

Gly Thr Gly Ser Gly Thr Gly Gly Ser Thr Asp Ile Gln Met Thr Gln
    130                 135                 140

Ser Pro Ser Ser Leu Ser Ala Ser Val Gly Asp Arg Val Thr Ile Thr
145                 150                 155                 160

Cys Arg Ala Ser Gln Gly Ile Ser Ser Ala Leu Ala Trp Tyr Gln Gln
                165                 170                 175

Lys Pro Gly Lys Ala Pro Lys Leu Leu Ile Tyr Asp Ala Ser Ser Leu
            180                 185                 190

Glu Ser Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Thr Tyr
    210                 215                 220

Tyr Cys Gln Gln Phe Asn Ser Tyr Pro Leu Thr Phe Gly Gly Gly Thr
225                 230                 235                 240

Lys Val Glu Ile Lys Arg Ala Ala Ala
                245

<210> SEQ ID NO 199
<211> LENGTH: 744
<212> TYPE: DNA
<213> ORGANISM: Artificial sequence
<220> FEATURE:
```

<223> OTHER INFORMATION: SC04-144
<220> FEATURE:
<221> NAME/KEY: CDS
<222> LOCATION: (1)..(744)

<400> SEQUENCE: 199

| | | | | | | | | | | | | | | | | |
|---|---|---|---|---|---|---|---|---|---|---|---|---|---|---|---|---|
| gcc | atg | gcc | cag | gtg | cag | ctg | cag | gag | ttg | ggg | gga | ggc | gtg | gtc | cag | 48 |
| Ala | Met | Ala | Gln | Val | Gln | Leu | Gln | Glu | Leu | Gly | Gly | Gly | Val | Val | Gln | |
| 1 | | | | 5 | | | | | 10 | | | | | 15 | | |
| cct | ggg | agg | tcc | ctg | aga | ctc | tcc | tgt | gca | gcc | tct | gga | ttc | acc | ttc | 96 |
| Pro | Gly | Arg | Ser | Leu | Arg | Leu | Ser | Cys | Ala | Ala | Ser | Gly | Phe | Thr | Phe | |
| | | | 20 | | | | | 25 | | | | | 30 | | | |
| ggt | agc | tat | ggc | atg | cac | tgg | gtc | cgc | cag | gct | ccg | ggc | aag | ggg | ctg | 144 |
| Gly | Ser | Tyr | Gly | Met | His | Trp | Val | Arg | Gln | Ala | Pro | Gly | Lys | Gly | Leu | |
| | | | 35 | | | | | 40 | | | | | 45 | | | |
| gag | tgg | gtg | gca | act | ata | tca | tat | gat | gga | agt | att | aaa | gac | tat | gca | 192 |
| Glu | Trp | Val | Ala | Thr | Ile | Ser | Tyr | Asp | Gly | Ser | Ile | Lys | Asp | Tyr | Ala | |
| | 50 | | | | | 55 | | | | | 60 | | | | | |
| gac | tcc | gag | aag | ggc | cga | ttc | acc | atc | tcc | aga | gac | aat | tcc | aag | aac | 240 |
| Asp | Ser | Glu | Lys | Gly | Arg | Phe | Thr | Ile | Ser | Arg | Asp | Asn | Ser | Lys | Asn | |
| 65 | | | | | 70 | | | | | 75 | | | | | 80 | |
| aca | ctg | tat | ctg | caa | atg | aac | agc | ctg | aga | gct | gag | gac | acg | gct | gtg | 288 |
| Thr | Leu | Tyr | Leu | Gln | Met | Asn | Ser | Leu | Arg | Ala | Glu | Asp | Thr | Ala | Val | |
| | | | | 85 | | | | | 90 | | | | | 95 | | |
| tat | tac | tgt | gcg | aaa | ggg | ggg | aag | act | gga | gag | ttt | gac | tac | tgg | ggc | 336 |
| Tyr | Tyr | Cys | Ala | Lys | Gly | Gly | Lys | Thr | Gly | Glu | Phe | Asp | Tyr | Trp | Gly | |
| | | | 100 | | | | | 105 | | | | | 110 | | | |
| cag | gga | acc | ctg | gtc | acc | gtc | tcg | agc | ggt | acg | ggc | ggt | tca | ggc | gga | 384 |
| Gln | Gly | Thr | Leu | Val | Thr | Val | Ser | Ser | Gly | Thr | Gly | Gly | Ser | Gly | Gly | |
| | | | 115 | | | | | 120 | | | | | 125 | | | |
| acc | ggc | agc | ggc | act | ggc | ggg | tcg | acg | gac | atc | cag | ttg | acg | cag | tct | 432 |
| Thr | Gly | Ser | Gly | Thr | Gly | Gly | Ser | Thr | Asp | Ile | Gln | Leu | Thr | Gln | Ser | |
| | | 130 | | | | | 135 | | | | | 140 | | | | |
| cca | tcc | tcc | ctg | tct | gca | tct | gta | gga | gac | aga | gtc | acc | atc | act | tgc | 480 |
| Pro | Ser | Ser | Leu | Ser | Ala | Ser | Val | Gly | Asp | Arg | Val | Thr | Ile | Thr | Cys | |
| 145 | | | | | 150 | | | | | 155 | | | | | 160 | |
| cgg | gcc | agt | cag | ggc | att | agc | agt | tat | tta | gcc | tgg | tat | cag | caa | aaa | 528 |
| Arg | Ala | Ser | Gln | Gly | Ile | Ser | Ser | Tyr | Leu | Ala | Trp | Tyr | Gln | Gln | Lys | |
| | | | | 165 | | | | | 170 | | | | | 175 | | |
| cca | ggg | aaa | ggc | cct | aag | ctc | ctg | atc | tat | gct | gca | tcc | act | tta | caa | 576 |
| Pro | Gly | Lys | Gly | Pro | Lys | Leu | Leu | Ile | Tyr | Ala | Ala | Ser | Thr | Leu | Gln | |
| | | | 180 | | | | | 185 | | | | | 190 | | | |
| agt | ggg | gtc | cca | tca | agg | ttc | agc | ggc | agt | gga | tct | ggg | aca | gac | ttc | 624 |
| Ser | Gly | Val | Pro | Ser | Arg | Phe | Ser | Gly | Ser | Gly | Ser | Gly | Thr | Asp | Phe | |
| | | | | 195 | | | | | 200 | | | | | 205 | | |
| agt | ctc | acc | atc | agt | agc | ctg | cag | cct | gaa | gat | tta | gca | act | tat | tac | 672 |
| Ser | Leu | Thr | Ile | Ser | Ser | Leu | Gln | Pro | Glu | Asp | Leu | Ala | Thr | Tyr | Tyr | |
| | | 210 | | | | | 215 | | | | | 220 | | | | |
| tgc | caa | cag | tat | gat | agt | tac | cct | ctc | act | ttc | ggc | gga | ggg | acc | aag | 720 |
| Cys | Gln | Gln | Tyr | Asp | Ser | Tyr | Pro | Leu | Thr | Phe | Gly | Gly | Gly | Thr | Lys | |
| 225 | | | | | 230 | | | | | 235 | | | | | 240 | |
| gtg | gaa | atc | aaa | cgt | gcg | gcc | gca | | | | | | | | | 744 |
| Val | Glu | Ile | Lys | Arg | Ala | Ala | Ala | | | | | | | | | |
| | | | 245 | | | | | | | | | | | | | |

<210> SEQ ID NO 200
<211> LENGTH: 248
<212> TYPE: PRT
<213> ORGANISM: Artificial sequence
<220> FEATURE:
<223> OTHER INFORMATION: Synthetic Construct -continued

```
<400> SEQUENCE: 200

Ala Met Ala Gln Val Gln Leu Gln Glu Leu Gly Gly Gly Val Val Gln
1               5                   10                  15

Pro Gly Arg Ser Leu Arg Leu Ser Cys Ala Ala Ser Gly Phe Thr Phe
            20                  25                  30

Gly Ser Tyr Gly Met His Trp Val Arg Gln Ala Pro Gly Lys Gly Leu
        35                  40                  45

Glu Trp Val Ala Thr Ile Ser Tyr Asp Gly Ser Ile Lys Asp Tyr Ala
    50                  55                  60

Asp Ser Glu Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Lys Gly Gly Lys Thr Gly Glu Phe Asp Tyr Trp Gly
            100                 105                 110

Gln Gly Thr Leu Val Thr Val Ser Ser Gly Thr Gly Gly Ser Gly Gly
        115                 120                 125

Thr Gly Ser Gly Thr Gly Gly Ser Thr Asp Ile Gln Leu Thr Gln Ser
130                 135                 140

Pro Ser Ser Leu Ser Ala Ser Val Gly Asp Arg Val Thr Ile Thr Cys
145                 150                 155                 160

Arg Ala Ser Gln Gly Ile Ser Ser Tyr Leu Ala Trp Tyr Gln Gln Lys
                165                 170                 175

Pro Gly Lys Gly Pro Lys Leu Leu Ile Tyr Ala Ala Ser Thr Leu Gln
            180                 185                 190

Ser Gly Val Pro Ser Arg Phe Ser Gly Ser Gly Ser Gly Thr Asp Phe
        195                 200                 205

Ser Leu Thr Ile Ser Ser Leu Gln Pro Glu Asp Leu Ala Thr Tyr Tyr
    210                 215                 220

Cys Gln Gln Tyr Asp Ser Tyr Pro Leu Thr Phe Gly Gly Gly Thr Lys
225                 230                 235                 240

Val Glu Ile Lys Arg Ala Ala Ala
                245

<210> SEQ ID NO 201
<211> LENGTH: 744
<212> TYPE: DNA
<213> ORGANISM: Artificial sequence
<220> FEATURE:
<223> OTHER INFORMATION: SC04-146
<220> FEATURE:
<221> NAME/KEY: CDS
<222> LOCATION: (1)..(744)

<400> SEQUENCE: 201 gcc atg gcc gaa gtg cag ctg gtg cag tct ggg gga ggc gtg gtc cag         48
Ala Met Ala Glu Val Gln Leu Val Gln Ser Gly Gly Gly Val Val Gln
1               5                   10                  15 cct ggg agg tcc ctg aga ctc tcc tgt gca gcc tct gga ttc acc ttc         96
Pro Gly Arg Ser Leu Arg Leu Ser Cys Ala Ala Ser Gly Phe Thr Phe
            20                  25                  30 agt agc tat ggc atg cac tgg gtc cgc cag gct ccg ggc aag ggg ctg        144
Ser Ser Tyr Gly Met His Trp Val Arg Gln Ala Pro Gly Lys Gly Leu
        35                  40                  45 gag tgg gtg gca act ata tca tat gat gga agt att aaa gac tat gca        192
Glu Trp Val Ala Thr Ile Ser Tyr Asp Gly Ser Ile Lys Asp Tyr Ala
    50                  55                  60
```

| | | | | | | | | | | | | | | | |
|---|---|---|---|---|---|---|---|---|---|---|---|---|---|---|---|
| gac | tcc | gag | gag | ggc | cga | ttc | acc | atc | tcc | aga | gac | aat | tcc | aag | aac | 240 |
| Asp | Ser | Glu | Glu | Gly | Arg | Phe | Thr | Ile | Ser | Arg | Asp | Asn | Ser | Lys | Asn | |
| 65 | | | | 70 | | | | | 75 | | | | | 80 | | |

| aca | ctg | tat | ctg | caa | atg | aac | agc | ctg | aga | gct | gag | gac | acg | gct | gtg | 288 |
| Thr | Leu | Tyr | Leu | Gln | Met | Asn | Ser | Leu | Arg | Ala | Glu | Asp | Thr | Ala | Val | |
| | | | | 85 | | | | | 90 | | | | | 95 | | |

| tat | tac | tgt | gcg | aaa | ggg | ggg | aag | act | gga | gag | ttt | gac | tac | tgg | ggc | 336 |
| Tyr | Tyr | Cys | Ala | Lys | Gly | Gly | Lys | Thr | Gly | Glu | Phe | Asp | Tyr | Trp | Gly | |
| | | | | 100 | | | | | 105 | | | | | 110 | | |

| cag | ggc | acc | ctg | gtc | acc | gtc | tcg | agc | ggt | acg | ggc | ggt | tca | ggc | gga | 384 |
| Gln | Gly | Thr | Leu | Val | Thr | Val | Ser | Ser | Gly | Thr | Gly | Gly | Ser | Gly | Gly | |
| | | | 115 | | | | | 120 | | | | | 125 | | | |

| acc | ggc | agc | ggc | act | ggc | ggg | tcg | acg | gat | gtt | gtg | atg | act | cag | tct | 432 |
| Thr | Gly | Ser | Gly | Thr | Gly | Gly | Ser | Thr | Asp | Val | Val | Met | Thr | Gln | Ser | |
| | | | 130 | | | | | 135 | | | | | 140 | | | |

| cca | gcc | acc | ctg | tct | gtg | tct | cca | ggg | gaa | agc | gcc | aca | ctc | ttc | tgc | 480 |
| Pro | Ala | Thr | Leu | Ser | Val | Ser | Pro | Gly | Glu | Ser | Ala | Thr | Leu | Phe | Cys | |
| 145 | | | | | 150 | | | | | 155 | | | | | 160 | |

| agg | gcc | agt | gag | agt | gtt | tat | agc | aac | ttg | gcc | tgg | tat | cag | cac | aaa | 528 |
| Arg | Ala | Ser | Glu | Ser | Val | Tyr | Ser | Asn | Leu | Ala | Trp | Tyr | Gln | His | Lys | |
| | | | | 165 | | | | | 170 | | | | | 175 | | |

| cct | ggc | cgg | gct | ccc | agg | ctc | ctc | atc | tat | ggt | gca | tcc | acc | agg | gcc | 576 |
| Pro | Gly | Arg | Ala | Pro | Arg | Leu | Leu | Ile | Tyr | Gly | Ala | Ser | Thr | Arg | Ala | |
| | | | 180 | | | | | 185 | | | | | 190 | | | |

| act | ggt | atc | cca | gcc | agg | ttc | gat | ggc | act | ggg | tct | ggg | aca | gac | ttc | 624 |
| Thr | Gly | Ile | Pro | Ala | Arg | Phe | Asp | Gly | Thr | Gly | Ser | Gly | Thr | Asp | Phe | |
| | | | 195 | | | | | 200 | | | | | 205 | | | |

| aca | ctc | acc | atc | agc | agc | ctg | cag | tct | gaa | gat | ttt | gca | gtt | tat | tac | 672 |
| Thr | Leu | Thr | Ile | Ser | Ser | Leu | Gln | Ser | Glu | Asp | Phe | Ala | Val | Tyr | Tyr | |
| | | | 210 | | | | | 215 | | | | | 220 | | | |

| tgt | cag | caa | tat | aat | gac | tgg | ccg | atc | acc | ttc | ggc | caa | ggg | aca | cga | 720 |
| Cys | Gln | Gln | Tyr | Asn | Asp | Trp | Pro | Ile | Thr | Phe | Gly | Gln | Gly | Thr | Arg | |
| 225 | | | | | 230 | | | | | 235 | | | | | 240 | |

| ctg | gag | att | aaa | cgt | gcg | gcc | gca | | | | | | | | | 744 |
| Leu | Glu | Ile | Lys | Arg | Ala | Ala | Ala | | | | | | | | | |
| | | | | 245 | | | | | | | | | | | | |

<210> SEQ ID NO 202
<211> LENGTH: 248
<212> TYPE: PRT
<213> ORGANISM: Artificial sequence
<220> FEATURE:
<223> OTHER INFORMATION: Synthetic Construct

<400> SEQUENCE: 202

Ala Met Ala Glu Val Gln Leu Val Gln Ser Gly Gly Gly Val Val Gln
1               5                   10                  15

Pro Gly Arg Ser Leu Arg Leu Ser Cys Ala Ala Ser Gly Phe Thr Phe
            20                  25                  30

Ser Ser Tyr Gly Met His Trp Val Arg Gln Ala Pro Gly Lys Gly Leu
        35                  40                  45

Glu Trp Val Ala Thr Ile Ser Tyr Asp Gly Ser Ile Lys Asp Tyr Ala
    50                  55                  60

Asp Ser Glu Glu Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Lys Gly Gly Lys Thr Gly Glu Phe Asp Tyr Trp Gly
            100                 105                 110

```
Gln Gly Thr Leu Val Thr Val Ser Gly Thr Gly Ser Gly Gly
        115                 120                 125

Thr Gly Ser Gly Thr Gly Gly Ser Thr Asp Val Val Met Thr Gln Ser
    130                 135                 140

Pro Ala Thr Leu Ser Val Ser Pro Gly Glu Ser Ala Thr Leu Phe Cys
145                 150                 155                 160

Arg Ala Ser Glu Ser Val Tyr Ser Asn Leu Ala Trp Tyr Gln His Lys
                165                 170                 175

Pro Gly Arg Ala Pro Arg Leu Leu Ile Tyr Gly Ala Ser Thr Arg Ala
            180                 185                 190

Thr Gly Ile Pro Ala Arg Phe Asp Gly Thr Gly Ser Gly Thr Asp Phe
        195                 200                 205

Thr Leu Thr Ile Ser Ser Leu Gln Ser Glu Asp Phe Ala Val Tyr Tyr
    210                 215                 220

Cys Gln Gln Tyr Asn Asp Trp Pro Ile Thr Phe Gly Gln Gly Thr Arg
225                 230                 235                 240

Leu Glu Ile Lys Arg Ala Ala Ala
                245

<210> SEQ ID NO 203
<211> LENGTH: 747
<212> TYPE: DNA
<213> ORGANISM: Artificial sequence
<220> FEATURE:
<223> OTHER INFORMATION: SC04-164
<220> FEATURE:
<221> NAME/KEY: CDS
<222> LOCATION: (1)..(747)

<400> SEQUENCE: 203
```

| | | | | | | | | | | | | | | | | |
|---|---|---|---|---|---|---|---|---|---|---|---|---|---|---|---|---|
| gcc | atg | gcc | gag | gtg | cag | ctg | gtg | gag | tct | ggg | gga | ggc | gtg | gtc | cag | 48 |
| Ala | Met | Ala | Glu | Val | Gln | Leu | Val | Glu | Ser | Gly | Gly | Gly | Val | Val | Gln | |
| 1 | | | | 5 | | | | | 10 | | | | | 15 | | |
| cct | ggg | agg | tcc | ctg | aga | ctc | tcc | tgt | gca | gcc | tct | gga | ttc | acc | ttc | 96 |
| Pro | Gly | Arg | Ser | Leu | Arg | Leu | Ser | Cys | Ala | Ala | Ser | Gly | Phe | Thr | Phe | |
| | | 20 | | | | | 25 | | | | | 30 | | | | |
| agt | agc | tat | ggc | atg | cac | tgg | gtc | cgc | cag | gct | cca | ggc | aag | ggg | ctg | 144 |
| Ser | Ser | Tyr | Gly | Met | His | Trp | Val | Arg | Gln | Ala | Pro | Gly | Lys | Gly | Leu | |
| | 35 | | | | | 40 | | | | | 45 | | | | | |
| gag | tgg | gtg | gca | gtt | ata | tca | tat | gat | gga | agc | agt | aaa | tac | tac | gca | 192 |
| Glu | Trp | Val | Ala | Val | Ile | Ser | Tyr | Asp | Gly | Ser | Ser | Lys | Tyr | Tyr | Ala | |
| 50 | | | | | 55 | | | | | 60 | | | | | | |
| gac | tcc | gtg | aag | ggc | cga | ttc | acc | atc | tcc | aga | gac | aat | tcc | aag | aac | 240 |
| Asp | Ser | Val | Lys | Gly | Arg | Phe | Thr | Ile | Ser | Arg | Asp | Asn | Ser | Lys | Asn | |
| 65 | | | | 70 | | | | | 75 | | | | | 80 | | |
| acg | ctg | tat | ctg | caa | atg | aac | agc | ctg | aga | gct | gag | gac | acg | gct | gtg | 288 |
| Thr | Leu | Tyr | Leu | Gln | Met | Asn | Ser | Leu | Arg | Ala | Glu | Asp | Thr | Ala | Val | |
| | | | 85 | | | | | 90 | | | | | 95 | | | |
| tat | tac | tgt | gcg | aaa | ggg | tcc | gtc | ctc | ggt | gat | gct | ttt | gat | atc | tgg | 336 |
| Tyr | Tyr | Cys | Ala | Lys | Gly | Ser | Val | Leu | Gly | Asp | Ala | Phe | Asp | Ile | Trp | |
| | | | 100 | | | | | 105 | | | | | 110 | | | |
| ggc | caa | ggg | aca | atg | gtc | acc | gtc | tcg | agc | ggt | acg | ggc | ggt | tca | ggc | 384 |
| Gly | Gln | Gly | Thr | Met | Val | Thr | Val | Ser | Ser | Gly | Thr | Gly | Gly | Ser | Gly | |
| | | 115 | | | | | 120 | | | | | 125 | | | | |
| gga | acc | ggc | agc | ggc | act | ggc | ggg | tcg | acg | gac | atc | cag | ttg | acc | cag | 432 |
| Gly | Thr | Gly | Ser | Gly | Thr | Gly | Gly | Ser | Thr | Asp | Ile | Gln | Leu | Thr | Gln | |
| | 130 | | | | | 135 | | | | | 140 | | | | | |
| tct | cca | tct | tct | gtg | tct | gca | tct | gta | gga | gac | aga | gtc | acc | atc | act | 480 |
| Ser | Pro | Ser | Ser | Val | Ser | Ala | Ser | Val | Gly | Asp | Arg | Val | Thr | Ile | Thr | |
| 145 | | | | | 150 | | | | | 155 | | | | | 160 | |

```
tgt cgg gcg agt cag ggt att agc agc tgg tta gcc tgg tat cag cag       528
Cys Arg Ala Ser Gln Gly Ile Ser Ser Trp Leu Ala Trp Tyr Gln Gln
            165                 170                 175 aaa cca ggg aaa gcc cct aag ctc ctg atc tat gct gca tcc agt ttg       576
Lys Pro Gly Lys Ala Pro Lys Leu Leu Ile Tyr Ala Ala Ser Ser Leu
        180                 185                 190 caa agt ggg gtc cca tca agg ttc agc ggc agt gga tct ggg aca gat       624
Gln Ser Gly Val Pro Ser Arg Phe Ser Gly Ser Gly Ser Gly Thr Asp
    195                 200                 205 ttc act ctc act atc agc agc ctg cag cct gaa gat ttt gca act tac       672
Phe Thr Leu Thr Ile Ser Ser Leu Gln Pro Glu Asp Phe Ala Thr Tyr
210                 215                 220 tat tgt caa cag gct aac agt ttc ccg ctc act ttc ggc gga ggg acc       720
Tyr Cys Gln Gln Ala Asn Ser Phe Pro Leu Thr Phe Gly Gly Gly Thr
225                 230                 235                 240 aaa gtg gat atc aaa cgt gcg gcc gca                                   747
Lys Val Asp Ile Lys Arg Ala Ala Ala
                245

<210> SEQ ID NO 204
<211> LENGTH: 249
<212> TYPE: PRT
<213> ORGANISM: Artificial sequence
<220> FEATURE:
<223> OTHER INFORMATION: Synthetic Construct

<400> SEQUENCE: 204

Ala Met Ala Glu Val Gln Leu Val Glu Ser Gly Gly Gly Val Val Gln
1               5                   10                  15

Pro Gly Arg Ser Leu Arg Leu Ser Cys Ala Ala Ser Gly Phe Thr Phe
            20                  25                  30

Ser Ser Tyr Gly Met His Trp Val Arg Gln Ala Pro Gly Lys Gly Leu
        35                  40                  45

Glu Trp Val Ala Val Ile Ser Tyr Asp Gly Ser Ser Lys Tyr Tyr Ala
    50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Lys Gly Ser Val Leu Gly Asp Ala Phe Asp Ile Trp
            100                 105                 110

Gly Gln Gly Thr Met Val Thr Val Ser Ser Gly Thr Gly Gly Ser Gly
        115                 120                 125

Gly Thr Gly Ser Gly Thr Gly Gly Ser Thr Asp Ile Gln Leu Thr Gln
    130                 135                 140

Ser Pro Ser Ser Val Ser Ala Ser Val Gly Asp Arg Val Thr Ile Thr
145                 150                 155                 160

Cys Arg Ala Ser Gln Gly Ile Ser Ser Trp Leu Ala Trp Tyr Gln Gln
                165                 170                 175

Lys Pro Gly Lys Ala Pro Lys Leu Leu Ile Tyr Ala Ala Ser Ser Leu
            180                 185                 190

Gln Ser Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Thr Tyr
    210                 215                 220

Tyr Cys Gln Gln Ala Asn Ser Phe Pro Leu Thr Phe Gly Gly Gly Thr
225                 230                 235                 240
```

Lys Val Asp Ile Lys Arg Ala Ala Ala
                245

<210> SEQ ID NO 205
<211> LENGTH: 786
<212> TYPE: DNA
<213> ORGANISM: Artificial sequence
<220> FEATURE:
<223> OTHER INFORMATION: SO57
<220> FEATURE:
<221> NAME/KEY: CDS
<222> LOCATION: (1)..(786)

<400> SEQUENCE: 205

| gcc | atg | gcc | cag | gtg | cag | ctg | gtg | cag | agc | gga | gcc | gag | gtg | aag | aag | 48 |
|---|---|---|---|---|---|---|---|---|---|---|---|---|---|---|---|---|
| Ala | Met | Ala | Gln | Val | Gln | Leu | Val | Gln | Ser | Gly | Ala | Glu | Val | Lys | Lys | |
| 1 | | | | 5 | | | | | 10 | | | | | 15 | | |

| ccc | ggc | agc | agc | gtg | aag | gtg | agc | tgc | aag | gcc | agc | ggc | ggc | acc | ttc | 96 |
|---|---|---|---|---|---|---|---|---|---|---|---|---|---|---|---|---|
| Pro | Gly | Ser | Ser | Val | Lys | Val | Ser | Cys | Lys | Ala | Ser | Gly | Gly | Thr | Phe | |
| | | | 20 | | | | 25 | | | | | 30 | | | | |

| aac | agg | tac | acc | gtg | aac | tgg | gtg | aga | cag | gcc | cca | ggc | cag | ggc | ctg | 144 |
|---|---|---|---|---|---|---|---|---|---|---|---|---|---|---|---|---|
| Asn | Arg | Tyr | Thr | Val | Asn | Trp | Val | Arg | Gln | Ala | Pro | Gly | Gln | Gly | Leu | |
| | | 35 | | | | | 40 | | | | | 45 | | | | |

| gag | tgg | atg | ggc | ggc | atc | atc | cct | atc | ttc | ggc | acc | gcc | aac | tac | gcc | 192 |
|---|---|---|---|---|---|---|---|---|---|---|---|---|---|---|---|---|
| Glu | Trp | Met | Gly | Gly | Ile | Ile | Pro | Ile | Phe | Gly | Thr | Ala | Asn | Tyr | Ala | |
| 50 | | | | | 55 | | | | | 60 | | | | | | |

| cag | aga | ttc | cag | ggc | agg | ctc | acc | atc | acc | gcc | gac | gag | agc | acc | agc | 240 |
|---|---|---|---|---|---|---|---|---|---|---|---|---|---|---|---|---|
| Gln | Arg | Phe | Gln | Gly | Arg | Leu | Thr | Ile | Thr | Ala | Asp | Glu | Ser | Thr | Ser | |
| 65 | | | | | 70 | | | | | 75 | | | | | 80 | |

| acc | gcc | tac | atg | gag | ctg | agc | agc | ctg | aga | agc | gat | gac | acc | gcc | gtg | 288 |
|---|---|---|---|---|---|---|---|---|---|---|---|---|---|---|---|---|
| Thr | Ala | Tyr | Met | Glu | Leu | Ser | Ser | Leu | Arg | Ser | Asp | Asp | Thr | Ala | Val | |
| | | | | 85 | | | | | 90 | | | | | 95 | | |

| tac | ttc | tgc | gcc | agg | gag | aac | ctg | gat | aac | agc | ggc | acc | tac | tac | tac | 336 |
|---|---|---|---|---|---|---|---|---|---|---|---|---|---|---|---|---|
| Tyr | Phe | Cys | Ala | Arg | Glu | Asn | Leu | Asp | Asn | Ser | Gly | Thr | Tyr | Tyr | Tyr | |
| | | | 100 | | | | | 105 | | | | | 110 | | | |

| ttc | agc | ggc | tgg | ttc | gac | ccc | tgg | ggc | cag | ggc | acc | ctg | gtg | acc | gtc | 384 |
|---|---|---|---|---|---|---|---|---|---|---|---|---|---|---|---|---|
| Phe | Ser | Gly | Trp | Phe | Asp | Pro | Trp | Gly | Gln | Gly | Thr | Leu | Val | Thr | Val | |
| | | 115 | | | | | 120 | | | | | 125 | | | | |

| tcg | agc | ggt | acg | ggc | ggt | tca | ggc | gga | acc | ggc | agc | ggc | act | ggc | ggg | 432 |
|---|---|---|---|---|---|---|---|---|---|---|---|---|---|---|---|---|
| Ser | Ser | Gly | Thr | Gly | Gly | Ser | Gly | Gly | Thr | Gly | Ser | Gly | Thr | Gly | Gly | |
| | 130 | | | | | 135 | | | | | 140 | | | | | |

| tcg | acg | cag | agc | gcc | ctc | acc | cag | ccc | aga | agc | gtg | agc | ggc | agc | cct | 480 |
|---|---|---|---|---|---|---|---|---|---|---|---|---|---|---|---|---|
| Ser | Thr | Gln | Ser | Ala | Leu | Thr | Gln | Pro | Arg | Ser | Val | Ser | Gly | Ser | Pro | |
| 145 | | | | | 150 | | | | | 155 | | | | | 160 | |

| ggc | cag | agc | gtg | acc | atc | agc | tgc | acc | ggc | acc | agc | agc | gac | atc | ggc | 528 |
|---|---|---|---|---|---|---|---|---|---|---|---|---|---|---|---|---|
| Gly | Gln | Ser | Val | Thr | Ile | Ser | Cys | Thr | Gly | Thr | Ser | Ser | Asp | Ile | Gly | |
| | | | | 165 | | | | | 170 | | | | | 175 | | |

| ggc | tac | aac | ttc | gtg | agc | tgg | tat | cag | cag | cac | ccc | ggc | aag | gcc | cct | 576 |
|---|---|---|---|---|---|---|---|---|---|---|---|---|---|---|---|---|
| Gly | Tyr | Asn | Phe | Val | Ser | Trp | Tyr | Gln | Gln | His | Pro | Gly | Lys | Ala | Pro | |
| | | | 180 | | | | | 185 | | | | | 190 | | | |

| aag | ctc | atg | atc | tac | gac | gcc | acc | aag | aga | ccc | agc | ggc | gtg | ccc | gac | 624 |
|---|---|---|---|---|---|---|---|---|---|---|---|---|---|---|---|---|
| Lys | Leu | Met | Ile | Tyr | Asp | Ala | Thr | Lys | Arg | Pro | Ser | Gly | Val | Pro | Asp | |
| | | 195 | | | | | 200 | | | | | 205 | | | | |

| aga | ttc | agc | ggc | agc | aag | agc | ggc | aac | acc | gcc | agc | ctc | acc | atc | agc | 672 |
|---|---|---|---|---|---|---|---|---|---|---|---|---|---|---|---|---|
| Arg | Phe | Ser | Gly | Ser | Lys | Ser | Gly | Asn | Thr | Ala | Ser | Leu | Thr | Ile | Ser | |
| | 210 | | | | | 215 | | | | | 220 | | | | | |

| gga | ctg | cag | gcc | gag | gac | gag | gcc | gac | tac | tac | tgc | tgc | agc | tac | gcc | 720 |
|---|---|---|---|---|---|---|---|---|---|---|---|---|---|---|---|---|
| Gly | Leu | Gln | Ala | Glu | Asp | Glu | Ala | Asp | Tyr | Tyr | Cys | Cys | Ser | Tyr | Ala | |
| 225 | | | | | 230 | | | | | 235 | | | | | 240 | |

| ggc | gac | tac | acc | cct | ggc | gtg | gtg | ttc | ggc | gga | ggc | acc | aag | ctt | acc | 768 |
|---|---|---|---|---|---|---|---|---|---|---|---|---|---|---|---|---|
| Gly | Asp | Tyr | Thr | Pro | Gly | Val | Val | Phe | Gly | Gly | Gly | Thr | Lys | Leu | Thr | |

```
                245                 250                 255 gtg cta ggt gcg gcc gca                                                 786
Val Leu Gly Ala Ala Ala
            260

<210> SEQ ID NO 206
<211> LENGTH: 262
<212> TYPE: PRT
<213> ORGANISM: Artificial sequence
<220> FEATURE:
<223> OTHER INFORMATION: Synthetic Construct
<400> SEQUENCE: 206

Ala Met Ala Gln Val Gln Leu Val Gln Ser Gly Ala Glu Val Lys Lys
1               5                   10                  15

Pro Gly Ser Ser Val Lys Val Ser Cys Lys Ala Ser Gly Gly Thr Phe
            20                  25                  30

Asn Arg Tyr Thr Val Asn Trp Val Arg Gln Ala Pro Gly Gln Gly Leu
        35                  40                  45

Glu Trp Met Gly Gly Ile Ile Pro Ile Phe Gly Thr Ala Asn Tyr Ala
    50                  55                  60

Gln Arg Phe Gln Gly Arg Leu Thr Ile Thr Ala Asp Glu Ser Thr Ser
65                  70                  75                  80

Thr Ala Tyr Met Glu Leu Ser Ser Leu Arg Ser Asp Asp Thr Ala Val
                85                  90                  95

Tyr Phe Cys Ala Arg Glu Asn Leu Asp Asn Ser Gly Thr Tyr Tyr Tyr
            100                 105                 110

Phe Ser Gly Trp Phe Asp Pro Trp Gly Gln Gly Thr Leu Val Thr Val
        115                 120                 125

Ser Ser Gly Thr Gly Gly Ser Gly Gly Thr Gly Ser Gly Thr Gly Gly
    130                 135                 140

Ser Thr Gln Ser Ala Leu Thr Gln Pro Arg Ser Val Ser Gly Ser Pro
145                 150                 155                 160

Gly Gln Ser Val Thr Ile Ser Cys Thr Gly Thr Ser Ser Asp Ile Gly
                165                 170                 175

Gly Tyr Asn Phe Val Ser Trp Tyr Gln Gln His Pro Gly Lys Ala Pro
            180                 185                 190

Lys Leu Met Ile Tyr Asp Ala Thr Lys Arg Pro Ser Gly Val Pro Asp
        195                 200                 205

Arg Phe Ser Gly Ser Lys Ser Gly Asn Thr Ala Ser Leu Thr Ile Ser
    210                 215                 220

Gly Leu Gln Ala Glu Asp Glu Ala Asp Tyr Tyr Cys Cys Ser Tyr Ala
225                 230                 235                 240

Gly Asp Tyr Thr Pro Gly Val Val Phe Gly Gly Gly Thr Lys Leu Thr
                245                 250                 255

Val Leu Gly Ala Ala Ala
            260

<210> SEQ ID NO 207
<211> LENGTH: 524
<212> TYPE: PRT
<213> ORGANISM: Lyssavirus Rabies
<220> FEATURE:
<221> NAME/KEY: MISC_FEATURE
<223> OTHER INFORMATION: G protein of rabies virus ERA strain
<400> SEQUENCE: 207

Met Val Pro Gln Ala Leu Leu Phe Val Pro Leu Leu Val Phe Pro Leu
```

-continued

```
1               5                   10                  15
Cys Phe Gly Lys Phe Pro Ile Tyr Thr Ile Leu Asp Lys Leu Gly Pro
                20                  25                  30

Trp Ser Pro Ile Asp Ile His His Leu Ser Cys Pro Asn Asn Leu Val
                35                  40                  45

Val Glu Asp Glu Gly Cys Thr Asn Leu Ser Gly Phe Ser Tyr Met Glu
 50                         55                  60

Leu Lys Val Gly Tyr Ile Leu Ala Ile Lys Met Asn Gly Phe Thr Cys
 65                 70                  75                  80

Thr Gly Val Val Thr Glu Ala Glu Asn Tyr Thr Asn Phe Val Gly Tyr
                85                  90                  95

Val Thr Thr Thr Phe Lys Arg Lys His Phe Arg Pro Thr Pro Asp Ala
                100                 105                 110

Cys Arg Ala Ala Tyr Asn Trp Lys Met Ala Gly Asp Pro Arg Tyr Glu
                115                 120                 125

Glu Ser Leu His Asn Pro Tyr Pro Asp Tyr Arg Trp Leu Arg Thr Val
 130                        135                 140

Lys Thr Thr Lys Glu Ser Leu Val Ile Ile Ser Pro Ser Val Ala Asp
145                 150                 155                 160

Leu Asp Pro Tyr Asp Arg Ser Leu His Ser Arg Val Phe Pro Ser Gly
                165                 170                 175

Lys Cys Ser Gly Val Ala Val Ser Ser Thr Tyr Cys Ser Thr Asn His
                180                 185                 190

Asp Tyr Thr Ile Trp Met Pro Glu Asn Pro Arg Leu Gly Met Ser Cys
                195                 200                 205

Asp Ile Phe Thr Asn Ser Arg Gly Lys Arg Ala Ser Lys Gly Ser Glu
 210                        215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asn Glu Thr Lys Trp Cys Pro
                260                 265                 270

Pro Asp Gln Leu Val Asn Leu His Asp Phe Arg Ser Asp Glu Ile Glu
                275                 280                 285

His Leu Val Val Glu Glu Leu Val Arg Lys Arg Glu Glu Cys Leu Asp
 290                        295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Arg
                340                 345                 350

Thr Trp Asn Glu Ile Leu Pro Ser Lys Gly Cys Leu Arg Val Gly Gly
                355                 360                 365

Arg Cys His Pro His Val Asn Gly Val Phe Phe Asn Gly Ile Ile Leu
                370                 375                 380

Gly Pro Asp Gly Asn Val Leu Ile Pro Glu Met Gln Ser Ser Leu Leu
385                 390                 395                 400

Gln Gln His Met Glu Leu Leu Glu Ser Ser Val Ile Pro Leu Val His
                405                 410                 415

Pro Leu Ala Asp Pro Ser Thr Val Phe Lys Asp Gly Asp Glu Ala Glu
                420                 425                 430
```

```
Asp Phe Val Glu Val His Leu Pro Asp Val His Asn Gln Val Ser Gly
        435                 440                 445
Val Asp Leu Gly Leu Pro Asn Trp Gly Lys Tyr Val Leu Leu Ser Ala
    450                 455                 460
Gly Ala Leu Thr Ala Leu Met Leu Ile Ile Phe Leu Met Thr Cys Cys
465                 470                 475                 480
Arg Arg Val Asn Arg Ser Glu Pro Thr Gln His Asn Leu Arg Gly Thr
                485                 490                 495
Gly Arg Glu Val Ser Val Thr Pro Gln Ser Gly Lys Ile Ile Ser Ser
            500                 505                 510
Trp Glu Ser His Lys Ser Gly Gly Glu Thr Arg Leu
            515                 520
```

<210> SEQ ID NO 208
<211> LENGTH: 23
<212> TYPE: DNA
<213> ORGANISM: Artificial sequence
<220> FEATURE:
<223> OTHER INFORMATION: Primer HuVlambda1A

<400> SEQUENCE: 208
cagtctgtgc tgactcagcc acc                                23

<210> SEQ ID NO 209
<211> LENGTH: 23
<212> TYPE: DNA
<213> ORGANISM: Artificial sequence
<220> FEATURE:
<223> OTHER INFORMATION: Primer HuVlambda1B

<400> SEQUENCE: 209
cagtctgtgy tgacgcagcc gcc                                23

<210> SEQ ID NO 210
<211> LENGTH: 23
<212> TYPE: DNA
<213> ORGANISM: Artificial sequence
<220> FEATURE:
<223> OTHER INFORMATION: Primer HuVlambda1C

<400> SEQUENCE: 210
cagtctgtcg tgacgcagcc gcc                                23

<210> SEQ ID NO 211
<211> LENGTH: 21
<212> TYPE: DNA
<213> ORGANISM: Artificial sequence
<220> FEATURE:
<223> OTHER INFORMATION: Primer HuVlambda2

<400> SEQUENCE: 211
cartctgccc tgactcagcc t                                  21

<210> SEQ ID NO 212
<211> LENGTH: 23
<212> TYPE: DNA
<213> ORGANISM: Artificial sequence
<220> FEATURE:
<223> OTHER INFORMATION: Primer HuVlambda3A

<400> SEQUENCE: 212
tcctatgwgc tgactcagcc acc                                23

<210> SEQ ID NO 213
<211> LENGTH: 23
<212> TYPE: DNA
<213> ORGANISM: Artificial sequence
<220> FEATURE:
<223> OTHER INFORMATION: Primer HuVlambda3B

<400> SEQUENCE: 213
tcttctgagc tgactcagga ccc                                              23

<210> SEQ ID NO 214
<211> LENGTH: 23
<212> TYPE: DNA
<213> ORGANISM: Artificial sequence
<220> FEATURE:
<223> OTHER INFORMATION: Primer HuVlambda4

<400> SEQUENCE: 214
cacgttatac tgactcaacc gcc                                              23

<210> SEQ ID NO 215
<211> LENGTH: 23
<212> TYPE: DNA
<213> ORGANISM: Artificial sequence
<220> FEATURE:
<223> OTHER INFORMATION: Primer HuVlambda5

<400> SEQUENCE: 215
caggctgtgc tgactcagcc gtc                                              23

<210> SEQ ID NO 216
<211> LENGTH: 23
<212> TYPE: DNA
<213> ORGANISM: Artificial sequence
<220> FEATURE:
<223> OTHER INFORMATION: Primer HuVlambda6

<400> SEQUENCE: 216
aattttatgc tgactcagcc cca                                              23

<210> SEQ ID NO 217
<211> LENGTH: 23
<212> TYPE: DNA
<213> ORGANISM: Artificial sequence
<220> FEATURE:
<223> OTHER INFORMATION: Primer HuVlambda7/8

<400> SEQUENCE: 217
cagrctgtgg tgacycagga gcc                                              23

<210> SEQ ID NO 218
<211> LENGTH: 23
<212> TYPE: DNA
<213> ORGANISM: Artificial sequence
<220> FEATURE:
<223> OTHER INFORMATION: Primer HuVlambda9

<400> SEQUENCE: 218
cwgcctgtgc tgactcagcc mcc                                              23

<210> SEQ ID NO 219
<211> LENGTH: 23
<212> TYPE: DNA
<213> ORGANISM: Artificial sequence
<220> FEATURE:
<223> OTHER INFORMATION: Primer HuVkappa1B

<400> SEQUENCE: 219
gacatccagw tgacccagtc tcc    23

<210> SEQ ID NO 220
<211> LENGTH: 23
<212> TYPE: DNA
<213> ORGANISM: Artificial sequence
<220> FEATURE:
<223> OTHER INFORMATION: Primer HuVkappa2

<400> SEQUENCE: 220
gatgttgtga tgactcagtc tcc    23

<210> SEQ ID NO 221
<211> LENGTH: 23
<212> TYPE: DNA
<213> ORGANISM: Artificial sequence
<220> FEATURE:
<223> OTHER INFORMATION: Primer HuVkappa3

<400> SEQUENCE: 221
gaaattgtgw tgacrcagtc tcc    23

<210> SEQ ID NO 222
<211> LENGTH: 23
<212> TYPE: DNA
<213> ORGANISM: Artificial sequence
<220> FEATURE:
<223> OTHER INFORMATION: Primer HuVkappa4

<400> SEQUENCE: 222
gatattgtga tgacccacac tcc    23

<210> SEQ ID NO 223
<211> LENGTH: 23
<212> TYPE: DNA
<213> ORGANISM: Artificial sequence
<220> FEATURE:
<223> OTHER INFORMATION: Primer HuVkappa5

<400> SEQUENCE: 223
gaaacgacac tcacgcagtc tcc    23

<210> SEQ ID NO 224
<211> LENGTH: 23
<212> TYPE: DNA
<213> ORGANISM: Artificial sequence
<220> FEATURE:
<223> OTHER INFORMATION: Primer HuVkappa6

<400> SEQUENCE: 224
gaaattgtgc tgactcagtc tcc    23

<210> SEQ ID NO 225
<211> LENGTH: 41
<212> TYPE: DNA
<213> ORGANISM: Artificial sequence
<220> FEATURE:
<223> OTHER INFORMATION: Primer HuVkappa1B-SalI

<400> SEQUENCE: 225
tgagcacaca ggtcgacgga catccagwtg acccagtctc c    41

<210> SEQ ID NO 226

```
<211> LENGTH: 41
<212> TYPE: DNA
<213> ORGANISM: Artificial sequence
<220> FEATURE:
<223> OTHER INFORMATION: Primer HuVkappa2-SalI

<400> SEQUENCE: 226
tgagcacaca ggtcgacgga tgttgtgatg actcagtctc c                    41

<210> SEQ ID NO 227
<211> LENGTH: 41
<212> TYPE: DNA
<213> ORGANISM: Artificial sequence
<220> FEATURE:
<223> OTHER INFORMATION: Primer HuVkappa3B-SalI

<400> SEQUENCE: 227
tgagcacaca ggtcgacgga aattgtgwtg acrcagtctc c                    41

<210> SEQ ID NO 228
<211> LENGTH: 41
<212> TYPE: DNA
<213> ORGANISM: Artificial sequence
<220> FEATURE:
<223> OTHER INFORMATION: Primer HuVkappa4B-SalI

<400> SEQUENCE: 228
tgagcacaca ggtcgacgga tattgtgatg acccacactc c                    41

<210> SEQ ID NO 229
<211> LENGTH: 41
<212> TYPE: DNA
<213> ORGANISM: Artificial sequence
<220> FEATURE:
<223> OTHER INFORMATION: Primer HuVkappa5-SalI

<400> SEQUENCE: 229
tgagcacaca ggtcgacgga aacgacactc acgcagtctc c                    41

<210> SEQ ID NO 230
<211> LENGTH: 41
<212> TYPE: DNA
<213> ORGANISM: Artificial sequence
<220> FEATURE:
<223> OTHER INFORMATION: Primer HuVkappa6-SalI

<400> SEQUENCE: 230
tgagcacaca ggtcgacgga aattgtgctg actcagtctc c                    41

<210> SEQ ID NO 231
<211> LENGTH: 48
<212> TYPE: DNA
<213> ORGANISM: Artificial sequence
<220> FEATURE:
<223> OTHER INFORMATION: Primer HuJkappa1-NotI

<400> SEQUENCE: 231
gagtcattct cgacttgcgg ccgcacgttt gatttccacc ttggtccc             48

<210> SEQ ID NO 232
<211> LENGTH: 48
<212> TYPE: DNA
<213> ORGANISM: Artificial sequence
<220> FEATURE:
<223> OTHER INFORMATION: Primer HuJkappa2-NotI

<400> SEQUENCE: 232
```
gagtcattct cgacttgcgg ccgcacgttt gatctccagc ttggtccc                48

<210> SEQ ID NO 233
<211> LENGTH: 48
<212> TYPE: DNA
<213> ORGANISM: Artificial sequence
<220> FEATURE:
<223> OTHER INFORMATION: Primer HuJkappa3-NotI

<400> SEQUENCE: 233
gagtcattct cgacttgcgg ccgcacgttt gatatccact ttggtccc                48

<210> SEQ ID NO 234
<211> LENGTH: 48
<212> TYPE: DNA
<213> ORGANISM: Artificial sequence
<220> FEATURE:
<223> OTHER INFORMATION: Primer HuJkappa4-NotI

<400> SEQUENCE: 234
gagtcattct cgacttgcgg ccgcacgttt gatctccacc ttggtccc                48

<210> SEQ ID NO 235
<211> LENGTH: 48
<212> TYPE: DNA
<213> ORGANISM: Artificial sequence
<220> FEATURE:
<223> OTHER INFORMATION: Primer HuJkappa5-NotI

<400> SEQUENCE: 235
gagtcattct cgacttgcgg ccgcacgttt aatctccagt cgtgtccc                48

<210> SEQ ID NO 236
<211> LENGTH: 41
<212> TYPE: DNA
<213> ORGANISM: Artificial sequence
<220> FEATURE:
<223> OTHER INFORMATION: Primer HuVlambda1A-SalI

<400> SEQUENCE: 236
tgagcacaca ggtcgacgca gtctgtgctg actcagccac c                      41

<210> SEQ ID NO 237
<211> LENGTH: 41
<212> TYPE: DNA
<213> ORGANISM: Artificial sequence
<220> FEATURE:
<223> OTHER INFORMATION: Primer HuVlambda1B-SalI

<400> SEQUENCE: 237
tgagcacaca ggtcgacgca gtctgtgytg acgcagccgc c                      41

<210> SEQ ID NO 238
<211> LENGTH: 41
<212> TYPE: DNA
<213> ORGANISM: Artificial sequence
<220> FEATURE:
<223> OTHER INFORMATION: Primer HuVlambda1C-SalI

<400> SEQUENCE: 238
tgagcacaca ggtcgacgca gtctgtcgtg acgcagccgc c                      41

<210> SEQ ID NO 239
<211> LENGTH: 39
<212> TYPE: DNA

```
<213> ORGANISM: Artificial sequence
<220> FEATURE:
<223> OTHER INFORMATION: Primer HuVlambda2-SalI

<400> SEQUENCE: 239
tgagcacaca ggtcgacgca rtctgccctg actcagcct                    39

<210> SEQ ID NO 240
<211> LENGTH: 41
<212> TYPE: DNA
<213> ORGANISM: Artificial sequence
<220> FEATURE:
<223> OTHER INFORMATION: Primer HuVlambda3A-SalI

<400> SEQUENCE: 240
tgagcacaca ggtcgacgtc ctatgwgctg actcagccac c                 41

<210> SEQ ID NO 241
<211> LENGTH: 41
<212> TYPE: DNA
<213> ORGANISM: Artificial sequence
<220> FEATURE:
<223> OTHER INFORMATION: Primer HuVlambda3B-SalI

<400> SEQUENCE: 241
tgagcacaca ggtcgacgtc ttctgagctg actcaggacc c                 41

<210> SEQ ID NO 242
<211> LENGTH: 41
<212> TYPE: DNA
<213> ORGANISM: Artificial sequence
<220> FEATURE:
<223> OTHER INFORMATION: Primer HuVlambda4-SalI

<400> SEQUENCE: 242
tgagcacaca ggtcgacgca cgttatactg actcaaccgc c                 41

<210> SEQ ID NO 243
<211> LENGTH: 41
<212> TYPE: DNA
<213> ORGANISM: Artificial sequence
<220> FEATURE:
<223> OTHER INFORMATION: Primer HuVlambda5-SalI

<400> SEQUENCE: 243
tgagcacaca ggtcgacgca ggctgtgctg actcagccgt c                 41

<210> SEQ ID NO 244
<211> LENGTH: 41
<212> TYPE: DNA
<213> ORGANISM: Artificial sequence
<220> FEATURE:
<223> OTHER INFORMATION: Primer HuVlambda6-SalI

<400> SEQUENCE: 244
tgagcacaca ggtcgacgaa ttttatgctg actcagcccc a                 41

<210> SEQ ID NO 245
<211> LENGTH: 41
<212> TYPE: DNA
<213> ORGANISM: Artificial sequence
<220> FEATURE:
<223> OTHER INFORMATION: Primer HuVlambda7/8-SalI

<400> SEQUENCE: 245
tgagcacaca ggtcgacgca grctgtggtg acycaggagc c                 41
```

<210> SEQ ID NO 246
<211> LENGTH: 41
<212> TYPE: DNA
<213> ORGANISM: Artificial sequence
<220> FEATURE:
<223> OTHER INFORMATION: Primer HuVlambda9-SalI

<400> SEQUENCE: 246
tgagcacaca ggtcgacgcw gcctgtgctg actcagccmc c                41

<210> SEQ ID NO 247
<211> LENGTH: 48
<212> TYPE: DNA
<213> ORGANISM: Artificial sequence
<220> FEATURE:
<223> OTHER INFORMATION: Primer HuJlambda1-NotI

<400> SEQUENCE: 247
gagtcattct cgacttgcgg ccgcacctag gacggtgacc ttggtccc         48

<210> SEQ ID NO 248
<211> LENGTH: 48
<212> TYPE: DNA
<213> ORGANISM: Artificial sequence
<220> FEATURE:
<223> OTHER INFORMATION: Primer HuJlambda2/3-NotI

<400> SEQUENCE: 248
gagtcattct cgacttgcgg ccgcacctag gacggtcagc ttggtccc         48

<210> SEQ ID NO 249
<211> LENGTH: 48
<212> TYPE: DNA
<213> ORGANISM: Artificial sequence
<220> FEATURE:
<223> OTHER INFORMATION: Primer HuJlambda4/5-NotI

<400> SEQUENCE: 249
gagtcattct cgacttgcgg ccgcacytaa aacggtgagc tgggtccc         48

<210> SEQ ID NO 250
<211> LENGTH: 23
<212> TYPE: DNA
<213> ORGANISM: Artificial sequence
<220> FEATURE:
<223> OTHER INFORMATION: Primer HuVH1B/7A

<400> SEQUENCE: 250
cagrtgcagc tggtgcartc tgg                                    23

<210> SEQ ID NO 251
<211> LENGTH: 23
<212> TYPE: DNA
<213> ORGANISM: Artificial sequence
<220> FEATURE:
<223> OTHER INFORMATION: Primer HuVH1C

<400> SEQUENCE: 251
saggtccagc tggtrcagtc tgg                                    23

<210> SEQ ID NO 252
<211> LENGTH: 23
<212> TYPE: DNA
<213> ORGANISM: Artificial sequence
<220> FEATURE:

<223> OTHER INFORMATION: Primer HuVH2B

<400> SEQUENCE: 252
saggtgcagc tggtggagtc tgg                                              23

<210> SEQ ID NO 253
<211> LENGTH: 23
<212> TYPE: DNA
<213> ORGANISM: Artificial sequence
<220> FEATURE:
<223> OTHER INFORMATION: Primer HuVH3B

<400> SEQUENCE: 253
saggtgcagc tggtggagtc tgg                                              23

<210> SEQ ID NO 254
<211> LENGTH: 23
<212> TYPE: DNA
<213> ORGANISM: Artificial sequence
<220> FEATURE:
<223> OTHER INFORMATION: Primer HuVH3C

<400> SEQUENCE: 254
gaggtgcagc tggtggagwc ygg                                              23

<210> SEQ ID NO 255
<211> LENGTH: 23
<212> TYPE: DNA
<213> ORGANISM: Artificial sequence
<220> FEATURE:
<223> OTHER INFORMATION: Primer HuVH4B

<400> SEQUENCE: 255
caggtgcagc tacagcagtg ggg                                              23

<210> SEQ ID NO 256
<211> LENGTH: 23
<212> TYPE: DNA
<213> ORGANISM: Artificial sequence
<220> FEATURE:
<223> OTHER INFORMATION: Primer HuVH4C

<400> SEQUENCE: 256
cagstgcagc tgcaggagtc sgg                                              23

<210> SEQ ID NO 257
<211> LENGTH: 23
<212> TYPE: DNA
<213> ORGANISM: Artificial sequence
<220> FEATURE:
<223> OTHER INFORMATION: Primer HuVH5B

<400> SEQUENCE: 257
gargtgcagc tggtgcagtc tgg                                              23

<210> SEQ ID NO 258
<211> LENGTH: 23
<212> TYPE: DNA
<213> ORGANISM: Artificial sequence
<220> FEATURE:
<223> OTHER INFORMATION: Primer HuVH6A

<400> SEQUENCE: 258
caggtacagc tgcagcagtc agg                                              23

<210> SEQ ID NO 259
<211> LENGTH: 56
<212> TYPE: DNA
<213> ORGANISM: Artificial sequence
<220> FEATURE:
<223> OTHER INFORMATION: Primer HuVH1B/7A-SfiI

<400> SEQUENCE: 259
gtcctcgcaa ctgcggccca gccggccatg gcccagrtgc agctggtgca rtctgg      56

<210> SEQ ID NO 260
<211> LENGTH: 56
<212> TYPE: DNA
<213> ORGANISM: Artificial sequence
<220> FEATURE:
<223> OTHER INFORMATION: Primer HuVH1C-SfiI

<400> SEQUENCE: 260
gtcctcgcaa ctgcggccca gccggccatg gccsaggtcc agctggtrca gtctgg      56

<210> SEQ ID NO 261
<211> LENGTH: 56
<212> TYPE: DNA
<213> ORGANISM: Artificial sequence
<220> FEATURE:
<223> OTHER INFORMATION: Primer HuVH2B-SfiI

<400> SEQUENCE: 261
gtcctcgcaa ctgcggccca gccggccatg gcccagrtca ccttgaagga gtctgg      56

<210> SEQ ID NO 262
<211> LENGTH: 56
<212> TYPE: DNA
<213> ORGANISM: Artificial sequence
<220> FEATURE:
<223> OTHER INFORMATION: Primer HuVH3B-SfiI

<400> SEQUENCE: 262
gtcctcgcaa ctgcggccca gccggccatg gccsaggtgc agctggtgga gtctgg      56

<210> SEQ ID NO 263
<211> LENGTH: 56
<212> TYPE: DNA
<213> ORGANISM: Artificial sequence
<220> FEATURE:
<223> OTHER INFORMATION: Primer HuVH3C-SfiI

<400> SEQUENCE: 263
gtcctcgcaa ctgcggccca gccggccatg gccgaggtgc agctggtgga gwcygg      56

<210> SEQ ID NO 264
<211> LENGTH: 56
<212> TYPE: DNA
<213> ORGANISM: Artificial sequence
<220> FEATURE:
<223> OTHER INFORMATION: Primer HuVH4B-SfiI

<400> SEQUENCE: 264
gtcctcgcaa ctgcggccca gccggccatg gcccaggtgc agctacagca gtgggg      56

<210> SEQ ID NO 265
<211> LENGTH: 56
<212> TYPE: DNA
<213> ORGANISM: Artificial sequence
<220> FEATURE:
<223> OTHER INFORMATION: Primer HuVH4C-SfiI

<400> SEQUENCE: 265
gtcctcgcaa ctgcggccca gccggccatg gcccagstgc agctgcagga gtcsgg    56

<210> SEQ ID NO 266
<211> LENGTH: 56
<212> TYPE: DNA
<213> ORGANISM: Artificial sequence
<220> FEATURE:
<223> OTHER INFORMATION: Primer HuVH5B-SfiI

<400> SEQUENCE: 266
gtcctcgcaa ctgcggccca gccggccatg gccgargtgc agctggtgca gtctgg    56

<210> SEQ ID NO 267
<211> LENGTH: 56
<212> TYPE: DNA
<213> ORGANISM: Artificial sequence
<220> FEATURE:
<223> OTHER INFORMATION: Primer HuVH6A-SfiI

<400> SEQUENCE: 267
gtcctcgcaa ctgcggccca gccggccatg gcccaggtac agctgcagca gtcagg    56

<210> SEQ ID NO 268
<211> LENGTH: 36
<212> TYPE: DNA
<213> ORGANISM: Artificial sequence
<220> FEATURE:
<223> OTHER INFORMATION: Primer HuJH1/2-XhoI

<400> SEQUENCE: 268
gagtcattct cgactcgaga cggtgaccag ggtgcc    36

<210> SEQ ID NO 269
<211> LENGTH: 36
<212> TYPE: DNA
<213> ORGANISM: Artificial sequence
<220> FEATURE:
<223> OTHER INFORMATION: Primer HuJH3-XhoI

<400> SEQUENCE: 269
gagtcattct cgactcgaga cggtgaccat tgtccc    36

<210> SEQ ID NO 270
<211> LENGTH: 36
<212> TYPE: DNA
<213> ORGANISM: Artificial sequence
<220> FEATURE:
<223> OTHER INFORMATION: Primer HuJH4/5-XhoI

<400> SEQUENCE: 270
gagtcattct cgactcgaga cggtgaccag ggttcc    36

<210> SEQ ID NO 271
<211> LENGTH: 36
<212> TYPE: DNA
<213> ORGANISM: Artificial sequence
<220> FEATURE:
<223> OTHER INFORMATION: Primer HuJH6-XhoI

<400> SEQUENCE: 271
gagtcattct cgactcgaga cggtgaccgt ggtccc    36

<210> SEQ ID NO 272
<211> LENGTH: 381

<212> TYPE: DNA
<213> ORGANISM: Artificial sequence
<220> FEATURE:
<223> OTHER INFORMATION: Heavy chain variable region of CR57

<400> SEQUENCE: 272

```
caggtgcagc tggtgcagag cggagccgag gtgaagaagc ccggcagcag cgtgaaggtg      60
agctgcaagg ccagcggcgg caccttcaac aggtacaccg tgaactgggt gagacaggcc     120
ccaggccagg gcctggagtg gatgggcggc atcatcccta tcttcggcac cgccaactac     180
gcccagagat ccagggcag gctcaccatc accgccgacg agagcaccag caccgcctac     240
atggagctga gcagcctgag aagcgatgac accgccgtgt acttctgcgc cagggagaac     300
ctggataaca gcggcaccta ctactacttc agcggctggt tcgacccctg gggccagggc     360
accctggtga ccgtgagctc a                                                381
```

<210> SEQ ID NO 273
<211> LENGTH: 127
<212> TYPE: PRT
<213> ORGANISM: Artificial sequence
<220> FEATURE:
<223> OTHER INFORMATION: Heavy chain variable region of CR57

<400> SEQUENCE: 273

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Arg Tyr
            20                  25                  30

Thr Val Asn Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Arg Phe
    50                  55                  60

Gln Gly Arg Leu Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Phe Cys
                85                  90                  95

Ala Arg Glu Asn Leu Asp Asn Ser Gly Thr Tyr Tyr Tyr Phe Ser Gly
            100                 105                 110

Trp Phe Asp Pro Trp Gly Gln Gly Thr Leu Val Thr Val Ser Ser
        115                 120                 125
```

<210> SEQ ID NO 274
<211> LENGTH: 336
<212> TYPE: DNA
<213> ORGANISM: Artificial sequence
<220> FEATURE:
<223> OTHER INFORMATION: Light chain variable region of CR57

<400> SEQUENCE: 274

```
cagagcgccc tcacccagcc cagaagcgtg agcggcagcc tggccagag cgtgaccatc      60
agctgcaccg gcaccagcag cgacatcggc ggctacaact cgtgagctg gtatcagcag     120
caccccggca aggcccctaa gctcatgatc tacgacgcca ccaagagacc cagcggcgtg     180
cccgacagat tcagcggcag caagagcggc aacaccgcca gcctcaccat cagcggactg     240
caggccgagg acgaggccga ctactactgc tgcagctacg ccggcgacta caccccctggc     300
gtggtgttcg gcggaggcac caagcttacc gtccta                                336
```

<210> SEQ ID NO 275

<211> LENGTH: 112
<212> TYPE: PRT
<213> ORGANISM: Artificial sequence
<220> FEATURE:
<223> OTHER INFORMATION: Light chain variable region of CR57

<400> SEQUENCE: 275

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Ile Gly Gly Tyr
            20                  25                  30

Asn Phe Val Ser Trp Tyr Gln Gln His Pro Gly Lys Ala Pro Lys Leu
        35                  40                  45

Met Ile Tyr Asp Ala Thr Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Asp
                85                  90                  95

Tyr Thr Pro Gly Val Val Phe Gly Gly Gly Thr Lys Leu Thr Val Leu
            100                 105                 110

<210> SEQ ID NO 276
<211> LENGTH: 12
<212> TYPE: PRT
<213> ORGANISM: Artificial sequence
<220> FEATURE:
<223> OTHER INFORMATION: CDR3 of CRJB

<400> SEQUENCE: 276

Arg Gln His Ile Ser Ser Phe Pro Trp Phe Asp Ser
1               5                   10

<210> SEQ ID NO 277
<211> LENGTH: 6778
<212> TYPE: DNA
<213> ORGANISM: Artificial sequence
<220> FEATURE:
<223> OTHER INFORMATION: Vector pSyn-C03-HCgamma1

<400> SEQUENCE: 277
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgct aggtggtcaa tattggccat tagccatatt     240
attcattggt tatatagcat aaatcaatat tggctattgg ccattgcata cgttgtatcc     300
atatcataat atgtacattt atattggctc atgtccaaca ttaccgccat gttgacattg     360
attattgact agttattaat agtaatcaat tacggggtca ttagttcata gcccatatat     420
ggagttccgc gttacataac ttacggtaaa tggcccgcct ggctgaccgc ccaacgaccc     480
ccgcccattg acgtcaataa tgacgtatgt tcccatagta acgccaatag ggactttcca     540
ttgacgtcaa tggtggagt atttacggta aactgcccac ttggcagtac atcaagtgta     600
tcatatgcca gtacgcccc ctattgacgt caatgacggt aaatggcccg cctggcatta     660
tgcccagtac atgaccttat gggactttcc tacttggcag tacatctacg tattagtcat     720
cgctattacc atggtgatgc ggttttggca gtacatcaat gggcgtggat agcggtttga     780
ctcacgggga tttccaagtc tccaccccat tgacgtcaat gggagtttgt tttggcacca     840

```
aaatcaacgg gactttccaa aatgtcgtaa caactccgcc ccattgacgc aaatgggcgg    900
taggcgtgta cggtgggagg tctatataag cagagctcgt ttagtgaacc gtcagatcgc    960
ctggagacgc catccacgct gttttgacct ccatagaaga caccgggacc gatccagcct   1020
ccgcggccgg gaacggtgca ttggaagctg gcctggatgg cctgactctc ttaggtagcc   1080
ttgcagaagt tggtcgtgag gcactgggca ggtaagtatc aaggttacaa gacaggttta   1140
aggagatcaa tagaaactgg gcttgtcgag acagagaaga ctcttgcgtt tctgataggc   1200
acctattggt cttactgaca tccactttgc ctttctctcc acaggtgtcc actcccagtt   1260
caattacagc tcgccaccat ggcctgcccc ggcttcctgt gggccctggt gatcagcacc   1320
tgcctggaat tcagcatgag cagcgctagc accaagggcc ccagcgtgtt cccctggcc    1380 cccagcagca gagcaccag cggcggcaca gccgccctgg gctgcctggt gaaggactac   1440
ttccccgagc ccgtgaccgt gagctggaac agcggcgcct tgaccagcgg cgtgcacacc   1500
ttccccgccg tgctgcagag cagcggcctg tacagcctga gcagcgtggt gaccgtgccc   1560
agcagcagcc tgggcaccca gacctacatc tgcaacgtga accacaagcc cagcaacacc   1620
aaggtggaca acgcgtgga gcccaagagc tgcgacaaga cccacacctg ccccccctgc   1680
cctgcccccg agctgctggg cggacccctcc gtgttcctgt tccccccaa gcccaaggac   1740 accctcatga tcagccggac ccccgaggtg acctgcgtgg tggtggacgt gagccacgag   1800
gaccccgagg tgaagttcaa ctggtacgtg gacggcgtgg aggtgcacaa cgccaagacc   1860
aagccccggg aggagcagta caacagcacc taccgggtgg tgagcgtgct caccgtgctg   1920
caccaggact ggctgaacgg caaggagtac aagtgcaagg tgagcaacaa ggccctgcct   1980 gccccatcg agaagaccat cagcaaggcc aagggccagc ccggagcc ccaggtgtac   2040 accctgcccc ccagccggga ggagatgacc aagaaccagg tgtccctcac ctgtctggtg   2100
aagggcttct accccagcga catcgccgtg gagtgggaga gcaacggcca gcccgagaac   2160
aactacaaga ccaccccccc tgtgctggac agcgacggca gcttcttcct gtacagcaag   2220
ctcaccgtgg acaagagccg gtggcagcag ggcaacgtgt tcagctgcag cgtgatgcac   2280
gaggccctgc acaaccacta cacccagaag agcctgagcc tgagccccgg caagtgataa   2340
tctagagggc ccgtttaaac ccgctgatca gcctcgactg tgccttctag ttgccagcca   2400
tctgttgttt gcccctcccc cgtgccttcc ttgaccctgg aaggtgccac tcccactgtc   2460
ctttcctaat aaaatgagga aattgcatcg cattgtctga gtaggtgtca ttctattctg   2520 ggggtgggg tggggcagga cagcaagggg gaggattggg aagacaatag caggcatgct   2580
ggggatgcgg tgggctctat ggcttctgag gcggaaagaa ccagctgggg ctctaggggg   2640
tatccccacg cgccctgtag cggcgcatta agcgcggcgg gtgtggtggt tacgcgcagc   2700
gtgaccgcta cacttgccag cgccctagcg cccgctcctt tcgctttctt cccttccttt   2760
ctcgccacgt tcgccggctt tccccgtcaa gctctaaatc gggggctccc tttagggttc   2820
cgatttagtg ctttacggca cctcgacccc aaaaaacttg attagggtga tggttcacgt   2880
agtgggccat cgccctgata acggtttttt cgcccttga cgttggagtc cacgttcttt   2940
aatagtggac tcttgttcca aactggaaca acactcaacc ctatctcggt ctattctttt   3000
gatttataag ggattttgcc gatttcggcc tattggttaa aaaatgagct gatttaacaa   3060
aaatttaacg cgaattaatt ctgtggaatg tgtgtcagtt agggtgtgga agtccccag   3120 gctccccagc aggcagaagt atgcaaagca tgcatctcaa ttagtcagca accaggtgtg   3180
```

```
gaaagtcccc aggctcccca gcaggcagaa gtatgcaaag catgcatctc aattagtcag    3240
caaccatagt cccgccccta actccgccca tcccgcccct aactccgccc agttccgccc    3300
attctccgcc ccatggctga ctaattttt ttatttatgc agaggccgag gccgcctctg    3360
cctctgagct attccagaag tagtgaggag gcttttttgg aggcctaggc ttttgcaaaa    3420
agctcccggg agcttgtata tccatttcg gatctgatca agagacagga tgaggatcgt    3480
ttcgcatgat tgaacaagat ggattgcacg caggttctcc ggccgcttgg gtggagaggc    3540
tattcggcta tgactgggca caacagacaa tcggctgctc tgatgccgcc gtgttccggc    3600
tgtcagcgca ggggcgcccg gttcttttg tcaagaccga cctgtccggt gccctgaatg    3660
aactgcagga cgaggcagcg cggctatcgt ggctggccac gacgggcgtt ccttgcgcag    3720
ctgtgctcga cgttgtcact gaagcggaa gggactggct gctattgggc gaagtgccgg    3780
ggcaggatct cctgtcatct caccttgctc ctgccgagaa agtatccatc atggctgatg    3840
caatgcggcg gctgcatacg cttgatccgg ctacctgccc attcgaccac caagcgaaac    3900
atcgcatcga gcgagcacgt actcggatgg aagccggtct tgtcgatcag gatgatctgg    3960
acgaagagca tcaggggctc gcgccagccg aactgttcgc caggctcaag gcgcgcatgc    4020
ccgacggcga ggatctcgtc gtgacccatg gcgatgcctg cttgccgaat atcatggtgg    4080
aaaatggccg cttttctgga ttcatcgact gtggccggct gggtgtggcg gatcgctatc    4140
aggacatagc gttggctacc cgtgatattg ctgaagagct tggcggcgaa tgggctgacc    4200
gcttcctcgt gctttacggt atcgccgctc ccgattcgca gcgcatcgcc ttctatcgcc    4260
ttcttgacga gttcttctga gcgggactct ggggttcgaa atgaccgacc aagcgacgcc    4320
caacctgcca tcacgagatt tcgattccac cgccgccttc tatgaaaggt tgggcttcgg    4380
aatcgttttc cgggacgccg gctggatgat cctccagcgc ggggatctca tgctggagtt    4440
cttcgcccac cccaacttgt ttattgcagc ttataatggt tacaaataaa gcaatagcat    4500
cacaaatttc acaaataaag catttttttc actgcattct agttgtggtt tgtccaaact    4560
catcaatgta tcttatcatg tctgtatacc gtcgacctct agctagagct tggcgtaatc    4620
atggtcatag ctgtttcctg tgtgaaattg ttatccgctc acaattccac acaacatacg    4680
agccggaagc ataaagtgta aagcctgggg tgcctaatga gtgagctaac tcacattaat    4740
tgcgttgcgc tcactgcccg ctttccagtc gggaaacctg tcgtgccagc tgcattaatg    4800
aatcggccaa cgcgcgggga gaggcggttt gcgtattggg cgctcttccg cttcctcgct    4860
cactgactcg ctgcgctcgg tcgttcggct gcggcgagcg gtatcagctc actcaaaggc    4920
ggtaatacgg ttatccacag aatcagggga taacgcagga aagaacatgt gagcaaaagg    4980
ccagcaaaag gccaggaacc gtaaaaaggc cgcgttgctg gcgttttcc ataggctccg    5040 cccccctgac gagcatcaca aaaatcgacg ctcaagtcag aggtggcgaa acccgacagg    5100
actataaaga taccaggcgt ttccccctgg aagctccctc gtgcgctctc ctgttccgac    5160
cctgccgctt accggatacc tgtccgcctt tctcccttcg ggaagcgtgg cgctttctca    5220
tagctcacgc tgtaggtatc tcagttcggt gtaggtcgtt cgctccaagc tgggctgtgt    5280
gcacgaaccc cccgttcagc ccgaccgctg cgccttatcc ggtaactatc gtcttgagtc    5340
caacccggta agacacgact tatcgccact ggcagcagcc actggtaaca ggattagcag    5400
agcgaggtat gtaggcggtg ctacagagtt cttgaagtgg tggcctaact acggctacac    5460
tagaagaaca gtatttggta tctgcgctct gctgaagcca gttaccttcg gaaaagagt    5520 tggtagctct tgatccggca aacaaaccac cgctggtagc ggttttttg tttgcaagca    5580
```

| | |
|---|---|
| gcagattacg cgcagaaaaa aaggatctca agaagatcct tgatctttt ctacgggtc | 5640 |
| tgacgctcag tggaacgaaa actcacgtta agggattttg gtcatgagat tatcaaaaag | 5700 |
| gatcttcacc tagatccttt taaattaaaa atgaagtttt aaatcaatct aaagtatata | 5760 |
| tgagtaaact tggtctgaca gttaccaatg cttaatcagt gaggcaccta tctcagcgat | 5820 |
| ctgtctattt cgttcatcca tagttgcctg actccccgtc gtgtagataa ctacgatacg | 5880 |
| ggagggctta ccatctggcc ccagtgctgc aatgataccg cgagacccac gctcaccggc | 5940 |
| tccagattta tcagcaataa accagccagc cggaagggcc gagcgcagaa gtggtcctgc | 6000 |
| aactttatcc gcctccatcc agtctattaa ttgttgccgg gaagctagag taagtagttc | 6060 |
| gccagttaat agtttgcgca acgttgttgc cattgctaca ggcatcgtgg tgtcacgctc | 6120 |
| gtcgtttggt atggcttcat tcagctccgg ttcccaacga tcaaggcgag ttacatgatc | 6180 |
| ccccatgttg tgcaaaaaag cggttagctc cttcggtcct ccgatcgttg tcagaagtaa | 6240 |
| gttggccgca gtgttatcac tcatggttat ggcagcactg cataattctc ttactgtcat | 6300 |
| gccatccgta agatgctttt ctgtgactgg tgagtactca accaagtcat tctgagaata | 6360 |
| gtgtatgcgg cgaccgagtt gctcttgccc ggcgtcaata cgggataata ccgcgccaca | 6420 |
| tagcagaact ttaaaagtgc tcatcattgg aaaacgttct cggggcgaaa actctcaag | 6480 |
| gatcttaccg ctgttgagat ccagttcgat gtaacccact cgtgcaccca actgatcttc | 6540 |
| agcatctttt actttcacca gcgtttctgg gtgagcaaaa acaggaaggc aaaatgccgc | 6600 |
| aaaaaaggga ataagggcga cacggaaatg ttgaatactc atactcttcc ttttcaata | 6660 |
| ttattgaagc atttatcagg gttattgtct catgagcgga tacatatttg aatgtattta | 6720 |
| gaaaaataaa caaataggg ttccgcgcac atttccccga aaagtgccac ctgacgtc | 6778 |

<210> SEQ ID NO 278
<211> LENGTH: 6283
<212> TYPE: DNA
<213> ORGANISM: Artificial sequence
<220> FEATURE:
<223> OTHER INFORMATION: Vector pSyn-C04-Clambda

<400> SEQUENCE: 278

| | |
|---|---|
| gacggatcgg gagatctccc gatccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgttaa ttaacatgaa | 180 |
| gaatctgctt agggttaggc gttttgcgct gcttcgctag gtggtcaata ttggccatta | 240 |
| gccatattat tcattggtta tatagcataa atcaatattg ctattggcc attgcatacg | 300 |
| ttgtatccta atcataatat gtacatttat attggctcat gtccaacatt accgccatgt | 360 |
| tgacattgat tattgactag ttattaatag taatcaatta cggggtcatt agttcatagc | 420 |
| ccatatatgg agttccgcgt tacataactt acggtaaatg gcccgcctgg ctgaccgccc | 480 |
| aacgaccccc gcccattgac gtcaataatg acgtatgttc ccatagtaac gccaataggg | 540 |
| actttccatt gacgtcaatg ggtggagtat ttacggtaaa ctgcccactt ggcagtacat | 600 |
| caagtgtatc atatgccaag tacgcccct attgacgtca atgacggtaa atggcccgcc | 660 |
| tggcattatg cccagtacat gaccttatgg gactttccta cttggcagta catctacgta | 720 |
| ttagtcatcg ctattaccat ggtgatgcgg ttttggcagt acatcaatgg gcgtggatag | 780 |
| cggtttgact cacggggatt tccaagtctc cacccccattg acgtcaatgg gagtttgttt | 840 |

```
tggcaccaaa atcaacggga ctttccaaaa tgtcgtaaca actccgcccc attgacgcaa    900
atgggcggta ggcgtgtacg gtgggaggtc tatataagca gagctcgttt agtgaaccgt    960
cagatcgcct ggagacgcca tccacgctgt tttgacctcc atagaagaca ccgggaccga   1020
tccagcctcc gcggcgggga acggtgcatt ggaatcgatg actctcttag gtagccttgc   1080
agaagttggt cgtgaggcac tgggcaggta agtatcaagg ttacaagaca ggtttaagga   1140
gatcaataga aactgggctt gtcgagacag agaagactct tgcgtttctg ataggcacct   1200
attggtctta ctgacatcca ctttgccttt ctctccacag gtgtccactc ccagttcaat   1260
tacagctcgc caccatggcc tgccccggct cctgtgggc cctggtgatc agcacctgcc    1320
tcgagatccc cggaccgcgg ccgcaagctt accgtgctgg gccagcccaa ggccgctccc   1380
agcgtgaccc tgttcccccc ctcctccgag gagctgcagg ccaacaaggc caccctggtg   1440
tgcctcatca gcgacttcta ccctggcgcc gtgaccgtgg cctggaaggc cgacagcagc   1500
cccgtgaagg ccggcgtgga gaccaccacc cccagcaagc agagcaacaa caagtacgcc   1560
gccagcagct acctgagcct cacccccgag cagtggaaga gccaccggag ctacagctgc   1620
caggtgaccc acgagggcag caccgtggag aagaccgtgg cccccaccga gtgcagctaa   1680
tagacttaag tttaaaccgc tgatcagcct cgactgtgcc ttctagttgc cagccatctg   1740
ttgtttgccc ctcccccgtg ccttccttga ccctggaagg tgccactccc actgtccttt   1800
cctaataaaa tgaggaaatt gcatcgcatt gtctgagtag gtgtcattct attctggggg   1860
gtggggtggg gcaggacagc aagggggagg attgggaaga caatagcagg catgctgggg   1920
atgcggtggg ctctatggct tctgaggcgg aaagaaccag ctggggctct agggggtatc   1980
cccacgcgcc ctgtagcggc gcattaagcg cggcgggtgt ggtggttacg cgcagcgtga   2040
ccgctacact tgccagcgcc ctagcgcccg ctcctttcgc tttcttccct tcctttctcg   2100
ccacgttcgc cggctttccc cgtcaagctc taaatcgggg gctcccttta gggttccgat   2160
ttagtgcttt acggcacctc gaccccaaaa aacttgatta gggtgatggt tcacgtagtg   2220
ggccatcgcc ctgatagacg gttttttcgcc ctttgacgtt ggagtccacg ttctttaata   2280
gtggactctt gttccaaact ggaacaacac tcaaccctat ctcggtctat tcttttgatt   2340
tataagggat tttggccatt tcggcctatt ggttaaaaaa tgagctgatt taacaaaaat   2400
ttaacgcgaa ttaattctgt ggaatgtgtg tcagttaggg tgtggaaagt ccccaggctc   2460
cccagcaggc agaagtatgc aaagcatgca tctcaattag tcagcaacca ggtgtggaaa   2520
gtccccaggc tccccagcag gcagaagtat gcaaagcatg catctcaatt agtcagcaac   2580
catagtcccg cccctaactc cgcccatccc gcccctaact ccgcccagtt ccgcccattc   2640
tccgccccat ggctgactaa ttttttttat ttatgcagag gccgaggccg cctctgcctc   2700
tgagctattc cagaagtagt gaggaggctt ttttggaggc ctaggctttt gcaaaaagct   2760
cccgggagct tgtatatcca ttttcggatc tgatcagcac gtgatgaaaa agcctgaact   2820
caccgcgacg tctgtcgaga agtttctgat cgaaaagttc gacagcgtct ccgacctgat   2880
gcagctctcg gagggcgaag aatctcgtgc tttcagcttc gatgtaggag ggcgtggata   2940
tgtcctgcgg gtaaatagct gcgccgatgg tttctacaaa gatcgttatg tttatcggca   3000
ctttgcatcg gccgcgctcc cgattccgga agtgcttgac attggggaat tcagcgagag   3060
cctgacctat tgcatctccc gccgtgcaca gggtgtcacg ttgcaagacc tgcctgaaac   3120
cgaactgccc gctgttctgc agccggtcgc ggaggccatg gatgcgatcg ctgcggccga   3180
tcttagccag acgagcgggt tcggcccatt cggaccgcaa ggaatcggtc aatacactac   3240
```

-continued

```
atggcgtgat ttcatatgcg cgattgctga tccccatgtg tatcactggc aaactgtgat   3300
ggacgacacc gtcagtgcgt ccgtcgcgca ggctctcgat gagctgatgc tttgggccga   3360
ggactgcccc gaagtccggc acctcgtgca cgcggatttc ggctccaaca atgtcctgac   3420
ggacaatggc cgcataacag cggtcattga ctggagcgag gcgatgttcg gggattccca   3480
atacgaggtc gccaacatct tcttctggag gccgtggttg gcttgtatgg agcagcagac   3540
gcgctacttc gagcggaggc atccggagct tgcaggatcg ccgcggctcc gggcgtatat   3600
gctccgcatt ggtcttgacc aactctatca gagcttggtt gacggcaatt cgatgatgc    3660 agcttgggcg cagggtcgat gcgacgcaat cgtccgatcc ggagccggga ctgtcgggcg   3720
tacacaaatc gcccgcagaa gcgcggccgt ctggaccgat ggctgtgtag aagtactcgc   3780
cgatagtgga aaccgacgcc ccagcactcg tccagggca aaggaatagc acgtgctacg    3840
agatttcgat tccaccgccg ccttctatga aggttgggc ttcggaatcg tttccggga     3900 cgccggctgg atgatcctcc agcgcgggga tctcatgctg gagttcttcg cccaccccaa   3960
cttgtttatt gcagcttata atggttacaa ataaagcaat agcatcacaa atttcacaaa   4020
taaagcattt ttttcactgc attctagttg tggtttgtcc aaactcatca atgtatctta   4080
tcatgtctgt ataccgtcga cctctagcta gagcttggcg taatcatggt catagctgtt   4140
tcctgtgtga aattgttatc cgctcacaat tccacacaac atacgagccg gaagcataaa   4200
gtgtaaagcc tggggtgcct aatgagtgag ctaactcaca ttaattgcgt tgcgctcact   4260
gcccgctttc cagtcgggaa acctgtcgtg ccagctgcat taatgaatcg gccaacgcgc   4320
ggggagaggc ggtttgcgta ttgggcgctc ttccgcttcc tcgctcactg actcgctgcg   4380
ctcggtcgtt cggctgcggc gagcggtatc agctcactca aaggcggtaa tacggttatc   4440
cacagaatca ggggataacg caggaaagaa catgtgagca aaaggccagc aaaaggccag   4500
gaaccgtaaa aaggccgcgt tgctggcgtt tttccatagg ctccgccccc ctgacgagca   4560
tcacaaaaat cgacgctcaa gtcagaggtg gcgaaacccg acaggactat aaagatacca   4620
ggcgtttccc cctggaagct ccctcgtgcg ctctcctgtt ccgaccctgc cgcttaccgg   4680
atacctgtcc gcctttctcc cttcgggaag cgtggcgctt tctcatagct cacgctgtag   4740
gtatctcagt tcggtgtagg tcgttcgctc caagctgggc tgtgtgcacg aaccccccgt   4800
tcagcccgac cgctgcgcct tatccggtaa ctatcgtctt gagtccaacc cggtaagaca   4860
cgacttatcg ccactggcag cagccactgg taacaggatt agcagagcga ggtatgtagg   4920
cggtgctaca gagttcttga agtggtggcc taactacggc tacactagaa gaacagtatt   4980
tggtatctgc gctctgctga agccagttac cttcggaaaa agagttggta gctcttgatc   5040
cggcaaacaa accaccgctg gtagcggttt ttttgtttgc aagcagcaga ttacgcgcag   5100
aaaaaaagga tctcaagaag atcctttgat cttttctacg gggtctgacg ctcagtggaa   5160
cgaaaactca cgttaaggga ttttggtcat gagattatca aaaaggatct tcacctagat   5220
ccttttaaat taaaatgaa gttttaaatc aatctaaagt atatatgagt aaacttggtc     5280
tgacagttac caatgcttaa tcagtgaggc acctatctca gcgatctgtc tatttcgttc   5340
atccatagtt gcctgactcc ccgtcgtgta gataactacg atacgggagg gcttaccatc   5400
tggccccagt gctgcaatga taccgcgaga cccacgctca ccggctccag atttatcagc   5460
aataaaccag ccagccggaa gggccgagcg cagaagtggg cctgcaactt tatccgcctc   5520
catccagtct attaattgtt gccgggaagc tagagtaagt agttcgccag ttaatagttt   5580
```

| | |
|---|---|
| gcgcaacgtt gttgccattg ctacaggcat cgtggtgtca cgctcgtcgt ttggtatggc | 5640 |
| ttcattcagc tccggttccc aacgatcaag gcgagttaca tgatccccca tgttgtgcaa | 5700 |
| aaaagcggtt agctccttcg gtcctccgat cgttgtcaga agtaagttgg ccgcagtgtt | 5760 |
| atcactcatg gttatggcag cactgcataa ttctcttact gtcatgccat ccgtaagatg | 5820 |
| cttttctgtg actggtgagt actcaaccaa gtcattctga aatagtgta tgcggcgacc | 5880 |
| gagttgctct tgcccggcgt caatacggga taataccgcg ccacatagca gaactttaaa | 5940 |
| agtgctcatc attggaaaac gttcttcggg gcgaaaactc tcaaggatct taccgctgtt | 6000 |
| gagatccagt tcgatgtaac ccactcgtgc acccaactga tcttcagcat cttttacttt | 6060 |
| caccagcgtt tctgggtgag caaaaacagg aaggcaaaat gccgcaaaaa agggaataag | 6120 |
| ggcgacacgg aaatgttgaa tactcatact cttcctttt caatattatt gaagcattta | 6180 |
| tcagggttat tgtctcatga gcggatacat atttgaatgt atttagaaaa ataaacaaat | 6240 |
| aggggttccg cgcacatttc cccgaaaagt gccacctgac gtc | 6283 |

<210> SEQ ID NO 279
<211> LENGTH: 6267
<212> TYPE: DNA
<213> ORGANISM: Artificial sequence
<220> FEATURE:
<223> OTHER INFORMATION: Vector pSyn-C05-Ckappa

<400> SEQUENCE: 279

| | |
|---|---|
| gacggatcgg gagatctccc gatccccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgttaa ttaacatgaa | 180 |
| gaatctgctt agggttaggc gttttgcgct gcttcgctag gtggtcaata ttggccatta | 240 |
| gccatattat tcattggtta tatagcataa atcaatattg gctattggcc attgcatacg | 300 |
| ttgtatccat atcataatat gtacatttat attggctcat gtccaacatt accgccatgt | 360 |
| tgacattgat tattgactag ttattaatag taatcaatta cggggtcatt agttcatagc | 420 |
| ccatatatgg agttccgcgt tacataactt acggtaaatg gcccgcctgg ctgaccgccc | 480 |
| aacgaccccc gcccattgac gtcaataatg acgtatgttc ccatagtaac gccaataggg | 540 |
| actttccatt gacgtcaatg ggtggagtat ttacggtaaa ctgcccactt ggcagtacat | 600 |
| caagtgtatc atatgccaag tacgccccct attgacgtca atgacggtaa atggcccgcc | 660 |
| tggcattatg cccagtacat gaccttatgg gactttccta cttggcagta catctacgta | 720 |
| ttagtcatcg ctattaccat ggtgatgcgg ttttggcagt acatcaatgg gcgtggatag | 780 |
| cggtttgact cacggggatt tccaagtctc cacccccattg acgtcaatgg gagtttgttt | 840 |
| tggcaccaaa atcaacggga ctttccaaaa tgtcgtaaca actccgcccc attgacgcaa | 900 |
| atgggcggta ggcgtgtacg gtgggaggtc tatataagca gagctcgttt agtgaaccgt | 960 |
| cagatcgcct ggagacgcca tccacgctgt tttgacctcc atagaagaca ccgggaccga | 1020 |
| tccagcctcc gcggccggga acggtgcatt ggaatcgatg actctcttag gtagccttgc | 1080 |
| agaagttggt cgtgaggcac tgggcaggta agtatcaagg ttacaagaca ggtttaagga | 1140 |
| gatcaataga aactgggctt gtcgagacag agaagactct gcgtttctg ataggcacct | 1200 |
| attggtctta ctgacatcca ctttgccttt ctctccacag gtgtccactc ccagttcaat | 1260 |
| tacagctcgc caccatggcc tgccccggct tcctgtgggc cctggtgatc agcacctgcc | 1320 |
| tcgagttcag cggccctaag cggaccgtgg ccgctcccag cgtgttcatc ttcccccct | 1380 |

```
ccgacgagca gctgaagagc ggcaccgcca gcgtggtgtg cctgctgaac aacttctacc    1440
cccgggaggc caaggtgcag tggaaggtgg acaacgccct gcagagcggc aacagccagg    1500
agagcgtgac cgagcaggac agcaaggact ccacctacag cctgagcagc accctcaccc    1560
tgagcaaggc cgactacgag aagcacaagg tgtacgcctg cgaggtgacc caccagggcc    1620
tgagcagccc cgtgaccaag agcttcaacc ggggcgagtg ttaatagact taagtttaaa    1680
ccgctgatca gcctcgactg tgccttctag ttgccagcca tctgttgttt gcccctcccc    1740
cgtgccttcc ttgaccctgg aaggtgccac tcccactgtc ctttcctaat aaaatgagga    1800
aattgcatcg cattgtctga gtaggtgtca ttctattctg gggggtgggg tgggcagga     1860 cagcaagggg gaggattggg aagacaatag caggcatgct ggggatgcgg tgggctctat    1920
ggcttctgag gcggaaagaa ccagctgggg ctctaggggg tatccccacg cgccctgtag    1980
cggcgcatta agcgcggcgg gtgtggtggt tacgcgcagc gtgaccgcta cacttgccag    2040
cgccctagcg cccgctcctt tcgctttctt cccttccttt ctcgccacgt tcgccggctt    2100
tccccgtcaa gctctaaatc ggggctccc tttagggttc cgatttagtg ctttacggca    2160
cctcgacccc aaaaaacttg attagggtga tggttcacgt agtgggccat cgccctgata    2220
gacggttttt cgccctttga cgttggagtc cacgttcttt aatagtggac tcttgttcca    2280
aactggaaca cactcaacc ctatctcggt ctattctttt gatttataag ggattttggc     2340
catttcggcc tattggttaa aaaatgagct gatttaacaa aaatttaacg cgaattaatt    2400
ctgtggaatg tgtgtcagtt agggtgtgga aagtccccag gctccccagc aggcagaagt    2460
atgcaaagca tgcatctcaa ttagtcagca accaggtgtg gaaagtcccc aggctcccca    2520
gcaggcagaa gtatgcaaag catgcatctc aattagtcag caaccatagt cccgccccta    2580
actccgccca tcccgcccct aactccgccc agttccgccc attctccgcc ccatggctga    2640 ctaattttt ttatttatgc agaggccgag gccgcctctg cctctgagct attccagaag     2700
tagtgaggag gcttttttgg aggcctaggc ttttgcaaaa agctcccggg agcttgtata    2760
tccattttcg gatctgatca gcacgtgatg aaaaagcctg aactcaccgc gacgtctgtc    2820
gagaagtttc tgatcgaaaa gttcgacagc gtctccgacc tgatgcagct ctcggagggc    2880
gaagaatctc gtgctttcag cttcgatgta ggagggcgtg gatatgtcct gcgggtaaat    2940
agctgcgccg atggtttcta caaagatcgt tatgtttatc ggcactttgc atcggccgcg    3000
ctcccgattc cggaagtgct tgacattggg gaattcagcg agagcctgac ctattgcatc    3060
tcccgccgtg cacagggtgt cacgttgcaa gacctgcctg aaaccgaact gcccgctgtt    3120
ctgcagccgg tcgcggaggc catggatgcg atcgctgcgg ccgatcttag ccagacgagc    3180
gggttcggcc cattcggacc acaaggaatc ggtcaataca ctacatgcg tgatttcata     3240 tgcgcgattg ctgatcccca tgtgtatcac tggcaaactg tgatggacga caccgtcagt    3300
gcgtccgtcg cgcaggctct cgatgagctg atgctttggg ccgaggactg ccccgaagtc    3360
cggcacctcg tgcacgcgga tttcggctcc aacaatgtcc tgacggacaa tggccgcata    3420
acagcggtca ttgactggag cgaggcgatg ttcggggatt cccaatacga ggtcgccaac    3480
atcttcttct ggaggccgtg gttggcttgt atggagcagc agacgcgcta cttcgagcgg    3540
aggcatccgg agcttgcagg atcgccgcgg ctccgggcgt atatgctccg cattggtctt    3600
gaccaactct atcagagctt ggttgacggc aatttcgatg atgcagcttg gcgcagggt     3660 cgatgcgacg caatcgtccg atccggagcc gggactgtcg ggcgtacaca aatcgcccgc    3720
```

```
agaagcgcgg ccgtctggac cgatggctgt gtagaagtac tcgccgatag tggaaaccga    3780
cgccccagca ctcgtccgag ggcaaaggaa tagcacgtgc tacgagattt cgattccacc    3840
gccgccttct atgaaaggtt gggcttcgga atcgttttcc gggacgccgg ctggatgatc    3900
ctccagcgcg gggatctcat gctggagttc ttcgcccacc ccaacttgtt tattgcagct    3960
tataatggtt acaaataaag caatagcatc acaaatttca caaataaagc attttttca    4020 ctgcattcta gttgtggttt gtccaaactc atcaatgtat cttatcatgt ctgtataccg    4080
tcgacctcta gctagagctt ggcgtaatca tggtcatagc tgtttcctgt gtgaaattgt    4140
tatccgctca caattccaca acatacga gccggaagca taagtgtaa agcctggggt       4200 gcctaatgag tgagctaact cacattaatt gcgttgcgct cactgcccgc tttccagtcg    4260
ggaaacctgt cgtgccagct gcattaatga atcggccaac gcgcggggag aggcggtttg    4320
cgtattgggc gctcttccgc ttcctcgctc actgactcgc tgcgctcggt cgttcggctg    4380
cggcgagcgg tatcagctca ctcaaaggcg gtaatacggt tatccacaga atcaggggat    4440
aacgcaggaa agaacatgtg agcaaaaggc cagcaaaagg ccaggaaccg taaaaaggcc    4500
gcgttgctgg cgtttttcca taggctccgc cccctgacg agcatcacaa aaatcgacgc    4560
tcaagtcaga ggtggcgaaa cccgacagga ctataaagat accaggcgtt ccccctgga    4620 agctccctcg tgcgctctcc tgttccgacc ctgccgctta ccggatacct gtccgccttt    4680
ctcccttcgg gaagcgtggc gctttctcat agctcacgct gtaggtatct cagttcggtg    4740
taggtcgttc gctccaagct gggctgtgtg cacgaacccc ccgttcagcc cgaccgctgc    4800
gccttatccg gtaactatcg tcttgagtcc aacccggtaa gacacgactt atcgccactg    4860
gcagcagcca ctggtaacag gattagcaga gcgaggtatg taggcggtgc tacagagttc    4920
ttgaagtggt ggcctaacta cggctacact agaagaacag tatttggtat ctgcgctctg    4980
ctgaagccag ttaccttcgg aaaaagagtt ggtagctctt gatccggcaa acaaaccacc    5040
gctggtagcg gtttttttgt ttgcaagcag cagattacgc gcagaaaaaa aggatctcaa    5100
gaagatcctt tgatctttc tacggggtct gacgctcagt ggaacgaaaa ctcacgttaa    5160
gggattttgg tcatgagatt atcaaaaagg atcttcacct agatccttt aaattaaaaa    5220 tgaagtttta aatcaatcta agtatatat gagtaaactt ggtctgacag ttaccaatgc    5280
ttaatcagtg aggcacctat ctcagcgatc tgtctatttc gttcatccat agttgcctga    5340
ctccccgtcg tgtagataac tacgatacgg gagggcttac catctggccc cagtgctgca    5400
atgataccgc gagacccacg ctcaccggct ccagatttat cagcaataaa ccagccagcc    5460
ggaagggccg agcgcagaag tggtcctgca actttatccg cctccatcca gtctattaat    5520
tgttgccggg aagctagagt aagtagttcg ccagttaata gtttgcgcaa cgttgttgcc    5580
attgctacag gcatcgtggt gtcacgctcg tcgtttggta tggcttcatt cagctccggt    5640
tcccaacgat caaggcgagt tacatgatcc cccatgttgt gcaaaaaagc ggttagctcc    5700
ttcggtcctc cgatcgttgt cagaagtaag ttggccgcag tgttatcact catggttatg    5760
gcagcactgc ataattctct tactgtcatg ccatccgtaa gatgcttttc tgtgactggt    5820
gagtactcaa ccaagtcatt ctgagaatag tgtatgcggc gaccgagttg ctcttgcccg    5880
gcgtcaatac gggataatac cgcgccacat agcagaactt aaaagtgct catcattgga    5940 aaacgttctt cggggcgaaa actctcaagg atcttaccgc tgttgagatc cagttcgatg    6000
taacccactc gtgcacccaa ctgatcttca gcatcttta ctttcaccag cgtttctggg    6060
tgagcaaaaa caggaaggca aaatgccgca aaaaagggaa taagggcgac acggaaatgt    6120
```

-continued tgaatactca tactcttcct ttttcaatat tattgaagca tttatcaggg ttattgtctc      6180
atgagcggat acatatttga atgtatttag aaaaataaac aaatagggt tccgcgcaca       6240 tttccccgaa aagtgccacc tgacgtc                                          6267

<210> SEQ ID NO 280
<211> LENGTH: 46
<212> TYPE: DNA
<213> ORGANISM: Artificial sequence
<220> FEATURE:
<223> OTHER INFORMATION: Oligonucleotide 5H-B

<400> SEQUENCE: 280
acctgtcttg aattctccat ggccgaggtg cagctggtgg agtctg                  46

<210> SEQ ID NO 281
<211> LENGTH: 47
<212> TYPE: DNA
<213> ORGANISM: Artificial sequence
<220> FEATURE:
<223> OTHER INFORMATION: Oligonucleotide 5H-C

<400> SEQUENCE: 281
acctgtcttg aattctccat ggcccaggtg cagctggtgg agtctgg                 47

<210> SEQ ID NO 282
<211> LENGTH: 49
<212> TYPE: DNA
<213> ORGANISM: Artificial sequence
<220> FEATURE:
<223> OTHER INFORMATION: Oligonucleotide 5H-C-long

<400> SEQUENCE: 282
acctgtcttg aattctccat ggcccaggtg cagctggtgg agtctgggg               49

<210> SEQ ID NO 283
<211> LENGTH: 50
<212> TYPE: DNA
<213> ORGANISM: Artificial sequence
<220> FEATURE:
<223> OTHER INFORMATION: Oligonucleotide 5H-F

<400> SEQUENCE: 283
acctgtcttg aattctccat ggcccaggtg cagctgcagg agtccggccc              50

<210> SEQ ID NO 284
<211> LENGTH: 47
<212> TYPE: DNA
<213> ORGANISM: Artificial sequence
<220> FEATURE:
<223> OTHER INFORMATION: Oligonucleotide 5H-H

<400> SEQUENCE: 284
acctgtcttg aattctccat ggccgaggtg cagctggtgc agtctgg                 47

<210> SEQ ID NO 285
<211> LENGTH: 47
<212> TYPE: DNA
<213> ORGANISM: Artificial sequence
<220> FEATURE:
<223> OTHER INFORMATION: Oligonucleotide 5H-I

<400> SEQUENCE: 285
acctgtcttg aattctccat ggccgaggtg cagctgctgg agtctgg                 47

<210> SEQ ID NO 286
<211> LENGTH: 47
<212> TYPE: DNA
<213> ORGANISM: Artificial sequence
<220> FEATURE:
<223> OTHER INFORMATION: Oligonucleotide 5H-M

<400> SEQUENCE: 286
acctgtcttg aattctccat ggcccaggtg accttgaagg agtctgg    47

<210> SEQ ID NO 287
<211> LENGTH: 47
<212> TYPE: DNA
<213> ORGANISM: Artificial sequence
<220> FEATURE:
<223> OTHER INFORMATION: Oligonucleotide sy3H-A

<400> SEQUENCE: 287
gcccttggtg ctagcgctgg agacggtcac cagggtgccc tggcccc    47

<210> SEQ ID NO 288
<211> LENGTH: 47
<212> TYPE: DNA
<213> ORGANISM: Artificial sequence
<220> FEATURE:
<223> OTHER INFORMATION: Oligonucleotide sy3H-C

<400> SEQUENCE: 288
gcccttggtg ctagcgctgg agacggtcac ggtggtgccc tggcccc    47

<210> SEQ ID NO 289
<211> LENGTH: 54
<212> TYPE: DNA
<213> ORGANISM: Artificial sequence
<220> FEATURE:
<223> OTHER INFORMATION: Oligonucleotide sy3H-C-long

<400> SEQUENCE: 289
gcccttggtg ctagcgctgg agacggtcac ggtggtgccc ttgccccaga cgtc    54

<210> SEQ ID NO 290
<211> LENGTH: 47
<212> TYPE: DNA
<213> ORGANISM: Artificial sequence
<220> FEATURE:
<223> OTHER INFORMATION: Oligonucleotide sy3H-D

<400> SEQUENCE: 290
gcccttggtg ctagcgctgg acacggtcac catggtgccc tggcccc    47

<210> SEQ ID NO 291
<211> LENGTH: 47
<212> TYPE: DNA
<213> ORGANISM: Artificial sequence
<220> FEATURE:
<223> OTHER INFORMATION: Oligonucleotide sy3H-E

<400> SEQUENCE: 291
gcccttggtg ctagcgctgg acacggtcac cagggtgccc cggcccc    47

<210> SEQ ID NO 292
<211> LENGTH: 44
<212> TYPE: DNA
<213> ORGANISM: Artificial sequence
<220> FEATURE:
<223> OTHER INFORMATION: Oligonucleotide 3L-B

<400> SEQUENCE: 292
ttttccttag cggccgcgac tcacctagga cggtcagctt ggtc                          44

<210> SEQ ID NO 293
<211> LENGTH: 44
<212> TYPE: DNA
<213> ORGANISM: Artificial sequence
<220> FEATURE:
<223> OTHER INFORMATION: Oligonucleotide 5K-B

<400> SEQUENCE: 293
acctgtctcg agttttccat ggctgacatc cagatgaccc agtc                          44

<210> SEQ ID NO 294
<211> LENGTH: 55
<212> TYPE: DNA
<213> ORGANISM: Artificial sequence
<220> FEATURE:
<223> OTHER INFORMATION: Oligonucleotide 5K-C

<400> SEQUENCE: 294
acctgtctcg agttttccat ggctgacatc cagatgaccc agtctccatc ctccc             55

<210> SEQ ID NO 295
<211> LENGTH: 47
<212> TYPE: DNA
<213> ORGANISM: Artificial sequence
<220> FEATURE:
<223> OTHER INFORMATION: Oligonucleotide 5K-G

<400> SEQUENCE: 295
acctgtctcg agttttccat ggctgacatc gtgatgaccc agtctcc                       47

<210> SEQ ID NO 296
<211> LENGTH: 47
<212> TYPE: DNA
<213> ORGANISM: Artificial sequence
<220> FEATURE:
<223> OTHER INFORMATION: Oligonucleotide 5K-K

<400> SEQUENCE: 296
acctgtctcg agttttccat ggctgccatc cagatgaccc agtctcc                       47

<210> SEQ ID NO 297
<211> LENGTH: 44
<212> TYPE: DNA
<213> ORGANISM: Artificial sequence
<220> FEATURE:
<223> OTHER INFORMATION: Oligonucleotide 5K-M

<400> SEQUENCE: 297
acctgtctcg agttttccat ggctgacatc cagctgaccc agtc                          44

<210> SEQ ID NO 298
<211> LENGTH: 44
<212> TYPE: DNA
<213> ORGANISM: Artificial sequence
<220> FEATURE:
<223> OTHER INFORMATION: Oligonucleotide 5K-N

<400> SEQUENCE: 298
acctgtctcg agttttccat ggctgacatc cagatgactc agtc                          44

<210> SEQ ID NO 299

```
<211> LENGTH: 44
<212> TYPE: DNA
<213> ORGANISM: Artificial sequence
<220> FEATURE:
<223> OTHER INFORMATION: Oligonucleotide 5K-O

<400> SEQUENCE: 299
acctgtctcg agttttccat ggctgccatc cagctgaccc agtc            44

<210> SEQ ID NO 300
<211> LENGTH: 44
<212> TYPE: DNA
<213> ORGANISM: Artificial sequence
<220> FEATURE:
<223> OTHER INFORMATION: Oligonucleotide 5K-Q

<400> SEQUENCE: 300
acctgtctcg agttttccat ggctgagatc gtgatgactc agtc            44

<210> SEQ ID NO 301
<211> LENGTH: 45
<212> TYPE: DNA
<213> ORGANISM: Artificial sequence
<220> FEATURE:
<223> OTHER INFORMATION: Oligonucleotide 5L-E

<400> SEQUENCE: 301
acctgtctcg agttttccat ggcttcctac gtgctgactc agccg           45

<210> SEQ ID NO 302
<211> LENGTH: 44
<212> TYPE: DNA
<213> ORGANISM: Artificial sequence
<220> FEATURE:
<223> OTHER INFORMATION: Oligonucleotide 5L-F

<400> SEQUENCE: 302
acctgtctcg agttttccat ggctcagtcc gtgctgactc agcc            44

<210> SEQ ID NO 303
<211> LENGTH: 44
<212> TYPE: DNA
<213> ORGANISM: Artificial sequence
<220> FEATURE:
<223> OTHER INFORMATION: Oligoucleotide 5L-G

<400> SEQUENCE: 303
acctgtctcg agttttccat ggcttcctac gtgctgactc agcc            44

<210> SEQ ID NO 304
<211> LENGTH: 42
<212> TYPE: DNA
<213> ORGANISM: Artificial sequence
<220> FEATURE:
<223> OTHER INFORMATION: Oligonucleotide sy3K-F

<400> SEQUENCE: 304
gctgggggcg gccacggtcc gcttgatctc caccttggtc cc              42

<210> SEQ ID NO 305
<211> LENGTH: 42
<212> TYPE: DNA
<213> ORGANISM: Artificial sequence
<220> FEATURE:
<223> OTHER INFORMATION: Oligonucleotide sy3K-I

<400> SEQUENCE: 305
```
gctgggggcg gccacggtcc gcttgatctc cagccgtgtc cc    42

<210> SEQ ID NO 306
<211> LENGTH: 42
<212> TYPE: DNA
<213> ORGANISM: Artificial sequence
<220> FEATURE:
<223> OTHER INFORMATION: Oligonucleotide sy3K-J

<400> SEQUENCE: 306
gctgggggcg gccacggtcc gcttgatctc cagcttggtc cc    42

<210> SEQ ID NO 307
<211> LENGTH: 42
<212> TYPE: DNA
<213> ORGANISM: Artificial sequence
<220> FEATURE:
<223> OTHER INFORMATION: Oligonucleotide sy3K-K

<400> SEQUENCE: 307
gctgggggcg gccacggtcc gcttgatgtc caccttggtc cc    42

<210> SEQ ID NO 308
<211> LENGTH: 43
<212> TYPE: DNA
<213> ORGANISM: Artificial sequence
<220> FEATURE:
<223> OTHER INFORMATION: Oligonucleotide sy3L-A

<400> SEQUENCE: 308
ccagcacggt aagcttcagc acggtcacct tggtgccagt tcc    43

<210> SEQ ID NO 309
<211> LENGTH: 43
<212> TYPE: DNA
<213> ORGANISM: Artificial sequence
<220> FEATURE:
<223> OTHER INFORMATION: Oligonucleotide sy3L-C

<400> SEQUENCE: 309
ccagcacggt aagcttcagc acggtcagct tggtgcctcc gcc    43

<210> SEQ ID NO 310
<211> LENGTH: 37
<212> TYPE: DNA
<213> ORGANISM: Artificial sequence
<220> FEATURE:
<223> OTHER INFORMATION: Oligonucleotide sy3L-D

<400> SEQUENCE: 310
ccagcacggt aagcttcaac acggtcagct gggtccc    37

<210> SEQ ID NO 311
<211> LENGTH: 52
<212> TYPE: DNA
<213> ORGANISM: Artificial sequence
<220> FEATURE:
<223> OTHER INFORMATION: Oligonucleotide sy5L-A

<400> SEQUENCE: 311
acctgtctcg agttttccat ggcttcctcc gagctgaccc aggaccctgc tg    52

<210> SEQ ID NO 312
<211> LENGTH: 756
<212> TYPE: DNA

<213> ORGANISM: Artificial sequence
<220> FEATURE:
<223> OTHER INFORMATION: scFv SOJB

<400> SEQUENCE: 312

```
gccatggccc agatcaccct gaaggagacc ggccccaccc tggtgaagcc cacccagacc      60
ctcaccctca cctgcacctt cagcggcttc agcctgagca ccagcggcgt gggcgtgggc     120
tggatcagac agcccctgg caaggccctg gagtgggtga ccctcatcta ctggacgac      180
gacaagagat acagccccag cctggagaac agggtgacca tccggaagga caccagcaag     240
aaccaggtgg ccctcaccat gaccaacatg gaccccctgg ataccggcac ctactactgc     300
gcccacaggc agcacatcag cagcttcccc tggttcgaca gctggggcca gggcacactg     360
gtgaccgtct cgagcggtac gggcggttca ggcggaaccg gcagcggcac tggcgggtcg     420
acgagctacg tgctcaccca gcccccagc gtgagcgtgg ccctggcaa gaccgccaga     480
atcaactgcg gcggcaacaa catcgagtac cggagcgtgc actggtatca gcagaagagc     540
ggccaggccc ccgtggccgt gatctacgac aacagcgaca gacctagcgg catccccgag     600
agattcagcg gcagcaagag cggcaacacc gccaccctca ccatcagcag agtggaggcc     660
ggcgacgagg ccgactacta ctgccaggtg tgggacatca gcagcgatgt ggtgttcggc     720
ggaggcacca gcttaccgt gctaggtgcg ccgca                                  756
```

<210> SEQ ID NO 313
<211> LENGTH: 252
<212> TYPE: PRT
<213> ORGANISM: Artificial sequence
<220> FEATURE:
<223> OTHER INFORMATION: scFv SOJB

<400> SEQUENCE: 313

```
Ala Met Ala Gln Ile Thr Leu Lys Glu Thr Gly Pro Thr Leu Val Lys
1               5                   10                  15
Pro Thr Gln Thr Leu Thr Leu Thr Cys Thr Phe Ser Gly Phe Ser Leu
            20                  25                  30
Ser Thr Ser Gly Val Gly Val Gly Trp Ile Arg Gln Pro Pro Gly Lys
        35                  40                  45
Ala Leu Glu Trp Val Thr Leu Ile Tyr Trp Asp Asp Asp Lys Arg Tyr
    50                  55                  60
Ser Pro Ser Leu Glu Asn Arg Val Thr Ile Arg Lys Asp Thr Ser Lys
65                  70                  75                  80
Asn Gln Val Ala Leu Thr Met Thr Asn Met Asp Pro Leu Asp Thr Gly
                85                  90                  95
Thr Tyr Tyr Cys Ala His Arg Gln His Ile Ser Ser Phe Pro Trp Phe
            100                 105                 110
Asp Ser Trp Gly Gln Gly Thr Leu Val Thr Val Ser Ser Gly Thr Gly
        115                 120                 125
Gly Ser Gly Gly Thr Gly Ser Gly Thr Gly Gly Ser Thr Ser Tyr Val
    130                 135                 140
Leu Thr Gln Pro Pro Ser Val Ser Val Ala Pro Gly Lys Thr Ala Arg
145                 150                 155                 160
Ile Asn Cys Gly Gly Asn Asn Ile Glu Tyr Arg Ser Val His Trp Tyr
                165                 170                 175
Gln Gln Lys Ser Gly Gln Ala Pro Val Ala Val Ile Tyr Asp Asn Ser
            180                 185                 190
Asp Arg Pro Ser Gly Ile Pro Glu Arg Phe Ser Gly Ser Lys Ser Gly
```

```
                195                 200                 205
Asn Thr Ala Thr Leu Thr Ile Ser Arg Val Glu Ala Gly Asp Glu Ala
    210                 215                 220

Asp Tyr Tyr Cys Gln Val Trp Asp Ile Ser Ser Asp Val Val Phe Gly
225                 230                 235                 240

Gly Gly Thr Lys Leu Thr Val Leu Gly Ala Ala Ala
                245                 250

<210> SEQ ID NO 314
<211> LENGTH: 15
<212> TYPE: PRT
<213> ORGANISM: Artificial sequence
<220> FEATURE:
<223> OTHER INFORMATION: Peptide

<400> SEQUENCE: 314

Ser Leu Lys Gly Ala Cys Lys Leu Lys Leu Cys Gly Val Leu Gly
1               5                   10                  15

<210> SEQ ID NO 315
<211> LENGTH: 15
<212> TYPE: PRT
<213> ORGANISM: Artificial sequence
<220> FEATURE:
<223> OTHER INFORMATION: Peptide

<400> SEQUENCE: 315

Leu Lys Gly Ala Cys Lys Leu Lys Leu Cys Gly Val Leu Gly Leu
1               5                   10                  15

<210> SEQ ID NO 316
<211> LENGTH: 15
<212> TYPE: PRT
<213> ORGANISM: Artificial sequence
<220> FEATURE:
<223> OTHER INFORMATION: Peptide

<400> SEQUENCE: 316

Lys Gly Ala Cys Lys Leu Lys Leu Cys Gly Val Leu Gly Leu Arg
1               5                   10                  15

<210> SEQ ID NO 317
<211> LENGTH: 15
<212> TYPE: PRT
<213> ORGANISM: Artificial sequence
<220> FEATURE:
<223> OTHER INFORMATION: Peptide

<400> SEQUENCE: 317

Gly Ala Cys Lys Leu Lys Leu Cys Gly Val Leu Gly Leu Arg Leu
1               5                   10                  15

<210> SEQ ID NO 318
<211> LENGTH: 15
<212> TYPE: PRT
<213> ORGANISM: Artificial sequence
<220> FEATURE:
<223> OTHER INFORMATION: Peptide

<400> SEQUENCE: 318

Ala Cys Lys Leu Lys Leu Cys Gly Val Leu Gly Leu Arg Leu Met
1               5                   10                  15

<210> SEQ ID NO 319
<211> LENGTH: 15
```

```
<212> TYPE: PRT
<213> ORGANISM: Artificial sequence
<220> FEATURE:
<223> OTHER INFORMATION: Peptide

<400> SEQUENCE: 319

Cys Lys Leu Lys Leu Cys Gly Val Leu Gly Leu Arg Leu Met Asp
1               5                   10                  15

<210> SEQ ID NO 320
<211> LENGTH: 15
<212> TYPE: PRT
<213> ORGANISM: Artificial sequence
<220> FEATURE:
<223> OTHER INFORMATION: Peptide

<400> SEQUENCE: 320

Lys Leu Lys Leu Cys Gly Val Leu Gly Leu Arg Leu Met Asp Gly
1               5                   10                  15

<210> SEQ ID NO 321
<211> LENGTH: 15
<212> TYPE: PRT
<213> ORGANISM: Artificial sequence
<220> FEATURE:
<223> OTHER INFORMATION: Peptide

<400> SEQUENCE: 321

Leu Lys Leu Cys Gly Val Leu Gly Leu Arg Leu Met Asp Gly Thr
1               5                   10                  15

<210> SEQ ID NO 322
<211> LENGTH: 15
<212> TYPE: PRT
<213> ORGANISM: Artificial sequence
<220> FEATURE:
<223> OTHER INFORMATION: Peptide

<400> SEQUENCE: 322

Lys Leu Cys Gly Val Leu Gly Leu Arg Leu Met Asp Gly Thr Trp
1               5                   10                  15

<210> SEQ ID NO 323
<211> LENGTH: 15
<212> TYPE: PRT
<213> ORGANISM: Artificial sequence
<220> FEATURE:
<223> OTHER INFORMATION: Peptide

<400> SEQUENCE: 323

Gly Phe Gly Lys Ala Tyr Thr Ile Phe Asn Lys Thr Leu Met Glu
1               5                   10                  15

<210> SEQ ID NO 324
<211> LENGTH: 15
<212> TYPE: PRT
<213> ORGANISM: Artificial sequence
<220> FEATURE:
<223> OTHER INFORMATION: Peptide

<400> SEQUENCE: 324

Phe Gly Lys Ala Tyr Thr Ile Phe Asn Lys Thr Leu Met Glu Ala
1               5                   10                  15

<210> SEQ ID NO 325
<211> LENGTH: 15
<212> TYPE: PRT
```

```
<213> ORGANISM: Artificial sequence
<220> FEATURE:
<223> OTHER INFORMATION: Peptide

<400> SEQUENCE: 325

Gly Lys Ala Tyr Thr Ile Phe Asn Lys Thr Leu Met Glu Ala Asp
1               5                   10                  15

<210> SEQ ID NO 326
<211> LENGTH: 15
<212> TYPE: PRT
<213> ORGANISM: Artificial sequence
<220> FEATURE:
<223> OTHER INFORMATION: Peptide

<400> SEQUENCE: 326

Lys Ala Tyr Thr Ile Phe Asn Lys Thr Leu Met Glu Ala Asp Ala
1               5                   10                  15

<210> SEQ ID NO 327
<211> LENGTH: 15
<212> TYPE: PRT
<213> ORGANISM: Artificial sequence
<220> FEATURE:
<223> OTHER INFORMATION: Peptide

<400> SEQUENCE: 327

Ala Tyr Thr Ile Phe Asn Lys Thr Leu Met Glu Ala Asp Ala His
1               5                   10                  15

<210> SEQ ID NO 328
<211> LENGTH: 15
<212> TYPE: PRT
<213> ORGANISM: Artificial sequence
<220> FEATURE:
<223> OTHER INFORMATION: Peptide

<400> SEQUENCE: 328

Tyr Thr Ile Phe Asn Lys Thr Leu Met Glu Ala Asp Ala His Tyr
1               5                   10                  15

<210> SEQ ID NO 329
<211> LENGTH: 15
<212> TYPE: PRT
<213> ORGANISM: Artificial sequence
<220> FEATURE:
<223> OTHER INFORMATION: Peptide

<400> SEQUENCE: 329

Thr Ile Phe Asn Lys Thr Leu Met Glu Ala Asp Ala His Tyr Lys
1               5                   10                  15

<210> SEQ ID NO 330
<211> LENGTH: 15
<212> TYPE: PRT
<213> ORGANISM: Artificial sequence
<220> FEATURE:
<223> OTHER INFORMATION: Peptide

<400> SEQUENCE: 330

Ile Phe Asn Lys Thr Leu Met Glu Ala Asp Ala His Tyr Lys Ser
1               5                   10                  15

<210> SEQ ID NO 331
<211> LENGTH: 15
<212> TYPE: PRT
<213> ORGANISM: Artificial sequence
```

<220> FEATURE:
<223> OTHER INFORMATION: Peptide

<400> SEQUENCE: 331

Phe Asn Lys Thr Leu Met Glu Ala Asp Ala His Tyr Lys Ser Val
1               5                   10                  15

<210> SEQ ID NO 332
<211> LENGTH: 23
<212> TYPE: PRT
<213> ORGANISM: Artificial sequence
<220> FEATURE:
<223> OTHER INFORMATION: Peptide

<400> SEQUENCE: 332

Ser Leu Lys Gly Ala Cys Lys Leu Lys Leu Cys Gly Val Leu Gly Leu
1               5                   10                  15

Arg Leu Met Asp Gly Thr Trp
            20

<210> SEQ ID NO 333
<211> LENGTH: 23
<212> TYPE: PRT
<213> ORGANISM: Artificial sequence
<220> FEATURE:
<223> OTHER INFORMATION: Peptide

<400> SEQUENCE: 333

Gly Phe Gly Lys Ala Tyr Thr Ile Phe Asn Lys Thr Leu Met Glu Ala
1               5                   10                  15

Asp Ala His Tyr Lys Ser Val
            20

<210> SEQ ID NO 334
<211> LENGTH: 2083
<212> TYPE: DNA
<213> ORGANISM: Artificial sequence
<220> FEATURE:
<223> OTHER INFORMATION: Heavy chain of CR04-098
<220> FEATURE:
<221> NAME/KEY: Intron
<222> LOCATION: (358)..(484)
<220> FEATURE:
<221> NAME/KEY: Intron
<222> LOCATION: (779)..(1169)
<220> FEATURE:
<221> NAME/KEY: Intron
<222> LOCATION: (1215)..(1332)
<220> FEATURE:
<221> NAME/KEY: Intron
<222> LOCATION: (1663)..(1759)

<400> SEQUENCE: 334
caggtgcagc tggtggagtc tgggggaggc gcggtccagc tgggaggtc cctgagactc      60 tcctgtgcag cctctggatt caccttcagt agctatggca tgcactgggt ccgccaggct    120
ccaggcaagg ggctggagtg ggtggctgtt atattatatg atggaagtga taaattctat    180
gcagactccg tgaagggccg attcaccatc tccagagaca attccaagaa cacgctgtat    240
ctgcagatga acagcctgag agctgaggac acggctgtgt attactgtgc gaaagtagca    300
gtggctggta cgcactttga ctactgggc cagggcaccc tggtgaccgt cagctcaggt    360
gagtgcggcc gcgagcccag acactggacg ctgaacctcg cggacagtta agaacccagg    420
ggcctctgcg ccctgggccc agctctgtcc cacaccgcgg tcacatggca ccacctctct    480
tgcagcctcc accaagggcc catcggtctt ccccctggca ccctcctcca agagcacctc    540

```
tgggggcaca gcggccctgg gctgcctggt caaggactac ttccccgaac cggtgacggt   600
gtcgtggaac tcaggcgccc tgaccagcgg cgtgcacacc ttcccggctg tcctacagtc   660
ctcaggactc tactccctca gcagcgtggt gaccgtgccc tccagcagct tgggcaccca   720
gacctacatc tgcaacgtga atcacaagcc cagcaacacc aaggtggaca gagagttgg   780
tgagaggcca gcacagggag ggagggtgtc tgctggaagc caggctcagc gctcctgcct   840
ggacgcatcc cggctatgca gtcccagtcc agggcagcaa gcaggccccc gtctgcctct   900
tcacccggag gcctctgccc gccccactca tgctcaggga gggtcttc tggctttttc    960
cccaggctct gggcaggcac aggctaggtg cccctaaccc aggccctgca cacaaagggg  1020
caggtgctgg gctcagacct gccaagagcc atatccggga ggaccctgcc cctgacctaa  1080
gcccacccca aaggccaaac ctctccactcc ctcagctcgg acaccttctc tcctcccaga  1140
ttccagtaac tcccaatctt ctctctgcag agcccaaatc ttgtgacaaa actcacacat  1200
gcccaccgtg cccaggtaag ccagcccagg cctcgccctc cagctcaagg cgggacaggt  1260
gccctagagt agcctgcatc cagggacagg ccccagccgg gtgctgacac gtccacctcc  1320
atctcttcct cagcacctga actcctgggg ggaccgtcag tcttcctctt ccccccaaaa  1380
cccaaggaca ccctcatgat ctcccggacc cctgaggtca catgcgtggt ggtggacgtg  1440
agccacgaag accctgaggt caagttcaac tggtacgtgg acggcgtgga ggtgcataat  1500
gccaagacaa agccgcggga ggagcagtac aacagcacgt accgtgtggt cagcgtcctc  1560
accgtcctgc accaggactg gctgaatggc aaggagtaca agtgcaaggt ctccaacaaa  1620
gccctcccag cccccatcga gaaaaccatc tccaaagcca aggtgggac ccgtgggtg   1680
cgagggccac atggacagag gccggctcgg cccaccctct gccctgagag tgaccgctgt  1740
accaacctct gtccctacag ggcagccccg agaaccacag gtgtacaccc tgcccccatc  1800
ccggaggag atgaccaaga accaggtcag cctgacctgc ctggtcaaag gcttctatcc  1860
cagcgacatc gccgtggagt gggagagcaa tgggcagccg gagaacaact acaagaccac  1920
gcctcccgtg ctggactccg acggctcctt cttcctctat agcaagctca ccgtggacaa  1980
gagcaggtgg cagcagggga acgtcttctc atgctccgtg atgcatgagg ctctgcacaa  2040
ccactacacg cagaagagcc tctccctgtc tccgggtaaa tga                    2083
```

<210> SEQ ID NO 335
<211> LENGTH: 449
<212> TYPE: PRT
<213> ORGANISM: Artificial sequence
<220> FEATURE:
<223> OTHER INFORMATION: Heavy chain of CR04-098

<400> SEQUENCE: 335

Gln Val Gln Leu Val Glu Ser Gly Gly Gly Ala Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Leu Tyr Asp Gly Ser Asp Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys 85                  90                  95
Ala Lys Val Ala Val Ala Gly Thr His Phe Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 336
<211> LENGTH: 847
<212> TYPE: DNA
<213> ORGANISM: Artificial sequence
<220> FEATURE:
<223> OTHER INFORMATION: Light chain of CR04-098
<220> FEATURE:
<221> NAME/KEY: Intron

<222> LOCATION: (322)..(526)

<400> SEQUENCE: 336

```
gacatccaga tgacccagtc tccatcctcc ctgtctgcat ctgtaggaga cagagtcacc      60
atcacttgcc gggcaagtca gggcattaga aatgatttag ctggtatca gcagaaacca     120
gggaaagccc ctaagctcct gatctatgct gcatccagtt tgcaaagtgg ggtcccatca    180
aggttcagcg gcagtggatc tgggacagat ttcactctca ccatcagcag cctgcagcct    240
gaagattttg caacttatta ctgtcaacag cttaatagtt accctcccac tttcggcgga    300
gggaccaagg tggagatcaa acgtaagtgc actttgcggc cgctaggaag aaactcaaaa    360
catcaagatt ttaaatacgc ttcttggtct ccttgctata attatctggg ataagcatgc    420
tgttttctgt ctgtccctaa catgccctgt gattatccgc aaacaacaca cccaagggca    480
gaactttgtt acttaaacac catcctgttt gcttctttcc tcaggaactg tggctgcacc    540
atctgtcttc atcttcccgc catctgatga gcagttgaaa tctggaactg cctctgttgt    600
gtgcctgctg aataacttct atcccagaga ggccaaagta cagtggaagg tggataacgc    660
cctccaatcg ggtaactccc aggagagtgt cacagagcag gacagcaagg acagcaccta    720
cagcctcagc agcaccctga cgctgagcaa agcagactac gagaaacaca agtctacgc    780
ctgcgaagtc acccatcagg gcctgagctc gcccgtcaca aagagcttca caggggaga    840
gtgttag                                                              847
```

<210> SEQ ID NO 337
<211> LENGTH: 213
<212> TYPE: PRT
<213> ORGANISM: Artificial sequence
<220> FEATURE:
<223> OTHER INFORMATION: Light chain of CR04-098

<400> SEQUENCE: 337

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Pro
                85                  90                  95

Thr Phe Gly Gly Gly Thr Lys Val Glu Ile Lys Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190
```

Cys Glu Val Thr His Gln Gly Leu Ser Ser Pro Val Thr Lys Ser Phe
            195                 200                 205
Asn Arg Gly Glu Cys
        210

<210> SEQ ID NO 338
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 338

Lys Phe Pro Ile Tyr Thr Ile Leu Asp Lys Leu Gly Pro Trp Ser
1               5                   10                  15

<210> SEQ ID NO 339
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 339

Phe Pro Ile Tyr Thr Ile Leu Asp Lys Leu Gly Pro Trp Ser Pro
1               5                   10                  15

<210> SEQ ID NO 340
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 340

Pro Ile Tyr Thr Ile Leu Asp Lys Leu Gly Pro Trp Ser Pro Ile
1               5                   10                  15

<210> SEQ ID NO 341
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 341

Ile Tyr Thr Ile Leu Asp Lys Leu Gly Pro Trp Ser Pro Ile Asp
1               5                   10                  15

<210> SEQ ID NO 342
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain ERA (SEQ ID NO:207), wherein the extracellular domain of
glycoprotein G consists of amino acids 20-458 of SEQ ID NO:207.

<400> SEQUENCE: 342

Tyr Thr Ile Leu Asp Lys Leu Gly Pro Trp Ser Pro Ile Asp Ile
1               5                   10                  15

<210> SEQ ID NO 343
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 343

Thr Ile Leu Asp Lys Leu Gly Pro Trp Ser Pro Ile Asp Ile His
1               5                   10                  15

<210> SEQ ID NO 344
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 344

Ile Leu Asp Lys Leu Gly Pro Trp Ser Pro Ile Asp Ile His His
1               5                   10                  15

<210> SEQ ID NO 345
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 345

Leu Asp Lys Leu Gly Pro Trp Ser Pro Ile Asp Ile His His Leu
1               5                   10                  15

<210> SEQ ID NO 346
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 346

Asp Lys Leu Gly Pro Trp Ser Pro Ile Asp Ile His His Leu Ser
1               5                   10                  15

<210> SEQ ID NO 347
<211> LENGTH: 15
<212> TYPE: PRT
<213> ORGANISM: Artificial Sequence
<220> FEATURE:
<223> OTHER INFORMATION: 15 contiguous and consecutive amino acids from -continued the extracellular domain of glycoprotein G of rabies virus strain
    ERA (SEQ ID NO:207), wherein the extracellular domain of
    glycoprotein G consists of amino acids 20-458 of SEQ ID NO:207.

<400> SEQUENCE: 347

Lys Leu Gly Pro Trp Ser Pro Ile Asp Ile His His Leu Ser Cys
1               5                   10                  15

<210> SEQ ID NO 348
<211> LENGTH: 15
<212> TYPE: PRT
<213> ORGANISM: Artificial Sequence
<220> FEATURE:
<223> OTHER INFORMATION: 15 contiguous and consecutive amino acids from
    the extracellular domain of glycoprotein G of rabies virus strain
    ERA (SEQ ID NO:207), wherein the extracellular domain of
    glycoprotein G consists of amino acids 20-458 of SEQ ID NO:207.

<400> SEQUENCE: 348

Leu Gly Pro Trp Ser Pro Ile Asp Ile His His Leu Ser Cys Pro
1               5                   10                  15

<210> SEQ ID NO 349
<211> LENGTH: 15
<212> TYPE: PRT
<213> ORGANISM: Artificial Sequence
<220> FEATURE:
<223> OTHER INFORMATION: 15 contiguous and consecutive amino acids from
    the extracellular domain of glycoprotein G of rabies virus strain
    ERA (SEQ ID NO:207), wherein the extracellular domain of
    glycoprotein G consists of amino acids 20-458 of SEQ ID NO:207.

<400> SEQUENCE: 349

Gly Pro Trp Ser Pro Ile Asp Ile His His Leu Ser Cys Pro Asn
1               5                   10                  15

<210> SEQ ID NO 350
<211> LENGTH: 15
<212> TYPE: PRT
<213> ORGANISM: Artificial Sequence
<220> FEATURE:
<223> OTHER INFORMATION: 15 contiguous and consecutive amino acids from
    the extracellular domain of glycoprotein G of rabies virus strain
    ERA (SEQ ID NO:207), wherein the extracellular domain of
    glycoprotein G consists of amino acids 20-458 of SEQ ID NO:207.

<400> SEQUENCE: 350

Pro Trp Ser Pro Ile Asp Ile His His Leu Ser Cys Pro Asn Asn
1               5                   10                  15

<210> SEQ ID NO 351
<211> LENGTH: 15
<212> TYPE: PRT
<213> ORGANISM: Artificial Sequence
<220> FEATURE:
<223> OTHER INFORMATION: 15 contiguous and consecutive amino acids from
    the extracellular domain of glycoprotein G of rabies virus strain
    ERA (SEQ ID NO:207), wherein the extracellular domain of
    glycoprotein G consists of amino acids 20-458 of SEQ ID NO:207.

<400> SEQUENCE: 351

Trp Ser Pro Ile Asp Ile His His Leu Ser Cys Pro Asn Asn Leu
1               5                   10                  15

<210> SEQ ID NO 352
<211> LENGTH: 15
<212> TYPE: PRT
<213> ORGANISM: Artificial Sequence
<220> FEATURE:

<223> OTHER INFORMATION: 15 contiguous and consecutive amino acids from
     the extracellular domain of glycoprotein G of rabies virus strain
     ERA (SEQ ID NO:207), wherein the extracellular domain of
     glycoprotein G consists of amino acids 20-458 of SEQ ID NO:207.

<400> SEQUENCE: 352

Ser Pro Ile Asp Ile His His Leu Ser Cys Pro Asn Asn Leu Val
1               5                   10                  15

<210> SEQ ID NO 353
<211> LENGTH: 15
<212> TYPE: PRT
<213> ORGANISM: Artificial Sequence
<220> FEATURE:
<223> OTHER INFORMATION: 15 contiguous and consecutive amino acids from
     the extracellular domain of glycoprotein G of rabies virus strain
     ERA (SEQ ID NO:207), wherein the extracellular domain of
     glycoprotein G consists of amino acids 20-458 of SEQ ID NO:207.

<400> SEQUENCE: 353

Pro Ile Asp Ile His His Leu Ser Cys Pro Asn Asn Leu Val Val
1               5                   10                  15

<210> SEQ ID NO 354
<211> LENGTH: 15
<212> TYPE: PRT
<213> ORGANISM: Artificial Sequence
<220> FEATURE:
<223> OTHER INFORMATION: 15 contiguous and consecutive amino acids from
     the extracellular domain of glycoprotein G of rabies virus strain
     ERA (SEQ ID NO:207), wherein the extracellular domain of
     glycoprotein G consists of amino acids 20-458 of SEQ ID NO:207.

<400> SEQUENCE: 354

Ile Asp Ile His His Leu Ser Cys Pro Asn Asn Leu Val Val Glu
1               5                   10                  15

<210> SEQ ID NO 355
<211> LENGTH: 15
<212> TYPE: PRT
<213> ORGANISM: Artificial Sequence
<220> FEATURE:
<223> OTHER INFORMATION: 15 contiguous and consecutive amino acids from
     the extracellular domain of glycoprotein G of rabies virus strain
     ERA (SEQ ID NO:207), wherein the extracellular domain of
     glycoprotein G consists of amino acids 20-458 of SEQ ID NO:207.

<400> SEQUENCE: 355

Asp Ile His His Leu Ser Cys Pro Asn Asn Leu Val Val Glu Asp
1               5                   10                  15

<210> SEQ ID NO 356
<211> LENGTH: 15
<212> TYPE: PRT
<213> ORGANISM: Artificial Sequence
<220> FEATURE:
<223> OTHER INFORMATION: 15 contiguous and consecutive amino acids from
     the extracellular domain of glycoprotein G of rabies virus strain
     ERA (SEQ ID NO:207), wherein the extracellular domain of
     glycoprotein G consists of amino acids 20-458 of SEQ ID NO:207.

<400> SEQUENCE: 356

Ile His His Leu Ser Cys Pro Asn Asn Leu Val Val Glu Asp Glu
1               5                   10                  15

<210> SEQ ID NO 357
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 357

His His Leu Ser Cys Pro Asn Asn Leu Val Val Glu Asp Glu Gly
1               5                   10                  15

<210> SEQ ID NO 358
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 358

His Leu Ser Cys Pro Asn Asn Leu Val Val Glu Asp Glu Gly Cys
1               5                   10                  15

<210> SEQ ID NO 359
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 359

Leu Ser Cys Pro Asn Asn Leu Val Val Glu Asp Glu Gly Cys Thr
1               5                   10                  15

<210> SEQ ID NO 360
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 360

Ser Cys Pro Asn Asn Leu Val Val Glu Asp Glu Gly Cys Thr Asn
1               5                   10                  15

<210> SEQ ID NO 361
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 361

Cys Pro Asn Asn Leu Val Val Glu Asp Glu Gly Cys Thr Asn Leu
1               5                   10                  15

<210> SEQ ID NO 362
<211> LENGTH: 15
<212> TYPE: PRT

-continued

```
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 362

Pro Asn Asn Leu Val Val Glu Asp Glu Gly Cys Thr Asn Leu Ser
1               5                   10                  15

<210> SEQ ID NO 363
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 363

Asn Asn Leu Val Val Glu Asp Glu Gly Cys Thr Asn Leu Ser Gly
1               5                   10                  15

<210> SEQ ID NO 364
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 364

Asn Leu Val Val Glu Asp Glu Gly Cys Thr Asn Leu Ser Gly Phe
1               5                   10                  15

<210> SEQ ID NO 365
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 365

Leu Val Val Glu Asp Glu Gly Cys Thr Asn Leu Ser Gly Phe Ser
1               5                   10                  15

<210> SEQ ID NO 366
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 366

Val Val Glu Asp Glu Gly Cys Thr Asn Leu Ser Gly Phe Ser Tyr
1               5                   10                  15

<210> SEQ ID NO 367
<211> LENGTH: 15
```

```
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 367

Val Glu Asp Glu Gly Cys Thr Asn Leu Ser Gly Phe Ser Tyr Met
1               5                   10                  15

<210> SEQ ID NO 368
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 368

Glu Asp Glu Gly Cys Thr Asn Leu Ser Gly Phe Ser Tyr Met Glu
1               5                   10                  15

<210> SEQ ID NO 369
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 369

Asp Glu Gly Cys Thr Asn Leu Ser Gly Phe Ser Tyr Met Glu Leu
1               5                   10                  15

<210> SEQ ID NO 370
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 370

Glu Gly Cys Thr Asn Leu Ser Gly Phe Ser Tyr Met Glu Leu Lys
1               5                   10                  15

<210> SEQ ID NO 371
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 371

Gly Cys Thr Asn Leu Ser Gly Phe Ser Tyr Met Glu Leu Lys Val
1               5                   10                  15

<210> SEQ ID NO 372
```

```
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 372

Cys Thr Asn Leu Ser Gly Phe Ser Tyr Met Glu Leu Lys Val Gly
1               5                   10                  15

<210> SEQ ID NO 373
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 373

Thr Asn Leu Ser Gly Phe Ser Tyr Met Glu Leu Lys Val Gly Tyr
1               5                   10                  15

<210> SEQ ID NO 374
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 374

Asn Leu Ser Gly Phe Ser Tyr Met Glu Leu Lys Val Gly Tyr Ile
1               5                   10                  15

<210> SEQ ID NO 375
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 375

Leu Ser Gly Phe Ser Tyr Met Glu Leu Lys Val Gly Tyr Ile Leu
1               5                   10                  15

<210> SEQ ID NO 376
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 376

Ser Gly Phe Ser Tyr Met Glu Leu Lys Val Gly Tyr Ile Leu Ala
1               5                   10                  15
```

```
<210> SEQ ID NO 377
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 377

Gly Phe Ser Tyr Met Glu Leu Lys Val Gly Tyr Ile Leu Ala Ile
1               5                   10                  15

<210> SEQ ID NO 378
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 378

Phe Ser Tyr Met Glu Leu Lys Val Gly Tyr Ile Leu Ala Ile Lys
1               5                   10                  15

<210> SEQ ID NO 379
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 379

Ser Tyr Met Glu Leu Lys Val Gly Tyr Ile Leu Ala Ile Lys Met
1               5                   10                  15

<210> SEQ ID NO 380
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 380

Tyr Met Glu Leu Lys Val Gly Tyr Ile Leu Ala Ile Lys Met Asn
1               5                   10                  15

<210> SEQ ID NO 381
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 381

Met Glu Leu Lys Val Gly Tyr Ile Leu Ala Ile Lys Met Asn Gly
1               5                   10                  15
```

```
<210> SEQ ID NO 382
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 382

Glu Leu Lys Val Gly Tyr Ile Leu Ala Ile Lys Met Asn Gly Phe
1               5                   10                  15

<210> SEQ ID NO 383
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 383

Leu Lys Val Gly Tyr Ile Leu Ala Ile Lys Met Asn Gly Phe Thr
1               5                   10                  15

<210> SEQ ID NO 384
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 384

Lys Val Gly Tyr Ile Leu Ala Ile Lys Met Asn Gly Phe Thr Cys
1               5                   10                  15

<210> SEQ ID NO 385
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 385

Val Gly Tyr Ile Leu Ala Ile Lys Met Asn Gly Phe Thr Cys Thr
1               5                   10                  15

<210> SEQ ID NO 386
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 386

Gly Tyr Ile Leu Ala Ile Lys Met Asn Gly Phe Thr Cys Thr Gly
1               5                   10                  15
```

```
<210> SEQ ID NO 387
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 387

Tyr Ile Leu Ala Ile Lys Met Asn Gly Phe Thr Cys Thr Gly Val
1               5                   10                  15

<210> SEQ ID NO 388
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 388

Ile Leu Ala Ile Lys Met Asn Gly Phe Thr Cys Thr Gly Val Val
1               5                   10                  15

<210> SEQ ID NO 389
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 389

Leu Ala Ile Lys Met Asn Gly Phe Thr Cys Thr Gly Val Val Thr
1               5                   10                  15

<210> SEQ ID NO 390
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 390

Ala Ile Lys Met Asn Gly Phe Thr Cys Thr Gly Val Val Thr Glu
1               5                   10                  15

<210> SEQ ID NO 391
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 391

Ile Lys Met Asn Gly Phe Thr Cys Thr Gly Val Val Thr Glu Ala
```

<210> SEQ ID NO 392
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 392

Lys Met Asn Gly Phe Thr Cys Thr Gly Val Val Thr Glu Ala Glu
1               5                   10                  15

<210> SEQ ID NO 393
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 393

Met Asn Gly Phe Thr Cys Thr Gly Val Val Thr Glu Ala Glu Asn
1               5                   10                  15

<210> SEQ ID NO 394
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 394

Asn Gly Phe Thr Cys Thr Gly Val Val Thr Glu Ala Glu Asn Tyr
1               5                   10                  15

<210> SEQ ID NO 395
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 395

Gly Phe Thr Cys Thr Gly Val Val Thr Glu Ala Glu Asn Tyr Thr
1               5                   10                  15

<210> SEQ ID NO 396
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 396

Phe Thr Cys Thr Gly Val Val Thr Glu Ala Glu Asn Tyr Thr Asn
1               5                   10                  15

<210> SEQ ID NO 397
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 397

Thr Cys Thr Gly Val Val Thr Glu Ala Glu Asn Tyr Thr Asn Phe
1               5                   10                  15

<210> SEQ ID NO 398
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 398

Cys Thr Gly Val Val Thr Glu Ala Glu Asn Tyr Thr Asn Phe Val
1               5                   10                  15

<210> SEQ ID NO 399
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 399

Thr Gly Val Val Thr Glu Ala Glu Asn Tyr Thr Asn Phe Val Gly
1               5                   10                  15

<210> SEQ ID NO 400
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 400

Gly Val Val Thr Glu Ala Glu Asn Tyr Thr Asn Phe Val Gly Tyr
1               5                   10                  15

<210> SEQ ID NO 401
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 401

```
Val Val Thr Glu Ala Glu Asn Tyr Thr Asn Phe Val Gly Tyr Val
1               5                   10                  15

<210> SEQ ID NO 402
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 402

Val Thr Glu Ala Glu Asn Tyr Thr Asn Phe Val Gly Tyr Val Thr
1               5                   10                  15

<210> SEQ ID NO 403
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 403

Thr Glu Ala Glu Asn Tyr Thr Asn Phe Val Gly Tyr Val Thr Thr
1               5                   10                  15

<210> SEQ ID NO 404
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 404

Glu Ala Glu Asn Tyr Thr Asn Phe Val Gly Tyr Val Thr Thr Thr
1               5                   10                  15

<210> SEQ ID NO 405
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 405

Ala Glu Asn Tyr Thr Asn Phe Val Gly Tyr Val Thr Thr Thr Phe
1               5                   10                  15

<210> SEQ ID NO 406
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.
```

```
<400> SEQUENCE: 406

Glu Asn Tyr Thr Asn Phe Val Gly Tyr Val Thr Thr Thr Phe Lys
1               5                   10                  15

<210> SEQ ID NO 407
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 407

Asn Tyr Thr Asn Phe Val Gly Tyr Val Thr Thr Thr Phe Lys Arg
1               5                   10                  15

<210> SEQ ID NO 408
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 408

Tyr Thr Asn Phe Val Gly Tyr Val Thr Thr Thr Phe Lys Arg Lys
1               5                   10                  15

<210> SEQ ID NO 409
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 409

Thr Asn Phe Val Gly Tyr Val Thr Thr Thr Phe Lys Arg Lys His
1               5                   10                  15

<210> SEQ ID NO 410
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 410

Asn Phe Val Gly Tyr Val Thr Thr Thr Phe Lys Arg Lys His Phe
1               5                   10                  15

<210> SEQ ID NO 411
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.
```

<400> SEQUENCE: 411

Phe Val Gly Tyr Val Thr Thr Thr Phe Lys Arg Lys His Phe Arg
1               5                   10                  15

<210> SEQ ID NO 412
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 412

Val Gly Tyr Val Thr Thr Thr Phe Lys Arg Lys His Phe Arg Pro
1               5                   10                  15

<210> SEQ ID NO 413
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 413

Gly Tyr Val Thr Thr Thr Phe Lys Arg Lys His Phe Arg Pro Thr
1               5                   10                  15

<210> SEQ ID NO 414
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 414

Tyr Val Thr Thr Thr Phe Lys Arg Lys His Phe Arg Pro Thr Pro
1               5                   10                  15

<210> SEQ ID NO 415
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 415

Val Thr Thr Thr Phe Lys Arg Lys His Phe Arg Pro Thr Pro Asp
1               5                   10                  15

<210> SEQ ID NO 416
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of glycoprotein G consists of amino acids 20-458 of SEQ ID NO:207.

<400> SEQUENCE: 416

Thr Thr Thr Phe Lys Arg Lys His Phe Arg Pro Thr Pro Asp Ala
1               5                   10                  15

<210> SEQ ID NO 417
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 417

Thr Thr Phe Lys Arg Lys His Phe Arg Pro Thr Pro Asp Ala Cys
1               5                   10                  15

<210> SEQ ID NO 418
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 418

Thr Phe Lys Arg Lys His Phe Arg Pro Thr Pro Asp Ala Cys Arg
1               5                   10                  15

<210> SEQ ID NO 419
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 419

Phe Lys Arg Lys His Phe Arg Pro Thr Pro Asp Ala Cys Arg Ala
1               5                   10                  15

<210> SEQ ID NO 420
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 420

Lys Arg Lys His Phe Arg Pro Thr Pro Asp Ala Cys Arg Ala Ala
1               5                   10                  15

<210> SEQ ID NO 421
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain -continued ERA (SEQ ID NO:207), wherein the extracellular domain of
glycoprotein G consists of amino acids 20-458 of SEQ ID NO:207.

<400> SEQUENCE: 421

Arg Lys His Phe Arg Pro Thr Pro Asp Ala Cys Arg Ala Ala Tyr
1               5                   10                  15

<210> SEQ ID NO 422
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 422

Lys His Phe Arg Pro Thr Pro Asp Ala Cys Arg Ala Ala Tyr Asn
1               5                   10                  15

<210> SEQ ID NO 423
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 423

His Phe Arg Pro Thr Pro Asp Ala Cys Arg Ala Ala Tyr Asn Trp
1               5                   10                  15

<210> SEQ ID NO 424
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 424

Phe Arg Pro Thr Pro Asp Ala Cys Arg Ala Ala Tyr Asn Trp Lys
1               5                   10                  15

<210> SEQ ID NO 425
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 425

Arg Pro Thr Pro Asp Ala Cys Arg Ala Ala Tyr Asn Trp Lys Met
1               5                   10                  15

<210> SEQ ID NO 426
<211> LENGTH: 15
<212> TYPE: PRT
<213> ORGANISM: Artificial Sequence
<220> FEATURE:
<223> OTHER INFORMATION: 15 contiguous and consecutive amino acids from -continued the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 426

Pro Thr Pro Asp Ala Cys Arg Ala Ala Tyr Asn Trp Lys Met Ala
1               5                   10                  15

<210> SEQ ID NO 427
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 427

Thr Pro Asp Ala Cys Arg Ala Ala Tyr Asn Trp Lys Met Ala Gly
1               5                   10                  15

<210> SEQ ID NO 428
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 428

Pro Asp Ala Cys Arg Ala Ala Tyr Asn Trp Lys Met Ala Gly Asp
1               5                   10                  15

<210> SEQ ID NO 429
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 429

Asp Ala Cys Arg Ala Ala Tyr Asn Trp Lys Met Ala Gly Asp Pro
1               5                   10                  15

<210> SEQ ID NO 430
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 430

Ala Cys Arg Ala Ala Tyr Asn Trp Lys Met Ala Gly Asp Pro Arg
1               5                   10                  15

<210> SEQ ID NO 431
<211> LENGTH: 15
<212> TYPE: PRT
<213> ORGANISM: Artificial Sequence
<220> FEATURE:

```
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 431

Cys Arg Ala Ala Tyr Asn Trp Lys Met Ala Gly Asp Pro Arg Tyr
1               5                   10                  15

<210> SEQ ID NO 432
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 432

Arg Ala Ala Tyr Asn Trp Lys Met Ala Gly Asp Pro Arg Tyr Glu
1               5                   10                  15

<210> SEQ ID NO 433
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 433

Ala Ala Tyr Asn Trp Lys Met Ala Gly Asp Pro Arg Tyr Glu Glu
1               5                   10                  15

<210> SEQ ID NO 434
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 434

Ala Tyr Asn Trp Lys Met Ala Gly Asp Pro Arg Tyr Glu Glu Ser
1               5                   10                  15

<210> SEQ ID NO 435
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 435

Tyr Asn Trp Lys Met Ala Gly Asp Pro Arg Tyr Glu Glu Ser Leu
1               5                   10                  15

<210> SEQ ID NO 436
<211> LENGTH: 15
<212> TYPE: PRT
<213> ORGANISM: Artificial Sequence
```

```
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 436

Asn Trp Lys Met Ala Gly Asp Pro Arg Tyr Glu Glu Ser Leu His
1               5                   10                  15

<210> SEQ ID NO 437
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 437

Trp Lys Met Ala Gly Asp Pro Arg Tyr Glu Glu Ser Leu His Asn
1               5                   10                  15

<210> SEQ ID NO 438
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 438

Lys Met Ala Gly Asp Pro Arg Tyr Glu Glu Ser Leu His Asn Pro
1               5                   10                  15

<210> SEQ ID NO 439
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 439

Met Ala Gly Asp Pro Arg Tyr Glu Glu Ser Leu His Asn Pro Tyr
1               5                   10                  15

<210> SEQ ID NO 440
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 440

Ala Gly Asp Pro Arg Tyr Glu Glu Ser Leu His Asn Pro Tyr Pro
1               5                   10                  15

<210> SEQ ID NO 441
<211> LENGTH: 15
<212> TYPE: PRT
```

<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 441

Gly Asp Pro Arg Tyr Glu Glu Ser Leu His Asn Pro Tyr Pro Asp
1               5                   10                  15

<210> SEQ ID NO 442
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 442

Asp Pro Arg Tyr Glu Glu Ser Leu His Asn Pro Tyr Pro Asp Tyr
1               5                   10                  15

<210> SEQ ID NO 443
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 443

Pro Arg Tyr Glu Glu Ser Leu His Asn Pro Tyr Pro Asp Tyr Arg
1               5                   10                  15

<210> SEQ ID NO 444
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 444

Arg Tyr Glu Glu Ser Leu His Asn Pro Tyr Pro Asp Tyr Arg Trp
1               5                   10                  15

<210> SEQ ID NO 445
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 445

Tyr Glu Glu Ser Leu His Asn Pro Tyr Pro Asp Tyr Arg Trp Leu
1               5                   10                  15

<210> SEQ ID NO 446
<211> LENGTH: 15

```
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 446

Glu Glu Ser Leu His Asn Pro Tyr Pro Asp Tyr Arg Trp Leu Arg
1               5                   10                  15

<210> SEQ ID NO 447
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 447

Glu Ser Leu His Asn Pro Tyr Pro Asp Tyr Arg Trp Leu Arg Thr
1               5                   10                  15

<210> SEQ ID NO 448
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 448

Ser Leu His Asn Pro Tyr Pro Asp Tyr Arg Trp Leu Arg Thr Val
1               5                   10                  15

<210> SEQ ID NO 449
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 449

Leu His Asn Pro Tyr Pro Asp Tyr Arg Trp Leu Arg Thr Val Lys
1               5                   10                  15

<210> SEQ ID NO 450
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 450

His Asn Pro Tyr Pro Asp Tyr Arg Trp Leu Arg Thr Val Lys Thr
1               5                   10                  15

<210> SEQ ID NO 451
```

```
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 451

Asn Pro Tyr Pro Asp Tyr Arg Trp Leu Arg Thr Val Lys Thr Thr
1               5                   10                  15

<210> SEQ ID NO 452
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 452

Pro Tyr Pro Asp Tyr Arg Trp Leu Arg Thr Val Lys Thr Thr Lys
1               5                   10                  15

<210> SEQ ID NO 453
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 453

Tyr Pro Asp Tyr Arg Trp Leu Arg Thr Val Lys Thr Thr Lys Glu
1               5                   10                  15

<210> SEQ ID NO 454
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 454

Pro Asp Tyr Arg Trp Leu Arg Thr Val Lys Thr Thr Lys Glu Ser
1               5                   10                  15

<210> SEQ ID NO 455
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 455

Asp Tyr Arg Trp Leu Arg Thr Val Lys Thr Thr Lys Glu Ser Leu
1               5                   10                  15
```

```
<210> SEQ ID NO 456
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 456

Tyr Arg Trp Leu Arg Thr Val Lys Thr Thr Lys Glu Ser Leu Val
1               5                   10                  15

<210> SEQ ID NO 457
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 457

Arg Trp Leu Arg Thr Val Lys Thr Thr Lys Glu Ser Leu Val Ile
1               5                   10                  15

<210> SEQ ID NO 458
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 458

Trp Leu Arg Thr Val Lys Thr Thr Lys Glu Ser Leu Val Ile Ile
1               5                   10                  15

<210> SEQ ID NO 459
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 459

Leu Arg Thr Val Lys Thr Thr Lys Glu Ser Leu Val Ile Ile Ser
1               5                   10                  15

<210> SEQ ID NO 460
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 460

Arg Thr Val Lys Thr Thr Lys Glu Ser Leu Val Ile Ile Ser Pro
1               5                   10                  15
```

<210> SEQ ID NO 461
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 461

Thr Val Lys Thr Thr Lys Glu Ser Leu Val Ile Ile Ser Pro Ser
1               5                   10                  15

<210> SEQ ID NO 462
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 462

Val Lys Thr Thr Lys Glu Ser Leu Val Ile Ile Ser Pro Ser Val
1               5                   10                  15

<210> SEQ ID NO 463
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 463

Lys Thr Thr Lys Glu Ser Leu Val Ile Ile Ser Pro Ser Val Ala
1               5                   10                  15

<210> SEQ ID NO 464
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 464

Thr Thr Lys Glu Ser Leu Val Ile Ile Ser Pro Ser Val Ala Asp
1               5                   10                  15

<210> SEQ ID NO 465
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 465

Thr Lys Glu Ser Leu Val Ile Ile Ser Pro Ser Val Ala Asp Leu
1               5                   10                  15

<210> SEQ ID NO 466
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 466

Lys Glu Ser Leu Val Ile Ile Ser Pro Ser Val Ala Asp Leu Asp
1               5                   10                  15

<210> SEQ ID NO 467
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 467

Glu Ser Leu Val Ile Ile Ser Pro Ser Val Ala Asp Leu Asp Pro
1               5                   10                  15

<210> SEQ ID NO 468
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 468

Ser Leu Val Ile Ile Ser Pro Ser Val Ala Asp Leu Asp Pro Tyr
1               5                   10                  15

<210> SEQ ID NO 469
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 469

Leu Val Ile Ile Ser Pro Ser Val Ala Asp Leu Asp Pro Tyr Asp
1               5                   10                  15

<210> SEQ ID NO 470
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 470

Val Ile Ile Ser Pro Ser Val Ala Asp Leu Asp Pro Tyr Asp Arg

```
<210> SEQ ID NO 471
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 471

Ile Ile Ser Pro Ser Val Ala Asp Leu Asp Pro Tyr Asp Arg Ser
1               5                   10                  15

<210> SEQ ID NO 472
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 472

Ile Ser Pro Ser Val Ala Asp Leu Asp Pro Tyr Asp Arg Ser Leu
1               5                   10                  15

<210> SEQ ID NO 473
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 473

Ser Pro Ser Val Ala Asp Leu Asp Pro Tyr Asp Arg Ser Leu His
1               5                   10                  15

<210> SEQ ID NO 474
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 474

Pro Ser Val Ala Asp Leu Asp Pro Tyr Asp Arg Ser Leu His Ser
1               5                   10                  15

<210> SEQ ID NO 475
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 475
```

Ser Val Ala Asp Leu Asp Pro Tyr Asp Arg Ser Leu His Ser Arg
1               5                   10                  15

<210> SEQ ID NO 476
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 476

Val Ala Asp Leu Asp Pro Tyr Asp Arg Ser Leu His Ser Arg Val
1               5                   10                  15

<210> SEQ ID NO 477
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 477

Ala Asp Leu Asp Pro Tyr Asp Arg Ser Leu His Ser Arg Val Phe
1               5                   10                  15

<210> SEQ ID NO 478
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 478

Asp Leu Asp Pro Tyr Asp Arg Ser Leu His Ser Arg Val Phe Pro
1               5                   10                  15

<210> SEQ ID NO 479
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 479

Leu Asp Pro Tyr Asp Arg Ser Leu His Ser Arg Val Phe Pro Ser
1               5                   10                  15

<210> SEQ ID NO 480
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 480

```
Asp Pro Tyr Asp Arg Ser Leu His Ser Arg Val Phe Pro Ser Gly
1               5                   10                  15
```

<210> SEQ ID NO 481
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 481

```
Pro Tyr Asp Arg Ser Leu His Ser Arg Val Phe Pro Ser Gly Lys
1               5                   10                  15
```

<210> SEQ ID NO 482
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 482

```
Tyr Asp Arg Ser Leu His Ser Arg Val Phe Pro Ser Gly Lys Cys
1               5                   10                  15
```

<210> SEQ ID NO 483
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 483

```
Asp Arg Ser Leu His Ser Arg Val Phe Pro Ser Gly Lys Cys Ser
1               5                   10                  15
```

<210> SEQ ID NO 484
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 484

```
Arg Ser Leu His Ser Arg Val Phe Pro Ser Gly Lys Cys Ser Gly
1               5                   10                  15
```

<210> SEQ ID NO 485
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

```
<400> SEQUENCE: 485

Ser Leu His Ser Arg Val Phe Pro Ser Gly Lys Cys Ser Gly Val
1               5                   10                  15

<210> SEQ ID NO 486
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 486

Leu His Ser Arg Val Phe Pro Ser Gly Lys Cys Ser Gly Val Ala
1               5                   10                  15

<210> SEQ ID NO 487
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 487

His Ser Arg Val Phe Pro Ser Gly Lys Cys Ser Gly Val Ala Val
1               5                   10                  15

<210> SEQ ID NO 488
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 488

Ser Arg Val Phe Pro Ser Gly Lys Cys Ser Gly Val Ala Val Ser
1               5                   10                  15

<210> SEQ ID NO 489
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 489

Arg Val Phe Pro Ser Gly Lys Cys Ser Gly Val Ala Val Ser Ser
1               5                   10                  15

<210> SEQ ID NO 490
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.
```

<400> SEQUENCE: 490

Val Phe Pro Ser Gly Lys Cys Ser Gly Val Ala Val Ser Ser Thr
1               5                   10                  15

<210> SEQ ID NO 491
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 491

Phe Pro Ser Gly Lys Cys Ser Gly Val Ala Val Ser Ser Thr Tyr
1               5                   10                  15

<210> SEQ ID NO 492
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 492

Pro Ser Gly Lys Cys Ser Gly Val Ala Val Ser Ser Thr Tyr Cys
1               5                   10                  15

<210> SEQ ID NO 493
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 493

Ser Gly Lys Cys Ser Gly Val Ala Val Ser Ser Thr Tyr Cys Ser
1               5                   10                  15

<210> SEQ ID NO 494
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 494

Gly Lys Cys Ser Gly Val Ala Val Ser Ser Thr Tyr Cys Ser Thr
1               5                   10                  15

<210> SEQ ID NO 495
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of -continued glycoprotein G consists of amino acids 20-458 of SEQ ID NO:207.

<400> SEQUENCE: 495

```
Lys Cys Ser Gly Val Ala Val Ser Ser Thr Tyr Cys Ser Thr Asn
1               5                   10                  15
```

<210> SEQ ID NO 496
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 496

```
Cys Ser Gly Val Ala Val Ser Ser Thr Tyr Cys Ser Thr Asn His
1               5                   10                  15
```

<210> SEQ ID NO 497
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 497

```
Ser Gly Val Ala Val Ser Ser Thr Tyr Cys Ser Thr Asn His Asp
1               5                   10                  15
```

<210> SEQ ID NO 498
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 498

```
Gly Val Ala Val Ser Ser Thr Tyr Cys Ser Thr Asn His Asp Tyr
1               5                   10                  15
```

<210> SEQ ID NO 499
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 499

```
Val Ala Val Ser Ser Thr Tyr Cys Ser Thr Asn His Asp Tyr Thr
1               5                   10                  15
```

<210> SEQ ID NO 500
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain ERA (SEQ ID NO:207), wherein the extracellular domain of
glycoprotein G consists of amino acids 20-458 of SEQ ID NO:207.

<400> SEQUENCE: 500

Ala Val Ser Ser Thr Tyr Cys Ser Thr Asn His Asp Tyr Thr Ile
1               5                   10                  15

<210> SEQ ID NO 501
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 501

Val Ser Ser Thr Tyr Cys Ser Thr Asn His Asp Tyr Thr Ile Trp
1               5                   10                  15

<210> SEQ ID NO 502
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 502

Ser Ser Thr Tyr Cys Ser Thr Asn His Asp Tyr Thr Ile Trp Met
1               5                   10                  15

<210> SEQ ID NO 503
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 503

Ser Thr Tyr Cys Ser Thr Asn His Asp Tyr Thr Ile Trp Met Pro
1               5                   10                  15

<210> SEQ ID NO 504
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 504

Thr Tyr Cys Ser Thr Asn His Asp Tyr Thr Ile Trp Met Pro Glu
1               5                   10                  15

<210> SEQ ID NO 505
<211> LENGTH: 15
<212> TYPE: PRT
<213> ORGANISM: Artificial Sequence
<220> FEATURE:
<223> OTHER INFORMATION: 15 contiguous and consecutive amino acids from the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 505

Tyr Cys Ser Thr Asn His Asp Tyr Thr Ile Trp Met Pro Glu Asn
1               5                   10                  15

<210> SEQ ID NO 506
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 506

Cys Ser Thr Asn His Asp Tyr Thr Ile Trp Met Pro Glu Asn Pro
1               5                   10                  15

<210> SEQ ID NO 507
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 507

Ser Thr Asn His Asp Tyr Thr Ile Trp Met Pro Glu Asn Pro Arg
1               5                   10                  15

<210> SEQ ID NO 508
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 508

Thr Asn His Asp Tyr Thr Ile Trp Met Pro Glu Asn Pro Arg Leu
1               5                   10                  15

<210> SEQ ID NO 509
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 509

Asn His Asp Tyr Thr Ile Trp Met Pro Glu Asn Pro Arg Leu Gly
1               5                   10                  15

<210> SEQ ID NO 510
<211> LENGTH: 15
<212> TYPE: PRT
<213> ORGANISM: Artificial Sequence
<220> FEATURE:

<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 510

His Asp Tyr Thr Ile Trp Met Pro Glu Asn Pro Arg Leu Gly Met
1               5                   10                  15

<210> SEQ ID NO 511
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 511

Asp Tyr Thr Ile Trp Met Pro Glu Asn Pro Arg Leu Gly Met Ser
1               5                   10                  15

<210> SEQ ID NO 512
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 512

Tyr Thr Ile Trp Met Pro Glu Asn Pro Arg Leu Gly Met Ser Cys
1               5                   10                  15

<210> SEQ ID NO 513
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 513

Thr Ile Trp Met Pro Glu Asn Pro Arg Leu Gly Met Ser Cys Asp
1               5                   10                  15

<210> SEQ ID NO 514
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 514

Ile Trp Met Pro Glu Asn Pro Arg Leu Gly Met Ser Cys Asp Ile
1               5                   10                  15

<210> SEQ ID NO 515
<211> LENGTH: 15
<212> TYPE: PRT
<213> ORGANISM: Artificial Sequence

```
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 515

Trp Met Pro Glu Asn Pro Arg Leu Gly Met Ser Cys Asp Ile Phe
1               5                   10                  15

<210> SEQ ID NO 516
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 516

Met Pro Glu Asn Pro Arg Leu Gly Met Ser Cys Asp Ile Phe Thr
1               5                   10                  15

<210> SEQ ID NO 517
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 517

Pro Glu Asn Pro Arg Leu Gly Met Ser Cys Asp Ile Phe Thr Asn
1               5                   10                  15

<210> SEQ ID NO 518
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 518

Glu Asn Pro Arg Leu Gly Met Ser Cys Asp Ile Phe Thr Asn Ser
1               5                   10                  15

<210> SEQ ID NO 519
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 519

Asn Pro Arg Leu Gly Met Ser Cys Asp Ile Phe Thr Asn Ser Arg
1               5                   10                  15

<210> SEQ ID NO 520
<211> LENGTH: 15
<212> TYPE: PRT
```

```
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 520

Pro Arg Leu Gly Met Ser Cys Asp Ile Phe Thr Asn Ser Arg Gly
1               5                   10                  15

<210> SEQ ID NO 521
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 521

Arg Leu Gly Met Ser Cys Asp Ile Phe Thr Asn Ser Arg Gly Lys
1               5                   10                  15

<210> SEQ ID NO 522
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 522

Leu Gly Met Ser Cys Asp Ile Phe Thr Asn Ser Arg Gly Lys Arg
1               5                   10                  15

<210> SEQ ID NO 523
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 523

Gly Met Ser Cys Asp Ile Phe Thr Asn Ser Arg Gly Lys Arg Ala
1               5                   10                  15

<210> SEQ ID NO 524
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 524

Met Ser Cys Asp Ile Phe Thr Asn Ser Arg Gly Lys Arg Ala Ser
1               5                   10                  15

<210> SEQ ID NO 525
<211> LENGTH: 15
```

```
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 525

Ser Cys Asp Ile Phe Thr Asn Ser Arg Gly Lys Arg Ala Ser Lys
1               5                   10                  15

<210> SEQ ID NO 526
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 526

Cys Asp Ile Phe Thr Asn Ser Arg Gly Lys Arg Ala Ser Lys Gly
1               5                   10                  15

<210> SEQ ID NO 527
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 527

Asp Ile Phe Thr Asn Ser Arg Gly Lys Arg Ala Ser Lys Gly Ser
1               5                   10                  15

<210> SEQ ID NO 528
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 528

Ile Phe Thr Asn Ser Arg Gly Lys Arg Ala Ser Lys Gly Ser Glu
1               5                   10                  15

<210> SEQ ID NO 529
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 529

Phe Thr Asn Ser Arg Gly Lys Arg Ala Ser Lys Gly Ser Glu Thr
1               5                   10                  15

<210> SEQ ID NO 530
```

```
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 530

Thr Asn Ser Arg Gly Lys Arg Ala Ser Lys Gly Ser Glu Thr Cys
1               5                   10                  15

<210> SEQ ID NO 531
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 531

Asn Ser Arg Gly Lys Arg Ala Ser Lys Gly Ser Glu Thr Cys Gly
1               5                   10                  15

<210> SEQ ID NO 532
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 532

Ser Arg Gly Lys Arg Ala Ser Lys Gly Ser Glu Thr Cys Gly Phe
1               5                   10                  15

<210> SEQ ID NO 533
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 533

Arg Gly Lys Arg Ala Ser Lys Gly Ser Glu Thr Cys Gly Phe Val
1               5                   10                  15

<210> SEQ ID NO 534
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 534

Gly Lys Arg Ala Ser Lys Gly Ser Glu Thr Cys Gly Phe Val Asp
1               5                   10                  15
```

```
<210> SEQ ID NO 535
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 535

Lys Arg Ala Ser Lys Gly Ser Glu Thr Cys Gly Phe Val Asp Glu
1               5                   10                  15

<210> SEQ ID NO 536
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 536

Arg Ala Ser Lys Gly Ser Glu Thr Cys Gly Phe Val Asp Glu Arg
1               5                   10                  15

<210> SEQ ID NO 537
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 537

Ala Ser Lys Gly Ser Glu Thr Cys Gly Phe Val Asp Glu Arg Gly
1               5                   10                  15

<210> SEQ ID NO 538
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 538

Ser Lys Gly Ser Glu Thr Cys Gly Phe Val Asp Glu Arg Gly Leu
1               5                   10                  15

<210> SEQ ID NO 539
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 539

Lys Gly Ser Glu Thr Cys Gly Phe Val Asp Glu Arg Gly Leu Tyr
1               5                   10                  15
```

```
<210> SEQ ID NO 540
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 540

Gly Ser Glu Thr Cys Gly Phe Val Asp Glu Arg Gly Leu Tyr Lys
1               5                   10                  15

<210> SEQ ID NO 541
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 541

Ser Glu Thr Cys Gly Phe Val Asp Glu Arg Gly Leu Tyr Lys Ser
1               5                   10                  15

<210> SEQ ID NO 542
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 542

Glu Thr Cys Gly Phe Val Asp Glu Arg Gly Leu Tyr Lys Ser Leu
1               5                   10                  15

<210> SEQ ID NO 543
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 543

Thr Cys Gly Phe Val Asp Glu Arg Gly Leu Tyr Lys Ser Leu Lys
1               5                   10                  15

<210> SEQ ID NO 544
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 544

Cys Gly Phe Val Asp Glu Arg Gly Leu Tyr Lys Ser Leu Lys Gly
1               5                   10                  15
```

```
<210> SEQ ID NO 545
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 545

Gly Phe Val Asp Glu Arg Gly Leu Tyr Lys Ser Leu Lys Gly Ala
1               5                   10                  15

<210> SEQ ID NO 546
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 546

Phe Val Asp Glu Arg Gly Leu Tyr Lys Ser Leu Lys Gly Ala Cys
1               5                   10                  15

<210> SEQ ID NO 547
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 547

Val Asp Glu Arg Gly Leu Tyr Lys Ser Leu Lys Gly Ala Cys Lys
1               5                   10                  15

<210> SEQ ID NO 548
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 548

Asp Glu Arg Gly Leu Tyr Lys Ser Leu Lys Gly Ala Cys Lys Leu
1               5                   10                  15

<210> SEQ ID NO 549
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 549

Glu Arg Gly Leu Tyr Lys Ser Leu Lys Gly Ala Cys Lys Leu Lys
```

<210> SEQ ID NO 550
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 550

Arg Gly Leu Tyr Lys Ser Leu Lys Gly Ala Cys Lys Leu Lys Leu
1               5                   10                  15

<210> SEQ ID NO 551
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 551

Gly Leu Tyr Lys Ser Leu Lys Gly Ala Cys Lys Leu Lys Leu Cys
1               5                   10                  15

<210> SEQ ID NO 552
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 552

Leu Tyr Lys Ser Leu Lys Gly Ala Cys Lys Leu Lys Leu Cys Gly
1               5                   10                  15

<210> SEQ ID NO 553
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 553

Tyr Lys Ser Leu Lys Gly Ala Cys Lys Leu Lys Leu Cys Gly Val
1               5                   10                  15

<210> SEQ ID NO 554
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 554

```
Lys Ser Leu Lys Gly Ala Cys Lys Leu Lys Leu Cys Gly Val Leu
1               5                   10                  15
```

<210> SEQ ID NO 555
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 555

```
Leu Cys Gly Val Leu Gly Leu Arg Leu Met Asp Gly Thr Trp Val
1               5                   10                  15
```

<210> SEQ ID NO 556
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 556

```
Cys Gly Val Leu Gly Leu Arg Leu Met Asp Gly Thr Trp Val Ala
1               5                   10                  15
```

<210> SEQ ID NO 557
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 557

```
Gly Val Leu Gly Leu Arg Leu Met Asp Gly Thr Trp Val Ala Met
1               5                   10                  15
```

<210> SEQ ID NO 558
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 558

```
Val Leu Gly Leu Arg Leu Met Asp Gly Thr Trp Val Ala Met Gln
1               5                   10                  15
```

<210> SEQ ID NO 559
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 559

Leu Gly Leu Arg Leu Met Asp Gly Thr Trp Val Ala Met Gln Thr
1               5                   10                  15

<210> SEQ ID NO 560
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 560

Gly Leu Arg Leu Met Asp Gly Thr Trp Val Ala Met Gln Thr Ser
1               5                   10                  15

<210> SEQ ID NO 561
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 561

Leu Arg Leu Met Asp Gly Thr Trp Val Ala Met Gln Thr Ser Asn
1               5                   10                  15

<210> SEQ ID NO 562
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 562

Arg Leu Met Asp Gly Thr Trp Val Ala Met Gln Thr Ser Asn Glu
1               5                   10                  15

<210> SEQ ID NO 563
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 563

Leu Met Asp Gly Thr Trp Val Ala Met Gln Thr Ser Asn Glu Thr
1               5                   10                  15

<210> SEQ ID NO 564
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

```
<400> SEQUENCE: 564

Met Asp Gly Thr Trp Val Ala Met Gln Thr Ser Asn Glu Thr Lys
 1               5                  10                  15

<210> SEQ ID NO 565
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 565

Asp Gly Thr Trp Val Ala Met Gln Thr Ser Asn Glu Thr Lys Trp
 1               5                  10                  15

<210> SEQ ID NO 566
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 566

Gly Thr Trp Val Ala Met Gln Thr Ser Asn Glu Thr Lys Trp Cys
 1               5                  10                  15

<210> SEQ ID NO 567
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 567

Thr Trp Val Ala Met Gln Thr Ser Asn Glu Thr Lys Trp Cys Pro
 1               5                  10                  15

<210> SEQ ID NO 568
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 568

Trp Val Ala Met Gln Thr Ser Asn Glu Thr Lys Trp Cys Pro Pro
 1               5                  10                  15

<210> SEQ ID NO 569
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.
```

```
<400> SEQUENCE: 569

Val Ala Met Gln Thr Ser Asn Glu Thr Lys Trp Cys Pro Pro Asp
1               5                   10                  15

<210> SEQ ID NO 570
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 570

Ala Met Gln Thr Ser Asn Glu Thr Lys Trp Cys Pro Pro Asp Gln
1               5                   10                  15

<210> SEQ ID NO 571
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 571

Met Gln Thr Ser Asn Glu Thr Lys Trp Cys Pro Pro Asp Gln Leu
1               5                   10                  15

<210> SEQ ID NO 572
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 572

Gln Thr Ser Asn Glu Thr Lys Trp Cys Pro Pro Asp Gln Leu Val
1               5                   10                  15

<210> SEQ ID NO 573
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 573

Thr Ser Asn Glu Thr Lys Trp Cys Pro Pro Asp Gln Leu Val Asn
1               5                   10                  15

<210> SEQ ID NO 574
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
``` glycoprotein G consists of amino acids 20-458 of SEQ ID NO:207.

<400> SEQUENCE: 574

Ser Asn Glu Thr Lys Trp Cys Pro Pro Asp Gln Leu Val Asn Leu
1               5                   10                  15

<210> SEQ ID NO 575
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 575

Asn Glu Thr Lys Trp Cys Pro Pro Asp Gln Leu Val Asn Leu His
1               5                   10                  15

<210> SEQ ID NO 576
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 576

Glu Thr Lys Trp Cys Pro Pro Asp Gln Leu Val Asn Leu His Asp
1               5                   10                  15

<210> SEQ ID NO 577
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 577

Thr Lys Trp Cys Pro Pro Asp Gln Leu Val Asn Leu His Asp Phe
1               5                   10                  15

<210> SEQ ID NO 578
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 578

Lys Trp Cys Pro Pro Asp Gln Leu Val Asn Leu His Asp Phe Arg
1               5                   10                  15

<210> SEQ ID NO 579
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain ERA (SEQ ID NO:207), wherein the extracellular domain of
glycoprotein G consists of amino acids 20-458 of SEQ ID NO:207.

<400> SEQUENCE: 579

Trp Cys Pro Pro Asp Gln Leu Val Asn Leu His Asp Phe Arg Ser
1               5                   10                  15

<210> SEQ ID NO 580
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 580

Cys Pro Pro Asp Gln Leu Val Asn Leu His Asp Phe Arg Ser Asp
1               5                   10                  15

<210> SEQ ID NO 581
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 581

Pro Pro Asp Gln Leu Val Asn Leu His Asp Phe Arg Ser Asp Glu
1               5                   10                  15

<210> SEQ ID NO 582
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 582

Pro Asp Gln Leu Val Asn Leu His Asp Phe Arg Ser Asp Glu Ile
1               5                   10                  15

<210> SEQ ID NO 583
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 583

Asp Gln Leu Val Asn Leu His Asp Phe Arg Ser Asp Glu Ile Glu
1               5                   10                  15

<210> SEQ ID NO 584
<211> LENGTH: 15
<212> TYPE: PRT
<213> ORGANISM: Artificial Sequence
<220> FEATURE:
<223> OTHER INFORMATION: 15 contiguous and consecutive amino acids from the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 584

Gln Leu Val Asn Leu His Asp Phe Arg Ser Asp Glu Ile Glu His
1               5                   10                  15

<210> SEQ ID NO 585
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 585

Leu Val Asn Leu His Asp Phe Arg Ser Asp Glu Ile Glu His Leu
1               5                   10                  15

<210> SEQ ID NO 586
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 586

Val Asn Leu His Asp Phe Arg Ser Asp Glu Ile Glu His Leu Val
1               5                   10                  15

<210> SEQ ID NO 587
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 587

Asn Leu His Asp Phe Arg Ser Asp Glu Ile Glu His Leu Val Val
1               5                   10                  15

<210> SEQ ID NO 588
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 588

Leu His Asp Phe Arg Ser Asp Glu Ile Glu His Leu Val Val Glu
1               5                   10                  15

<210> SEQ ID NO 589
<211> LENGTH: 15
<212> TYPE: PRT
<213> ORGANISM: Artificial Sequence
<220> FEATURE:

```
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 589

His Asp Phe Arg Ser Asp Glu Ile Glu His Leu Val Val Glu Glu
1               5                   10                  15

<210> SEQ ID NO 590
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 590

Asp Phe Arg Ser Asp Glu Ile Glu His Leu Val Val Glu Glu Leu
1               5                   10                  15

<210> SEQ ID NO 591
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 591

Phe Arg Ser Asp Glu Ile Glu His Leu Val Val Glu Glu Leu Val
1               5                   10                  15

<210> SEQ ID NO 592
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 592

Arg Ser Asp Glu Ile Glu His Leu Val Val Glu Glu Leu Val Arg
1               5                   10                  15

<210> SEQ ID NO 593
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 593

Ser Asp Glu Ile Glu His Leu Val Val Glu Glu Leu Val Arg Lys
1               5                   10                  15

<210> SEQ ID NO 594
<211> LENGTH: 15
<212> TYPE: PRT
<213> ORGANISM: Artificial Sequence
```

```
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 594

Asp Glu Ile Glu His Leu Val Val Glu Glu Leu Val Arg Lys Arg
1               5                   10                  15

<210> SEQ ID NO 595
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 595

Glu Ile Glu His Leu Val Val Glu Glu Leu Val Arg Lys Arg Glu
1               5                   10                  15

<210> SEQ ID NO 596
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 596

Ile Glu His Leu Val Val Glu Glu Leu Val Arg Lys Arg Glu Glu
1               5                   10                  15

<210> SEQ ID NO 597
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 597

Glu His Leu Val Val Glu Glu Leu Val Arg Lys Arg Glu Glu Cys
1               5                   10                  15

<210> SEQ ID NO 598
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 598

His Leu Val Val Glu Glu Leu Val Arg Lys Arg Glu Glu Cys Leu
1               5                   10                  15

<210> SEQ ID NO 599
<211> LENGTH: 15
<212> TYPE: PRT
```

```
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 599

Leu Val Val Glu Glu Leu Val Arg Lys Arg Glu Glu Cys Leu Asp
1               5                   10                  15

<210> SEQ ID NO 600
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 600

Val Val Glu Glu Leu Val Arg Lys Arg Glu Glu Cys Leu Asp Ala
1               5                   10                  15

<210> SEQ ID NO 601
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 601

Val Glu Glu Leu Val Arg Lys Arg Glu Glu Cys Leu Asp Ala Leu
1               5                   10                  15

<210> SEQ ID NO 602
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 602

Glu Glu Leu Val Arg Lys Arg Glu Glu Cys Leu Asp Ala Leu Glu
1               5                   10                  15

<210> SEQ ID NO 603
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 603

Glu Leu Val Arg Lys Arg Glu Glu Cys Leu Asp Ala Leu Glu Ser
1               5                   10                  15

<210> SEQ ID NO 604
<211> LENGTH: 15
```

```
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 604

Leu Val Arg Lys Arg Glu Glu Cys Leu Asp Ala Leu Glu Ser Ile
1               5                   10                  15

<210> SEQ ID NO 605
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 605

Val Arg Lys Arg Glu Glu Cys Leu Asp Ala Leu Glu Ser Ile Met
1               5                   10                  15

<210> SEQ ID NO 606
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 606

Arg Lys Arg Glu Glu Cys Leu Asp Ala Leu Glu Ser Ile Met Thr
1               5                   10                  15

<210> SEQ ID NO 607
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 607

Lys Arg Glu Glu Cys Leu Asp Ala Leu Glu Ser Ile Met Thr Thr
1               5                   10                  15

<210> SEQ ID NO 608
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 608

Arg Glu Glu Cys Leu Asp Ala Leu Glu Ser Ile Met Thr Thr Lys
1               5                   10                  15

<210> SEQ ID NO 609
```

```
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 609

Glu Glu Cys Leu Asp Ala Leu Glu Ser Ile Met Thr Thr Lys Ser
1               5                   10                  15

<210> SEQ ID NO 610
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 610

Glu Cys Leu Asp Ala Leu Glu Ser Ile Met Thr Thr Lys Ser Val
1               5                   10                  15

<210> SEQ ID NO 611
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 611

Cys Leu Asp Ala Leu Glu Ser Ile Met Thr Thr Lys Ser Val Ser
1               5                   10                  15

<210> SEQ ID NO 612
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 612

Leu Asp Ala Leu Glu Ser Ile Met Thr Thr Lys Ser Val Ser Phe
1               5                   10                  15

<210> SEQ ID NO 613
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 613

Asp Ala Leu Glu Ser Ile Met Thr Thr Lys Ser Val Ser Phe Arg
1               5                   10                  15
```

```
<210> SEQ ID NO 614
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 614

Ala Leu Glu Ser Ile Met Thr Thr Lys Ser Val Ser Phe Arg Arg
1               5                   10                  15

<210> SEQ ID NO 615
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 615

Leu Glu Ser Ile Met Thr Thr Lys Ser Val Ser Phe Arg Arg Leu
1               5                   10                  15

<210> SEQ ID NO 616
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 616

Glu Ser Ile Met Thr Thr Lys Ser Val Ser Phe Arg Arg Leu Ser
1               5                   10                  15

<210> SEQ ID NO 617
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 617

Ser Ile Met Thr Thr Lys Ser Val Ser Phe Arg Arg Leu Ser His
1               5                   10                  15

<210> SEQ ID NO 618
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 618

Ile Met Thr Thr Lys Ser Val Ser Phe Arg Arg Leu Ser His Leu
1               5                   10                  15
```

<210> SEQ ID NO 619
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 619

Met Thr Thr Lys Ser Val Ser Phe Arg Arg Leu Ser His Leu Arg
1               5                   10                  15

<210> SEQ ID NO 620
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 620

Thr Thr Lys Ser Val Ser Phe Arg Arg Leu Ser His Leu Arg Lys
1               5                   10                  15

<210> SEQ ID NO 621
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 621

Thr Lys Ser Val Ser Phe Arg Arg Leu Ser His Leu Arg Lys Leu
1               5                   10                  15

<210> SEQ ID NO 622
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 622

Lys Ser Val Ser Phe Arg Arg Leu Ser His Leu Arg Lys Leu Val
1               5                   10                  15

<210> SEQ ID NO 623
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 623

Ser Val Ser Phe Arg Arg Leu Ser His Leu Arg Lys Leu Val Pro
1               5                   10                  15

```
<210> SEQ ID NO 624
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 624

Val Ser Phe Arg Arg Leu Ser His Leu Arg Lys Leu Val Pro Gly
1               5                   10                  15

<210> SEQ ID NO 625
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 625

Ser Phe Arg Arg Leu Ser His Leu Arg Lys Leu Val Pro Gly Phe
1               5                   10                  15

<210> SEQ ID NO 626
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 626

Phe Arg Arg Leu Ser His Leu Arg Lys Leu Val Pro Gly Phe Gly
1               5                   10                  15

<210> SEQ ID NO 627
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 627

Arg Arg Leu Ser His Leu Arg Lys Leu Val Pro Gly Phe Gly Lys
1               5                   10                  15

<210> SEQ ID NO 628
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 628

Arg Leu Ser His Leu Arg Lys Leu Val Pro Gly Phe Gly Lys Ala
```

<210> SEQ ID NO 629
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 629

Leu Ser His Leu Arg Lys Leu Val Pro Gly Phe Gly Lys Ala Tyr
1               5                   10                  15

<210> SEQ ID NO 630
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 630

Ser His Leu Arg Lys Leu Val Pro Gly Phe Gly Lys Ala Tyr Thr
1               5                   10                  15

<210> SEQ ID NO 631
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 631

His Leu Arg Lys Leu Val Pro Gly Phe Gly Lys Ala Tyr Thr Ile
1               5                   10                  15

<210> SEQ ID NO 632
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 632

Leu Arg Lys Leu Val Pro Gly Phe Gly Lys Ala Tyr Thr Ile Phe
1               5                   10                  15

<210> SEQ ID NO 633
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 633

Arg Lys Leu Val Pro Gly Phe Gly Lys Ala Tyr Thr Ile Phe Asn
1               5                   10                  15

<210> SEQ ID NO 634
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 634

Lys Leu Val Pro Gly Phe Gly Lys Ala Tyr Thr Ile Phe Asn Lys
1               5                   10                  15

<210> SEQ ID NO 635
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 635

Leu Val Pro Gly Phe Gly Lys Ala Tyr Thr Ile Phe Asn Lys Thr
1               5                   10                  15

<210> SEQ ID NO 636
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 636

Val Pro Gly Phe Gly Lys Ala Tyr Thr Ile Phe Asn Lys Thr Leu
1               5                   10                  15

<210> SEQ ID NO 637
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 637

Pro Gly Phe Gly Lys Ala Tyr Thr Ile Phe Asn Lys Thr Leu Met
1               5                   10                  15

<210> SEQ ID NO 638
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 638

Asn Lys Thr Leu Met Glu Ala Asp Ala His Tyr Lys Ser Val Arg
1               5                   10                  15

<210> SEQ ID NO 639
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 639

Lys Thr Leu Met Glu Ala Asp Ala His Tyr Lys Ser Val Arg Thr
1               5                   10                  15

<210> SEQ ID NO 640
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 640

Thr Leu Met Glu Ala Asp Ala His Tyr Lys Ser Val Arg Thr Trp
1               5                   10                  15

<210> SEQ ID NO 641
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 641

Leu Met Glu Ala Asp Ala His Tyr Lys Ser Val Arg Thr Trp Asn
1               5                   10                  15

<210> SEQ ID NO 642
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 642

Met Glu Ala Asp Ala His Tyr Lys Ser Val Arg Thr Trp Asn Glu
1               5                   10                  15

<210> SEQ ID NO 643
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

```
<400> SEQUENCE: 643

Glu Ala Asp Ala His Tyr Lys Ser Val Arg Thr Trp Asn Glu Ile
1               5                   10                  15

<210> SEQ ID NO 644
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 644

Ala Asp Ala His Tyr Lys Ser Val Arg Thr Trp Asn Glu Ile Leu
1               5                   10                  15

<210> SEQ ID NO 645
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 645

Asp Ala His Tyr Lys Ser Val Arg Thr Trp Asn Glu Ile Leu Pro
1               5                   10                  15

<210> SEQ ID NO 646
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 646

Ala His Tyr Lys Ser Val Arg Thr Trp Asn Glu Ile Leu Pro Ser
1               5                   10                  15

<210> SEQ ID NO 647
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 647

His Tyr Lys Ser Val Arg Thr Trp Asn Glu Ile Leu Pro Ser Lys
1               5                   10                  15

<210> SEQ ID NO 648
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.
```

<400> SEQUENCE: 648

Tyr Lys Ser Val Arg Thr Trp Asn Glu Ile Leu Pro Ser Lys Gly
1               5                   10                  15

<210> SEQ ID NO 649
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 649

Lys Ser Val Arg Thr Trp Asn Glu Ile Leu Pro Ser Lys Gly Cys
1               5                   10                  15

<210> SEQ ID NO 650
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 650

Ser Val Arg Thr Trp Asn Glu Ile Leu Pro Ser Lys Gly Cys Leu
1               5                   10                  15

<210> SEQ ID NO 651
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 651

Val Arg Thr Trp Asn Glu Ile Leu Pro Ser Lys Gly Cys Leu Arg
1               5                   10                  15

<210> SEQ ID NO 652
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 652

Arg Thr Trp Asn Glu Ile Leu Pro Ser Lys Gly Cys Leu Arg Val
1               5                   10                  15

<210> SEQ ID NO 653
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of -continued glycoprotein G consists of amino acids 20-458 of SEQ ID NO:207.

<400> SEQUENCE: 653

Thr Trp Asn Glu Ile Leu Pro Ser Lys Gly Cys Leu Arg Val Gly
1               5                   10                  15

<210> SEQ ID NO 654
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 654

Trp Asn Glu Ile Leu Pro Ser Lys Gly Cys Leu Arg Val Gly Gly
1               5                   10                  15

<210> SEQ ID NO 655
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 655

Asn Glu Ile Leu Pro Ser Lys Gly Cys Leu Arg Val Gly Gly Arg
1               5                   10                  15

<210> SEQ ID NO 656
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 656

Glu Ile Leu Pro Ser Lys Gly Cys Leu Arg Val Gly Gly Arg Cys
1               5                   10                  15

<210> SEQ ID NO 657
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 657

Ile Leu Pro Ser Lys Gly Cys Leu Arg Val Gly Gly Arg Cys His
1               5                   10                  15

<210> SEQ ID NO 658
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain -continued ERA (SEQ ID NO:207), wherein the extracellular domain of
glycoprotein G consists of amino acids 20-458 of SEQ ID NO:207.

<400> SEQUENCE: 658

Leu Pro Ser Lys Gly Cys Leu Arg Val Gly Gly Arg Cys His Pro
1               5                   10                  15

<210> SEQ ID NO 659
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 659

Pro Ser Lys Gly Cys Leu Arg Val Gly Gly Arg Cys His Pro His
1               5                   10                  15

<210> SEQ ID NO 660
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 660

Ser Lys Gly Cys Leu Arg Val Gly Gly Arg Cys His Pro His Val
1               5                   10                  15

<210> SEQ ID NO 661
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 661

Lys Gly Cys Leu Arg Val Gly Gly Arg Cys His Pro His Val Asn
1               5                   10                  15

<210> SEQ ID NO 662
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 662

Gly Cys Leu Arg Val Gly Gly Arg Cys His Pro His Val Asn Gly
1               5                   10                  15

<210> SEQ ID NO 663
<211> LENGTH: 15
<212> TYPE: PRT
<213> ORGANISM: Artificial Sequence
<220> FEATURE:
<223> OTHER INFORMATION: 15 contiguous and consecutive amino acids from -continued the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 663

```
Cys Leu Arg Val Gly Gly Arg Cys His Pro His Val Asn Gly Val
1               5                   10                  15
```

<210> SEQ ID NO 664
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 664

```
Leu Arg Val Gly Gly Arg Cys His Pro His Val Asn Gly Val Phe
1               5                   10                  15
```

<210> SEQ ID NO 665
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 665

```
Arg Val Gly Gly Arg Cys His Pro His Val Asn Gly Val Phe Phe
1               5                   10                  15
```

<210> SEQ ID NO 666
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 666

```
Val Gly Gly Arg Cys His Pro His Val Asn Gly Val Phe Phe Asn
1               5                   10                  15
```

<210> SEQ ID NO 667
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 667

```
Gly Gly Arg Cys His Pro His Val Asn Gly Val Phe Phe Asn Gly
1               5                   10                  15
```

<210> SEQ ID NO 668
<211> LENGTH: 15
<212> TYPE: PRT
<213> ORGANISM: Artificial Sequence
<220> FEATURE:

<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 668

Gly Arg Cys His Pro His Val Asn Gly Val Phe Phe Asn Gly Ile
1               5                   10                  15

<210> SEQ ID NO 669
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 669

Arg Cys His Pro His Val Asn Gly Val Phe Phe Asn Gly Ile Ile
1               5                   10                  15

<210> SEQ ID NO 670
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 670

Cys His Pro His Val Asn Gly Val Phe Phe Asn Gly Ile Ile Leu
1               5                   10                  15

<210> SEQ ID NO 671
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 671

His Pro His Val Asn Gly Val Phe Phe Asn Gly Ile Ile Leu Gly
1               5                   10                  15

<210> SEQ ID NO 672
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 672

Pro His Val Asn Gly Val Phe Phe Asn Gly Ile Ile Leu Gly Pro
1               5                   10                  15

<210> SEQ ID NO 673
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 673

His Val Asn Gly Val Phe Phe Asn Gly Ile Ile Leu Gly Pro Asp
1               5                   10                  15

<210> SEQ ID NO 674
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 674

Val Asn Gly Val Phe Phe Asn Gly Ile Ile Leu Gly Pro Asp Gly
1               5                   10                  15

<210> SEQ ID NO 675
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 675

Asn Gly Val Phe Phe Asn Gly Ile Ile Leu Gly Pro Asp Gly Asn
1               5                   10                  15

<210> SEQ ID NO 676
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 676

Gly Val Phe Phe Asn Gly Ile Ile Leu Gly Pro Asp Gly Asn Val
1               5                   10                  15

<210> SEQ ID NO 677
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 677

Val Phe Phe Asn Gly Ile Ile Leu Gly Pro Asp Gly Asn Val Leu
1               5                   10                  15

<210> SEQ ID NO 678
<211> LENGTH: 15
<212> TYPE: PRT

```
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 678

Phe Phe Asn Gly Ile Ile Leu Gly Pro Asp Gly Asn Val Leu Ile
1               5                   10                  15

<210> SEQ ID NO 679
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 679

Phe Asn Gly Ile Ile Leu Gly Pro Asp Gly Asn Val Leu Ile Pro
1               5                   10                  15

<210> SEQ ID NO 680
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 680

Asn Gly Ile Ile Leu Gly Pro Asp Gly Asn Val Leu Ile Pro Glu
1               5                   10                  15

<210> SEQ ID NO 681
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 681

Gly Ile Ile Leu Gly Pro Asp Gly Asn Val Leu Ile Pro Glu Met
1               5                   10                  15

<210> SEQ ID NO 682
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 682

Ile Ile Leu Gly Pro Asp Gly Asn Val Leu Ile Pro Glu Met Gln
1               5                   10                  15

<210> SEQ ID NO 683
<211> LENGTH: 15
```

```
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 683

Ile Leu Gly Pro Asp Gly Asn Val Leu Ile Pro Glu Met Gln Ser
1               5                   10                  15

<210> SEQ ID NO 684
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 684

Leu Gly Pro Asp Gly Asn Val Leu Ile Pro Glu Met Gln Ser Ser
1               5                   10                  15

<210> SEQ ID NO 685
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 685

Gly Pro Asp Gly Asn Val Leu Ile Pro Glu Met Gln Ser Ser Leu
1               5                   10                  15

<210> SEQ ID NO 686
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 686

Pro Asp Gly Asn Val Leu Ile Pro Glu Met Gln Ser Ser Leu Leu
1               5                   10                  15

<210> SEQ ID NO 687
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 687

Asp Gly Asn Val Leu Ile Pro Glu Met Gln Ser Ser Leu Leu Gln
1               5                   10                  15

<210> SEQ ID NO 688
```

```
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 688

Gly Asn Val Leu Ile Pro Glu Met Gln Ser Ser Leu Leu Gln Gln
1               5                   10                  15

<210> SEQ ID NO 689
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 689

Asn Val Leu Ile Pro Glu Met Gln Ser Ser Leu Leu Gln Gln His
1               5                   10                  15

<210> SEQ ID NO 690
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 690

Val Leu Ile Pro Glu Met Gln Ser Ser Leu Leu Gln Gln His Met
1               5                   10                  15

<210> SEQ ID NO 691
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 691

Leu Ile Pro Glu Met Gln Ser Ser Leu Leu Gln Gln His Met Glu
1               5                   10                  15

<210> SEQ ID NO 692
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 692

Ile Pro Glu Met Gln Ser Ser Leu Leu Gln Gln His Met Glu Leu
1               5                   10                  15
```

-continued

```
<210> SEQ ID NO 693
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 693

Pro Glu Met Gln Ser Ser Leu Leu Gln Gln His Met Glu Leu Leu
1               5                   10                  15

<210> SEQ ID NO 694
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 694

Glu Met Gln Ser Ser Leu Leu Gln Gln His Met Glu Leu Leu Glu
1               5                   10                  15

<210> SEQ ID NO 695
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 695

Met Gln Ser Ser Leu Leu Gln Gln His Met Glu Leu Leu Glu Ser
1               5                   10                  15

<210> SEQ ID NO 696
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 696

Gln Ser Ser Leu Leu Gln Gln His Met Glu Leu Leu Glu Ser Ser
1               5                   10                  15

<210> SEQ ID NO 697
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 697

Ser Ser Leu Leu Gln Gln His Met Glu Leu Leu Glu Ser Ser Val
1               5                   10                  15
```

<210> SEQ ID NO 698
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 698

Ser Leu Leu Gln Gln His Met Glu Leu Leu Glu Ser Ser Val Ile
1               5                   10                  15

<210> SEQ ID NO 699
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 699

Leu Leu Gln Gln His Met Glu Leu Leu Glu Ser Ser Val Ile Pro
1               5                   10                  15

<210> SEQ ID NO 700
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 700

Leu Gln Gln His Met Glu Leu Leu Glu Ser Ser Val Ile Pro Leu
1               5                   10                  15

<210> SEQ ID NO 701
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 701

Gln Gln His Met Glu Leu Leu Glu Ser Ser Val Ile Pro Leu Val
1               5                   10                  15

<210> SEQ ID NO 702
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 702

Gln His Met Glu Leu Leu Glu Ser Ser Val Ile Pro Leu Val His
1               5                   10                  15

<210> SEQ ID NO 703
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 703

His Met Glu Leu Leu Glu Ser Ser Val Ile Pro Leu Val His Pro
1               5                   10                  15

<210> SEQ ID NO 704
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 704

Met Glu Leu Leu Glu Ser Ser Val Ile Pro Leu Val His Pro Leu
1               5                   10                  15

<210> SEQ ID NO 705
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 705

Glu Leu Leu Glu Ser Ser Val Ile Pro Leu Val His Pro Leu Ala
1               5                   10                  15

<210> SEQ ID NO 706
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 706

Leu Leu Glu Ser Ser Val Ile Pro Leu Val His Pro Leu Ala Asp
1               5                   10                  15

<210> SEQ ID NO 707
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 707

Leu Glu Ser Ser Val Ile Pro Leu Val His Pro Leu Ala Asp Pro

<210> SEQ ID NO 708
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 708

Glu Ser Ser Val Ile Pro Leu Val His Pro Leu Ala Asp Pro Ser
1               5                   10                  15

<210> SEQ ID NO 709
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 709

Ser Ser Val Ile Pro Leu Val His Pro Leu Ala Asp Pro Ser Thr
1               5                   10                  15

<210> SEQ ID NO 710
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 710

Ser Val Ile Pro Leu Val His Pro Leu Ala Asp Pro Ser Thr Val
1               5                   10                  15

<210> SEQ ID NO 711
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 711

Val Ile Pro Leu Val His Pro Leu Ala Asp Pro Ser Thr Val Phe
1               5                   10                  15

<210> SEQ ID NO 712
<211> LENGTH: 15
<212> TYPE: PRT
<213> ORGANISM: Artificial Sequence
<220> FEATURE:
<223> OTHER INFORMATION: 15 contiguous and consecutive amino acids from
the extracellular domain of glycoprotein G of rabies virus strain
ERA (SEQ ID NO:207), wherein the extracellular domain of
glycoprotein G consists of amino acids 20-458 of SEQ ID NO:207.

<400> SEQUENCE: 712

```
Ile Pro Leu Val His Pro Leu Ala Asp Pro Ser Thr Val Phe Lys
1               5                   10                  15
```

<210> SEQ ID NO 713
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain ERA (SEQ ID NO:207), where-
in the extracellular domain of
      glycoprotein G consists of amino acids 20-458 of SEQ ID NO:207.

<400> SEQUENCE: 713

```
Pro Leu Val His Pro Leu Ala Asp Pro Ser Thr Val Phe Lys Asp
1               5                   10                  15
```

<210> SEQ ID NO 714
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 714

```
Leu Val His Pro Leu Ala Asp Pro Ser Thr Val Phe Lys Asp Gly
1               5                   10                  15
```

<210> SEQ ID NO 715
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 715

```
Val His Pro Leu Ala Asp Pro Ser Thr Val Phe Lys Asp Gly Asp
1               5                   10                  15
```

<210> SEQ ID NO 716
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 716

```
His Pro Leu Ala Asp Pro Ser Thr Val Phe Lys Asp Gly Asp Glu
1               5                   10                  15
```

<210> SEQ ID NO 717
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 717

```
Pro Leu Ala Asp Pro Ser Thr Val Phe Lys Asp Gly Asp Glu Ala
1               5                   10                  15
```

<210> SEQ ID NO 718
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 718

```
Leu Ala Asp Pro Ser Thr Val Phe Lys Asp Gly Asp Glu Ala Glu
1               5                   10                  15
```

<210> SEQ ID NO 719
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 719

```
Ala Asp Pro Ser Thr Val Phe Lys Asp Gly Asp Glu Ala Glu Asp
1               5                   10                  15
```

<210> SEQ ID NO 720
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 720

```
Asp Pro Ser Thr Val Phe Lys Asp Gly Asp Glu Ala Glu Asp Phe
1               5                   10                  15
```

<210> SEQ ID NO 721
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 721

```
Pro Ser Thr Val Phe Lys Asp Gly Asp Glu Ala Glu Asp Phe Val
1               5                   10                  15
```

<210> SEQ ID NO 722
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 722

```
Ser Thr Val Phe Lys Asp Gly Asp Glu Ala Glu Asp Phe Val Glu
1               5                   10                  15

<210> SEQ ID NO 723
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 723

Thr Val Phe Lys Asp Gly Asp Glu Ala Glu Asp Phe Val Glu Val
1               5                   10                  15

<210> SEQ ID NO 724
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 724

Val Phe Lys Asp Gly Asp Glu Ala Glu Asp Phe Val Glu Val His
1               5                   10                  15

<210> SEQ ID NO 725
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 725

Phe Lys Asp Gly Asp Glu Ala Glu Asp Phe Val Glu Val His Leu
1               5                   10                  15

<210> SEQ ID NO 726
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 726

Lys Asp Gly Asp Glu Ala Glu Asp Phe Val Glu Val His Leu Pro
1               5                   10                  15

<210> SEQ ID NO 727
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.
```

```
<400> SEQUENCE: 727

Asp Gly Asp Glu Ala Glu Asp Phe Val Glu Val His Leu Pro Asp
1               5                   10                  15

<210> SEQ ID NO 728
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 728

Gly Asp Glu Ala Glu Asp Phe Val Glu Val His Leu Pro Asp Val
1               5                   10                  15

<210> SEQ ID NO 729
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 729

Asp Glu Ala Glu Asp Phe Val Glu Val His Leu Pro Asp Val His
1               5                   10                  15

<210> SEQ ID NO 730
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 730

Glu Ala Glu Asp Phe Val Glu Val His Leu Pro Asp Val His Asn
1               5                   10                  15

<210> SEQ ID NO 731
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 731

Ala Glu Asp Phe Val Glu Val His Leu Pro Asp Val His Asn Gln
1               5                   10                  15

<210> SEQ ID NO 732
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.
```

<400> SEQUENCE: 732

Glu Asp Phe Val Glu Val His Leu Pro Asp Val His Asn Gln Val
1               5                   10                  15

<210> SEQ ID NO 733
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 733

Asp Phe Val Glu Val His Leu Pro Asp Val His Asn Gln Val Ser
1               5                   10                  15

<210> SEQ ID NO 734
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 734

Phe Val Glu Val His Leu Pro Asp Val His Asn Gln Val Ser Gly
1               5                   10                  15

<210> SEQ ID NO 735
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 735

Val Glu Val His Leu Pro Asp Val His Asn Gln Val Ser Gly Val
1               5                   10                  15

<210> SEQ ID NO 736
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 736

Glu Val His Leu Pro Asp Val His Asn Gln Val Ser Gly Val Asp
1               5                   10                  15

<210> SEQ ID NO 737
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of -continued glycoprotein G consists of amino acids 20-458 of SEQ ID NO:207.

<400> SEQUENCE: 737

Val His Leu Pro Asp Val His Asn Gln Val Ser Gly Val Asp Leu
1               5                   10                  15

<210> SEQ ID NO 738
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 738

His Leu Pro Asp Val His Asn Gln Val Ser Gly Val Asp Leu Gly
1               5                   10                  15

<210> SEQ ID NO 739
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 739

Leu Pro Asp Val His Asn Gln Val Ser Gly Val Asp Leu Gly Leu
1               5                   10                  15

<210> SEQ ID NO 740
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 740

Pro Asp Val His Asn Gln Val Ser Gly Val Asp Leu Gly Leu Pro
1               5                   10                  15

<210> SEQ ID NO 741
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 741

Asp Val His Asn Gln Val Ser Gly Val Asp Leu Gly Leu Pro Asn
1               5                   10                  15

<210> SEQ ID NO 742
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain ERA (SEQ ID NO:207), wherein the extracellular domain of
glycoprotein G consists of amino acids 20-458 of SEQ ID NO:207.

<400> SEQUENCE: 742

Val His Asn Gln Val Ser Gly Val Asp Leu Gly Leu Pro Asn Trp
1               5                   10                  15

<210> SEQ ID NO 743
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 743

His Asn Gln Val Ser Gly Val Asp Leu Gly Leu Pro Asn Trp Gly
1               5                   10                  15

<210> SEQ ID NO 744
<211> LENGTH: 15
<212> TYPE: PRT
<213> ORGANISM: Artificial Sequence
<220> FEATURE:
<223> OTHER INFORMATION: 15 contiguous and consecutive amino acids from
      the extracellular domain of glycoprotein G of rabies virus strain
      ERA (SEQ ID NO:207), wherein the extracellular domain of
      glycoprotein G consists of amino acids 20-458 of SEQ ID NO:207.

<400> SEQUENCE: 744

Asn Gln Val Ser Gly Val Asp Leu Gly Leu Pro Asn Trp Gly Lys
1               5                   10                  15

<210> SEQ ID NO 745
<211> LENGTH: 21
<212> TYPE: DNA
<213> ORGANISM: Lyssavirus Rabies
<220> FEATURE:
<221> NAME/KEY: misc_feature
<223> OTHER INFORMATION: Part of glycoprotein of CVS-11

<400> SEQUENCE: 745
cggacctgga atgagatcat c                                          21

<210> SEQ ID NO 746
<211> LENGTH: 21
<212> TYPE: DNA
<213> ORGANISM: Lyssavirus Rabies
<220> FEATURE:
<221> NAME/KEY: misc_feature
<223> OTHER INFORMATION: Part of glycoprotein of E98-2, 4, 5, 6, 7

<400> SEQUENCE: 746
cggacctggg atgagatcat c                                          21

<210> SEQ ID NO 747
<211> LENGTH: 18
<212> TYPE: PRT
<213> ORGANISM: Lyssavirus Rabies
<220> FEATURE:
<221> NAME/KEY: misc_feature
<223> OTHER INFORMATION: Part of glycoprotein of CVS-11

<400> SEQUENCE: 747

His Tyr Lys Ser Val Arg Thr Trp Asn Glu Ile Ile Pro Ser Lys Gly
1               5                   10                  15

```
<210> SEQ ID NO 748
<211> LENGTH: 18
<212> TYPE: PRT
<213> ORGANISM: Lyssavirus Rabies
<220> FEATURE:
<221> NAME/KEY: misc_feature
<223> OTHER INFORMATION: Part of glycoprotein of E98-2, 4, 5, 6, 7

<400> SEQUENCE: 748

His Tyr Lys Ser Val Arg Thr Trp Asp Glu Ile Ile Pro Ser Lys Gly
1               5                   10                  15

Cys Leu
```

What is claimed is:

1. A composition comprising first and second human monoclonal antibodies binding to a first and second epitope of a rabies virus,
   wherein both the first and second human monoclonal antibodies are able to neutralize the rabies virus,
   wherein the first and second epitopes are different from one another and are non-competing,
   wherein either the first or second human monoclonal antibodies are CR04-098, comprising the heavy chain sequence, SEQ ID NO:335, and the light chain sequence, SEQ ID NO:337,
   and wherein the antibodies have isoelectric points as measured by isoelectric focusing that differ by less than 1.5 pI units.

2. A composition comprising first and second human monoclonal antibodies binding to a first and second epitope of a rabies virus,
   wherein both the first and second human monoclonal antibodies are able to neutralize the rabies virus,
   wherein the first and second epitopes are different from one another and are non-competing,
   wherein either the first or second human monoclonal antibodies are CR-57, comprising the heavy chain sequence, SEQ ID NO:123, and the light chain sequence, SEQ ID NO:125,
   and wherein the antibodies have isoelectric points as measured by isoelectric focusing that differ by less than 1.5 pI units.

3. A composition comprising first and second human monoclonal antibodies binding to a first and second epitope of a rabies virus,
   wherein both the first and second human monoclonal antibodies are able to neutralize the rabies virus,
   wherein the first and second epitopes are different from one another and are non-competing,
   wherein the first human monoclonal antibodies are CR04-098, comprising the heavy chain sequence, SEQ ID NO:335, and the light chain sequence, SEQ ID NO:337, and the second human monoclonal antibodies are CR-57, comprising the heavy chain sequence, SEQ ID NO:123, and the light chain sequence, SEQ ID NO:125,
   and wherein the antibodies have isoelectric points as measured by isoelectric focusing that differ by less than 1.5 pI units.

* * * * *